US012419970B2

(12) United States Patent
Hirano et al.

(10) Patent No.: US 12,419,970 B2
(45) Date of Patent: Sep. 23, 2025

(54) GENE THERAPY FOR DISEASES CAUSED BY UNBALANCED NUCLEOTIDE POOLS INCLUDING MITOCHONDRIAL DNA DEPLETION SYNDROMES

(71) Applicant: The Trustees of Columbia University in the City of New York, New York, NY (US)

(72) Inventors: Michio Hirano, New York, NY (US); Hasan O. Akman, Haworth, NJ (US); Carlos Lopez-Gomez, Fuengirola (ES)

(73) Assignee: The Trustees of Columbia University in the City of New York, New York, NY (US)

( * ) Notice: Subject to any disclaimer, the term of this patent is extended or adjusted under 35 U.S.C. 154(b) by 1190 days.

(21) Appl. No.: 17/048,236

(22) PCT Filed: Apr. 18, 2019

(86) PCT No.: PCT/US2019/028108
§ 371 (c)(1),
(2) Date: Oct. 16, 2020

(87) PCT Pub. No.: WO2019/204593
PCT Pub. Date: Oct. 24, 2019

(65) Prior Publication Data
US 2021/0100917 A1   Apr. 8, 2021

Related U.S. Application Data

(60) Provisional application No. 62/659,281, filed on Apr. 18, 2018.

(51) Int. Cl.
*A61K 38/45* (2006.01)
*A61K 48/00* (2006.01)
*C07K 14/705* (2006.01)
*C12N 15/86* (2006.01)

(52) U.S. Cl.
CPC .......... *A61K 48/005* (2013.01); *A61K 38/45* (2013.01); *C07K 14/705* (2013.01); *C12N 15/86* (2013.01); *C12N 2750/14143* (2013.01); *C12Y 207/01021* (2013.01); *C12Y 207/01076* (2013.01); *C12Y 207/01113* (2013.01)

(58) Field of Classification Search
CPC .............................................. C12Y 207/01021
See application file for complete search history.

(56) References Cited

U.S. PATENT DOCUMENTS

| | | | |
|---|---|---|---|
| 5,658,785 | A | 8/1997 | Johnson |
| 5,843,742 | A | 12/1998 | Natsoulis et al. |
| 6,632,670 | B1 | 10/2003 | Wadsworth et al. |
| 2016/0058890 | A1* | 3/2016 | Buj Bello ............... C12N 9/16 435/320.1 |
| 2016/0279159 | A1* | 9/2016 | Hirano ................ A61K 31/7072 |

FOREIGN PATENT DOCUMENTS

| | | |
|---|---|---|
| WO | WO 2007/118245 | 10/2007 |
| WO | WO 2016/205671 | 12/2016 |
| WO | WO-2017191274 A2 * | 11/2017 ......... A61K 31/7088 |

OTHER PUBLICATIONS

Bottani, E et al., "AAV-mediated Liver-specific MPV17 Expression Restores mtDNA Levels and Prevents Diet-induced Liver Failure". Molecular Therapy. Nov. 19, 2013; vol. 22, No. 1; pp. 1-8; abstract; p. 4, col. 1, paragraph 2; p. 7, col. 1, paragraph 2; DOI: 10.1038/mt.2013.230.

Hosseini, SH et al., "Targeted Transgenic Overexpression of Mitochondrial Thymidine Kinase (TK2) Alters Mitochondrial DNA (mtDNA) and Mitochondrial. Polypeptide Abundance: Transgenic TK2, mtDNA, and Antiretrovirals". The American Journal of Pathology. Mar. 2007; vol. 170, No. 3; pp. 865-874; abstract; p. 866, col. 1, paragraphs 1-3; p. 866, col. 2, paragraph 2; p. 872, col. 2, paragraphs 2-3; DOI: 10.2353/ajpath.2007.060655.

El-Hattab, AW et al., "Mitochondrial DNA Depletion Syndromes: Review and Updates of Genetic Basis, Manifestations, and Therapeutic Options". Neurotherapeutics. Apr. 2013; vol. 10, No. 2; pp. 186-198; abstract; p. 187, col. 1, paragraph 2; DOI: 10.1007/s13311-013-0177-6.

Sun, R et al., "Thymidine Kinase 2 Enzyme Kinetics Elucidate the Mechanism of Thymidine-Induced Mitochondrial DNA Depletion". Biochemistry. Sep. 23, 2014; vol. 53, No. 39; abstract; Genbank Supplemental pp. 1-5; DOI: 10.1021/bi5006877.

Krishnan, Shuba, et al. "Long term expression of *Drosophila melanogaster* nucleoside kinase in thymidine kinase 2-deficient mice with No. lethal effects caused by nucleotide pool imbalances." Journal of Biological Chemistry 289.47 (2014): 32835-32844.

(Continued)

*Primary Examiner* — Ekaterina Poliakova-Georgantas
(74) *Attorney, Agent, or Firm* — Amster, Rothstein & Ebenstein LLP

(57) ABSTRACT

The invention relates generally to a method of treatment for a human genetic disease, such as diseases characterized by unbalanced nucleotide pools, e.g., mitochondrial DNA depletion syndromes, and more specifically, thymidine kinase 2 (TK2) deficiency, using gene therapy. The gene therapy may involve administration of one or more constructs, such as a viral vector, containing a nucleic acid encoding a functional protein. The functional protein may correspond to a nuclear gene. For treatment of TK2 deficiency, the gene therapy may involve administration of one or more constructs, such as a viral vector, containing a nucleic acid encoding a functional TK2 enzyme. The treatment may also involve the administration of pharmacological therapy in conjunction with the gene therapy. The treatment protocols of the disclosure, such as those involving gene therapy alone or in combination with pharmacological therapy, can be used to treat, prevent, and/or cure various other disorders of unbalanced nucleoside pools, especially those found in mitochondrial DNA depletion syndrome.

6 Claims, 31 Drawing Sheets

Specification includes a Sequence Listing.

(56) References Cited

OTHER PUBLICATIONS

Van Poecke, Sara, et al. "Synthesis, modeling and evaluation of 3'-(1-aryl-1 H-tetrazol-5-ylamino)-substituted 3'-deoxythymidine derivatives as potent and selective human mitochondrial thymidine kinase inhibitors." Organic & Biomolecular Chemistry 9.3 (2011): 892-901.
Sara Van Poecke et al., "Synthesis, modeling and evaluation of 3'-(1-aryl-1 H-tetrazol-5-ylamino )substituted 3'-dcoxythymidinc derivatives as potent and selective human mitochondrial thymidine kinase inhibitorst", Org Biomol Chem. Feb. 7, 2011;9(3):892-901. doi: 10.1039/c0ob00591f. Epub Dec. 2, 2010.
Krishnan et al., "Long Term Expression of Drosophila melanogaster Nucleoside Kinase in Thymidine Kinase 2-deficient Mice with No Lethal Effects Caused by Nucleotide Pool Imbalances", J Biol Chem Nov. 21, 2014;289(47):32835-44. doi: 10.1074/jbc.M114. 588921. Epub Oct. 8, 2014.
Akman, et al. (May 6, 2008) Thymidine kinase 2 (H126N) knock in mice show the essential role of balanced deoxynucleotide pools for mitochondrial DNA maintenance. Hum Mol Genet 17:2433-2440.
Bourdon, et al. (May 7, 2007) Mutation of RRM2B, encoding p53-controlled ribonucleotide reductase (p53R2), causes severe mitochondrial DNA depletion. Nat Genet 39: 776-780.
Chanprasert, et al. (Dec. 6, 2012) TK2-Related Mitochondrial DNA Depletion Syndrome, Myopathic Form. GeneReviews® Internet.
Copeland (Mar. 21, 2008) Inherited mitochondrial diseases of DNA replication. Ann. Rev. Med. 59:131-146.
DiMauro, et al. (Feb. 20, 1987) Cytochrome c oxidase deficiency in Leigh syndrome. Ann Neurol 22: 498-506.
DiMauro, Schon. (Jul. 1, 2003) Mitochondrial respiratory-chain diseases. N Engl J Med 348:2656-2668.
DiMauro, Hirano. (2005) Mitochondrial encephalomyopathies: an update. Neuromuscul Disord 15:276-286. Accepted Dec. 10, 2004.
Dorado, et al. (2011) Onset and organ specificity of Tk2 deficiency depends on Tk1 down-regulation and transcriptional compensation. Hum Mol Genet. 20:155-64. Accepted Oct. 6, 2010.
Elpeleg, et al. (Apr. 7, 2005) Deficiency of the ADP-forming succinyl-CoA synthase activity is associated with encephalomyopathy and mitochondrial DNA depletion. Am J Hum Genet 76: 1081-1086.
Galbiati, et al. (2006) New mutations in TK2 gene associated with mitochondrial DNA depletion. Pediatr Neurol 34: 177-185. Accepted Jul. 11, 2005.
Garone, et al. (Sep. 10, 2012). MPV17 Mutations Causing Adult-Onset Multisystemic Disorder With Multiple Mitochondrial DNA Deletions. Arch Neurol 69:1648-1651.
Gotz, et al. (Sep. 3, 2008) Thymidine kinase 2 defects can cause multi-tissue mtDNA depletion syndrome. Brain 131:2841-2850.
Hirano, et al. (Dec. 2001) Defects of intergenomic communication: autosomal disorders that cause multiple deletions and depletion of mitochondrial DNA. Semin Cell Develop Biol 12:417-427.
Mandel, et al. (Nov. 2001) The deoxyguanosine kinase gene is mutated in individuals with depleted hepatocerebral mitochondrial DNA. Nat Genet 29: 337-341.
Naviaux, Nguyen. (Feb. 4, 2004) POLG mutations associated with Alpers' syndrome and mitochondrial DNA depletion. Ann Neurol 55: 706-712.
Ostergaard, et al. (Apr. 26, 2007) Deficiency of the alpha subunit of succinate-coenzyme A ligase causes fatal infantile lactic acidosis with mitochondrial DNA depletion. Am J Hum Genet 81: 383-387.
Paradas, et al. (2012) TK2 mutation presenting as indolent myopathy. Neurology 29:504-506. Jan. 9, 2013.
Saada, et al. (Aug. 7, 2003) Mitochondrial deoxyribonucleoside triphosphate pools in thymidine kinase 2 deficiency. Biochem Biophys Res Commun 310:963-966.
Spinazzola, et al. (Apr. 2, 2006) MPV17 encodes an inner mitochondrial membrane protein and is mutated in infantile hepatic mitochondrial DNA depletion. Nat Genet 38: 570-575.
Tyynismaa, et al. (2012) Thymidine kinase 2 mutations in autosomal recessive progressive external ophthalmoplegia with multiple mitochondrial DNA deletions. Hum Mol Genet 21:66-75. Accepted Sep. 19, 2011.
Garone et al., "Deoxypyrimidine monophosphate bypass therapy for thymidine kinase 2 deficiency". EMBO Mol Med Jun. 26, 2014 vol. 6 No. 8 pp. 1016-1027. Especially abstract, p. 1016 col. 2, p. 1017 col. 1 para 2, para 2, p. 1024 col. 1 para 1, p. 1024 col. 1 para 5.
Van Goethem, et al. (Jul. 2001) Mutation of POLG is associated with progressive external ophthalmoplegia characterized by mtDNA deletions. Nature Genet. 28:211-212.
Spelbrink, et al. (Jul. 2001). Human mitochondrial DNA deletions associated with mutations in the gene encoding Twinkle, a phage T7 gene 4-like protein localized in mitochondria. Nature Genet. 28:223-231.
Franzolin, et al. (Mar. 23, 2006) Bromovinyl-deoxyuridine: a selective substrate for mitochondrial thymidine kinase in cell extracts. Biochem. Biophy. Res. Commun. 344(1):30-6.
Sarzi, et al. (Dec. 2007) Twinkle helicase (PEO1) gene mutation causes mitochondrial DNA depletion. Ann. Neurol. 62: 579-587.
Ronchi, et al. (Jun. 28, 2012). Next-generation sequencing reveals DGUOK mutations in adult atients with mitochondrial DNA multiple deletions. Brain 135:3404-3415.
Quinzii, et al. (Feb. 2013) Tissue-specific oxidative stress and loss of mitochondria in CoQ-deficient Pdss2 mutant mice. FASEB J. 27:612-621.
Nishino, et al. (Jan. 29, 1999). Thymidine phosphorylase gene mutations in MNGIE, a human mitochondrial disorder. Science 283:689-692.
Longley, et al. (Jun. 2006). Mutant POLG2 disrupts DNA polymerase gamma subunits and causes progressive external ophthalmoplegia. Am J Hum Genet. 78:1026-1034.
Garone, et al. (2018) Retrospective Natural History of Thymidine Kinase 2 Deficiency. J. Med. Genetics 55:515-21. Received Oct. 3, 2017.
Birch-Machin, et al. (Feb. 1994) An evaluation of the measurement of the activities of complexes I-IV in the respiratory chain of human skeletal muscle mitochondria. Biochem Med Metab Biol 51:35-42.
Béhin, et al. (Feb. 2012) Adult cases of mitochondrial DNA depletion due to TKZ defect an expanding spectrum. Neurology 78:644-648.
Sandmair et al., "Thymidine kinase gene therapy for human malignant glioma, using replication-deficient retroviruses or adenoviruses", Hum Gen Ther, vol. 11 / Issue 16 pp. 2197-2205, Nov. 1, 2000.
Sangro et al., "A phase I clinical trial of thymidine kinase-based gene therapy in advanced hepatocellular carcinoma", Cancer Gene Ther, vol. 17 / Issue 12, pp. 837-843, Dec. 2010.
Tyynela et al., "Adenovirus-mediated herpes simplex Virus thymidine kinase gene therapy in BT4C rat glioma model", Cancer Gene Therapy (Aug. 8, 2002) 9, 917-924.
Tyynismaa, et al. (Aug. 14, 2009). A heterozygous truncating mutation in RRMZB causes autosomal-dominant progressive external ophthalmoplegia with multiple mtDNA deletions. Am. J. Hum. Genet. 85: 290-295.
El-Hattab Ayman W et al: "Therapies for mitochondrial diseases and current clinical trials", Molecular Genetics and Metabolism, Academic Press, Amsterdam, NL, vol. 122, No. 3, Sep. 18, 2017 (Sep. 18, 2017), pp. 1-9, XP085292053, ISSN: 1096-7192, DOI: 10.1016/J.YMGME.2017.09.009 p. 7, paragraph 11.
Keeler et al., "Gene Therapy 2017: Progress and Future Directions," Clin. Transl. Sci., vol. 10, published online May 23, 2017, pp. 242-248.
Khan et al., "Molecular Genetics and Metabolism," Mol. Genet. Metab., vol. 121, No. 3, Jul. 2017, pp. 227-240.
https://grantome.com/grant/NIH/P01-HD080642-01-5121, May 31, 2015 publication date asserted by SIPO in counterpart China Divisional Patent Application No. 2023107576092.
NCBI, GenBank Accession No. AAQ02499.1, "Thymidine Kinase 2, Mitochondrial, Partial (Synthetic Construct)", Jun. 8, 2005.

* cited by examiner

GENE THERAPY FOR DISEASES CAUSED BY UNBALANCED NUCLEOTIDE POOLS INCLUDING MITOCHONDRIAL DNA DEPLETION SYNDROMES

CROSS-REFERENCE TO RELATED APPLICATIONS

This present application is a U.S. National Phase Application under 35 U.S.C. § 371 of International Patent Application No. PCT/US2019/028108, filed on Apr. 18, 2019, which claims priority to U.S. Provisional Application Ser. No. 62/659,281, filed on Apr. 18, 2018, each of which are incorporated by reference as if expressly set forth in its entirety herein.

STATEMENT OF GOVERNMENT SUPPORT

This invention was made with government support under HD080642 awarded by NIH. The government has certain rights in the invention.

FIELD OF THE INVENTION

The invention relates to the field of gene therapy for the treatment of genetic diseases, including human diseases characterized by unbalanced nucleotide pools. Examples of such diseases are mitochondrial DNA depletion syndromes, such as thymidine kinase 2 (TK2) deficiency.

BACKGROUND OF THE INVENTION

Mitochondrial diseases are clinically heterogeneous diseases due to defects of the mitochondrial respiratory chain (RC) and oxidative phosphorylation, the biochemical pathways that convert energy in electrons into adenosine triphosphate (ATP). The respiratory chain is comprised of four multi-subunit enzymes (complexes I-IV) that transfer electrons to generate a proton gradient across the inner membrane of mitochondria. The flow of protons down this concentration gradient through complex V subsequently drives ATP synthesis (DiMauro and Schon 2003; DiMauro and Hirano 2005). Coenzyme $Q_{10}$ ($CoQ_{10}$) is an essential molecule that shuffles electrons from complexes I and II to complex III. The respiratory chain is unique in eukaryotic, e.g., mammalian, cells by virtue of being controlled by two genomes: one composed of mitochondrial DNA (mtDNA) and another composed of nuclear DNA (nDNA). As a consequence, mutations in either genome can cause mitochondrial diseases.

Mitochondrial DNA depletion syndrome (MDS), which is a subgroup of mitochondrial disease, is a frequent cause of severe childhood encephalomyopathy characterized molecularly by reduction of mitochondrial DNA (mtDNA) copy number in tissues and insufficient synthesis of mitochondrial RC complexes (Hirano, et al. 2001). Mutations in several nuclear genes have been identified as causes of infantile MDS, including TK2, DGUOK, POLG, POLG2, SCLA25A4, MPV17, RRM2B, SUCLA2, SUCLG1, TYMP, OPA1, and C10orf2 (PEO1). (Bourdon, et al. 2007; Copeland 2008; Elpeleg, et al. 2005; Mandel, et al. 2001; Naviaux and Nguyen 2004; Ostergaard, et at, 2007; Saada, et al. 2003; Sarzi, et al. 2007; Spinazzola, et al, 2006). In addition, mutations in these nuclear genes can also cause multiple deletions of mtDNA with or without mtDNA depletion (Béhin, et al. 2012; Garone, et al. 2012; Longley, et al. 2006; Nishino, et al. 1999; Paradas, et al. 2012; Ronchi, et al. 2012; Spelbrink, et al. 2001; Tyynismaa, et at 2012; Tyynismaa, et al, 2009; Van Goethem, et at 2001).

Most mitochondrial diseases affect multiple body organs and are typically fatal in childhood or early adult life. There are no proven effective treatments or cures for mitochondriat diseases, only supportive therapies. There remains a need for compositions and methods for treating and preventing mitochondrial diseases, such as MDS.

SUMMARY OF THE INVENTION

The present disclosure relates to compositions and methods that can be used to treat a subject (e.g., a mammalian subject, such as a human subject) that has or is at risk of developing a disease characterized by unbalanced nucleotide pools. Exemplary pathologies that may be treated, prevented, and/or cured using the compositions and methods of the disclosure are mitochondrial diseases, including mitochondrial DNA depletion syndromes, such as deficiencies in a gene selected from TK2, encoding thymidine kinase 2 protein; DGUOK, encoding deoxyguanosine kinase protein; RRM2B, encoding p53R2, p53 inducible subunit of ribonucleotide reductase; TYMP, encoding thymidine phosphorylase; SUCLA2, encoding succinate-CoA ligase ADP-forming beta subunit; SUCLG1, encoding succinate-CoA ligase ADP-forming alpha subunit; MPV17, encoding mitochondrial inner membrane protein MPV17; and POLG, encoding DNA polymerase gamma, catalytic subunit.

Using the compositions and methods of the disclosure, a subject (e.g., a mammalian subject, such as a human subject) that has or is at risk of developing a disease described above may be administered a composition containing a transgene encoding one or more of the foregoing proteins. The composition may be a vector, for example, a viral vector, such as an adeno-associated virus (AAV) vector. In some embodiments, the subject is administered a second composition containing a transgene encoding one or more of the foregoing proteins. The second composition may be a vector, for example, a viral vector, such as an AAV vector. In some embodiments, the subject is additionally administered one or more subsequent compositions, such as a third, fourth, fifth, sixth, seventh, eighth, ninth, and/or tenth composition, containing a transgene encoding one or more of the foregoing proteins. The one or more subsequent compositions may each be, independently, a vector, for example, a viral vector, such as an AAV vector.

In a first aspect, the disclosure features a method of treating, preventing, and/or curing a disease or disorder characterized by unbalanced nucleotide pools in a subject in need thereof. The method includes administering to the subject a therapeutically effective amount of a composition containing a transgene encoding thymidine kinase 2 (TK2), deoxyguanosine kinase (dGK), thymidine phosphorylase (TP), p53 inducible small subunit of ribonucleotide reductase (p53R2), succinyl-CoA ligase ADP-forming subunit beta (SUCLA2), succinyl-CoA ligase GDP-forming subunit alpha (SUCLG1), mitochondrial inner membrane protein MPV17 (MPV17), and/or DNA polymerase subunit gamma (POLG).

In a further aspect, the disclosure features a method of restoring enzyme activity in a subject having a disease or disorder characterized by unbalanced nucleotide pools. The method includes administering to the subject a therapeutically effective amount of a composition containing a transgene encoding TK2, dGK, TP, p53R2, SUCLA2, SUCLG1, MPV17, and/or POLG.

In an additional aspect, the disclosure features a method of alleviating one or more symptoms associated with a disease or disorder characterized by unbalanced nucleotide pools in a subject in need thereof. The method includes administering to the subject a therapeutically effective amount of a composition containing a transgene encoding TK2, dGK, TP, p53R2, SUCLA2, SUCLG1, MPV17, and/or POLG.

In any of the aspects of this invention, the disclosure also provides a composition as described herein for use in a method as described herein. The disclosure also provides the use of a composition as described herein for the manufacture of a medicament for a method as described herein. The transgene may encode TK2, dGK, TP, p53R2, SUCLA2, SUCLG1, MPV17, and/or POLG. For example, the transgene may encode TK2, dGK, TP, p53R2, SUCLA2, SUCLG1 and/or MPV17.

As part of the foregoing aspects, the disclosure therefore also provides a composition containing a transgene encoding TK2, dGK, TP, p53R2, SUCLA2, SUCLG1, MPV17, and/or POLG for use in treating, preventing, and/or curing a disease or disorder characterized by unbalanced nucleotide pools. Also provided is a composition containing a transgene encoding TK2, dGK, TP, p53R2, SUCLA2, SUCLG1, MPV17, and/or POLG for use in restoring enzyme activity in a subject having a disease or disorder characterized by unbalanced nucleotide pools. Furthermore provided is a composition containing a transgene encoding TK2, dGK, TP, p53R2, SUCLA2, SUCLG1, MPV17, and/or POLG for use in alleviating one or more symptoms associated with a disease or disorder characterized by unbalanced nucleotide pools.

As part of the foregoing aspects, the disclosure also provides the use of a composition containing a transgene encoding TK2, dGK, TP, p53R2, SUCLA2, SUCLG1, MPV17, and/or POLG for the manufacture of a medicament for treating, preventing, and/or curing a disease or disorder characterized by unbalanced nucleotide pools. Also provided is the use of a composition containing a transgene encoding TK2, dGK, TP, p53R2, SUCLA2, SUCLG1, MPV17, and/or POLG for the manufacture of a medicament for restoring enzyme activity in a subject having a disease or disorder characterized by unbalanced nucleotide pools. Furthermore provided is the use of a composition containing a transgene encoding TK2, dGK, TP, p53R2, SUCLA2, SUCLG1, MPV17, and/or POLG for the manufacture of a medicament for alleviating one or more symptoms associated with a disease or disorder characterized by unbalanced nucleotide pools.

In some embodiments of any of the foregoing aspects, the disease or disorder is a mitochondrial disease, such as a mitochondrial DNA depletion syndrome (MDS). In some embodiments, the MDS is a myopathic MDS characterized by one or more mutations in an endogenous gene encoding TK2. In some embodiments, the MDS is an encephalomyopathic form characterized by one or more mutations in an endogenous gene encoding SUCLA2. In some embodiments, the MDS is a neurogastrointestinal encephalopathic form characterized by one or more mutations in an endogenous gene encoding TP. In some embodiments, the MDS is a hepatopathic form characterized by one or more mutations in an endogenous gene encoding dGK, MPV17, and/or POLG.

In some embodiments, the transgene encodes TK2. The TK2 may have an amino acid sequence that is at least 85% identical to the amino acid sequence of SEQ ID NO: 1 (e.g., an amino acid sequence that is 85%, 86%, 87%, 88%, 89%, 90%, 91%, 92%, 93%, 94%, 95%, 96%, 97%, 98%, 99%, or 100% identical to the amino acid sequence of SEQ ID NO: 1). In some embodiments, the TK2 has an amino acid sequence that is at least 90% identical to the amino acid sequence of SEQ ID NO: 1 (e.g., an amino acid sequence that is 90%, 91%, 92%, 93%, 94%, 95%, 96%, 97%, 98%, 99%, or 100% identical to the amino acid sequence of SEQ ID NO: 1). In some embodiments, the TK2 has an amino acid sequence that is at least 95% identical to the amino acid sequence of SEQ ID NO: 1 (e.g., an amino acid sequence that is 95%, 96%, 97%, 98%, 99%, or 100% identical to the amino acid sequence of SEQ ID NO: 1). In some embodiments, the TK2 has an amino acid sequence that differs from SEQ ID NO: 1 by way of one or more amino acid substitutions, insertions, and/or deletions, such as by from 1 to 10, 1 to 15, 1 to 20, 1 to 25, or more, amino acid substitutions, insertions, and/or deletions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions). In some embodiments, the TK2 has an amino acid sequence that differs from SEQ ID NO: 1 by way of one or more conservative amino acid substitutions, such as by from 1 to 10, 1 to 15, 1 to 20, 1 to 25, or more, conservative amino acid substitutions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions).

In some embodiments, the transgene encoding TK2 has a nucleic acid sequence that is at least 70% identical to the nucleic acid sequence of SEQ ID NO: 2 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of SEQ ID NO: 2). In some embodiments, the transgene encoding TK2 has a nucleic acid sequence that is at least 85% identical to the nucleic acid sequence of SEQ ID NO: 2 (e.g., a nucleic acid sequence that is 85%, 86%, 87%, 88%, 89%, 90%, 91%, 92%, 93%, 94%, 95%, 96%, 97%, 98%, 99%, or 100% identical to the nucleic acid sequence of SEQ ID NO: 2). In some embodiments, the transgene encoding TK2 has a nucleic acid sequence that is at least 90% identical to the nucleic acid sequence of SEQ ID NO: 2 (e.g., a nucleic acid sequence that is 90%, 91%, 92%, 93%, 94%, 95%, 96%, 97%, 98%, 99%, or 100% identical to the nucleic acid sequence of SEQ ID NO: 2). In some embodiments, the transgene encoding TK2 has a nucleic acid sequence that is at least 95% identical to the nucleic acid sequence of SEQ ID NO: 2 (e.g., a nucleic acid sequence that is 95%, 96%, 97%, 98%, 99%, or 100% identical to the nucleic acid sequence of SEQ ID NO: 2). In some embodiments, the transgene encoding TK2 is codon optimized to increase efficiency. In some embodiments, the nucleic acid of the transgene encoding TK2 is at least at least 70% identical to coding sequence of the transgene that encodes TK2 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of the coding sequence). In some embodiments, the nucleic acid sequence of the transgene encoding TK2 has the nucleic acid sequence of SEQ ID NO: 17.

In some embodiments, the transgene encodes dGK. The dGK may have an amino acid sequence that is at least 85% identical to the amino acid sequence of SEQ ID NO: 3 (e.g., an amino acid sequence that is 85%, 86%, 87%, 88%, 89%, 90%, 91%, 92%, 93%, 94%, 95%, 96%, 97%, 98%, 99%, or 100% identical to the amino acid sequence of SEQ ID NO: 3). In some embodiments, the dGK has an amino acid sequence that is at least 90% identical to the amino acid sequence of SEQ ID NO: 3 (e.g., an amino acid sequence that is 90%, 91%, 92%, 93%, 94%, 95%, 96%, 97%, 98%, 99%, or 100% identical to the amino acid sequence of SEQ ID NO: 3). In some embodiments, the dGK has an amino acid sequence that is at least 95% identical to the amino acid sequence of SEQ ID NO: 3 (e.g., an amino acid sequence that is 95%, 96%, 97%, 98%, 99%, or 100% identical to the amino acid sequence of SEQ ID NO: 3). In some embodiments, the dGK has an amino acid sequence that differs from SEQ ID NO: 3 by way of one or more amino acid substitutions, insertions, and/or deletions, such as by from 1 to 10, 1 to 15, 1 to 20, 1 to 25, or more, amino acid substitutions, insertions, and/or deletions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions). In some embodiments, the dGK has an amino acid sequence that differs from SEQ ID NO: 3 by way of one or more conservative amino acid substitutions, such as by from 1 to 10, 1 to 15, 1 to 20, 1 to 25, or more, conservative amino acid substitutions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions).

In some embodiments, the transgene encoding dGK has a nucleic acid sequence that is at least 70% identical to the nucleic acid sequence of SEQ ID NO: 4 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of SEQ ID NO: 4). In some embodiments, the transgene encoding dGK has a nucleic acid sequence that is at least 85% identical to the nucleic acid sequence of SEQ ID NO: 4 (e.g., a nucleic acid sequence that is 85%, 86%, 87%, 88%, 89%, 90%, 91%, 92%, 93%, 94%, 95%, 96%, 97%, 98%, 99%, or 100% identical to the nucleic acid sequence of SEQ ID NO: 4). In some embodiments, the transgene encoding dGK has a nucleic acid sequence that is at least 90% identical to the nucleic acid sequence of SEQ ID NO: 4 (e.g., a nucleic acid sequence that is 90%, 91%, 92%, 93%, 94%, 95%, 96%, 97%, 98%, 99%, or 100% identical to the nucleic acid sequence of SEQ ID NO: 4). In some embodiments, the transgene encoding dGK has a nucleic acid sequence that is at least 95% identical to the nucleic acid sequence of SEQ ID NO: 4 (e.g., a nucleic acid sequence that is 95%, 96%, 97%, 98%, 99%, or 100% identical to the nucleic acid sequence of SEQ ID NO: 4). In some embodiments, the transgene encoding dGK is codon optimized to increase efficiency. In some embodiments, the nucleic acid of the transgene encoding dGK is at least at least 70% identical to coding sequence of the transgene that encodes dGK (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of the coding sequence). In some embodiments, the nucleic acid sequence of the transgene encoding dGK has the nucleic acid sequence of SEQ ID NO: 18.

In some embodiments, the transgene encodes TP. The TP may have an amino acid sequence that is at least 85% identical to the amino acid sequence of SEQ ID NO: 5 (e.g., an amino acid sequence that is 85%, 86%, 87%, 88%, 89%, 90%, 91%, 92%, 93%, 94%, 95%, 96%, 97%, 98%, 99%, or 100% identical to the amino acid sequence of SEQ ID NO: 5). In some embodiments, the TP has an amino acid sequence that is at least 90% identical to the amino acid sequence of SEQ ID NO: 5 (e.g., an amino acid sequence that is 90%, 91%, 92%, 93%, 94%, 95%, 96%, 97%, 98%, 99%, or 100% identical to the amino acid sequence of SEQ ID NO: 5). In some embodiments, the TP has an amino acid sequence that is at least 95% identical to the amino acid sequence of SEQ ID NO: 5 (e.g., an amino acid sequence that is 95%, 96%, 97%, 98%, 99%, or 100% identical to the amino acid sequence of SEQ ID NO: 5). In some embodiments, the TP has an amino acid sequence that differs from SEQ ID NO: 5 by way of one or more amino acid substitutions, insertions, and/or deletions, such as by from 1 to 10, 1 to 15, 1 to 20, 1 to 25, or more, amino acid substitutions, insertions, and/or deletions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions). In some embodiments, the TP has an amino acid sequence that differs from SEQ ID NO: 5 by way of one or more conservative amino acid substitutions, such as by from 1 to 10, 1 to 15, 1 to 20, 1 to 25, or more, conservative amino acid substitutions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions).

In some embodiments, the transgene encoding TP has a nucleic acid sequence that is at least 70% identical to the nucleic acid sequence of SEQ ID NO: 6 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of SEQ ID NO: 6). In some embodiments, the transgene encoding TP has a nucleic acid sequence that is at least 85% identical to the nucleic acid sequence of SEQ ID NO: 6 (e.g., a nucleic acid sequence that is 85%, 86%, 87%, 88%, 89%, 90%, 91%, 92%, 93%, 94%, 95%, 96%, 97%, 98%, 99%, or 100% identical to the nucleic acid sequence of SEQ ID NO: 6). In some embodiments, the transgene encoding TP has a nucleic acid sequence that is at least 90% identical to the nucleic acid sequence of SEQ ID NO: 6 (e.g., a nucleic acid sequence that is 90%, 91%, 92%, 93%, 94%, 95%, 96%, 97%, 98%, 99%, or 100% identical to the nucleic acid sequence of SEQ ID NO: 6). In some embodiments, the transgene encoding TP has a nucleic acid sequence that is at least 95% identical to the nucleic acid sequence of SEQ ID NO: 6 (e.g., a nucleic acid sequence that is 95%, 96%, 97%, 98%, 99%, or 100% identical to the nucleic acid sequence of SEQ ID NO: 6). In some embodiments, the transgene encoding TP is codon optimized to increase efficiency. In some embodiments, the nucleic acid of the transgene encoding TP is at least at least 70% identical to coding sequence of the transgene that encodes TP (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of the coding sequence). In some embodiments, the nucleic acid sequence of the transgene encoding TP has the nucleic acid sequence of SEQ ID NO: 19.

In some embodiments, the transgene encodes p53R2. The p53R2 may have an amino acid sequence that is at least 85% identical to the amino acid sequence of SEQ ID NO: 7 (e.g., an amino acid sequence that is 85%, 86%, 87%, 88%, 89%, 90%, 91%, 92%, 93%, 94%, 95%, 96%, 97%, 98%, 99%, or 100% identical to the amino acid sequence of SEQ ID NO: 7). In some embodiments, the p53R2 has an amino acid sequence that is at least 90% identical to the amino acid sequence of SEQ ID NO: 7 (e.g., an amino acid sequence that is 90%, 91%, 92%, 93%, 94%, 95%, 96%, 97%, 98%, 99%, or 100% identical to the amino acid sequence of SEQ ID NO: 7). In some embodiments, the p53R2 has an amino acid sequence that is at least 95% identical to the amino acid sequence of SEQ ID NO: 7 (e.g., an amino acid sequence that is 95%, 96%, 97%, 98%, 99%, or 100% identical to the amino acid sequence of SEQ ID NO: 7). In some embodiments, the p53R2 has an amino acid sequence that differs from SEQ ID NO: 7 by way of one or more amino acid substitutions, insertions, and/or deletions, such as by from 1 to 10, 1 to 15, 1 to 20, 1 to 25, or more, amino acid substitutions, insertions, and/or deletions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions). In some embodiments, the p53R2 has an amino acid sequence that differs from SEQ ID NO: 7 by way of one or more conservative amino acid substitutions, such as by from 1 to 10, 1 to 15, 1 to 20, 1 to 25, or more, conservative amino acid substitutions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions).

In some embodiments, the transgene encoding p53R2 has a nucleic acid sequence that is at least 70% identical to the nucleic acid sequence of SEQ ID NO: 8 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of SEQ ID NO: 8). In some embodiments, the transgene encoding p53R2 has a nucleic acid sequence that is at least 85% identical to the nucleic acid sequence of SEQ ID NO: 8 (e.g., a nucleic acid sequence that is 85%, 86%, 87%, 88%, 89%, 90%, 91%, 92%, 93%, 94%, 95%, 96%, 97%, 98%, 99%, or 100% identical to the nucleic acid sequence of SEQ ID NO: 8). In some embodiments, the transgene encoding p53R2 has a nucleic acid sequence that is at least 90% identical to the nucleic acid sequence of SEQ ID NO: 8 (e.g., a nucleic acid sequence that is 90%, 91%, 92%, 93%, 94%, 95%, 96%, 97%, 98%, 99%, or 100% identical to the nucleic acid sequence of SEQ ID NO: 8). In some embodiments, the transgene encoding p53R2 has a nucleic acid sequence that is at least 95% identical to the nucleic acid sequence of SEQ ID NO: 8 (e.g., a nucleic acid sequence that is 95%, 96%, 97%, 98%, 99%, or 100% identical to the nucleic acid sequence of SEQ ID NO: 8). In some embodiments, the transgene encoding p53R2 is codon optimized to increase efficiency. In some embodiments, the nucleic acid of the transgene encoding p53R2 is at least at least 70% identical to coding sequence of the transgene that encodes p53R2 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of the coding sequence). In some embodiments, the nucleic acid sequence of the transgene encoding p53R2 has the nucleic acid sequence of SEQ ID NO: 20.

In some embodiments, the transgene encodes SUCLA2. The SUCLA2 may have an amino acid sequence that is at least 85% identical to the amino acid sequence of SEQ ID NO: 9 (e.g., an amino acid sequence that is 85%, 86%, 87%, 88%, 89%, 90%, 91%, 92%, 93%, 94%, 95%, 96%, 97%, 98%, 99%, or 100% identical to the amino acid sequence of SEQ ID NO: 9). In some embodiments, the SUCLA2 has an amino acid sequence that is at least 90% identical to the amino acid sequence of SEQ ID NO: 9 (e.g., an amino acid sequence that is 90%, 91%, 92%, 93%, 94%, 95%, 96%, 97%, 98%, 99%, or 100% identical to the amino acid sequence of SEQ ID NO: 9). In some embodiments, the SUCLA2 has an amino acid sequence that is at least 95% identical to the amino acid sequence of SEQ ID NO: 9 (e.g., an amino acid sequence that is 95%, 96%, 97%, 98%, 99%, or 100% identical to the amino acid sequence of SEQ ID NO: 9). In some embodiments, the SUCLA2 has an amino acid sequence that differs from SEQ ID NO: 9 by way of one or more amino acid substitutions, insertions, and/or deletions, such as by from 1 to 10, 1 to 15, 1 to 20, 1 to 25, or more, amino acid substitutions, insertions, and/or deletions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions). In some embodiments, the SUCLA2 has an amino acid sequence that differs from SEQ ID NO: 9 by way of one or more conservative amino acid substitutions, such as by from 1 to 10, 1 to 15, 1 to 20, 1 to 25, or more, conservative amino acid substitutions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions). In some embodiments, the transgene encoding SUCLA2 has a nucleic acid sequence that is at least 70% identical to the nucleic acid sequence of SEQ ID NO: 10 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of SEQ ID NO: 10). In some embodiments, the transgene encoding SUCLA2 has a nucleic acid sequence that is at least 85% identical to the nucleic acid sequence of SEQ ID NO: 10 (e.g., a nucleic acid sequence that is 85%, 86%, 87%, 88%, 89%, 90%, 91%, 92%, 93%, 94%, 95%, 96%, 97%, 98%, 99%, or 100% identical to the nucleic acid sequence of SEQ ID NO: 10). In some embodiments, the transgene encoding SUCLA2 has a nucleic acid sequence that is at least 90% identical to the nucleic acid sequence of SEQ ID NO: 10 (e.g., a nucleic acid sequence that is 90%, 91%, 92%, 93%, 94%, 95%, 96%, 97%, 98%, 99%, or 100% identical to the nucleic acid sequence of SEQ ID NO: 10). In some embodiments, the transgene encoding SUCLA2 has a nucleic acid sequence that is at least 95% identical to the nucleic acid sequence of SEQ ID NO: 10 (e.g., a nucleic acid sequence that is 95%, 96%, 97%, 98%, 99%, or 100% identical to the nucleic acid sequence of SEQ ID NO: 10). In some embodiments, the transgene encoding SUCLA2 is codon optimized to increase efficiency. In some embodiments, the nucleic acid of the transgene encoding SUCLA2 is at least at least 70% identical to coding sequence of the transgene that encodes SUCLA2 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of the coding sequence). In some embodiments, the nucleic acid sequence of the transgene encoding SUCLA2 has the nucleic acid sequence of SEQ ID NO: 21.

In some embodiments, the transgene encodes SUCLG1. The SUCLG1 may have an amino acid sequence that is at least 85% identical to the amino acid sequence of SEQ ID NO: 11 (e.g., an amino acid sequence that is 85%, 86%, 87%, 88%, 89%, 90%, 91%, 92%, 93%, 94%, 95%, 96%, 97%, 98%, 99%, or 100% identical to the amino acid sequence of SEQ ID NO: 11). In some embodiments, the SUCLG1 has an amino acid sequence that is at least 90% identical to the amino acid sequence of SEQ ID NO: 11 (e.g., an amino acid sequence that is 90%, 91%, 92%, 93%, 94%, 95%, 96%, 97%, 98%, 99%, or 100% identical to the amino acid sequence of SEQ ID NO: 11). In some embodiments, the SUCLG1 has an amino acid sequence that is at least 95% identical to the amino acid sequence of SEQ ID NO: 11 (e.g., an amino acid sequence that is 95%, 96%, 97%, 98%, 99%, or 100% identical to the amino acid sequence of SEQ ID NO: 11). In some embodiments, the SUCLG1 has an amino acid sequence that differs from SEQ ID NO: 11 by way of one or more amino acid substitutions, insertions, and/or deletions, such as by from 1 to 10, 1 to 15, 1 to 20, 1 to 25, or more, amino acid substitutions, insertions, and/or deletions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions). In some embodiments, the SUCLG1 has an amino acid sequence that differs from SEQ ID NO: 11 by way of one or more conservative amino acid substitutions, such as by from 1 to 10, 1 to 15, 1 to 20, 1 to 25, or more, conservative amino acid substitutions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions).

In some embodiments, the transgene encoding SUCLG1 has a nucleic acid sequence that is at least 70% identical to the nucleic acid sequence of SEQ ID NO: 12 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of SEQ ID NO: 12). In some embodiments, the transgene encoding SUCLG1 has a nucleic acid sequence that is at least 85% identical to the nucleic acid sequence of SEQ ID NO: 12 (e.g., a nucleic acid sequence that is 85%, 86%, 87%, 88%, 89%, 90%, 91%, 92%, 93%, 94%, 95%, 96%, 97%, 98%, 99%, or 100% identical to the nucleic acid sequence of SEQ ID NO: 12). In some embodiments, the transgene encoding SUCLG1 has a nucleic acid sequence that is at least 90% identical to the nucleic acid sequence of SEQ ID NO: 12 (e.g., a nucleic acid sequence that is 90%, 91%, 92%, 93%, 94%, 95%, 96%, 97%, 98%, 99%, or 100% identical to the nucleic acid sequence of SEQ ID NO: 12). In some embodiments, the transgene encoding SUCLG1 has a nucleic acid sequence that is at least 95% identical to the nucleic acid sequence of SEQ ID NO: 12 (e.g., a nucleic acid sequence that is 95%, 96%, 97%, 98%, 99%, or 100% identical to the nucleic acid sequence of SEQ ID NO: 12). In some embodiments, the transgene encoding SUCLG1 is codon optimized to increase efficiency. In some embodiments, the nucleic acid of the transgene encoding SUCLG1 is at least at least 70% identical to coding sequence of the transgene that encodes SUCLG1 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of the coding sequence). In some embodiments, the nucleic acid sequence of the transgene encoding SUCLG1 has the nucleic acid sequence of SEQ ID NO: 22.

In some embodiments, the transgene encodes MPV17. The MPV17 may have an amino acid sequence that is at least 85% identical to the amino acid sequence of SEQ ID NO: 13 (e.g., an amino acid sequence that is 85%, 86%, 87%, 88%, 89%, 90%, 91%, 92%, 93%, 94%, 95%, 96%, 97%, 98%, 99%, or 100% identical to the amino acid sequence of SEQ ID NO: 13). In some embodiments, the MPV17 has an amino acid sequence that is at least 90% identical to the amino acid sequence of SEQ ID NO: 13 (e.g., an amino acid sequence that is 90%, 91%, 92%, 93%, 94%, 95%, 96%, 97%, 98%, 99%, or 100% identical to the amino acid sequence of SEQ ID NO: 13). In some embodiments, the MPV17 has an amino acid sequence that is at least 95% identical to the amino acid sequence of SEQ ID NO: 13 (e.g., an amino acid sequence that is 95%, 96%, 97%, 98%, 99%, or 100% identical to the amino acid sequence of SEQ ID NO: 13). In some embodiments, the MPV17 has an amino acid sequence that differs from SEQ ID NO: 13 by way of one or more amino acid substitutions, insertions, and/or deletions, such as by from 1 to 10, 1 to 15, 1 to 20, 1 to 25, or more, amino acid substitutions, insertions, and/or deletions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions). In some embodiments, the MPV17 has an amino acid sequence that differs from SEQ ID NO: 13 by way of one or more conservative amino acid substitutions, such as by from 1 to 10, 1 to 15, 1 to 20, 1 to 25, or more, conservative amino acid substitutions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions).

In some embodiments, the transgene encoding MPV17 has a nucleic acid sequence that is at least 70% identical to the nucleic acid sequence of SEQ ID NO: 14 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of SEQ ID NO: 14). In some embodiments, the transgene encoding MPV17 has a nucleic acid sequence that is at least 85% identical to the nucleic acid sequence of SEQ ID NO: 14 (e.g., a nucleic acid sequence that is 85%, 86%, 87%, 88%, 89%, 90%, 91%, 92%, 93%, 94%, 95%, 96%, 97%, 98%, 99%, or 100% identical to the nucleic acid sequence of SEQ ID NO: 14). In some embodiments, the transgene encoding MPV17 has a nucleic acid sequence that is at least 90% identical to the nucleic acid sequence of SEQ ID NO: 14 (e.g., a nucleic acid sequence that is 90%, 91%, 92%, 93%, 94%, 95%, 96%, 97%, 98%, 99%, or 100% identical to the nucleic acid sequence of SEQ ID NO: 14). In some embodiments, the transgene encoding MPV17 has a nucleic acid sequence that is at least 95% identical to the nucleic acid sequence of SEQ ID NO: 14 (e.g., a nucleic acid sequence that is 95%, 96%, 97%, 98%, 99%, or 100% identical to the nucleic acid sequence of SEQ ID NO: 14). In some embodiments, the transgene encoding MPV17 is codon optimized to increase efficiency. In some embodiments, the nucleic acid of the transgene encoding MPV17 is at least at least 70% identical to coding sequence of the transgene that encodes MPV17 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of the coding sequence). In some embodiments, the nucleic acid sequence of the transgene encoding MPV17 has the nucleic acid sequence of SEQ ID NO: 23.

In some embodiments, the transgene encodes POLG. The POLG may have an amino acid sequence that is at least 85% identical to the amino acid sequence of SEQ ID NO: 15 (e.g., an amino acid sequence that is 85%, 86%, 87%, 88%, 89%, 90%, 91%, 92%, 93%, 94%, 95%, 96%, 97%, 98%, 99%, or 100% identical to the amino acid sequence of SEQ ID NO: 15). In some embodiments, the POLG has an amino acid sequence that is at least 90% identical to the amino acid sequence of SEQ ID NO: 15 (e.g., an amino acid sequence that is 90%, 91%, 92%, 93%, 94%, 95%, 96%, 97%, 98%, 99%, or 100% identical to the amino acid sequence of SEQ ID NO: 15). In some embodiments, the POLG has an amino acid sequence that is at least 95% identical to the amino acid sequence of SEQ ID NO: 15 (e.g., an amino acid sequence that is 95%, 96%, 97%, 98%, 99%, or 100% identical to the amino acid sequence of SEQ ID NO: 15). In some embodiments, the POLG has an amino acid sequence that differs from SEQ ID NO: 15 by way of one or more amino acid substitutions, insertions, and/or deletions, such as by from 1 to 10, 1 to 15, 1 to 20, 1 to 25, or more, amino acid substitutions, insertions, and/or deletions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions). In some embodiments, the POLG has an amino acid sequence that differs from SEQ ID NO: 15 by way of one or more conservative amino acid substitutions, such as by from 1 to 10, 1 to 15, 1 to 20, 1 to 25, or more, conservative amino acid substitutions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions). In some embodiments, the transgene encoding POLG has a nucleic acid sequence that is at least 70% identical to the nucleic acid sequence of SEQ ID NO: 16 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of SEQ ID NO: 16). In some embodiments, the transgene encoding POLG has a nucleic acid sequence that is at least 85% identical to the nucleic acid sequence of SEQ ID NO: 16 (e.g., a nucleic acid sequence that is 85%, 86%, 87%, 88%, 89%, 90%, 91%, 92%, 93%, 94%, 95%, 96%, 97%, 98%, 99%, or 100% identical to the nucleic acid sequence of SEQ ID NO: 16). In some embodiments, the transgene encoding POLG has a nucleic acid sequence that is at least 90% identical to the nucleic acid sequence of SEQ ID NO: 16 (e.g., a nucleic acid sequence that is 90%, 91%, 92%, 93%, 94%, 95%, 96%, 97%, 98%, 99%, or 100% identical to the nucleic acid sequence of SEQ ID NO: 16). In some embodiments, the transgene encoding POLG has a nucleic acid sequence that is at least 95% identical to the nucleic acid sequence of SEQ ID NO: 16 (e.g., a nucleic acid sequence that is 95%, 96%, 97%, 98%, 99%, or 100% identical to the nucleic acid sequence of SEQ ID NO: 16). In some embodiments, the transgene encoding POLG is codon optimized to increase efficiency. In some embodiments, the nucleic acid of the transgene encoding POLG is at least at least 70% identical to coding sequence of the transgene that encodes POLG (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of the coding sequence). In some embodiments, the nucleic acid sequence of the transgene encoding POLG has the nucleic acid sequence of SEQ ID NO: 24.

In another aspect, the disclosure features a method of treating, preventing, and/or curing TK2 deficiency in a subject in need thereof. The method includes administering to the subject a therapeutically effective amount of a composition containing a transgene encoding TK2.

In a further aspect, the disclosure features a method of restoring TK2 enzyme activity in a subject in need thereof. The method includes administering to the subject a therapeutically effective amount of a composition containing a transgene encoding TK2.

In another aspect, the disclosure features a method of alleviating one or more symptoms associated with a TK2 deficiency in a subject in need thereof. The method includes administering to the subject a therapeutically effective amount of a composition containing a transgene encoding TK2.

As part of these aspects, the disclosure also provides a composition containing a transgene encoding TK2 for use in treating, preventing, and/or curing TK2 deficiency. Also provided is a composition containing a transgene encoding TK2 for use in restoring TK2 enzyme activity in a subject having a TK2 deficiency. Furthermore provided is a composition containing a transgene encoding TK2 for use in alleviating one or more symptoms associated with a TK2 deficiency. Typically the subject has a TK2 deficiency.

As part of these aspects, the disclosure also provides the use of a composition containing a transgene encoding TK2 for the manufacture of a medicament for treating, preventing, and/or curing TK2 deficiency. Also provided is the use of a composition containing a transgene encoding TK2 for the manufacture of a medicament for restoring TK2 enzyme activity in a subject having a TK2 deficiency. Furthermore provided is the use of a composition containing a transgene encoding TK2 for the manufacture of a medicament for alleviating one or more symptoms associated with a TK2 deficiency. Typically the subject has a TK2 deficiency.

In some embodiments of any of the preceding three aspects, the subject has or is at risk of developing a MDS. The TK2 may have an amino acid sequence that is at least 85% identical to the amino acid sequence of SEQ ID NO: 1 (e.g., an amino acid sequence that is 85%, 86%, 87%, 88%, 89%, 90%, 91%, 92%, 93%, 94%, 95%, 96%, 97%, 98%, 99%, or 100% identical to the amino acid sequence of SEQ ID NO: 1). In some embodiments, the TK2 has an amino acid sequence that is at least 90% identical to the amino acid sequence of SEQ ID NO: 1 (e.g., an amino acid sequence that is 90%, 91%, 92%, 93%, 94%, 95%, 96%, 97%, 98%, 99%, or 100% identical to the amino acid sequence of SEQ ID NO: 1). In some embodiments, the TK2 has an amino acid sequence that is at least 95% identical to the amino acid sequence of SEQ ID NO: 1 (e.g., an amino acid sequence that is 95%, 96%, 97%, 98%, 99%, or 100% identical to the amino acid sequence of SEQ ID NO: 1). In some embodiments, the TK2 has an amino acid sequence that differs from SEQ ID NO: 1 by way of one or more amino acid substitutions, insertions, and/or deletions, such as by from 1 to 10, 1 to 15, 1 to 20, 1 to 25, or more, amino acid substitutions, insertions, and/or deletions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions). In some embodiments, the TK2 has an amino acid sequence that differs from SEQ ID NO: 1 by way of one or more conservative amino acid substitutions, such as by from 1 to 10, 1 to 15, 1 to 20, 1 to 25, or more, conservative amino acid substitutions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions).

In some embodiments, the transgene encoding TK2 has a nucleic acid sequence that is at least 70% identical to the nucleic acid sequence of SEQ ID NO: 2 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of SEQ ID NO: 2). In some embodiments, the transgene encoding TK2 has a nucleic acid sequence that is at least 85% identical to the nucleic acid sequence of SEQ ID NO: 2 (e.g., a nucleic acid sequence that is 85%, 86%, 87%, 88%, 89%, 90%, 91%, 92%, 93%, 94%, 95%, 96%, 97%, 98%, 99%, or 100% identical to the nucleic acid sequence of SEQ ID NO: 2). In some embodiments, the transgene encoding TK2 has a nucleic acid sequence that is at least 90% identical to the nucleic acid sequence of SEQ ID NO: 2 (e.g., a nucleic acid sequence that is 90%, 91%, 92%, 93%, 94%, 95%, 96%, 97%, 98%, 99%, or 100% identical to the nucleic acid sequence of SEQ ID NO: 2). In some embodiments, the transgene encoding TK2 has a nucleic acid sequence that is at least 95% identical to the nucleic acid sequence of SEQ ID NO: 2 (e.g., a nucleic acid sequence that is 95%, 96%, 97%, 98%, 99%, or 100% identical to the nucleic acid sequence of SEQ ID NO: 2). In some embodiments, the transgene encoding TK2 is codon optimized to increase efficiency. In some embodiments, the nucleic acid of the transgene encoding TK2 is at least at least 70% identical to coding sequence of the transgene that encodes TK2 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of the coding sequence). In some embodiments, the nucleic acid sequence of the transgene encoding TK2 has the nucleic acid sequence of SEQ ID NO: 17.

In some embodiments of any of the above aspects of the disclosure, the composition comprises a vector, such as a viral vector. The viral vector may be, for example, an AAV, adenovirus, lentivirus, retrovirus, poxvirus, baculovirus, herpes simplex virus, vaccinia virus, or a synthetic virus (e.g., a chimeric virus, mosaic virus, or pseudotyped virus, and/or a virus that contains a foreign protein, synthetic polymer, nanoparticle, or small molecule).

In some embodiments, the viral vector is an AAV, such as an AAV1 (i.e., an AAV containing AAV1 inverted terminal repeats (ITRs) and AAV1 capsid proteins), AAV2 (i.e., an AAV containing AAV2 ITRs and AAV2 capsid proteins), AAV3 (i.e., an AAV containing AAV3 ITRs and AAV3 capsid proteins), AAV4 (i.e., an AAV containing AAV4 ITRs and AAV4 capsid proteins), AAV5 (i.e., an AAV containing AAV5 ITRs and AAV5 capsid proteins), AAV6 (i.e., an AAV containing AAV6 ITRs and AAV6 capsid proteins), AAV7 (i.e., an AAV containing AAV7 ITRs and AAV7 capsid proteins), AAV8 (i.e., an AAV containing AAV8 ITRs and AAV8 capsid proteins), AAV9 (i.e., an AAV containing AAV9 ITRs and AAV9 capsid proteins), AAVrh74 (i.e., an AAV containing AAVrh74 ITRs and AAVrh74 capsid proteins), AAVrh.8 (i.e., an AAV containing AAVrh.8 ITRs and AAVrh.8 capsid proteins), or AAVrh.10 (i.e., an AAV containing AAVrh.10 ITRs and AAVrh.10 capsid proteins).

In some embodiments, the viral vector is a pseudotyped AAV, containing ITRs from one AAV serotype and capsid proteins from a different AAV serotype. In some embodiments, the pseudotyped AAV is AAV2/9 (i.e., an AAV containing AAV2 ITRs and AAV9 capsid proteins). In some embodiments, the pseudotyped AAV is AAV2/8 (i.e., an AAV containing AAV2 ITRs and AAV8 capsid proteins). In some embodiments, the pseudotyped AAV is AAV2/1 (i.e., an AAV containing AAV2 ITRs and AAV1 capsid proteins).

In some embodiments, the AAV contains a recombinant capsid protein, such as a capsid protein containing a chimera of one or more of capsid proteins from AAV1, AAV2, AAV3, AAV4, AAV5, AAV6, AAV7, AAV8, AAV9, AAVrh74, AAVrh.8, or AAVrh.10. In certain embodiments, the viral vector is AAV9. For example, the composition may comprise AAV9 comprising a nucleic acid sequence comprising a transgene encoding TK2, dGK, TP, p53R2, SUCLA2, SUCLG1, MPV17, and/or POLG. In certain embodiments, the composition comprises AAV9 comprising a nucleic acid sequence comprising a transgene encoding TK2, dGK, TP, p53R2, SUCLA2, SUCLG1 or MPV17. In a particular embodiment, the composition comprises AAV9 comprising a nucleic acid sequence comprising a transgene encoding TK2.

In certain embodiments, the viral vector is an AAV and the transgene is TK2. For example, the composition may comprise a recombinant AAV (rAAV), such as AAV9, comprising a nucleic acid sequence comprising a transgene encoding a functional TK2 protein.

In some embodiments of any of the above aspects of the disclosure, the composition is a liposome, vesicle, synthetic vesicle, exosome, synthetic exosome, dendrimer, or nanoparticle.

In some embodiments of any of the above aspects of the disclosure, the transgene is operably linked to a promoter that induces expression of the transgene in a muscle cell. The promoter may be, for example, a chicken beta actin promoter, cytomegalovirus (CMV) promoter, myosin light chain-2 promoter, alpha actin promoter, troponin 1 promoter, Na+/Ca2+ exchanger promoter, dystrophin promoter, creatine kinase promoter, alpha7 integrin promoter, brain natriuretic peptide promoter, alpha B-crystallin/small heat shock protein promoter, alpha myosin heavy chain promoter, or atrial natriuretic factor promoter. In some embodiments of any of the above aspects of the disclosure, the transgene is operably linked to an enhancer that induces expression of the transgene in a muscle cell. Exemplary enhancers that may be used in conjunction with the compositions and methods of the disclosure are a CMV enhancer, a myocyte enhancer factor 2 (MEF2) enhancer, and a MyoD enhancer.

In some embodiments, the composition is administered to the subject as soon as, or immediately after, the subject is diagnosed as having a deficiency in an endogenous gene encoding TK2, dGK, TP, p53R2, SUCLA2, SUCLG1, MPV17, and/or POLG. In some embodiments, the composition is administered to the subject as soon as, or immediately after, the subject is diagnosed as having a deficiency in an endogenous gene encoding TK2.

In some embodiments, the method further includes administering to the subject a therapeutically effective amount of a second composition containing a transgene encoding TK2, dGK, TP, p53R2, SUCLA2, SUCLG1, MPV17, and/or POLG.

In some embodiments, the transgene of the second composition encodes TK2. The TK2 may have an amino acid sequence that is at least 85% identical to the amino acid sequence of SEQ ID NO: 1 (e.g., an amino acid sequence that is 85%, 86%, 87%, 88%, 89%, 90%, 91%, 92%, 93%, 94%, 95%, 96%, 97%, 98%, 99%, or 100% identical to the amino acid sequence of SEQ ID NO: 1). In some embodiments, the TK2 has an amino acid sequence that is at least 90% identical to the amino acid sequence of SEQ ID NO: 1 (e.g., an amino acid sequence that is 90%, 91%, 92%, 93%, 94%, 95%, 96%, 97%, 98%, 99%, or 100% identical to the amino acid sequence of SEQ ID NO: 1). In some embodiments, the TK2 has an amino acid sequence that is at least 95% identical to the amino acid sequence of SEQ ID NO: 1 (e.g., an amino acid sequence that is 95%, 96%, 97%, 98%, 99%, or 100% identical to the amino acid sequence of SEQ ID NO: 1). In some embodiments, the TK2 has an amino acid sequence that differs from SEQ ID NO: 1 by way of one or more amino acid substitutions, insertions, and/or deletions, such as by from 1 to 10, 1 to 15, 1 to 20, 1 to 25, or more, amino acid substitutions, insertions, and/or deletions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions). In some embodiments, the TK2 has an amino acid sequence that differs from SEQ ID NO: 1 by way of one or more conservative amino acid substitutions, such as by from 1 to 10, 1 to 15, 1 to 20, 1 to 25, or more, conservative amino acid substitutions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions).

In some embodiments, the transgene of the second composition encoding TK2 has a nucleic acid sequence that is at least 70% identical to the nucleic acid sequence of SEQ ID NO: 2 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of SEQ ID NO: 2). In some embodiments, the transgene of the second composition encoding TK2 has a nucleic acid sequence that is at least 85% identical to the nucleic acid sequence of SEQ ID NO: 2 (e.g., a nucleic acid sequence that is 85%, 86%, 87%, 88%, 89%, 90%, 91%, 92%, 93%, 94%, 95%, 96%, 97%, 98%, 99%, or 100% identical to the nucleic acid sequence of SEQ ID NO: 2). In some embodiments, the transgene encoding TK2 has a nucleic acid sequence that is at least 90% identical to the nucleic acid sequence of SEQ ID NO: 2 (e.g., a nucleic acid sequence that is 90%, 91%, 92%, 93%, 94%, 95%, 96%, 97%, 98%, 99%, or 100% identical to the nucleic acid sequence of SEQ ID NO: 2). In some embodiments, the transgene encoding TK2 has a nucleic acid sequence that is at least 95% identical to the nucleic acid sequence of SEQ ID NO: 2 (e.g., a nucleic acid sequence that is 95%, 96%, 97%, 98%, 99%, or 100% identical to the nucleic acid sequence of SEQ ID NO: 2). In some embodiments, the transgene encoding TK2 is codon optimized to increase efficiency. In some embodiments, the nucleic acid of the transgene encoding TK2 is at least at least 70% identical to coding sequence of the transgene that encodes TK2 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of the coding sequence). In some embodiments, the nucleic acid sequence of the transgene encoding TK2 has the nucleic acid sequence of SEQ ID NO: 17.

In some embodiments, the transgene of the second composition encodes dGK. The dGK may have an amino acid sequence that is at least 85% identical to the amino acid sequence of SEQ ID NO: 3 (e.g., an amino acid sequence that is 85%, 86%, 87%, 88%, 89%, 90%, 91%, 92%, 93%, 94%, 95%, 96%, 97%, 98%, 99%, or 100% identical to the amino acid sequence of SEQ ID NO: 3). In some embodiments, the dGK has an amino acid sequence that is at least 90% identical to the amino acid sequence of SEQ ID NO: 3 (e.g., an amino acid sequence that is 90%, 91%, 92%, 93%, 94%, 95%, 96%, 97%, 98%, 99%, or 100% identical to the amino acid sequence of SEQ ID NO: 3). In some embodiments, the dGK has an amino acid sequence that is at least 95% identical to the amino acid sequence of SEQ ID NO: 3 (e.g., an amino acid sequence that is 95%, 96%, 97%, 98%, 99%, or 100% identical to the amino acid sequence of SEQ ID NO: 3). In some embodiments, the dGK has an amino acid sequence that differs from SEQ ID NO: 3 by way of one or more amino acid substitutions, insertions, and/or deletions, such as by from 1 to 10, 1 to 15, 1 to 20, 1 to 25, or more, amino acid substitutions, insertions, and/or deletions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions). In some embodiments, the dGK has an amino acid sequence that differs from SEQ ID NO: 3 by way of one or more conservative amino acid substitutions, such as by from 1 to 10, 1 to 15, 1 to 20, 1 to 25, or more, conservative amino acid substitutions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions).

In some embodiments, the transgene of the second composition encoding dGK has a nucleic acid sequence that is at least 70% identical to the nucleic acid sequence of SEQ ID NO: 4 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of SEQ ID NO: 4). In some embodiments, the transgene of the second composition encoding dGK has a nucleic acid sequence that is at least 85% identical to the nucleic acid sequence of SEQ ID NO: 4 (e.g., a nucleic acid sequence that is 85%, 86%, 87%, 88%, 89%, 90%, 91%, 92%, 93%, 94%, 95%, 96%, 97%, 98%, 99%, or 100% identical to the nucleic acid sequence of SEQ ID NO: 4). In some embodiments, the transgene encoding dGK has a nucleic acid sequence that is at least 90% identical to the nucleic acid sequence of SEQ ID NO: 4 (e.g., a nucleic acid sequence that is 90%, 91%, 92%, 93%, 94%, 95%, 96%, 97%, 98%, 99%, or 100% identical to the nucleic acid sequence of SEQ ID NO: 4). In some embodiments, the transgene encoding dGK has a nucleic acid sequence that is at least 95% identical to the nucleic acid sequence of SEQ ID NO: 4 (e.g., a nucleic acid sequence that is 95%, 96%, 97%, 98%, 99%, or 100% identical to the nucleic acid sequence of SEQ ID NO: 4). In some embodiments, the transgene encoding dGK is codon optimized to increase efficiency. In some embodiments, the nucleic acid of the transgene encoding dGK is at least at least 70% identical to coding sequence of the transgene that encodes dGK (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of the coding sequence). In some embodiments, the nucleic acid sequence of the transgene encoding dGK has the nucleic acid sequence of SEQ ID NO: 18.

In some embodiments, the transgene of the second composition encodes TP. The TP may have an amino acid sequence that is at least 85% identical to the amino acid sequence of SEQ ID NO: 5 (e.g., an amino acid sequence that is 85%, 86%, 87%, 88%, 89%, 90%, 91%, 92%, 93%, 94%, 95%, 96%, 97%, 98%, 99%, or 100% identical to the amino acid sequence of SEQ ID NO: 5). In some embodiments, the TP has an amino acid sequence that is at least 90% identical to the amino acid sequence of SEQ ID NO: 5 (e.g., an amino acid sequence that is 90%, 91%, 92%, 93%, 94%, 95%, 96%, 97%, 98%, 99%, or 100% identical to the amino acid sequence of SEQ ID NO: 5). In some embodiments, the TP has an amino acid sequence that is at least 95% identical to the amino acid sequence of SEQ ID NO: 5 (e.g., an amino acid sequence that is 95%, 96%, 97%, 98%, 99%, or 100% identical to the amino acid sequence of SEQ ID NO: 5). In some embodiments, the TP has an amino acid sequence that differs from SEQ ID NO: 5 by way of one or more amino acid substitutions, insertions, and/or deletions, such as by from 1 to 10, 1 to 15, 1 to 20, 1 to 25, or more, amino acid substitutions, insertions, and/or deletions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions). In some embodiments, the TP has an amino acid sequence that differs from SEQ ID NO: 5 by way of one or more conservative amino acid substitutions, such as by from 1 to 10, 1 to 15, 1 to 20, 1 to 25, or more, conservative amino acid substitutions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions).

In some embodiments, the transgene of the second composition encoding TP has a nucleic acid sequence that is at least 70% identical to the nucleic acid sequence of SEQ ID NO: 6 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of SEQ ID NO: 6). In some embodiments, the transgene of the second composition encoding TP has a nucleic acid sequence that is at least 85% identical to the nucleic acid sequence of SEQ ID NO: 6 (e.g., a nucleic acid sequence that is 85%, 86%, 87%, 88%, 89%, 90%, 91%, 92%, 93%, 94%, 95%, 96%, 97%, 98%, 99%, or 100% identical to the nucleic acid sequence of SEQ ID NO: 6). In some embodiments, the transgene encoding TP has a nucleic acid sequence that is at least 90% identical to the nucleic acid sequence of SEQ ID NO: 6 (e.g., a nucleic acid sequence that is 90%, 91%, 92%, 93%, 94%, 95%, 96%, 97%, 98%, 99%, or 100% identical to the nucleic acid sequence of SEQ ID NO: 6). In some embodiments, the transgene encoding TP has a nucleic acid sequence that is at least 95% identical to the nucleic acid sequence of SEQ ID NO: 6 (e.g., a nucleic acid sequence that is 95%, 96%, 97%, 98%, 99%, or 100% identical to the nucleic acid sequence of SEQ ID NO: 6). In some embodiments, the transgene encoding TP is codon optimized to increase efficiency. In some embodiments, the nucleic acid of the transgene encoding TP is at least at least 70% identical to coding sequence of the transgene that encodes TP (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of the coding sequence). In some embodiments, the nucleic acid sequence of the transgene encoding TP has the nucleic acid sequence of SEQ ID NO: 19.

In some embodiments, the transgene of the second composition encodes p53R2. The p53R2 may have an amino acid sequence that is at least 85% identical to the amino acid sequence of SEQ ID NO: 7 (e.g., an amino acid sequence that is 85%, 86%, 87%, 88%, 89%, 90%, 91%, 92%, 93%, 94%, 95%, 96%, 97%, 98%, 99%, or 100% identical to the amino acid sequence of SEQ ID NO: 7). In some embodiments, the p53R2 has an amino acid sequence that is at least 90% identical to the amino acid sequence of SEQ ID NO: 7 (e.g., an amino acid sequence that is 90%, 91%, 92%, 93%, 94%, 95%, 96%, 97%, 98%, 99%, or 100% identical to the amino acid sequence of SEQ ID NO: 7). In some embodiments, the p53R2 has an amino acid sequence that is at least 95% identical to the amino acid sequence of SEQ ID NO: 7 (e.g., an amino acid sequence that is 95%, 96%, 97%, 98%, 99%, or 100% identical to the amino acid sequence of SEQ ID NO: 7). In some embodiments, the p53R2 has an amino acid sequence that differs from SEQ ID NO: 7 by way of one or more amino acid substitutions, insertions, and/or deletions, such as by from 1 to 10, 1 to 15, 1 to 20, 1 to 25, or more, amino acid substitutions, insertions, and/or deletions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions). In some embodiments, the p53R2 has an amino acid sequence that differs from SEQ ID NO: 7 by way of one or more conservative amino acid substitutions, such as by from 1 to 10, 1 to 15, 1 to 20, 1 to 25, or more, conservative amino acid substitutions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions).

In some embodiments, the transgene of the second composition encoding p53R2 has a nucleic acid sequence that is at least 70% identical to the nucleic acid sequence of SEQ ID NO: 8 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of SEQ ID NO: 8). In some embodiments, the transgene of the second composition encoding p53R2 has a nucleic acid sequence that is at least 85% identical to the nucleic acid sequence of SEQ ID NO: 8 (e.g., a nucleic acid sequence that is 85%, 86%, 87%, 88%, 89%, 90%, 91%, 92%, 93%, 94%, 95%, 96%, 97%, 98%, 99%, or 100% identical to the nucleic acid sequence of SEQ ID NO: 8). In some embodiments, the transgene encoding p53R2 has a nucleic acid sequence that is at least 90% identical to the nucleic acid sequence of SEQ ID NO: 8 (e.g., a nucleic acid sequence that is 90%, 91%, 92%, 93%, 94%, 95%, 96%, 97%, 98%, 99%, or 100% identical to the nucleic acid sequence of SEQ ID NO: 8). In some embodiments, the transgene encoding p53R2 has a nucleic acid sequence that is at least 95% identical to the nucleic acid sequence of SEQ ID NO: 8 (e.g., a nucleic acid sequence that is 95%, 96%, 97%, 98%, 99%, or 100% identical to the nucleic acid sequence of SEQ ID NO: 8). In some embodiments, the transgene encoding p53R2 is codon optimized to increase efficiency. In some embodiments, the nucleic acid of the transgene encoding p53R2 is at least at least 70% identical to coding sequence of the transgene that encodes p53R2 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of the coding sequence). In some embodiments, the nucleic acid sequence of the transgene encoding p53R2 has the nucleic acid sequence of SEQ ID NO: 20.

In some embodiments, the transgene of the second composition encodes SUCLA2. The SUCLA2 may have an amino acid sequence that is at least 85% identical to the amino acid sequence of SEQ ID NO: 9 (e.g., an amino acid sequence that is 85%, 86%, 87%, 88%, 89%, 90%, 91%, 92%, 93%, 94%, 95%, 96%, 97%, 98%, 99%, or 100% identical to the amino acid sequence of SEQ ID NO: 9). In some embodiments, the SUCLA2 has an amino acid sequence that is at least 90% identical to the amino acid sequence of SEQ ID NO: 9 (e.g., an amino acid sequence that is 90%, 91%, 92%, 93%, 94%, 95%, 96%, 97%, 98%, 99%, or 100% identical to the amino acid sequence of SEQ ID NO: 9). In some embodiments, the SUCLA2 has an amino acid sequence that is at least 95% identical to the amino acid sequence of SEQ ID NO: 9 (e.g., an amino acid sequence that is 95%, 96%, 97%, 98%, 99%, or 100% identical to the amino acid sequence of SEQ ID NO: 9). In some embodiments, the SUCLA2 has an amino acid sequence that differs from SEQ ID NO: 9 by way of one or more amino acid substitutions, insertions, and/or deletions, such as by from 1 to 10, 1 to 15, 1 to 20, 1 to 25, or more, amino acid substitutions, insertions, and/or deletions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions). In some embodiments, the SUCLA2 has an amino acid sequence that differs from SEQ ID NO: 9 by way of one or more conservative amino acid substitutions, such as by from 1 to 10, 1 to 15, 1 to 20, 1 to 25, or more, conservative amino acid substitutions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions).

In some embodiments, the transgene of the second composition encoding SUCLA2 has a nucleic acid sequence that is at least 70% identical to the nucleic acid sequence of SEQ ID NO: 10 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of SEQ ID NO: 10). In some embodiments, the transgene of the second composition encoding SUCLA2 has a nucleic acid sequence that is at least 85% identical to the nucleic acid sequence of SEQ ID NO: 10 (e.g., a nucleic acid sequence that is 85%, 86%, 87%, 88%, 89%, 90%, 91%, 92%, 93%, 94%, 95%, 96%, 97%, 98%, 99%, or 100% identical to the nucleic acid sequence of SEQ ID NO: 10). In some embodiments, the transgene encoding SUCLA2 has a nucleic acid sequence that is at least 90% identical to the nucleic acid sequence of SEQ ID NO: 10 (e.g., a nucleic acid sequence that is 90%, 91%, 92%, 93%, 94%, 95%, 96%, 97%, 98%, 99%, or 100% identical to the nucleic acid sequence of SEQ ID NO: 10). In some embodiments, the transgene encoding SUCLA2 has a nucleic acid sequence that is at least 95% identical to the nucleic acid sequence of SEQ ID NO: 10 (e.g., a nucleic acid sequence that is 95%, 96%, 97%, 98%, 99%, or 100% identical to the nucleic acid sequence of SEQ ID NO: 10). In some embodiments, the transgene encoding SUCLA2 is codon optimized to increase efficiency. In some embodiments, the nucleic acid of the transgene encoding SUCLA2 is at least at least 70% identical to coding sequence of the transgene that encodes SUCLA2 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of the coding sequence). In some embodiments, the nucleic acid sequence of the transgene encoding SUCLA2 has the nucleic acid sequence of SEQ ID NO: 21.

In some embodiments, the transgene of the second composition encodes SUCLG1. The SUCLG1 may have an amino acid sequence that is at least 85% identical to the amino acid sequence of SEQ ID NO: 11 (e.g., an amino acid sequence that is 85%, 86%, 87%, 88%, 89%, 90%, 91%, 92%, 93%, 94%, 95%, 96%, 97%, 98%, 99%, or 100% identical to the amino acid sequence of SEQ ID NO: 11). In some embodiments, the SUCLG1 has an amino acid sequence that is at least 90% identical to the amino acid sequence of SEQ ID NO: 11 (e.g., an amino acid sequence that is 90%, 91%, 92%, 93%, 94%, 95%, 96%, 97%, 98%, 99%, or 100% identical to the amino acid sequence of SEQ ID NO: 11). In some embodiments, the SUCLG1 has an amino acid sequence that is at least 95% identical to the amino acid sequence of SEQ ID NO: 11 (e.g., an amino acid sequence that is 95%, 96%, 97%, 98%, 99%, or 100% identical to the amino acid sequence of SEQ ID NO: 11). In some embodiments, the SUCLG1 has an amino acid sequence that differs from SEQ ID NO: 11 by way of one or more amino acid substitutions, insertions, and/or deletions, such as by from 1 to 10, 1 to 15, 1 to 20, 1 to 25, or more, amino acid substitutions, insertions, and/or deletions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions). In some embodiments, the SUCLG1 has an amino acid sequence that differs from SEQ ID NO: 11 by way of one or more conservative amino acid substitutions, such as by from 1 to 10, 1 to 15, 1 to 20, 1 to 25, or more, conservative amino acid substitutions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions).

In some embodiments, the transgene of the second composition encoding SUCLG1 has a nucleic acid sequence that is at least 70% identical to the nucleic acid sequence of SEQ ID NO: 12 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of SEQ ID NO: 12). In some embodiments, the transgene of the second composition encoding SUCLG1 has a nucleic acid sequence that is at least 85% identical to the nucleic acid sequence of SEQ ID NO: 12 (e.g., a nucleic acid sequence that is 85%, 86%, 87%, 88%, 89%, 90%, 91%, 92%, 93%, 94%, 95%, 96%, 97%, 98%, 99%, or 100% identical to the nucleic acid sequence of SEQ ID NO: 12). In some embodiments, the transgene encoding SUCLG1 has a nucleic acid sequence that is at least 90% identical to the nucleic acid sequence of SEQ ID NO: 12 (e.g., a nucleic acid sequence that is 90%, 91%, 92%, 93%, 94%, 95%, 96%, 97%, 98%, 99%, or 100% identical to the nucleic acid sequence of SEQ ID NO: 12). In some embodiments, the transgene encoding SUCLG1 has a nucleic acid sequence that is at least 95% identical to the nucleic acid sequence of SEQ ID NO: 12 (e.g., a nucleic acid sequence that is 95%, 96%, 97%, 98%, 99%, or 100% identical to the nucleic acid sequence of SEQ ID NO: 12). In some embodiments, the transgene encoding SUCLG1 is codon optimized to increase efficiency. In some embodiments, the nucleic acid of the transgene encoding SUCLG1 is at least at least 70% identical to coding sequence of the transgene that encodes SUCLG1 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of the coding sequence). In some embodiments, the nucleic acid sequence of the transgene encoding SUCLG1 has the nucleic acid sequence of SEQ ID NO: 22.

In some embodiments, the transgene of the second composition encodes MPV17. The MPV17 may have an amino acid sequence that is at least 85% identical to the amino acid sequence of SEQ ID NO: 13 (e.g., an amino acid sequence that is 85%, 86%, 87%, 88%, 89%, 90%, 91%, 92%, 93%, 94%, 95%, 96%, 97%, 98%, 99%, or 100% identical to the amino acid sequence of SEQ ID NO: 13). In some embodiments, the MPV17 has an amino acid sequence that is at least 90% identical to the amino acid sequence of SEQ ID NO: 13 (e.g., an amino acid sequence that is 90%, 91%, 92%, 93%, 94%, 95%, 96%, 97%, 98%, 99%, or 100% identical to the amino acid sequence of SEQ ID NO: 13). In some embodiments, the MPV17 has an amino acid sequence that is at least 95% identical to the amino acid sequence of SEQ ID NO: 13 (e.g., an amino acid sequence that is 95%, 96%, 97%, 98%, 99%, or 100% identical to the amino acid sequence of SEQ ID NO: 13). In some embodiments, the MPV17 has an amino acid sequence that differs from SEQ ID NO: 13 by way of one or more amino acid substitutions, insertions, and/or deletions, such as by from 1 to 10, 1 to 15, 1 to 20, 1 to 25, or more, amino acid substitutions, insertions, and/or deletions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions). In some embodiments, the MPV17 has an amino acid sequence that differs from SEQ ID NO: 13 by way of one or more conservative amino acid substitutions, such as by from 1 to 10, 1 to 15, 1 to 20, 1 to 25, or more, conservative amino acid substitutions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions).

In some embodiments, the transgene of the second composition encoding MPV17 has a nucleic acid sequence that is at least 70% identical to the nucleic acid sequence of SEQ ID NO: 14 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of SEQ ID NO: 14). In some embodiments, the transgene of the second composition encoding MPV17 has a nucleic acid sequence that is at least 85% identical to the nucleic acid sequence of SEQ ID NO: 14 (e.g., a nucleic acid sequence that is 85%, 86%, 87%, 88%, 89%, 90%, 91%, 92%, 93%, 94%, 95%, 96%, 97%, 98%, 99%, or 100% identical to the nucleic acid sequence of SEQ ID NO: 14). In some embodiments, the transgene encoding MPV17 has a nucleic acid sequence that is at least 90% identical to the nucleic acid sequence of SEQ ID NO: 14 (e.g., a nucleic acid sequence that is 90%, 91%, 92%, 93%, 94%, 95%, 96%, 97%, 98%, 99%, or 100% identical to the nucleic acid sequence of SEQ ID NO: 14). In some embodiments, the transgene encoding MPV17 has a nucleic acid sequence that is at least 95% identical to the nucleic acid sequence of SEQ ID NO: 14 (e.g., a nucleic acid sequence that is 95%, 96%, 97%, 98%, 99%, or 100% identical to the nucleic acid sequence of SEQ ID NO: 14). In some embodiments, the transgene encoding MPV17 is codon optimized to increase efficiency. In some embodiments, the nucleic acid of the transgene encoding MPV17 is at least at least 70% identical to coding sequence of the transgene that encodes MPV17 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of the coding sequence). In some embodiments, the nucleic acid sequence of the transgene encoding MPV17 has the nucleic acid sequence of SEQ ID NO: 23.

In some embodiments, the transgene of the second composition encodes POLG. The POLG may have an amino acid sequence that is at least 85% identical to the amino acid sequence of SEQ ID NO: 15 (e.g., an amino acid sequence that is 85%, 86%, 87%, 88%, 89%, 90%, 91%, 92%, 93%, 94%, 95%, 96%, 97%, 98%, 99%, or 100% identical to the amino acid sequence of SEQ ID NO: 15). In some embodiments, the POLG has an amino acid sequence that is at least 90% identical to the amino acid sequence of SEQ ID NO: 15 (e.g., an amino acid sequence that is 90%, 91%, 92%, 93%, 94%, 95%, 96%, 97%, 98%, 99%, or 100% identical to the amino acid sequence of SEQ ID NO: 15). In some embodiments, the POLG has an amino acid sequence that is at least 95% identical to the amino acid sequence of SEQ ID NO: 15 (e.g., an amino acid sequence that is 95%, 96%, 97%, 98%, 99%, or 100% identical to the amino acid sequence of SEQ ID NO: 15). In some embodiments, the POLG has an amino acid sequence that differs from SEQ ID NO: 15 by way of one or more amino acid substitutions, insertions, and/or deletions, such as by from 1 to 10, 1 to 15, 1 to 20, 1 to 25, or more, amino acid substitutions, insertions, and/or deletions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions). In some embodiments, the POLG has an amino acid sequence that differs from SEQ ID NO: 15 by way of one or more conservative amino acid substitutions, such as by from 1 to 10, 1 to 15, 1 to 20, 1 to 25, or more, conservative amino acid substitutions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions).

In some embodiments, the transgene of the second composition encoding POLG has a nucleic acid sequence that is at least 70% identical to the nucleic acid sequence of SEQ ID NO: 16 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of SEQ ID NO: 16). In some embodiments, the transgene of the second composition encoding POLG has a nucleic acid sequence that is at least 85% identical to the nucleic acid sequence of SEQ ID NO: 16 (e.g., a nucleic acid sequence that is 85%, 86%, 87%, 88%, 89%, 90%, 91%, 92%, 93%, 94%, 95%, 96%, 97%, 98%, 99%, or 100% identical to the nucleic acid sequence of SEQ ID NO: 16). In some embodiments, the transgene encoding POLG has a nucleic acid sequence that is at least 90% identical to the nucleic acid sequence of SEQ ID NO: 16 (e.g., a nucleic acid sequence that is 90%, 91%, 92%, 93%, 94%, 95%, 96%, 97%, 98%, 99%, or 100% identical to the nucleic acid sequence of SEQ ID NO: 16). In some embodiments, the transgene encoding POLG has a nucleic acid sequence that is at least 95% identical to the nucleic acid sequence of SEQ ID NO: 16 (e.g., a nucleic acid sequence that is 95%, 96%, 97%, 98%, 99%, or 100% identical to the nucleic acid sequence of SEQ ID NO: 16). In some embodiments, the transgene encoding POLG is codon optimized to increase efficiency. In some embodiments, the nucleic acid of the transgene encoding POLG is at least at least 70% identical to coding sequence of the transgene that encodes POLG (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of the coding sequence). In some embodiments, the nucleic acid sequence of the transgene encoding POLG has the nucleic acid sequence of SEQ ID NO: 24.

In some embodiments, the second composition is a vector, such as a viral vector. The viral vector may be, for example, an AAV, adenovirus, lentivirus, retrovirus, poxvirus, baculovirus, herpes simplex virus, vaccinia virus, or a synthetic virus (e.g., a chimeric virus, mosaic virus, or pseudotyped virus, and/or a virus that contains a foreign protein, synthetic polymer, nanoparticle, or small molecule).

In some embodiments, the second composition is an AAV, such as an AAV1 (i.e., an AAV containing AAV1 inverted terminal repeats (ITRs) and AAV1 capsid proteins), AAV2 (i.e., an AAV containing AAV2 ITRs and AAV2 capsid proteins), AAV3 (i.e., an AAV containing AAV3 ITRs and AAV3 capsid proteins), AAV4 (i.e., an AAV containing AAV4 ITRs and AAV4 capsid proteins), AAV5 (i.e., an AAV containing AAV5 ITRs and AAV5 capsid proteins), AAV6 (i.e., an AAV containing AAV6 ITRs and AAV6 capsid proteins), AAV7 (i.e., an AAV containing AAV7 ITRs and AAV7 capsid proteins), AAV8 (i.e., an AAV containing AAV8 ITRs and AAV8 capsid proteins), AAV9 (i.e., an AAV containing AAV9 ITRs and AAV9 capsid proteins), AAVrh74 (i.e., an AAV containing AAVrh74 ITRs and AAVrh74 capsid proteins), AAVrh.8 (i.e., an AAV containing AAVrh.8 ITRs and AAVrh.8 capsid proteins), or AAVrh.10 (i.e., an AAV containing AAVrh.10 ITRs and AAVrh.10 capsid proteins).

In some embodiments, the second composition is a pseudotyped AAV, containing ITRs from one AAV serotype and capsid proteins from a different AAV serotype. In some embodiments, the pseudotyped AAV is AAV2/9 (i.e., an AAV containing AAV2 ITRs and AAV9 capsid proteins). In some embodiments, the pseudotyped AAV is AAV2/8 (i.e., an AAV containing AAV2 ITRs and AAV8 capsid proteins). In some embodiments, the pseudotyped AAV is AAV2/1 (i.e., an AAV containing AAV2 ITRs and AAV1 capsid proteins).

In some embodiments, the second composition is an AAV that contains a recombinant capsid protein, such as a capsid protein containing a chimera of one or more of capsid proteins from AAV1, AAV2, AAV3, AAV4, AAV5, AAV6, AAV7, AAV8, AAV9, AAVrh74, AAVrh.8, or AAVrh.10.

In some embodiments, the second composition is a liposome, vesicle, synthetic vesicle, exosome, synthetic exosome, dendrimer, or nanoparticle. In some embodiments, the transgene of the second composition is operably linked to a promoter that induces expression of the transgene in a muscle cell. The promoter may be, for example, a chicken beta actin promoter, cytomegalovirus (CMV) promoter, myosin light chain-2 promoter, alpha actin promoter, troponin 1 promoter, Na+/Ca2+ exchanger promoter, dystrophin promoter, creatine kinase promoter, alpha7 integrin promoter, brain natriuretic peptide promoter, alpha B-crystallin/small heat shock protein promoter, alpha myosin heavy chain promoter, or atrial natriuretic factor promoter.

In some embodiments, the transgene of the second composition is operably linked to an enhancer that induces expression of the transgene in a muscle cell. Exemplary enhancers that may be used in conjunction with the compositions and methods of the disclosure are a CMV enhancer, a myocyte enhancer factor 2 (MEF2) enhancer, and a MyoD enhancer.

In some embodiments, the second composition is administered to the subject after administration of the first composition to the subject. The second composition may be administered to the subject, for example, within one or more days or weeks of administration of the first composition to the subject. In some embodiments, the second composition is administered to the subject at least one month after administration of the first composition to the subject. In some embodiments, administration of the first composition continues while the second composition is administered to the subject.

In some embodiments, the method further includes administering to the subject a therapeutically effective amount of a third composition containing a pharmacological agent. The pharmacological agent may be, for example, deoxycytidine (dC), deoxythymidine (dT), deoxyadenosine (dA), deoxyguanosine (dG), deoxycytidine monophosphate (dCMP), deoxythymidine monophosphate (TMP), deoxyadenosine monophosphate (dAMP), deoxyguanosine monophosphate (dGMP), or a mixture thereof. In some embodiments, the pharmacological agent is dC, dT, or a mixture thereof.

In some embodiments, the third composition is administered to the subject after administration of the first composition to the subject. The third composition may be administered to the subject, for example, within one or more days or weeks of administration of the first composition to the subject. In some embodiments, the third composition is administered to the subject at least one month after administration of the first composition to the subject.

In some embodiments, the third composition is administered to the subject after administration of the second composition to the subject. The third composition may be administered to the subject, for example, within one or more days or weeks of administration of the second composition to the subject. In some embodiments, the third composition is administered to the subject at least one month after administration of the second composition to the subject.

In some embodiments, administration of the first composition and administration of the second composition continue while the third composition is administered to the subject. In some embodiments, the third composition is administered to the subject in an amount of from about 100 mg/kg/day to about 1,000 mg/kg/day (e.g., about 100 mg/kg/day, 105 mg/kg/day, 110 mg/kg/day, 115 mg/kg/day, 120 mg/kg/day, 125 mg/kg/day, 130 mg/kg/day, 135 mg/kg/day, 140 mg/kg/day, 145 mg/kg/day, 150 mg/kg/day, 155 mg/kg/day, 160 mg/kg/day, 165 mg/kg/day, 170 mg/kg/day, 175 mg/kg/day, 180 mg/kg/day, 185 mg/kg/day, 190 mg/kg/day, 195 mg/kg/day, 200 mg/kg/day, 205 mg/kg/day, 210 mg/kg/day, 215 mg/kg/day, 220 mg/kg/day, 225 mg/kg/day, 230 mg/kg/day, 235 mg/kg/day, 240 mg/kg/day, 245 mg/kg/day, 250 mg/kg/day, 255 mg/kg/day, 260 mg/kg/day, 265 mg/kg/day, 270 mg/kg/day, 275 mg/kg/day, 280 mg/kg/day, 285 mg/kg/day, 290 mg/kg/day, 295 mg/kg/day, 300 mg/kg/day, 305 mg/kg/day, 310 mg/kg/day, 315 mg/kg/day, 320 mg/kg/day, 325 mg/kg/day, 330 mg/kg/day, 335 mg/kg/day, 340 mg/kg/day, 345 mg/kg/day, 350 mg/kg/day, 355 mg/kg/day, 360 mg/kg/day, 365 mg/kg/day, 370 mg/kg/day, 375 mg/kg/day, 380 mg/kg/day, 385 mg/kg/day, 390 mg/kg/day, 395 mg/kg/day,400 mg/kg/day, 405 mg/kg/day, 410 mg/kg/day, 415 mg/kg/day, 420 mg/kg/day, 425 mg/kg/day, 430 mg/kg/day, 435 mg/kg/day, 440 mg/kg/day, 445 mg/kg/day, 450 mg/kg/day, 455 mg/kg/day, 460 mg/kg/day, 465 mg/kg/day, 470 mg/kg/day, 475 mg/kg/day, 480 mg/kg/day, 485 mg/kg/day, 490 mg/kg/day, 495 mg/kg/day, 500 mg/kg/day, 505 mg/kg/day, 510 mg/kg/day, 515 mg/kg/day, 520 mg/kg/day, 525 mg/kg/day, 530 mg/kg/day, 535 mg/kg/day, 540 mg/kg/day, 545 mg/kg/day, 550 mg/kg/day, 555 mg/kg/day, 560 mg/kg/day, 565 mg/kg/day, 570 mg/kg/day, 575 mg/kg/day, 580 mg/kg/day, 585 mg/kg/day, 590 mg/kg/day, 595 mg/kg/day, 600 mg/kg/day, 605 mg/kg/day, 610 mg/kg/day, 615 mg/kg/day, 620 mg/kg/day, 625 mg/kg/day, 630 mg/kg/day, 635 mg/kg/day, 640 mg/kg/day, 645 mg/kg/day, 650 mg/kg/day, 655 mg/kg/day, 660 mg/kg/day, 665 mg/kg/day, 670 mg/kg/day, 675 mg/kg/day, 680 mg/kg/day, 685 mg/kg/day, 690 mg/kg/day, 695 mg/kg/day, 700 mg/kg/day, 705 mg/kg/day, 710 mg/kg/day, 715 mg/kg/day, 720 mg/kg/day, 725 mg/kg/day, 730 mg/kg/day, 735 mg/kg/day, 740 mg/kg/day, 745 mg/kg/day, 750 mg/kg/day, 755 mg/kg/day, 760 mg/kg/day, 765 mg/kg/day, 770 mg/kg/day, 775 mg/kg/day, 780 mg/kg/day, 785 mg/kg/day, 790 mg/kg/day, 795 mg/kg/day, 800 mg/kg/day, 805 mg/kg/day, 810 mg/kg/day, 815 mg/kg/day, 820 mg/kg/day, 825 mg/kg/day, 830 mg/kg/day, 835 mg/kg/day, 840 mg/kg/day, 845 mg/kg/day, 850 mg/kg/day, 855 mg/kg/day, 860 mg/kg/day, 865 mg/kg/day, 870 mg/kg/day, 875 mg/kg/day, 880 mg/kg/day, 885 mg/kg/day, 890 mg/kg/day, 895 mg/kg/day, 900 mg/kg/day, 905 mg/kg/day, 910 mg/kg/day, 915 mg/kg/day, 920 mg/kg/day, 925 mg/kg/ day, 930 mg/kg/day, 935 mg/kg/day, 940 mg/kg/day, 945 mg/kg/day, 950 mg/kg/day, 955 mg/kg/day, 960 mg/kg/day, 965 mg/kg/day, 970 mg/kg/day, 975 mg/kg/day, 980 mg/kg/day, 985 mg/kg/day, 990 mg/kg/day, 995 mg/kg/day, or 1,000 mg/kg/day).

In some embodiments, the third composition is administered to the subject in an amount of from about 200 mg/kg/day to about 800 mg/kg/day (e.g., about 200 mg/kg/day, 205 mg/kg/day, 210 mg/kg/day, 215 mg/kg/day, 220 mg/kg/day, 225 mg/kg/day, 230 mg/kg/day, 235 mg/kg/day, 240 mg/kg/day, 245 mg/kg/day, 250 mg/kg/day, 255 mg/kg/day, 260 mg/kg/day, 265 mg/kg/day, 270 mg/kg/day, 275 mg/kg/day, 280 mg/kg/day, 285 mg/kg/day, 290 mg/kg/day, 295 mg/kg/day, 300 mg/kg/day, 305 mg/kg/day, 310 mg/kg/day, 315 mg/kg/day, 320 mg/kg/day, 325 mg/kg/day, 330 mg/kg/day, 335 mg/kg/day, 340 mg/kg/day, 345 mg/kg/day, 350 mg/kg/day, 355 mg/kg/day, 360 mg/kg/day, 365 mg/kg/day, 370 mg/kg/day, 375 mg/kg/day, 380 mg/kg/day, 385 mg/kg/day, 390 mg/kg/day, 395 mg/kg/day, 400 mg/kg/day, 405 mg/kg/day, 410 mg/kg/day, 415 mg/kg/day, 420 mg/kg/day, 425 mg/kg/day, 430 mg/kg/day, 435 mg/kg/day, 440 mg/kg/day, 445 mg/kg/day, 450 mg/kg/day, 455 mg/kg/day, 460 mg/kg/day, 465 mg/kg/day, 470 mg/kg/day, 475 mg/kg/day, 480 mg/kg/day, 485 mg/kg/day, 490 mg/kg/day, 495 mg/kg/day, 500 mg/kg/day, 505 mg/kg/day, 510 mg/kg/day, 515 mg/kg/day, 520 mg/kg/day, 525 mg/kg/day, 530 mg/kg/day, 535 mg/kg/day, 540 mg/kg/day, 545 mg/kg/day, 550 mg/kg/day, 555 mg/kg/day, 560 mg/kg/day, 565 mg/kg/day, 570 mg/kg/day, 575 mg/kg/day, 580 mg/kg/day, 585 mg/kg/day, 590 mg/kg/day, 595 mg/kg/day, 600 mg/kg/day, 605 mg/kg/day, 610 mg/kg/day, 615 mg/kg/day, 620 mg/kg/day, 625 mg/kg/day, 630 mg/kg/day, 635 mg/kg/day, 640 mg/kg/day, 645 mg/kg/day, 650 mg/kg/day, 655 mg/kg/day, 660 mg/kg/day, 665 mg/kg/day, 670 mg/kg/day, 675 mg/kg/day, 680 mg/kg/day, 685 mg/kg/day, 690 mg/kg/day, 695 mg/kg/day, 700 mg/kg/day, 705 mg/kg/day, 710 mg/kg/day, 715 mg/kg/day, 720 mg/kg/day, 725 mg/kg/day, 730 mg/kg/day, 735 mg/kg/day, 740 mg/kg/day, 745 mg/kg/day, 750 mg/kg/day, 755 mg/kg/day, 760 mg/kg/day, 765 mg/kg/day, 770 mg/kg/day, 775 mg/kg/day, 780 mg/kg/day, 785 mg/kg/day, 790 mg/kg/day, 795 mg/kg/day, or 800 mg/kg/day).

In some embodiments, the third composition is administered to the subject in an amount of from about 250 mg/kg/day to about 400 mg/kg/day (e.g., about 250 mg/kg/day, 255 mg/kg/day, 260 mg/kg/day, 265 mg/kg/day, 270 mg/kg/day, 275 mg/kg/day, 280 mg/kg/day, 285 mg/kg/day, 290 mg/kg/day, 295 mg/kg/day, 300 mg/kg/day, 305 mg/kg/day, 310 mg/kg/day, 315 mg/kg/day, 320 mg/kg/day, 325 mg/kg/day, 330 mg/kg/day, 335 mg/kg/day, 340 mg/kg/day, 345 mg/kg/day, 350 mg/kg/day, 355 mg/kg/day, 360 mg/kg/day, 365 mg/kg/day, 370 mg/kg/day, 375 mg/kg/day, 380 mg/kg/day, 385 mg/kg/day, 390 mg/kg/day, 395 mg/kg/day, or 400 mg/kg/day).

In some embodiments, the third composition is administered to the subject once daily, twice daily, three times daily, four times daily, five times daily, or six times daily. The third composition may be administered to the subject orally in admixture with cow's milk, human breast milk, infant formula, and/or water.

In some embodiments, the first composition is administered to the subject by way of intravenous, intrathecal, intradermal, transdermal, parenteral, intramuscular, intranasal, subcutaneous, percutaneous, intratracheal, intraperitoneal, intraarterial, intravascular, inhalation, perfusion, lavage, and/or oral administration.

In some embodiments, the second composition is administered to the subject by way of intravenous, intrathecal, intradermal, transdermal, parenteral, intramuscular, intranasal, subcutaneous, percutaneous, intratracheal, intraperitoneal, intraarterial, intravascular, inhalation, perfusion, lavage, and/or oral administration.

In some embodiments, the third composition is administered to the subject by way of intravenous, intrathecal, intradermal, transdermal, parenteral, intramuscular, intranasal, subcutaneous, percutaneous, intratracheal, intraperitoneal, intraarterial, intravascular, inhalation, perfusion, lavage, and/or oral administration.

In some embodiments, the subject is a mammal, such as a human. In some embodiments, the subject is a pediatric human subject, such as a human subject of from about 1 month to about 12 years of age (e.g., a human subject of from about 1 month to about 1 year, 2 years, 3 years, 4 years, 5 years, 6 years, 7 years, 8 years, 9 years, 10 years, 11 years, or 12 years of age).

In a further aspect, the disclosure features a composition containing a transgene encoding TK2, dGK, TP, p53R2, SUCLA2, SUCLG1, MPV17, and/or POLG.

In some embodiments of the preceding aspect, the transgene encodes TK2. The TK2 may have an amino acid sequence that is at least 85% identical to the amino acid sequence of SEQ ID NO: 1 (e.g., an amino acid sequence that is 85%, 86%, 87%, 88%, 89%, 90%, 91%, 92%, 93%, 94%, 95%, 96%, 97%, 98%, 99%, or 100% identical to the amino acid sequence of SEQ ID NO: 1). In some embodiments, the TK2 has an amino acid sequence that is at least 90% identical to the amino acid sequence of SEQ ID NO: 1 (e.g., an amino acid sequence that is 90%, 91%, 92%, 93%, 94%, 95%, 96%, 97%, 98%, 99%, or 100% identical to the amino acid sequence of SEQ ID NO: 1). In some embodiments, the TK2 has an amino acid sequence that is at least 95% identical to the amino acid sequence of SEQ ID NO: 1 (e.g., an amino acid sequence that is 95%, 96%, 97%, 98%, 99%, or 100% identical to the amino acid sequence of SEQ ID NO: 1). In some embodiments, the TK2 has an amino acid sequence that differs from SEQ ID NO: 1 by way of one or more amino acid substitutions, insertions, and/or deletions, such as by from 1 to 10, 1 to 15, 1 to 20, 1 to 25, or more, amino acid substitutions, insertions, and/or deletions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions). In some embodiments, the TK2 has an amino acid sequence that differs from SEQ ID NO: 1 by way of one or more conservative amino acid substitutions, such as by from 1 to 10, 1 to 15, 1 to 20, 1 to 25, or more, conservative amino acid substitutions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions).

In some embodiments of the preceding aspect, the transgene encoding TK2 has a nucleic acid sequence that is at least 70% identical to the nucleic acid sequence of SEQ ID NO: 2 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of SEQ ID NO: 2). In some embodiments of the preceding aspect, the transgene encoding TK2 has a nucleic acid sequence that is at least 85% identical to the nucleic acid sequence of SEQ ID NO: 2 (e.g., a nucleic acid sequence that is 85%, 86%, 87%, 88%, 89%, 90%, 91%, 92%, 93%, 94%, 95%, 96%, 97%, 98%, 99%, or 100% identical to the nucleic acid sequence of SEQ ID NO: 2). In some embodiments, the transgene encoding TK2 has a nucleic acid sequence that is at least 90% identical to the nucleic acid sequence of SEQ ID NO: 2 (e.g., a nucleic acid sequence that is 90%, 91%, 92%, 93%, 94%, 95%, 96%, 97%, 98%, 99%, or 100% identical to the nucleic acid sequence of SEQ ID NO: 2). In some embodiments, the transgene encoding TK2 has a nucleic acid sequence that is at least 95% identical to the nucleic acid sequence of SEQ ID NO: 2 (e.g., a nucleic acid sequence that is 95%, 96%, 97%, 98%, 99%, or 100% identical to the nucleic acid sequence of SEQ ID NO: 2). In some embodiments, the transgene encoding TK2 is codon optimized to increase efficiency. In some embodiments, the nucleic acid of the transgene encoding TK2 is at least at least 70% identical to coding sequence of the transgene that encodes TK2 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of the coding sequence). In some embodiments, the nucleic acid sequence of the transgene encoding TK2 has the nucleic acid sequence of SEQ ID NO: 17.

In some embodiments of the preceding aspect, the transgene encodes dGK. The dGK may have an amino acid sequence that is at least 85% identical to the amino acid sequence of SEQ ID NO: 3 (e.g., an amino acid sequence that is 85%, 86%, 87%, 88%, 89%, 90%, 91%, 92%, 93%, 94%, 95%, 96%, 97%, 98%, 99%, or 100% identical to the amino acid sequence of SEQ ID NO: 3). In some embodiments, the dGK has an amino acid sequence that is at least 90% identical to the amino acid sequence of SEQ ID NO: 3 (e.g., an amino acid sequence that is 90%, 91%, 92%, 93%, 94%, 95%, 96%, 97%, 98%, 99%, or 100% identical to the amino acid sequence of SEQ ID NO: 3). In some embodiments, the dGK has an amino acid sequence that is at least 95% identical to the amino acid sequence of SEQ ID NO: 3 (e.g., an amino acid sequence that is 95%, 96%, 97%, 98%, 99%, or 100% identical to the amino acid sequence of SEQ ID NO: 3). In some embodiments, the dGK has an amino acid sequence that differs from SEQ ID NO: 3 by way of one or more amino acid substitutions, insertions, and/or deletions, such as by from 1 to 10, 1 to 15, 1 to 20, 1 to 25, or more, amino acid substitutions, insertions, and/or deletions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions). In some embodiments, the dGK has an amino acid sequence that differs from SEQ ID NO: 3 by way of one or more conservative amino acid substitutions, such as by from 1 to 10, 1 to 15, 1 to 20, 1 to 25, or more, conservative amino acid substitutions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions). In some embodiments of the preceding aspect, the transgene encoding dGK has a nucleic acid sequence that is at least 70% identical to the nucleic acid sequence of SEQ ID NO: 4 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of SEQ ID NO: 4). In some embodiments of the preceding aspect, the transgene encoding dGK has a nucleic acid sequence that is at least 85% identical to the nucleic acid sequence of SEQ ID NO: 4 (e.g., a nucleic acid sequence that is 85%, 86%, 87%, 88%, 89%, 90%, 91%, 92%, 93%, 94%, 95%, 96%, 97%, 98%, 99%, or 100% identical to the nucleic acid sequence of SEQ ID NO: 4). In some embodiments, the transgene encoding dGK has a nucleic acid sequence that is at least 90% identical to the nucleic acid sequence of SEQ ID NO: 4 (e.g., a nucleic acid sequence that is 90%, 91%, 92%, 93%, 94%, 95%, 96%, 97%, 98%, 99%, or 100% identical to the nucleic acid sequence of SEQ ID NO: 4). In some embodiments, the transgene encoding dGK has a nucleic acid sequence that is at least 95% identical to the nucleic acid sequence of SEQ ID NO: 4 (e.g., a nucleic acid sequence that is 95%, 96%, 97%, 98%, 99%, or 100% identical to the nucleic acid sequence of SEQ ID NO: 4). In some embodiments, the transgene encoding dGK is codon optimized to increase efficiency. In some embodiments, the nucleic acid of the transgene encoding dGK is at least at least 70% identical to coding sequence of the transgene that encodes dGK (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of the coding sequence). In some embodiments, the nucleic acid sequence of the transgene encoding dGK has the nucleic acid sequence of SEQ ID NO: 18.

In some embodiments of the preceding aspect, the transgene encodes TP. The TP may have an amino acid sequence that is at least 85% identical to the amino acid sequence of SEQ ID NO: 5 (e.g., an amino acid sequence that is 85%, 86%, 87%, 88%, 89%, 90%, 91%, 92%, 93%, 94%, 95%, 96%, 97%, 98%, 99%, or 100% identical to the amino acid sequence of SEQ ID NO: 5). In some embodiments, the TP has an amino acid sequence that is at least 90% identical to the amino acid sequence of SEQ ID NO: 5 (e.g., an amino acid sequence that is 90%, 91%, 92%, 93%, 94%, 95%, 96%, 97%, 98%, 99%, or 100% identical to the amino acid sequence of SEQ ID NO: 5). In some embodiments, the TP has an amino acid sequence that is at least 95% identical to the amino acid sequence of SEQ ID NO: 5 (e.g., an amino acid sequence that is 95%, 96%, 97%, 98%, 99%, or 100% identical to the amino acid sequence of SEQ ID NO: 5). In some embodiments, the TP has an amino acid sequence that differs from SEQ ID NO: 5 by way of one or more amino acid substitutions, insertions, and/or deletions, such as by from 1 to 10, 1 to 15, 1 to 20, 1 to 25, or more, amino acid substitutions, insertions, and/or deletions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions). In some embodiments, the TP has an amino acid sequence that differs from SEQ ID NO: 5 by way of one or more conservative amino acid substitutions, such as by from 1 to 10, 1 to 15, 1 to 20, 1 to 25, or more, conservative amino acid substitutions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions).

In some embodiments of the preceding aspect, the transgene encoding TP has a nucleic acid sequence that is at least 70% identical to the nucleic acid sequence of SEQ ID NO: 6 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of SEQ ID NO: 6). In some embodiments of the preceding aspect, the transgene encoding TP has a nucleic acid sequence that is at least 85% identical to the nucleic acid sequence of SEQ ID NO: 6 (e.g., a nucleic acid sequence that is 85%, 86%, 87%, 88%, 89%, 90%, 91%, 92%, 93%, 94%, 95%, 96%, 97%, 98%, 99%, or 100% identical to the nucleic acid sequence of SEQ ID NO: 6). In some embodiments, the transgene encoding TP has a nucleic acid sequence that is at least 90% identical to the nucleic acid sequence of SEQ ID NO: 6 (e.g., a nucleic acid sequence that is 90%, 91%, 92%, 93%, 94%, 95%, 96%, 97%, 98%, 99%, or 100% identical to the nucleic acid sequence of SEQ ID NO: 6). In some embodiments, the transgene encoding TP has a nucleic acid sequence that is at least 95% identical to the nucleic acid sequence of SEQ ID NO: 6 (e.g., a nucleic acid sequence that is 95%, 96%, 97%, 98%, 99%, or 100% identical to the nucleic acid sequence of SEQ ID NO: 6). In some embodiments, the transgene encoding TP is codon optimized to increase efficiency. In some embodiments, the nucleic acid of the transgene encoding TP is at least at least 70% identical to coding sequence of the transgene that encodes TP (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of the coding sequence). In some embodiments, the nucleic acid sequence of the transgene encoding TP has the nucleic acid sequence of SEQ ID NO: 19.

In some embodiments of the preceding aspect, the transgene encodes p53R2. The p53R2 may have an amino acid sequence that is at least 85% identical to the amino acid sequence of SEQ ID NO: 7 (e.g., an amino acid sequence that is 85%, 86%, 87%, 88%, 89%, 90%, 91%, 92%, 93%, 94%, 95%, 96%, 97%, 98%, 99%, or 100% identical to the amino acid sequence of SEQ ID NO: 7). In some embodiments, the p53R2 has an amino acid sequence that is at least 90% identical to the amino acid sequence of SEQ ID NO: 7 (e.g., an amino acid sequence that is 90%, 91%, 92%, 93%, 94%, 95%, 96%, 97%, 98%, 99%, or 100% identical to the amino acid sequence of SEQ ID NO: 7). In some embodiments, the p53R2 has an amino acid sequence that is at least 95% identical to the amino acid sequence of SEQ ID NO: 7 (e.g., an amino acid sequence that is 95%, 96%, 97%, 98%, 99%, or 100% identical to the amino acid sequence of SEQ ID NO: 7). In some embodiments, the p53R2 has an amino acid sequence that differs from SEQ ID NO: 7 by way of one or more amino acid substitutions, insertions, and/or deletions, such as by from 1 to 10, 1 to 15, 1 to 20, 1 to 25, or more, amino acid substitutions, insertions, and/or deletions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions). In some embodiments, the p53R2 has an amino acid sequence that differs from SEQ ID NO: 7 by way of one or more conservative amino acid substitutions, such as by from 1 to 10, 1 to 15, 1 to 20, 1 to 25, or more, conservative amino acid substitutions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions).

In some embodiments of the preceding aspect, the transgene encoding p53R2 has a nucleic acid sequence that is at least 70% identical to the nucleic acid sequence of SEQ ID NO: 8 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of SEQ ID NO: 8). In some embodiments of the preceding aspect, the transgene encoding p53R2 has a nucleic acid sequence that is at least 85% identical to the nucleic acid sequence of SEQ ID NO: 8 (e.g., a nucleic acid sequence that is 85%, 86%, 87%, 88%, 89%, 90%, 91%, 92%, 93%, 94%, 95%, 96%, 97%, 98%, 99%, or 100% identical to the nucleic acid sequence of SEQ ID NO: 8). In some embodiments, the transgene encoding p53R2 has a nucleic acid sequence that is at least 90% identical to the nucleic acid sequence of SEQ ID NO: 8 (e.g., a nucleic acid sequence that is 90%, 91%, 92%, 93%, 94%, 95%, 96%, 97%, 98%, 99%, or 100% identical to the nucleic acid sequence of SEQ ID NO: 8). In some embodiments, the transgene encoding p53R2 has a nucleic acid sequence that is at least 95% identical to the nucleic acid sequence of SEQ ID NO: 8 (e.g., a nucleic acid sequence that is 95%, 96%, 97%, 98%, 99%, or 100% identical to the nucleic acid sequence of SEQ ID NO: 8). In some embodiments, the transgene encoding p53R2 is codon optimized to increase efficiency. In some embodiments, the nucleic acid of the transgene encoding p53R2 is at least at least 70% identical to coding sequence of the transgene that encodes p53R2 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of the coding sequence). In some embodiments, the nucleic acid sequence of the transgene encoding p53R2 has the nucleic acid sequence of SEQ ID NO: 20.

In some embodiments of the preceding aspect, the transgene encodes SUCLA2. The SUCLA2 may have an amino acid sequence that is at least 85% identical to the amino acid sequence of SEQ ID NO: 9 (e.g., an amino acid sequence that is 85%, 86%, 87%, 88%, 89%, 90%, 91%, 92%, 93%, 94%, 95%, 96%, 97%, 98%, 99%, or 100% identical to the amino acid sequence of SEQ ID NO: 9). In some embodiments, the SUCLA2 has an amino acid sequence that is at least 90% identical to the amino acid sequence of SEQ ID NO: 9 (e.g., an amino acid sequence that is 90%, 91%, 92%, 93%, 94%, 95%, 96%, 97%, 98%, 99%, or 100% identical to the amino acid sequence of SEQ ID NO: 9). In some embodiments, the SUCLA2 has an amino acid sequence that is at least 95% identical to the amino acid sequence of SEQ ID NO: 9 (e.g., an amino acid sequence that is 95%, 96%, 97%, 98%, 99%, or 100% identical to the amino acid sequence of SEQ ID NO: 9). In some embodiments, the SUCLA2 has an amino acid sequence that differs from SEQ ID NO: 9 by way of one or more amino acid substitutions, insertions, and/or deletions, such as by from 1 to 10, 1 to 15, 1 to 20, 1 to 25, or more, amino acid substitutions, insertions, and/or deletions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions). In some embodiments, the SUCLA2 has an amino acid sequence that differs from SEQ ID NO: 9 by way of one or more conservative amino acid substitutions, such as by from 1 to 10, 1 to 15, 1 to 20, 1 to 25, or more, conservative amino acid substitutions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions).

In some embodiments of the preceding aspect, the transgene encoding SUCLA2 has a nucleic acid sequence that is at least 70% identical to the nucleic acid sequence of SEQ ID NO: 10 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of SEQ ID NO: 10). In some embodiments of the preceding aspect, the transgene encoding SUCLA2 has a nucleic acid sequence that is at least 85% identical to the nucleic acid sequence of SEQ ID NO: 10 (e.g., a nucleic acid sequence that is 85%, 86%, 87%, 88%, 89%, 90%, 91%, 92%, 93%, 94%, 95%, 96%, 97%, 98%, 99%, or 100% identical to the nucleic acid sequence of SEQ ID NO: 10). In some embodiments, the transgene encoding SUCLA2 has a nucleic acid sequence that is at least 90% identical to the nucleic acid sequence of SEQ ID NO: 10 (e.g., a nucleic acid sequence that is 90%, 91%, 92%, 93%, 94%, 95%, 96%, 97%, 98%, 99%, or 100% identical to the nucleic acid sequence of SEQ ID NO: 10). In some embodiments, the transgene encoding SUCLA2 has a nucleic acid sequence that is at least 95% identical to the nucleic acid sequence of SEQ ID NO: 10 (e.g., a nucleic acid sequence that is 95%, 96%, 97%, 98%, 99%, or 100% identical to the nucleic acid sequence of SEQ ID NO: 10). In some embodiments, the transgene encoding SUCLA2 is codon optimized to increase efficiency. In some embodiments, the nucleic acid of the transgene encoding SUCLA2 is at least at least 70% identical to coding sequence of the transgene that encodes SUCLA2 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of the coding sequence). In some embodiments, the nucleic acid sequence of the transgene encoding SUCLA2 has the nucleic acid sequence of SEQ ID NO: 21.

In some embodiments of the preceding aspect, the transgene encodes SUCLG1. The SUCLG1 may have an amino acid sequence that is at least 85% identical to the amino acid sequence of SEQ ID NO: 11 (e.g., an amino acid sequence that is 85%, 86%, 87%, 88%, 89%, 90%, 91%, 92%, 93%, 94%, 95%, 96%, 97%, 98%, 99%, or 100% identical to the amino acid sequence of SEQ ID NO: 11). In some embodiments, the SUCLG1 has an amino acid sequence that is at least 90% identical to the amino acid sequence of SEQ ID NO: 11 (e.g., an amino acid sequence that is 90%, 91%, 92%, 93%, 94%, 95%, 96%, 97%, 98%, 99%, or 100% identical to the amino acid sequence of SEQ ID NO: 11). In some embodiments, the SUCLG1 has an amino acid sequence that is at least 95% identical to the amino acid sequence of SEQ ID NO: 11 (e.g., an amino acid sequence that is 95%, 96%, 97%, 98%, 99%, or 100% identical to the amino acid sequence of SEQ ID NO: 11). In some embodiments, the SUCLG1 has an amino acid sequence that differs from SEQ ID NO: 11 by way of one or more amino acid substitutions, insertions, and/or deletions, such as by from 1 to 10, 1 to 15, 1 to 20, 1 to 25, or more, amino acid substitutions, insertions, and/or deletions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions). In some embodiments, the SUCLG1 has an amino acid sequence that differs from SEQ ID NO: 11 by way of one or more conservative amino acid substitutions, such as by from 1 to 10, 1 to 15, 1 to 20, 1 to 25, or more, conservative amino acid substitutions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions).

In some embodiments of the preceding aspect, the transgene encoding SUCLG1 has a nucleic acid sequence that is at least 70% identical to the nucleic acid sequence of SEQ ID NO: 12 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of SEQ ID NO: 12). In some embodiments of the preceding aspect, the transgene encoding SUCLG1 has a nucleic acid sequence that is at least 85% identical to the nucleic acid sequence of SEQ ID NO: 12 (e.g., a nucleic acid sequence that is 85%, 86%, 87%, 88%, 89%, 90%, 91%, 92%, 93%, 94%, 95%, 96%, 97%, 98%, 99%, or 100% identical to the nucleic acid sequence of SEQ ID NO: 12). In some embodiments, the transgene encoding SUCLG1 has a nucleic acid sequence that is at least 90% identical to the nucleic acid sequence of SEQ ID NO: 12 (e.g., a nucleic acid sequence that is 90%, 91%, 92%, 93%, 94%, 95%, 96%, 97%, 98%, 99%, or 100% identical to the nucleic acid sequence of SEQ ID NO: 12). In some embodiments, the transgene encoding SUCLG1 has a nucleic acid sequence that is at least 95% identical to the nucleic acid sequence of SEQ ID NO: 12 (e.g., a nucleic acid sequence that is 95%, 96%, 97%, 98%, 99%, or 100% identical to the nucleic acid sequence of SEQ ID NO: 12). In some embodiments, the transgene encoding SUCLG1 is codon optimized to increase efficiency. In some embodiments, the nucleic acid of the transgene encoding SUCLG1 is at least at least 70% identical to coding sequence of the transgene that encodes SUCLG1 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of the coding sequence). In some embodiments, the nucleic acid sequence of the transgene encoding SUCLG1 has the nucleic acid sequence of SEQ ID NO: 22.

In some embodiments of the preceding aspect, the transgene encodes MPV17. The MPV17 may have an amino acid sequence that is at least 85% identical to the amino acid sequence of SEQ ID NO: 13 (e.g., an amino acid sequence that is 85%, 86%, 87%, 88%, 89%, 90%, 91%, 92%, 93%, 94%, 95%, 96%, 97%, 98%, 99%, or 100% identical to the amino acid sequence of SEQ ID NO: 13). In some embodiments, the MPV17 has an amino acid sequence that is at least 90% identical to the amino acid sequence of SEQ ID NO: 13 (e.g., an amino acid sequence that is 90%, 91%, 92%, 93%, 94%, 95%, 96%, 97%, 98%, 99%, or 100% identical to the amino acid sequence of SEQ ID NO: 13). In some embodiments, the MPV17 has an amino acid sequence that is at least 95% identical to the amino acid sequence of SEQ ID NO: 13 (e.g., an amino acid sequence that is 95%, 96%, 97%, 98%, 99%, or 100% identical to the amino acid sequence of SEQ ID NO: 13). In some embodiments, the MPV17 has an amino acid sequence that differs from SEQ ID NO: 13 by way of one or more amino acid substitutions, insertions, and/or deletions, such as by from 1 to 10, 1 to 15, 1 to 20, 1 to 25, or more, amino acid substitutions, insertions, and/or deletions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions). In some embodiments, the MPV17 has an amino acid sequence that differs from SEQ ID NO: 13 by way of one or more conservative amino acid substitutions, such as by from 1 to 10, 1 to 15, 1 to 20, 1 to 25, or more, conservative amino acid substitutions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions).

In some embodiments of the preceding aspect, the transgene encoding MPV17 has a nucleic acid sequence that is at least 70% identical to the nucleic acid sequence of SEQ ID NO: 14 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of SEQ ID NO: 14). In some embodiments of the preceding aspect, the transgene encoding MPV17 has a nucleic acid sequence that is at least 85% identical to the nucleic acid sequence of SEQ ID NO: 14 (e.g., a nucleic acid sequence that is 85%, 86%, 87%, 88%, 89%, 90%, 91%, 92%, 93%, 94%, 95%, 96%, 97%, 98%, 99%, or 100% identical to the nucleic acid sequence of SEQ ID NO: 14). In some embodiments, the transgene encoding MPV17 has a nucleic acid sequence that is at least 90% identical to the nucleic acid sequence of SEQ ID NO: 14 (e.g., a nucleic acid sequence that is 90%, 91%, 92%, 93%, 94%, 95%, 96%, 97%, 98%, 99%, or 100% identical to the nucleic acid sequence of SEQ ID NO: 14). In some embodiments, the transgene encoding MPV17 has a nucleic acid sequence that is at least 95% identical to the nucleic acid sequence of SEQ ID NO: 14 (e.g., a nucleic acid sequence that is 95%, 96%, 97%, 98%, 99%, or 100% identical to the nucleic acid sequence of SEQ ID NO: 14). In some embodiments, the transgene encoding MPV17 is codon optimized to increase efficiency. In some embodiments, the nucleic acid of the transgene encoding MPV17 is at least at least 70% identical to coding sequence of the transgene that encodes MPV17 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of the coding sequence). In some embodiments, the nucleic acid sequence of the transgene encoding MPV17 has the nucleic acid sequence of SEQ ID NO: 23.

In some embodiments of the preceding aspect, the transgene encodes POLG. The POLG may have an amino acid sequence that is at least 85% identical to the amino acid sequence of SEQ ID NO: 15 (e.g., an amino acid sequence that is 85%, 86%, 87%, 88%, 89%, 90%, 91%, 92%, 93%, 94%, 95%, 96%, 97%, 98%, 99%, or 100% identical to the amino acid sequence of SEQ ID NO: 15). In some embodiments, the POLG has an amino acid sequence that is at least 90% identical to the amino acid sequence of SEQ ID NO: 15 (e.g., an amino acid sequence that is 90%, 91%, 92%, 93%, 94%, 95%, 96%, 97%, 98%, 99%, or 100% identical to the amino acid sequence of SEQ ID NO: 15). In some embodiments, the POLG has an amino acid sequence that is at least 95% identical to the amino acid sequence of SEQ ID NO: 15 (e.g., an amino acid sequence that is 95%, 96%, 97%, 98%, 99%, or 100% identical to the amino acid sequence of SEQ ID NO: 15). In some embodiments, the POLG has an amino acid sequence that differs from SEQ ID NO: 15 by way of one or more amino acid substitutions, insertions, and/or deletions, such as by from 1 to 10, 1 to 15, 1 to 20, 1 to 25, or more, amino acid substitutions, insertions, and/or deletions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions). In some embodiments, the POLG has an amino acid sequence that differs from SEQ ID NO: 15 by way of one or more conservative amino acid substitutions, such as by from 1 to 10, 1 to 15, 1 to 20, 1 to 25, or more, conservative amino acid substitutions (e.g., by 1, 2, 3, 4, 5, 6, 7, 8, 9, 10, 11, 12, 13, 14, 15, 16, 17, 18, 19, 20, 21, 22, 23, 24, 25, or more, conservative amino acid substitutions).

In some embodiments of the preceding aspect, the transgene encoding POLG has a nucleic acid sequence that is at least 70% identical to the nucleic acid sequence of SEQ ID NO: 16 (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of SEQ ID NO: 16). In some embodiments of the preceding aspect, the transgene encoding POLG has a nucleic acid sequence that is at least 85% identical to the nucleic acid sequence of SEQ ID NO: 16 (e.g., a nucleic acid sequence that is 85%, 86%, 87%, 88%, 89%, 90%, 91%, 92%, 93%, 94%, 95%, 96%, 97%, 98%, 99%, or 100% identical to the nucleic acid sequence of SEQ ID NO: 16). In some embodiments, the transgene encoding POLG has a nucleic acid sequence that is at least 90% identical to the nucleic acid sequence of SEQ ID NO: 16 (e.g., a nucleic acid sequence that is 90%, 91%, 92%, 93%, 94%, 95%, 96%, 97%, 98%, 99%, or 100% identical to the nucleic acid sequence of SEQ ID NO: 16). In some embodiments, the transgene encoding POLG has a nucleic acid sequence that is at least 95% identical to the nucleic acid sequence of SEQ ID NO: 16 (e.g., a nucleic acid sequence that is 95%, 96%, 97%, 98%, 99%, or 100% identical to the nucleic acid sequence of SEQ ID NO: 16). In some embodiments, the transgene encoding POLG is codon optimized to increase efficiency. In some embodiments, the nucleic acid of the transgene encoding POLG is at least at least 70% identical to coding sequence of the transgene that encodes POLG (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of the coding sequence). In some embodiments, the nucleic acid sequence of the transgene encoding POLG has the nucleic acid sequence of SEQ ID NO: 24.

In some embodiments of the preceding aspect, the composition is a vector, such as a viral vector. The viral vector may be, for example, an AAV, adenovirus, lentivirus, retrovirus, poxvirus, baculovirus, herpes simplex virus, vaccinia virus, or a synthetic virus (e.g., a chimeric virus, mosaic virus, or pseudotyped virus, and/or a virus that contains a foreign protein, synthetic polymer, nanoparticle, or small molecule).

In some embodiments of the preceding aspect, the viral vector is an AAV, such as an AAV1 (i.e., an AAV containing AAV1 inverted terminal repeats (ITRs) and AAV1 capsid proteins), AAV2 (i.e., an AAV containing AAV2 ITRs and AAV2 capsid proteins), AAV3 (i.e., an AAV containing AAV3 ITRs and AAV3 capsid proteins), AAV4 (i.e., an AAV containing AAV4 ITRs and AAV4 capsid proteins), AAV5 (i.e., an AAV containing AAV5 ITRs and AAV5 capsid proteins), AAV6 (i.e., an AAV containing AAV6 ITRs and AAV6 capsid proteins), AAV7 (i.e., an AAV containing AAV7 ITRs and AAV7 capsid proteins), AAV8 (i.e., an AAV containing AAV8 ITRs and AAV8 capsid proteins), AAV9 (i.e., an AAV containing AAV9 ITRs and AAV9 capsid proteins), AAVrh74 (i.e., an AAV containing AAVrh74 ITRs and AAVrh74 capsid proteins), AAVrh.8 (i.e., an AAV containing AAVrh.8 ITRs and AAVrh.8 capsid proteins), or AAVrh.10 (i.e., an AAV containing AAVrh.10 ITRs and AAVrh.10 capsid proteins).

In some embodiments of the preceding aspect, the viral vector is a pseudotyped AAV, containing ITRs from one AAV serotype and capsid proteins from a different AAV serotype. In some embodiments, the pseudotyped AAV is AAV2/9 (i.e., an AAV containing AAV2 ITRs and AAV9 capsid proteins). In some embodiments, the pseudotyped AAV is AAV2/8 (i.e., an AAV containing AAV2 ITRs and AAV8 capsid proteins). In some embodiments, the pseudotyped AAV is AAV2/1 (i.e., an AAV containing AAV2 ITRs and AAV1 capsid proteins).

In some embodiments of the preceding aspect, the AAV contains a recombinant capsid protein, such as a capsid protein containing a chimera of one or more of capsid proteins from AAV1, AAV2, AAV3, AAV4, AAV5, AAV6, AAV7, AAV8, AAV9, AAVrh74, AAVrh.8, or AAVrh.10.

In some embodiments of the preceding aspect, the composition is a liposome, vesicle, synthetic vesicle, exosome, synthetic exosome, dendrimer, or nanoparticle.

In some embodiments of the preceding aspect, the transgene is operably linked to a promoter that induces expression of the transgene in a muscle cell. The promoter may be, for example, a chicken beta actin promoter, cytomegalovirus (CMV) promoter, myosin light chain-2 promoter, alpha actin promoter, troponin 1 promoter, Na+/Ca2+ exchanger promoter, dystrophin promoter, creatine kinase promoter, alpha7 integrin promoter, brain natriuretic peptide promoter, alpha B-crystallin/small heat shock protein promoter, alpha myosin heavy chain promoter, or atrial natriuretic factor promoter.

In some embodiments of the preceding aspect, the transgene is operably linked to an enhancer that induces expression of the transgene in a muscle cell. Exemplary enhancers that may be used in conjunction with the compositions and methods of the disclosure are a CMV enhancer, a myocyte enhancer factor 2 (MEF2) enhancer, and a MyoD enhancer.

In another aspect, the disclosure features a kit containing the composition of the preceding aspect. The kit may further contain a package insert, such as a package insert instructing a user of the kit to administer the composition to a subject in accordance with the method of any of the above aspects or embodiments of the disclosure. The kit may further contain a pharmacological agent selected from the group consisting of dC, dT, dA, dG, dCMP, TMP, dAMP, dGMP, and mixtures thereof.

BRIEF DESCRIPTION OF THE DRAWINGS

For the purpose of illustrating the invention, there are depicted in drawings certain embodiments of the invention. However, the invention is not limited to the precise arrangements and instrumentalities of the embodiments depicted in the drawings.

In the drawings, certain abbreviations are used. "WT" means wild-type mice which are Tk2+. "Het" means mice heterozygous for the TK2 gene. "Mut" means $Tk2^{-/-}$ mice. "P #" means post-natal day #. "AAV2-hTK2" refers to an AAV2 vector containing a human TK2 transgene. "AAV9-hTK2" refers to an AAV9 vector containing a human TK2 transgene. "dC" refers to deoxycytidine. "dT" refers to deoxythymidine. "IV" refers to intravenous administration. "vc" refers to a quantity of vector genome copies.

Figure 16:
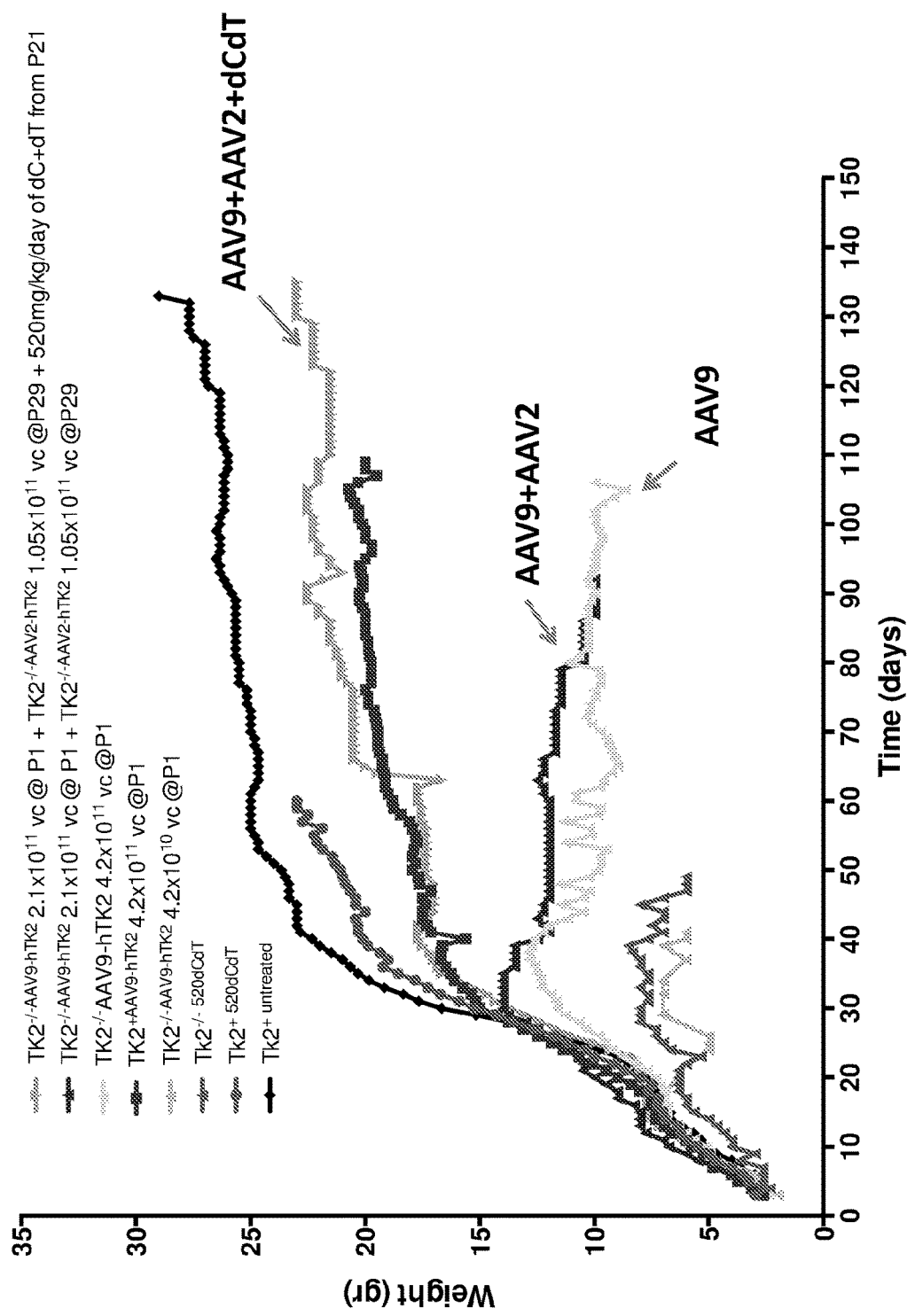

FIG. 16 shows weight versus time in the following female mice: Tk2⁺ untreated; Tk2⁺ treated with 520 mg of dC+dT; Tk2⁻/⁻ mice treated with 520 mg of dC+dT; Tk2⁺ treated AAV9–hTK2 at 4.2×10¹¹ vc by IV at postnatal day 1; Tk2⁻/⁻ mice treated with AAV9-hTK2 at 4.2×10¹¹ vc by IV at postnatal day 1 ("AAV9"); Tk2⁻/⁻ mice treated with AAV9-hTK2 at 4.2×10¹⁰ vc by IV at postnatal day 1; Tk2⁻/⁻ mice treated with AAV9-hTK2 at 2.1×10¹¹ vc by IV at postnatal day 1 and AAV2-hTK2 at 1.05×10¹¹ vc by IV at postnatal day 29 ("AAV9+AAV2"); and Tk2⁻/⁻ mice treated with AAV9-hTK2 at 2.1×10¹¹ vc by IV at postnatal day 1, AAV2-hTK2 at 1.05×10¹¹ vc by IV at postnatal day 29 and 520 mg/kg/day of oral dC+dT from day 21 (AAV9+ AAV2+ dCdT").

Figure 17:
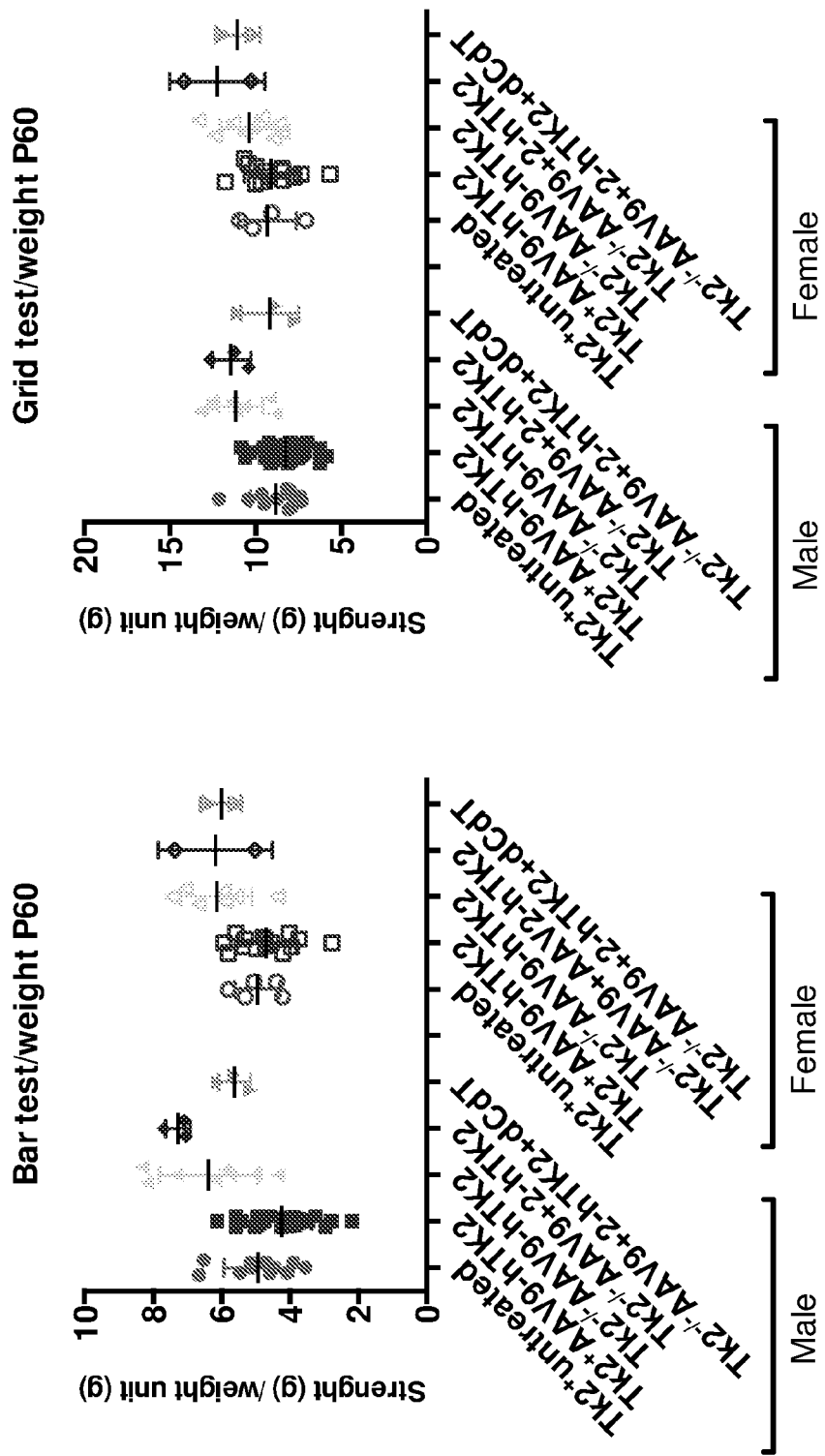

FIG. 17 shows graphs of the result of grip strength test of the fore limbs (bar test) and both fore and hind limbs (grid test) normalized by mouse weight at postnatal day 60 of male and female mice including untreated Tk2⁺, Tk2⁺ treated with AAV9-hTK2, Tk2⁻/⁻ mice treated with AAV9-hTK2, Tk2⁻/⁻ mice treated with AAV9-hTK2 and AAV2-hTK2, and Tk2⁻/⁻ mice treated with AAV9-hTK2, AAV2-hTK2 and dC+dT.

Figure 18:
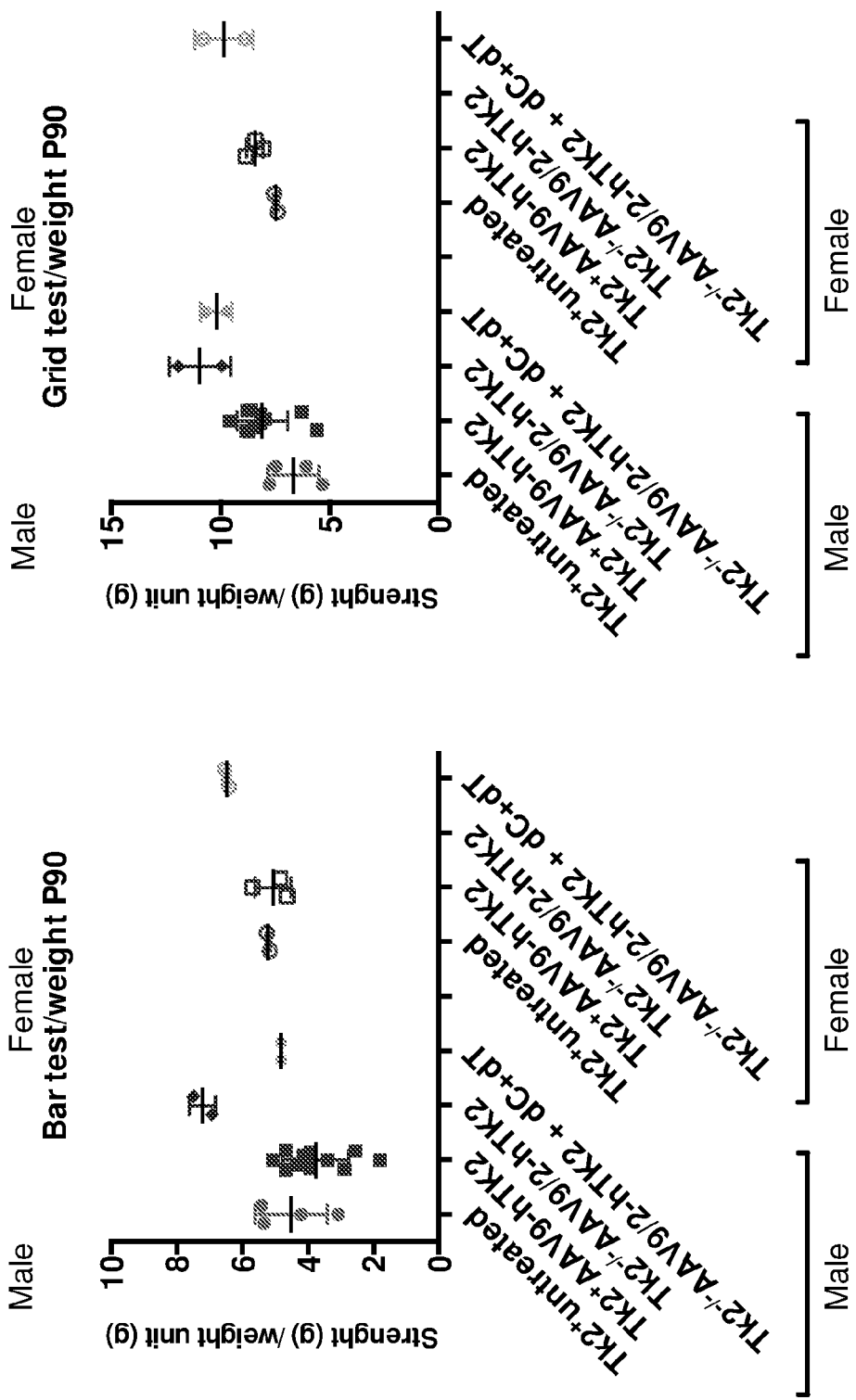

FIG. 18 shows graphs of the result of grip strength test of the fore limbs (bar test) and both fore and hind limbs (grid test) normalized by mouse weight at postnatal day 90 of male and female mice including untreated Tk2⁺, Tk2⁺ treated with AAV9-hTK2, Tk2⁻/⁻ mice treated with AAV9-hTK2, Tk2⁻/⁻ mice treated with AAV9-hTK2 and AAV2-hTK2, and Tk2⁻/⁻ mice treated with AAV9-hTK2, AAV2-hTK2 and dC+dT.

Figure 19:
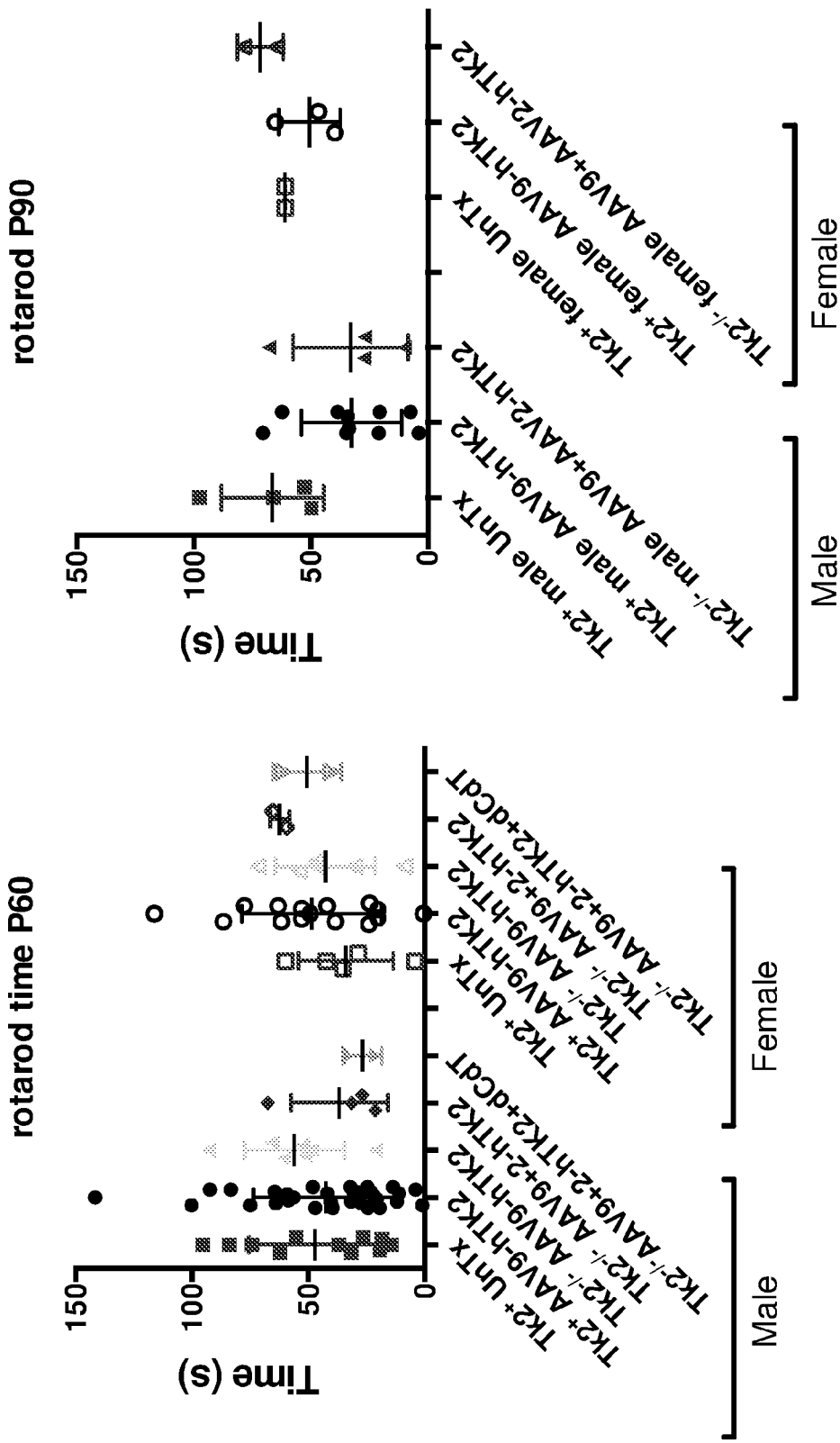

FIG. 19 shows graphs of the results of mice motor function as measured by accelerating rotarod performance test at postnatal day 60 and postnatal day 90 of male and female mice including untreated Tk2⁺, Tk2⁺ treated with AAV9-hTK2, Tk2⁻/⁻ mice treated with AAV9-hTK2, Tk2⁻/⁻ mice treated with AAV9-hTK2 and AAV2-hTK2, and Tk2⁻/⁻ mice treated with AAV9-hTK2, AAV2-hTK2 and dC+dT.

Figure 20:
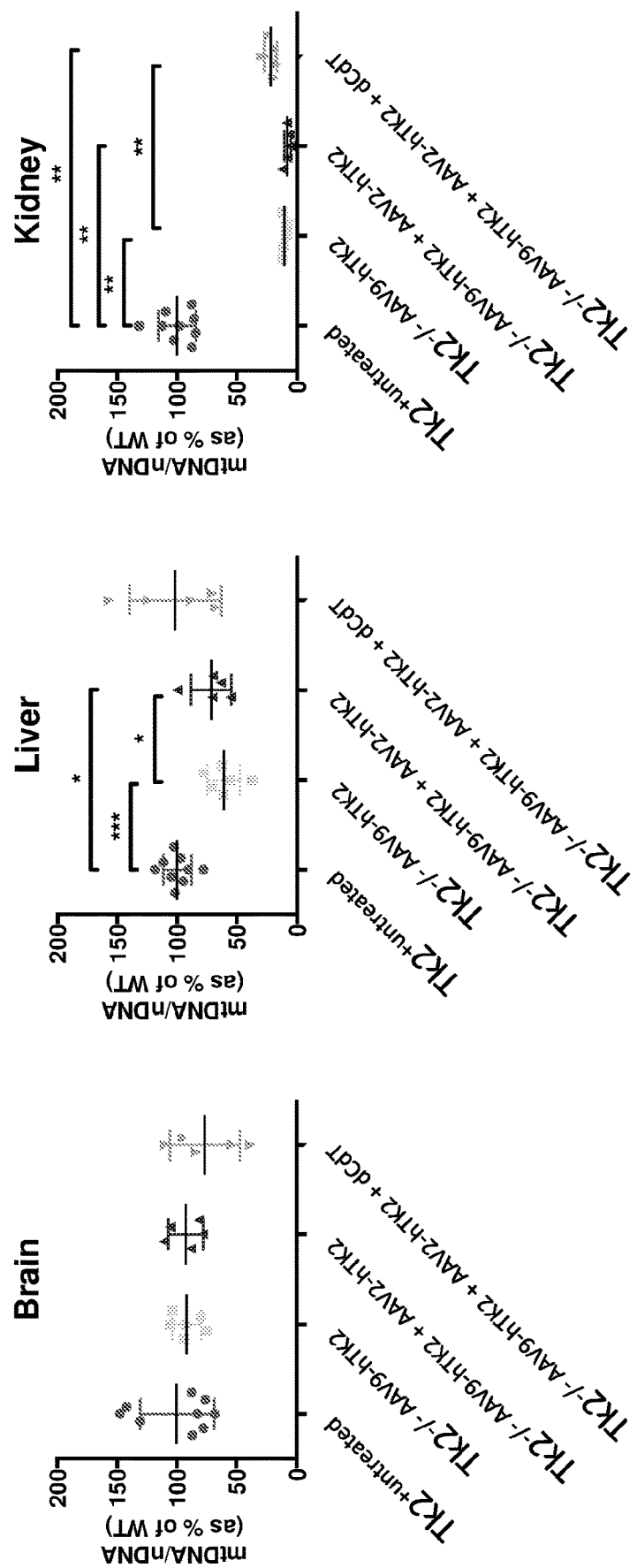
Figure 20:
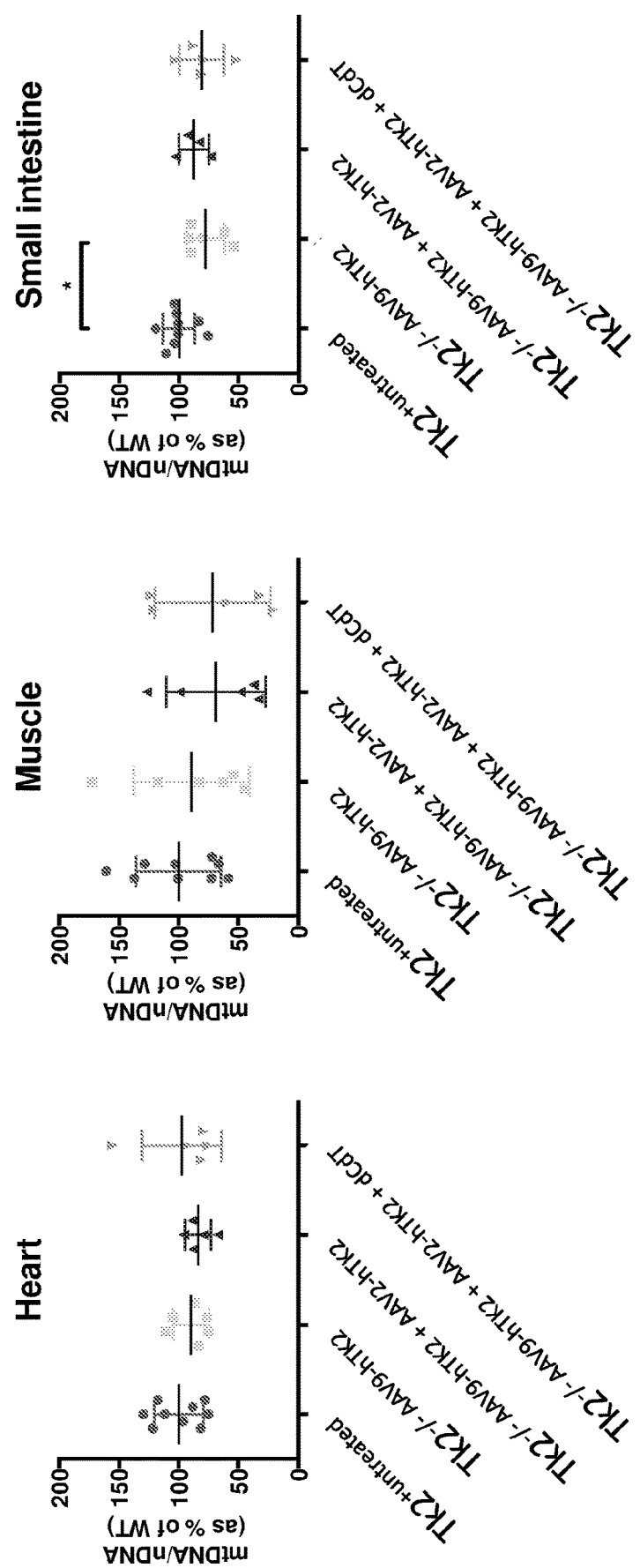

FIG. 20 shows graphs of showing mtDNA copy number (mtDNA/nDNA as a percent of untreated Tk2+) at postnatal day 60 in brain, liver, muscle, heart, kidney, and intestine tissue of the following mice: untreated Tk2⁺; Tk2⁻/⁻ mice treated with AAV9-hTK2; Tk2⁻/⁻ mice treated with AAV9-hTK2 and AAV2-hTK2; and Tk2⁻/⁻ mice treated with AAV9-hTK2, AAV2-hTK2 and dC+dT.

Figure 21:

FIG. 21 depicts the results from the protein test in a urine dip stick using urine from mice at age 21-29 days and age 60 days. All Tk2⁻/⁻ mice were treated with AAV9-hTK2 at day 1, while 3 out of the four Tk2⁻/⁻ mice were treated with AAV2-hTK2 at day 29.

Figure 22:
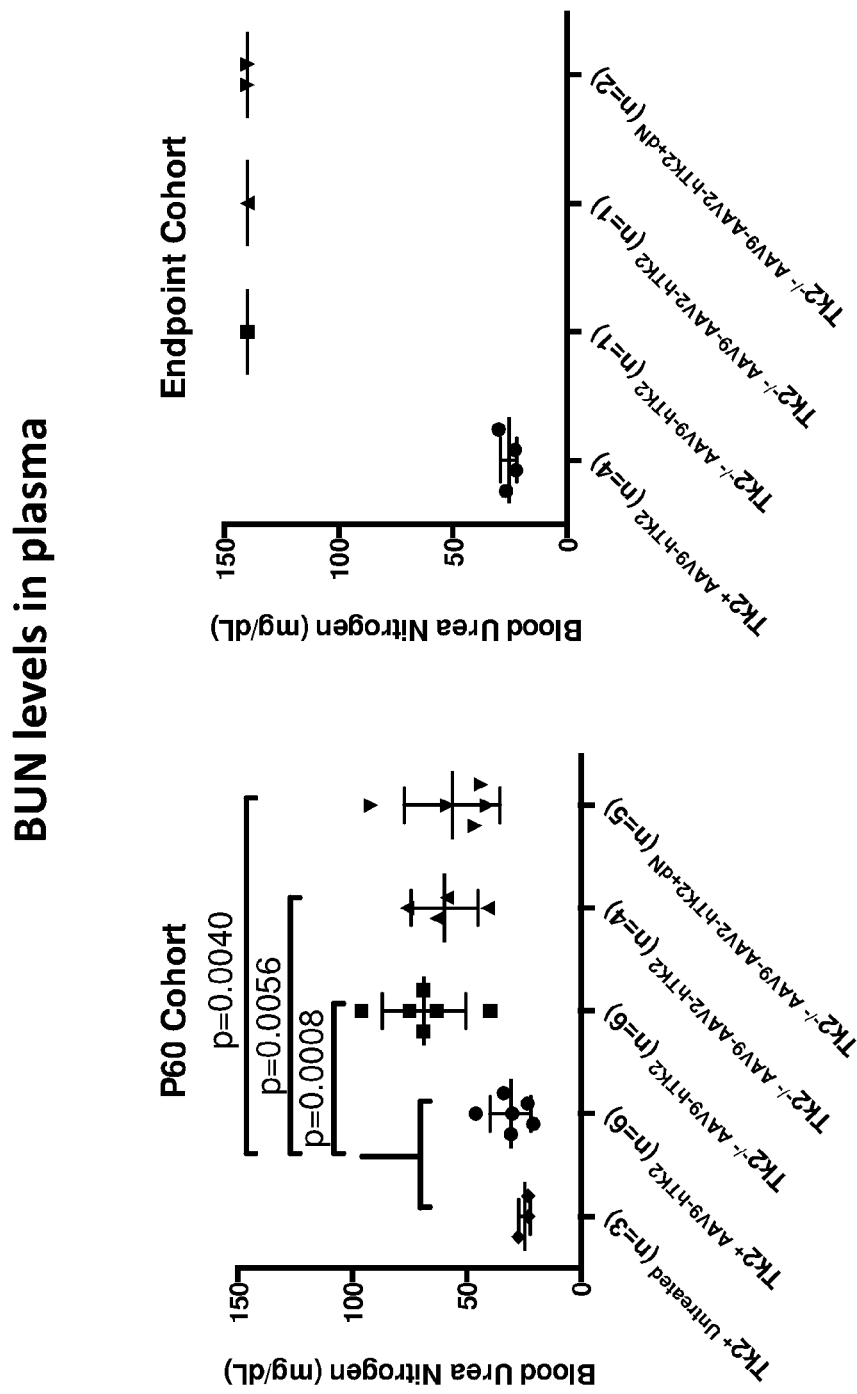

FIG. 22 shows graphs of BUN index in mice at day 60 and mice in an endpoint cohort including untreated Tk2⁺, Tk2⁺ treated with AAV9-hTK2, Tk2⁻/⁻ mice treated with AAV9-hTK2, Tk2⁻/⁻ mice treated with AAV9-hTK2 and AAV2-hTK2, and Tk2⁻/⁻ mice treated with AAV9-hTK2, AAV2-hTK2 and dC+dT.

Figure 23:
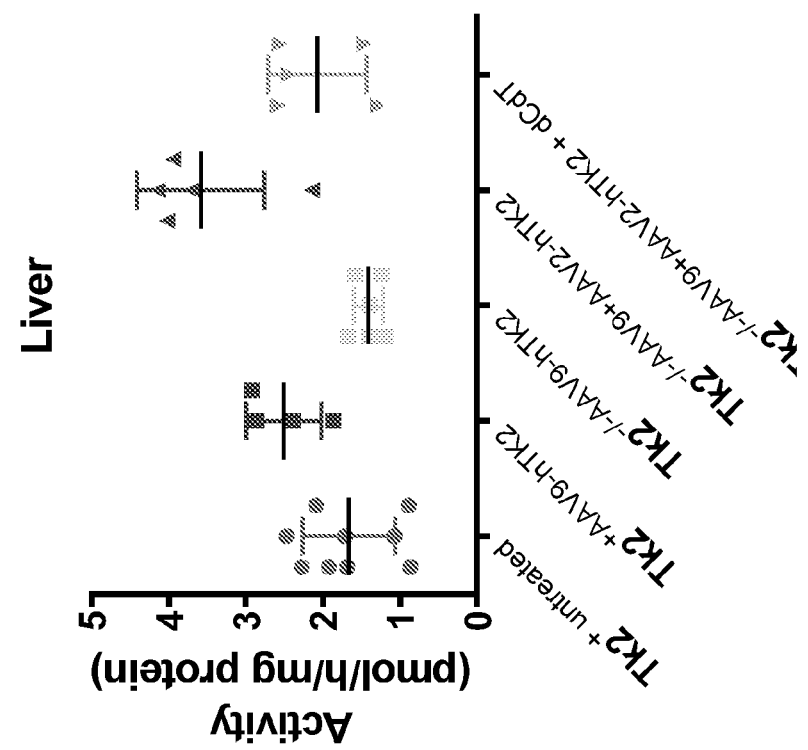
Figure 23:
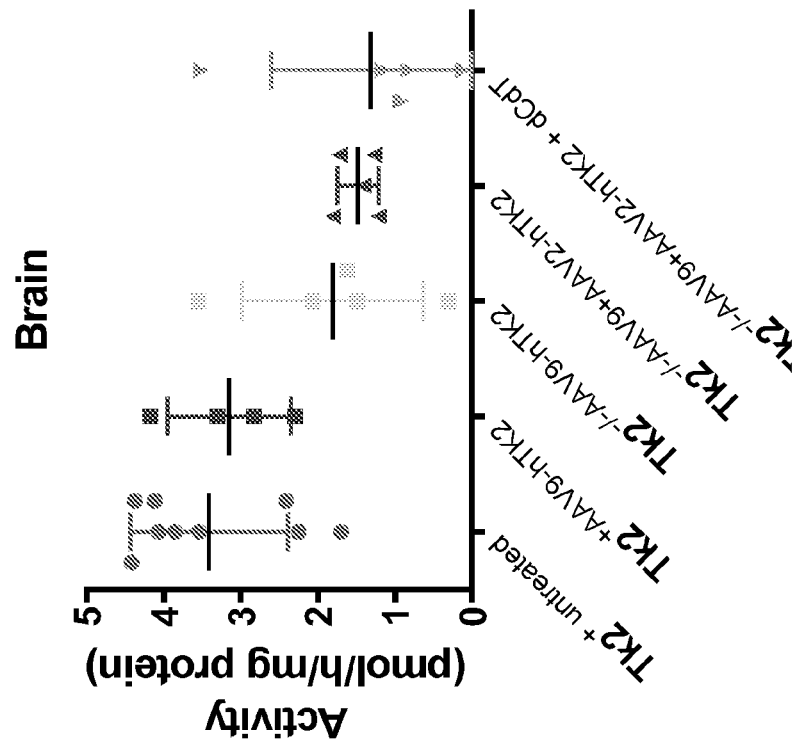
Figure 23:
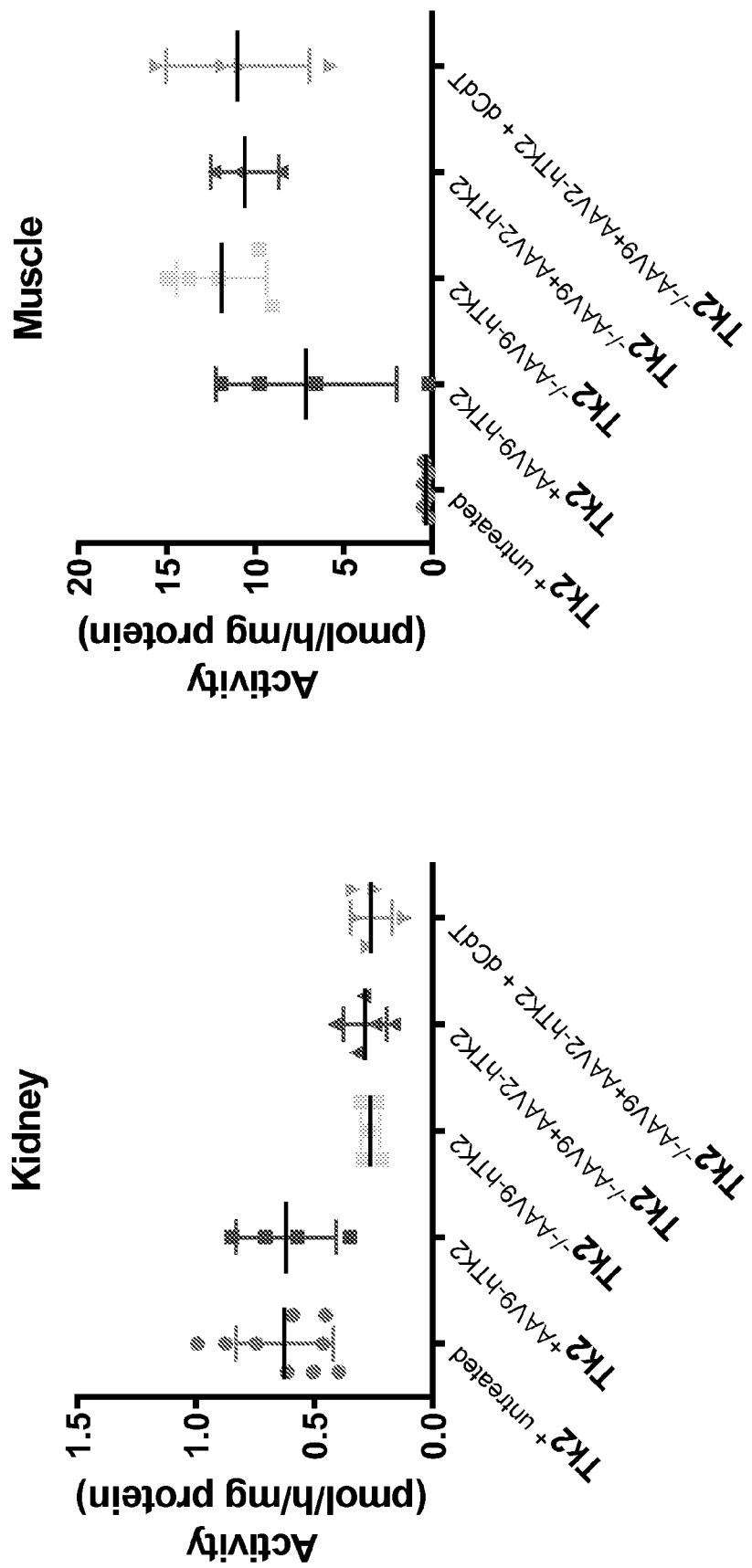

FIG. 23 shows graphs of the activity of TK2 enzyme measured as pmol/min/mg of protein at postnatal day 60 in brain, liver, muscle and kidney tissue of the following mice: untreated Tk2⁺; Tk2⁺ treated with AAV9-hTK2; Tk2⁻/⁻ mice treated with AAV9-hTK2; Tk2⁻/⁻ mice treated with AAV9-hTK2 and AAV2-hTK2; and Tk2⁻/⁻ mice treated with AAV9-hTK2, AAV2-hTK2 and dC+dT.

DETAILED DESCRIPTION OF THE INVENTION

The current invention is based, at least in part, upon the surprising discovery that mitochondrial DNA depletion syndromes, including TK2 deficiency, can be treated, prevented and/or cured via gene therapy by delivery of nucleic acids encoding for a functional protein, such as a functional protein encoded by a nuclear gene. Exemplary nucleic acids that can be used in conjunction with the compositions and methods of the disclosure encode thymidine kinase 2 (TK2), deoxyguanosine kinase (dGK), thymidine phosphorylase (TP), p53 inducible small subunit of ribonucleotide reductase (p53R2), succinyl-CoA ligase ADP-forming subunit beta (SUCLA2), succinyl-CoA ligase GDP-forming subunit alpha (SUCLG1), mitochondrial inner membrane protein MPV17 (MPV17), and/or DNA polymerase subunit gamma (POLG). Such nucleic acids can be delivered by way of one or more viral vectors, such as by way of an adeno-associated virus (AAV), among others described herein. The gene therapy can be administered alone or in combination with pharmacological therapy, such as deoxynucleoside or deoxyribonucleoside monophosphate therapy. The sections that follow describe the compositions and methods of the disclosure in further detail.

Definitions

The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere in the specification, including examples of any terms discussed herein, is illustrative only, and in no way limits the scope and meaning of the invention or any exemplified term. Likewise, the invention is not limited to its preferred embodiments.

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

The terms "mutant mouse", "TK2 knockin mouse" and "Tk2$^{-/-}$" refer to the homozygous Tk2 H126N knock-in mutant (Tk2$^{-/-}$) mouse model, described in Akman, et al. 2008. The terms "wild-type mouse", "WT", and "Tk2+" will be used interchangeably as well. In some cases, mice which are heterozygous for the Tk2 gene ("Tk2$^{+/-}$") are used for comparison and would be expected to behave the same as the wild-type mice. These mice are designated "Het."

The term "subject" as used in this application refers to animals in need of therapeutic or prophylactic treatment. Subjects include mammals, such as canines, felines, rodents, bovine, equines, porcines, ovines, and primates. Thus, the invention can be used in veterinary medicine, e.g., to treat companion animals, farm animals, laboratory animals in zoological parks, and animals in the wild. The invention is particularly desirable for human medical applications.

The term "patient" as used in this application means a human subject. In some embodiments of the present invention, the "patient" is known or suspected of having a disease or disorder characterized by unbalanced nucleotide pools, mitochondrial disease, mitochondrial DNA depletion syndrome, or TK2 deficiency.

The phrase "therapeutically effective amount" is used herein to mean an amount sufficient to cause an improvement in a clinically significant condition in the subject, or delays or minimizes or mitigates one or more symptoms associated with the disease or disorder, or results in a desired beneficial change of physiology in the subject. The terms "treat", "treatment", and the like refer to a means to slow down, relieve, ameliorate or alleviate at least one of the symptoms of the disease or disorder, or reverse the disease or disorder after its onset.

The terms "prevent", "prevention", and the like refer to acting prior to overt disease or disorder onset, to prevent the disease or disorder from developing or minimize the extent of the disease or disorder, or slow its course of development.

The term "cure" and the like means to heal, to make well, or to restore to good health or to allow a time without recurrence of disease so that the risk of recurrence is small.

The term "in need thereof" would be a subject known or suspected of having or being at risk of having a disease or disorder characterized by unbalanced nucleotide pools, mitochondrial disease, mitochondrial DNA depletion syndrome, or TK2 deficiency.

The term "agent" as used herein means a substance that produces or is capable of producing an effect and would include, but is not limited to, chemicals, pharmaceuticals, biologics, small organic molecules, antibodies, nucleic acids, peptides, and proteins.

The terms "deoxynucleoside" or "dN" as used herein means deoxythymidine or dT, deoxycytidine or dC, deoxyadenosine or dA, and deoxyguanosine or dG. The full length name and common abbreviation for each will be used interchangeably. Such deoxynucleosides also include physiologically functional derivatives of the deoxynucleosides.

The term "deoxyribonucleoside monophosphate" as used herein means thymidine-5'-monophosphate or (TMP) or 2'-deoxycytidine-5'-monophosphate (dCMP), deoxyadenosine monophosphate or dAMP, and deoxyguanosine monophosphate or dGMP. The full length name and common abbreviation for each will be used interchangeably.

The term "pharmacological agent" as used herein means deoxynucleosides or dNs and/or deoxyribonucleoside monophosphate or dNMPs, alone or in a composition or a pharmaceutical composition.

The terms "pharmacological therapy" or "pharmacological treatment" as used herein means the administration of dNs and/or dNMPs as disclosed herein and as fully described in co-owned U.S. application Ser. Nos.15/082,207 (hereinafter "the '207 application") and 15/736,092 (hereinafter the '092 application").

As used herein, the term "physiologically functional derivative" refers to a compound (e.g, a drug precursor) that is transformed in vivo to yield a deoxynucleoside. The transformation may occur by various mechanisms (e.g., by metabolic or chemical processes), such as, for example, through hydrolysis in blood. Prodrugs are such derivatives, and a discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

As used herein "an adverse effect" is an unwanted reaction caused by the administration of a drug. In most cases, the administration of the gene and pharmacological therapy caused no adverse effects.

As used herein, the term "carrier" refers to a diluent, adjuvant, excipient, or vehicle with which the therapeutic is administered, and includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art.

The term "pharmaceutically-acceptable" refers to molecular entities and compositions that do not produce an allergic or similar untoward reaction when administered to a host, such as gastric upset, dizziness and the like, when administered to a human, and approved by a regulatory agency of the Federal or a state government or listed in the U.S. Pharmacopeia or other generally recognized pharmacopeia for use in animals, and more particularly in humans.

"Isolated nucleic acid molecule" means a DNA or RNA of genomic, mRNA, cDNA, or synthetic origin or some combination thereof which is not associated with all or a portion of a polynucleotide in which the isolated polynucleotide is found in nature or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences.

The phrase "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

In some aspects, the invention provides isolated adeno-associated vectors (AAVs). As used herein with respect to AAVs, the term "isolated" refers to an AAV that has been isolated from its natural environment (e.g., from a host cell, tissue, or subject) or artificially produced. Isolated AAVs may be produced using recombinant methods. Such AAVs are referred to herein as "recombinant AAVs". Recombinant AAVs (rAAVs) preferably have tissue-specific targeting capabilities, such that a transgene of the rAAV will be delivered specifically to one or more predetermined tissue(s). The AAV capsid is an important element in determining these tissue-specific targeting capabilities.

Methods for obtaining recombinant AAVs having a desired capsid protein have been described (See, for example, U.S. Pat. No. 7,906,111). A number of different AAV capsid proteins have been described, for example, those disclosed in Gao, et al., *J. Virology* 78(12):6381-6388 (June 2004); Gao, et al., *Proc Natl Acad Sci USA* 100(10): 6081-6086 (May 13, 2003); and U.S. Pat. Nos. 7,906,111; 8,999,678. For the desired packaging of the presently described constructs and methods, the AAV9 vector and capsid, or the AAV2 vector and capsid, is preferred. However, it is noted that other suitable AAVs such as rAAVrh.8 and rAAVrh.10, or other similar vectors may be adapted for use in the present invention. Typically the methods involve culturing a host cell which contains a nucleic acid sequence encoding an AAV capsid protein or fragment thereof; a functional rep gene; a recombinant AAV vector composed of AAV inverted terminal repeats (ITRs) and a transgene; and sufficient helper functions to permit packaging of the recombinant AAV vector into the AAV capsid proteins.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters.

The recombinant AAV vector, rep sequences, cap sequences, and helper functions for producing the rAAV may be delivered to the packaging host cell using any appropriate genetic element (vector). The selected genetic element may be delivered by any suitable method, including those described herein. See, e.g., Fisher et al, *J. Virology* 70:520-532 (1993) and U.S. Pat. No. 5,478,745.

In some embodiments, recombinant AAVs may be produced using the triple transfection method (e.g., as described in detail in U.S. Pat. No. 6,001,650). Typically, the recombinant AAVs are produced by transfecting a host cell with a recombinant AAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Non-limiting examples of vectors suitable for use with the present invention include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

As used herein, the terms "AAV1," "AAV2," "AAV3," "AAV4," and the like refer to AAV vectors containing ITRs from AAV1, AAV2, AAV3, or AAV4, respectively, as well as capsid proteins from AAV1, AAV2, AAV3, or AAV4, respectively. The terms "AAV2/1," "AAV2/8," "AAV2/9," and the like refer to pseudotyped AAV vectors containing ITRs from AAV2 and capsid proteins from AAV1, AAV8, or AAV9, respectively.

With respect to transfected host cells, the term "transfection" is used to refer to the uptake of foreign DNA by a cell, and a cell has been "transfected" when exogenous DNA has been introduced inside the cell membrane. A number of transfection techniques are generally known in the art. See, e.g., Graham et al., *Virology* 52:456 (1973), Sambrook et al., *Molecular Cloning, a Laboratory Manual*, Cold Spring Harbor Laboratories, New York (1989), Davis et al., *Basic Methods in Molecular Biology*, Elsevier (1986), and Chu et al., *Gene* 13:197 (1981). Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

With respect to cells, the term "isolated" refers to a cell that has been isolated from its natural environment (e.g., from a tissue or subject). The term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants. As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

The term "vector" includes any genetic element, such as a plasmid, phage, transposon, cosmid, chromosome, artificial chromosome, virus, or virion, which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "operatively linked," "under control," or "under transcriptional control" means that the promoter is in the correct location and orientation in relation to the nucleic acid to control RNA polymerase initiation and expression of the gene.

The term "expression vector" or "expression construct" or "construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or inhibitory RNA from a transcribed gene.

As used herein, the term "TK2" refers to a gene encoding thymidine kinase 2, or the corresponding protein product. The terms "TK2" and "thymidine kinase 2" include wild-type forms of the TK2 gene or protein, as well as variants (e.g., splice variants, truncations, concatemers, and fusion constructs, among others) of wild-type TK2 proteins and nucleic acids encoding the same. Examples of such variants are proteins having at least 70% sequence identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.9% identity, or more) to any of the amino acid sequences of a wild-type TK2 protein (e.g., SEQ ID NO: 1), provided that the TK2 variant retains the function of a wild-type TK2. Additionally, the terms "TK2" and "thymidine kinase 2" may refer to fusion proteins, or nucleic acids encoding the same, in which the TK2 is operably linked to another polypeptide, half-life-modifying agent, or therapeutic agent. The term "TK2" may refer to the protein or the gene encoding this protein, depending upon the context, as will be appreciated by one of skill in the art.

```
Exemplary TK2 amino acid sequence (SEQ ID NO: 1):
MGAFCQRPSSDKEQEKEKKSVICVEGNIASGKTTCLEFFSNATDVEVLTEPVSKWRNVRGHNPLGLMY

HD

ASRWGLTLQTYVQLTMLDRHTRPQVSSVRLMERSIHSARYIFVENLYRSGKMPEVDYVVLSEWFDWIL

RN

MDVSVDLIVYLRTNPETCYQRLKKRCREEEKVIPLEYLEAIHHLHEEWLIKGSLFPMAAPVLVIEADHH

M

ERMLELFEQNRDRILTPENRKHCP

Exemplary TK2 nucleic acid sequence (SEQ ID NO: 2):
GCCAAGTTATGGGTGCGTTCTGCCAGCGTCCTAGCAGTGATAAAGAACAGGAAAAAGAGAAAAAATCAGT

GATCTGTGTCGAGGGCAATATTGCAAGTGGGAAGACGACATGCCTGGAATTCTTCTCCAACGCGACAGAC

GTCGAGGTGTTAACGGAGCCTGTGTCCAAGTGGAGAAATGTCCGTGGCCACAATCCTCTGGGCCTGATGT

ACCACGATGCCTCTCGCTGGGGTCTTACGCTACAGACTTATGTGCAGCTCACCATGCTGGACAGGCATAC

TCGTCCTCAGGTGTCATCTGTACGGTTGATGGAGAGGTCGATTCACAGCGCAAGATACATTTTTGTAGAA

AACCTGTATAGAAGTGGGAAGATGCCAGAAGTGGACTATGTAGTTCTGTCGGAATGGTTTGACTGGATCT

TGAGGAACATGGACGTGTCTGTTGATTTGATAGTTTACCTTCGGACCAATCCTGAGACTTGTTACCAGAG

GTTAAAGAAGAGATGCAGGGAAGAGGAGAAGGTCATTCCGCTGGAATACCTGGAAGCAATTCACCATCTC

CATGAGGAGTGGCTCATCAAAGGCAGCCTTTTCCCCATGGCAGCCCCTGTTCTGGTGATTGAGGCTGACC

ACCACATGGAGAGGATGTTAGAACTCTTTGAACAAAATCGGGATCGAATATTAACTCCAGAGAATCGGAA
```

-continued

```
GCATTGCCCATAGGAGGCAAAAGGTCTATGGCTCATGTCTGAAAAATGCCTGCTGCTGCCAAGTTAGCTA
TTGGGAGCAATCTGGAAAAACTTGCTCCCAGGAGGGCTTTGTGTCTGGCCAGCTTGATTTTCCTAATGGT
CTCATCTCCTTTGCTAGTGTCTTTGTCATGCGTCTCTGGCCCTCGTGGGTAAATGACAAACGGGACCAAT
GGGTTTGCCAAGCCCTTTGCTGTTCGCAGCCTCACATTCCCCCGGTGCCTCTCCCATGGCTTTGTGCTGC
TGAGTCGCTCTCATGAAGCCCTTAGGGAGAGCACCTGTTGTGTGCCTGACACCACGCTGGAGCTGTGTAC
CAATCGTCTCAGCCTTCATTAGGAGGCCGAGGTAGGAGTCTTATATCCCAGGTGAGGAATTTGAAGCTCA
GAAAGGTTGAGGGGCTCCCCAGAGGTCACACAGCCTGTGTGCAGTGGAGCTGGCACCATTCAGACTTTCA
GCCGACTCAGCAACTTTCCCTTGCCCTGGGCTGCCTCCTCCTGAGAGCTGTTCCCCACCGCCCTGCCTCT
TCCGGTTGGAGGCTCTCATGTCTCTTTGGGGAGAGCTGGCAGTGTGCGGAGCTGATAACATTTTCCCAAT
ATTGAGCAGTTCCCAAGGACAGTCAGCATTTCTAGACTTCCACAAAATTATGCTGCATTTGGCTGGAGCC
CGGTGTTCAGTGGTTTCCCTGCCCGAGGTCGCTGCAGCCCCATCTACCACATCTTCATGTGGACATTGAG
ATTCACATGCTGGCTCCTGAAGGGTGCTCAGTCTCCTTGGTGATTAAGGTCCTGCTTGAACTGCTGCCAA
CTCCATGTCAGGGAAGTCGCTTTTGGTGCCTGGCTGGTTTGCCCAGAGCCAAGCTGGGGCAAGGGGCAGC
CAGCCCTGGCTTCCAAGGCTCCCGTACTGTCTGTGTCCTTGTATAAGGAGCTTTGCTCTTGGAATTACTG
AAAGTCTGTGGCCCAAGAGAGAGACACAAGTGGCCTTAAGTCTTTTTGAAGTGTTATTTCATCCAGGGAA
ATGCCTCGAGCCATAGAGCCTGAAATCATCTTTGTTGGCTCAGAAAATACCTTAGCTTCACTCAGCTGGA
CTGCATTGAAGGCGAGGCTGCCCCTTGGATCAAGCAGAAAACAAGAGAAAGAAAGAACGTTCCCTTTGGG
GATAGTCTGGAAAGTTGGGATTTGCAAATAAAGGCTCTGGAAGCATTGCTGGTCCTGAAGCTTTGGAGGT
GGGCAGAGAGAGCTTCAAGAAGACTAGATGCAAACCCTGGAAAGGATTAAGGCTCAACTCTGGAGAAACA
GGCCACAGCCTCTCAGAGCAGCTGTTGGCTGTAAATAGAGGTAGCAAGGCCGCTCCCAGGCCCCTGTGAG
TGTGGGCACCTGTGCATGCAATGCTCCGACTCTGCAGAGGTGCCAAGTGCCCCTGCTGGGCCAGTCCCAG
AGAGTTAGGAAGTCAAGGCCTGCAACTCCTGGTTCTTCCTGTTTGGACCAGTTCTTGTGCCATTGGCAGG
ATGAGAGGCAGCAGCCAGGCGGGAGCTGTGTCTAGCAGCACCTGTAGCCCACGTGCTGCTAATTAGCTGG
AAAACTGGCGAAGGCAGAACCTTTGCTACCAGGAATCTTGACATGTGGGTCTGTCTTTGAGAATTTGTA
AATGAACAGTCCAATATTTCCTCTCGGCTCATTTTGCACATCCATTTTTGGGGAAATGTGATTTCTCTCT
CTTTTTTTTTTTTTTTTTGCCTAAGGCACAATCTCAAGAGGTCCTGAGACCACGTACCCATGATTTTT
TTCTTGCTCTGTGATACCCAATAACTCCTTCACCTAAGCCCTGTTGTTGATTTTGAAGTGCTTCCTAGGC
CAGTGATTTTAGCTTCTGCCAGCTGCTTTTGCCAGTAGATTAACGTGTTTTTATTTTTCAAACTCCGTGT
TTCCTAACGTGGAGTGTATGGGTCTAAGAGAGCCTGCTGTCCTCCCTGCCTTCCACCTTGGAGAGGAGGC
TGGACGCATCAGCAGTGGCCAGGGCAGGTCGCAAAATCTCCCAGCCTAGAGACCACACCTGAAACGGCTG
AAGCCAGCTTGCACAAGGGCTGCTGTCCCTCTGCGGCAGGCAGAGCTGGTGGGGCAGGGGTCACAGAGC
AGTCATAGACACCATGGACCAGGGCAGGAGAAGGGCAGATGGCACATGGGCACAACAGGGCCTTGTCCTT
AGAGCACTGGGGGGTCATGGCTGGAGGGGCATGGCAGGGGCTGGCATCCCTGTAGAGCCAGAGGGGCCA
CCCAGGGCAGTGACATTCCAGATATGTTGGGCTCACCTCATCCTTGCTGTGAGACTGGAGTTCCATGGGG
ACATGAAGTCAGTACACCGCAGAGCTGCTCAGCTGCTCTACCTCTCGCTGACTTTTTGTTGCACATATA
CATTTTCTTTCAATTAGCATTTATTTCAGCTTTTATTTAAGCTTTTTGACAGTACATGTAAAATATATGA
TTATAACCATTTAAAAATACCTTATGTACCTGGTTTTTTTTGGAAACTAGATAGAAATATATTTATCTTT
TACATAAAAGAAGTGTGTAGTGGGGTGGTCCAGGGCTTTGTGGTGGCTTAGTGGCCATCGGGGTCCCAGG
CTCTTCCCACCTTTCTCTTTTGGGTCCACCTCTTGGCTCCTGGCTTCCTTCCTCTGGGGCCTGACTGTCC
AGGATGGCAGCTGGAGCTCCTGCTCTGGGCACGGTTGGCATCAGAGCCCACTGCTCCCCATCCACTCTTT
AATCCAGATGCTGGTAATGTCCCTTTCCAAGGCATAACTAAGATAAGCTGGAAGGTTCTTACGAGGCTTT
```

```
GCTAGAGGCCCTGGGAGGTGGGGGGAAAGGCAAGAGGGCAGTGCCCACCCATAGACCGGGTCACATGACC

TGGCATCAGCGCCGTGGGGTCCTTTGGGCTTCACCTCCCTCTCCCCTCTGCCCCCACGTCATCCCACCCT

CATCCTCACCCTCACCATTCCCATCCCGTACCGTAATGTCCCTTGCAAGGCCTAACTCTGTGAGGAATGA

AACCACCTCATCCTTGTTCCAATAACATGAGTGACCGAATTTACAAACGAGTGAATGTGGACCTCTGGAA

ACATTACCCAGCTTGTTTTTACTTTTCACTTTCTCTTTCTGCCCCTTTCATTTCCGTAGGAGCCCTTTAC

CTAGATGAGAAGTGTCCCCCCGCCTGGGGAATATATCAGTCAGAACAATCTTCCTGCAGACATGCACCAT

TAGACCCGAGTGACGGTGGTGCCATTTAAACCTCAGAGCAGGTAAAAGGTGGTCCTGAAACCTGTCTACC

CACAGGGTGCTATGGAATCTGAATCACTTCTTTTTTCCTAGAGCCCTGGGGTGGGGAGCTCCCTCAAGTG

TTCACATGTGTGTGGAATGAGGAACACCCATCTCCTTGGCCCTCTCCACCCTGAAGAGTTAGTTATTAAA

ATAATTGGCAAGCTCTTGCAAATGTCAGTCATCCATTGTTCAGAATGGAATAGCAATAATACATCCCTGG

CTGCCCTGGGCTTGGCCAGGATTACTCACTGAAGGCCTCAGGGTTACTGGCACACACTTTCTTTTCCTAA

TAATCCCATCCCCTCAGCTTTCCTAAGGCTAGAGTGAATTTCGTGTTCCTTTAGTTTACATAAGATGGTG

AACTTGGCAAAAGCTATCATTAAACAGAAGCTAAGAGAAAGCCTATGTCGTGGAATCCAGAATGGGTATT

GCCATTCACTGCTGTCCACAGAAGCTGTCTTGAATTTCTTTCTGTGTCTTTTCTTTTTTTTCTTTAAGA

CTGTTGTTTACCAGACTGGGCTCTGTGGAACACAGGTGTCCTGGGAGATGGTTAATCATTACAAAATATT

GGTAACAATCTAAAGATGCATACATAAGAGAGTGGTCAAATAAACCATTTTCCATTCA
```

As used herein, the term "dGK" refers to a gene encoding deoxyguanosine kinase, or the corresponding protein product. The terms "dGK" and "deoxyguanosine kinase" include wild-type forms of the dGK gene or protein, as well as variants (e.g., splice variants, truncations, concatemers, and fusion constructs, among others) of wild-type dGK proteins and nucleic acids encoding the same. Examples of such variants are proteins having at least 70% sequence identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.9% identity, or more) to any of the amino acid sequences of a wild-type dGK protein (e.g., SEQ ID NO: 3), provided that the dGK variant retains the function of a wild-type dGK. Additionally, the terms "dGK" and "deoxyguanosine kinase" may refer to fusion proteins, or nucleic acids encoding the same, in which the dGK is operably linked to another polypeptide, half-life-modifying agent, or therapeutic agent. The term "dGK" may refer to the protein or the gene encoding this protein, depending upon the context, as will be appreciated by one of skill in the art.

```
Exemplary dGK amino acid sequence (SEQ ID NO: 3):
MAAGRLFLSRLRAPFSSMAKSPLEGVSSSRGLHAGRGPRRLSIEGNIAVG

KSTFVKLLTKTYPEWHVATEPVATWQNIQAAGTQKACTAQSLGNLLDMMY

REPARWSYTFQTFSFLSRLKVQLEPFPEKLLQARKPVQIFERLHFEALMN

IPVLVLDVNDDFSEEVTKQEDLMREVNTFVKNL

Exemplary dGK nucleic acid sequence (SEQ ID NO:
4):
AACGGTGCGCTGGAGCGAGTGAGCAGCGATACCTAGGGCGGAAGTGCTCT

CGGCGGAAGTGATCGCTGTGTGAATCGTGGGTGGGATGGCCGCGGGCCGC

CTCTTTCTAAGTCGGCTTCGAGCACCCTTCAGTTCCATGGCCAAGAGCCC

ACTCGAGGGCGTTTCCTCCTCCAGAGGCCTGCACGCGGGGCGCGGGCCCC

GAAGGCTCTCCATCGAAGGCAACATTGCTGTGGGAAAGTCCACGTTTGTG

AAGTTACTCACGAAAACTTACCCAGAATGGCACGTAGCTACAGAACCTGT

AGCAACATGGCAGAATATCCAGGCTGCTGGCACCCAAAAAGCCTGCACTG

CCCAAAGTCTTGGAAACTTGCTGGATATGATGTACCGGGAGCCAGCACGA

TGGTCCTACACATTCCAGACATTTTCCTTTTTGAGCCGCCTGAAAGTACA

GCTGGAGCCCTTCCCTGAGAAACTCTTACAGGCCAGGAAGCCAGTACAGA

TCTTTGAGAGGCTCCACTTTGAGGCTCTGATGAACATTCCAGTGCTGGTG

TTGGATGTCAATGATGATTTTTCTGAGGAAGTAACCAAACAAGAAGACCT

CATGAGAGAGGTAAACACCTTTGTAAAGAATCTGTAACCAATACCATGAA

GTTCAGGCTGTGATCTGGGCTCCCTGACTTTCTGAAGCTAGAAAAATGTT

GTGTCTCCCAACCACCTTTCCATCCCCAGCCCCTCTCATCCCTGGAGCAC

TCTGCCGCTCAAGAGCTGGTTTGTTAATTATTGTTAGACTTTGCCATTGT

TTTCTTTTGTACCTGAAGCATTTTGAAAATAAAGTTTACTTAAGTTATGC

TTGTTTTTCTAAAAAAAAAAAAAAAAAAA
```

As used herein, the term "p53R2" refers to a gene encoding p53 inducible subunit of ribonucleotide reductase, or the corresponding protein product. The terms "p53R2" and "p53 inducible subunit of ribonucleotide reductase" include wild-type forms of the p53R2 gene or protein, as well as variants (e.g., splice variants, truncations, concatemers, and fusion constructs, among others) of wild-type p53R2 proteins and nucleic acids encoding the same.

Examples of such variants are proteins having at least 70% sequence identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.9% identity, or more) to any of the amino acid sequences of a wild-type p53R2 protein (e.g., SEQ ID NO: 5), provided that the p53R2 variant retains the function of a wild-type p53R2. Additionally, the terms "p53R2" and "p53 inducible subunit of ribonucleotide reductase" may refer to fusion proteins, or nucleic acids encoding the same, in which the p53R2 is operably linked to another polypeptide, half-life-modifying agent, or therapeutic agent. The term "p53R2" may refer to the protein or the gene encoding this protein, depending upon the context, as will be appreciated by one of skill in the art.

```
Exemplary p53R2 amino acid sequence (SEQ ID NO: 5):
MLLLRLPPHRSHASPLDCKLQDRCRKCYSPRSGQACPPALAAAWLRRCERRGGRPRGGRRKELTLGLRPA

RCSAPGPAKDDAWRPQAGRSSSDTNESEIKSNEEPLLRKSSRRFVIFPIQYPDIWKMYKQAQASFWTAEE

VDLSKDLPHWNKLKADEKYFISHILAFFAASDGIVNENLVERFSQEVQVPEARCFYGFQILIENVHSEMY

SLLIDTYIRDPKKREFLFNAIETMPYVKKKADWALRWIADRKSTFGERVVAFAAVEGVFFSGSFAAIFWL

KKRGLMPGLTFSNELISRDEGLHCDFACLMFQYLVNKPSEERVREIIVDAVKIEQEFLTEALPVGLIGMN

CILMKQYIEFVADRLLVELGFSKVFQAENPFDFMENISLEGKTNFFEKRVSEYQRFAVNAETTDNVFTLD

ADF

Exemplary p53R2 nucleic acid sequence (SEQ ID NO: 6):
ATGAGGTAAATGTTGCTGTTGCGTCTTCCCCCTCACCGCAGTCACGCCAGCCCGTTAGATTGCAAGTTGC

AGGACCGCTGTAGGAAATGTTATTCGCCGCGGTCAGGACAGGCCTGTCCGCCCGCCCTCGCCGCAGCCTG

GCTTCGTCGTTGCGAGCGCCGGGGAGGCCGTCCCCGGGGAGGGCGGAGGAAGGAGCTGACTTTGGGTTTG

CGTCCCGCTCGCTGCTCTGCCCCGGGGCCAGCCAAGGACGACGCTTGGAGGCCTCAGGCCGGGAGATCAT

CTTCAGACACCAACGAAAGTGAAATAAAGTCAAATGAAGAGCCACTCCTAAGAAAGAGTTCTCGCCGGTT

TGTCATCTTTCCAATCCAGTACCCTGATATTTGGAAAATGTATAAACAGGCACAGGCTTCCTTCTGGACA

GCAGAAGAGGTCGACTTATCAAAGGATCTCCCTCACTGGAACAAGCTTAAAGCAGATGAGAAGTACTTCA

TCTCTCACATCTTAGCCTTTTTTGCAGCCAGTGATGGAATTGTAAATGAAAATTTGGTGGAGCGCTTTAG

TCAGGAGGTGCAGGTTCCAGAGGCTCGCTGTTTCTATGGCTTTCAAATTCTCATCGAGAATGTTCACTCA

GAGATGTACAGTTTGCTGATAGACACTTACATCAGAGATCCCAAGAAAAGGGAATTTTTATTTAATGCAA

TTGAAACCATGCCCTATGTTAAGAAAAAAGCAGATTGGGCCTTGCGATGGATAGCAGATAGAAAATCTAC

TTTTGGGGAAAGAGTGGTGGCCTTTGCTGCTGTAGAAGGAGTTTTCTTCTCAGGATCTTTTGCTGCTATA

TTCTGGCTAAAGAAGAGAGGTCTTATGCCAGGACTCACTTTTTCCAATGAACTCATCAGCAGAGATGAAG

GACTTCACTGTGACTTTGCTTGCCTGATGTTCCAATACTTAGTAAATAAGCCTTCAGAAGAAAGGGTCAG

GGAGATCATTGTTGATGCTGTCAAAATTGAGCAGGAGTTTTTAACAGAAGCCTTGCCAGTTGGCCTCATT

GGAATGAATTGCATTTTGATGAAACAGTACATTGAGTTTGTAGCTGACAGATTACTTGTGGAACTTGGAT

TCTCAAAGGTTTTTCAGGCAGAAAATCCTTTTGATTTTATGGAAAACATTTCTTTAGAAGGAAAAACAAA

TTTCTTTGAGAAACGAGTTTCAGAGTATCAGCGTTTTGCAGTTATGGCAGAAACCACAGATAACGTCTTC

ACCTTGGATGCAGATTTTTAAAAAACCTCTCGTTTTAAAACTCTATAAACTTGTCATTGGTAAATAGTAG

TCTATTTTCCTCTGCTTAAAAAAAATTTTAAGTATATCCTTTAAAGGACTGGGGGTTTGCTCAAAAGGAA

ATCCAAAACCTATTCTAAACAATTTGCATTTATATAATTTTCCTGTTTAACAACAAGAGTGTGACCTAAA

TGCTTTTGTCTTGTCACTGAAATAAAAGATGGCATTATGTGGTTAAGAGCATGGGGCGAGGGGTCAGACA

TGAGTCTAAGGTTCTGCCCTTACTCCAGTGTGTGACCCTTGGCAAGTCAGTTAATCTTGGTAAACCTCGG

TGTACTTATCTTTAAAATGGGAGTAATAGTAGGTCCTAAATTCATAGAGTGGATATTAGGATTAGGATGC

AAAAATAAATGCTTAACCAACACTACTACTGTTAGCACCACTACTAATTATCATTCATTGATAATATTAA

TTGCAATGATGTTGTAATAAAATACTCTCATTTCCTTAAAATAATTGTGATTCTAGGTCCTAGGATCTAG

AATTAGATCTTTGTATTTTTAATGCTTAGGGGAAGAATATAAGTATCTCCTTAAAAAGAACATAATTCTC

ATTCACGCAAGAATAAGTTCTTTGAATTCCTTAGTATGTAGTGAAGAAAATTTAGTTGTTAGTTGCTTTG

GGAAGCCTACTTATGGAGTGGAAACCAGGAGGTTATCATGGTAGTTGACCTTATAAGAAAAATGATTCTT
```

-continued
CTTCAGAAATTAAAAACATAACTATTGCCAGATTTAGCTCTGGAATGTTTAGAATCAGGCTAGAATAGCA

TTTTCCAAAGAATATTCTAAGAGCTATTAGCTCCTCTAGATATTTTTTTGGGGGAAAAAGGGGATTCTGT

GGTCAGATGAGTTTGGGAAATGCTGAACACTTCATTCTTCTTTAGCAAGTACAGTCAGTACATCAAAGAC

TGAGCAGTTCAGTGGTACATAAATTTATCTCGCCCTGCATATTCCCAACATACTTAACACAGATGTTTTT

TACCTGTTAACATCTCACCCAGCTAGTGTTCCTCAGAACAAAGATTGGAAAAAGCTGGCCGAGAACCATT

TATACATAGAGGAAGGGCTTATGGACTGAGAAAGGGAGAACATGGTAGGGATTATTGAATCATTTCAAAT

TTATACCAGCCTGAATAGTGTACCAGCAATTGACTTAGGCTGTGTTTCTTTATGGTTTTAAAACTCTTGA

GCTGTTATAAGAGATAGTTCTTTTAATGTGACTATGCAACATGATAGCCAATGGTGAGGGAAAAGGAGGT

TTCTCTAGAAGAGTCTGATGAAAGGCCGGGAACCAAGGTTTTTGAGAAGTCTGCCCCTATTTATTTTTAG

TAAGTATCAAGAGGTAGCCTGAGCCTAGTTAGAGTTAGACCTGTCTTTGGATGAAGAAGTCTTAATACTG

AAATACTGAATTTTTAATACATTATTATTTGGTATTCTGTATACCCCTTCAAGCAGTTGTTTCCCATTCC

CAACAAACTGTACTTTATACAATTCTGGATGCTAAAACTTAGAGATTTTCTCTTTGCATAAATTTTGGCT

CCATTCTTTCCATAACAATCTAATCAAACTGGGAGTTCTCAAGTGAATGCAAAAGGAGCAGGCCATAAC

TTTATTTGTTAGATACACTGTCAGAAACTTGAGATCTTTTGGCCTATGATAATACCATTAATTTTTGCAT

TGCTTCAGTTTGCCAAGTGTTTTTACATCATCTCATTTGATCTCAAAACAGCTTGACAGAGCAACTGTTA

TTGAAATATTACAGATGGAAAGAATGAGGCTCAGGGAAGTTAAATGACTTGGCCAAGATCTGCTCATCGT

CACTGTCTGTACAGTATTTTTTTTTAGAGGTTGTAATGTCTCAGATTTAGTCCTTTACCATCTATGTTGA

TTTGCTTTTGTCTATTTCCTCATTAATTGAATATACTTTAAATATATATATTAAAGTATCAAATATAGA

GAGACATTTGAACTGTATTCAGGTAATATGTTTAAAGATATTTATATATTGCCATACAAAAACTTAACAT

TTAAAACTGATAATATCTGTAATGACATCAGAATGAAAGAAAAAAAATTGTACAGTGTATATTCCTTTGT

TTTGAATCCAAATCTTTTTCATAGGTAATGACAGATGCCTTAATGTGAAGCTTATTTATAATAGCAATAA

ACCTAACTGGATTTGGATGAAGAAGTCTTAATACTGACATACTGGATTTTTAATGCACTGGTTTGTTATT

TGGTATTCTATCTCTTTTTCCAGGCCTCCAGGTTGCACATTTATTTATTATGTTCAATACTTTGGTTCTT

AGTTCTTAAAGAATCAAGAAGTTGTGTAATCTTTTAAAAATATTATCTTGCAGATAAAGAAAAAAATTAA

GAGTGTGTTTACAACTGTTTTCTCTTTTTTACAGTACATGTATTTAAATCATTGCTATAATAAAGTTAAG

TTCATTAGGAATATAAAAACTTGCAGTTCTATGATAGATTGCATTTATTAAAAATGTTTCATTGTATCAC

ATAGAAATATGGCCAGGAAGGACTTGAGAAGACAGTTTGATCCATTGCTTTTAGACAGGACTGGGTTTTG

CTGTCCAATTATATACAATAATAGTTTTTCTTACAACTAAGCTGGCCCCAGCCTTGTCTTGATATTAATA

CATGAAATTTTTATAATTGTCTCATTGTCTCATTTAGAAACATCCATATTTTTCTGCTTTTTCTATTGCC

ATTTTTTATTTGTGCATGAATTGATTATTGAGAAAATGTAGCAGTTTGCATATTTAAAAATTAATCATTT

TGCATTTTACATTTAAATATGCTAACATCACTGTCATAGAATTCCCAAATTTCATTTGTAGATACTGAAC

TAAGGGCTAATGTCAGGAGCTGATTTTTAATGATAAAGCTGCAGATGGGCTAAATAAAAGCCAAATTAAT

CCTACAATCAGGTATTATGTTTTTAAACCAAGTTGAGTGAATTGGTAGTGGACTTGGGAAATCTTCCCCA

GCAGAATCTGGATGAATGGCACAGAATTGAAATCTCTTTGTTTCCCACCATTTCCCTTTAAGTGCTCTGC

TCCTTTGTAAAAAGTTAAAGATTTGAAAGAGAATCTCATATTCCCGAGGCATTAGGAAGAAAGGATTTAA

TCCCTTCAATTTGGGGCTTAATCTTGTTTAAAAAAATGTAAGTGAAGATGGAAGGCTGGAGAGAATGATT

GCTTTTTGTACAGTTAAATAAGGTCACAATATTCTTACATACTTTGTTTTACAACTGTGTTTTCATTTTT

TCAAATGTCTGGCCATTTAGCAAAGTTATTTACTATTTACTGTGTACATAGAAAGCTTTATTATGTGTGG

```
-continued
TGTATCTAAATTTTTTTTGCTGAAATACATTATGGTCAATCAAGCCAAGCCTGCATGTACAGAATTTGTT

TTTTTTTCAAATAAATTAGTTGTTTTCTTATTTTTTTGGCTTAGTATGTTGAAATAAACTATGGTATCTT

CATCATTTTGTACATTTCCTTTTTGAGGAAGGTTTCTTTATAAGTGCAAGGGCTACCCTAATAAAGGAAT

GTATATACTTACT
```

As used herein, the term "TP" refers to a gene encoding thymidine phosphorylase, or the corresponding protein product. The terms "TP" and "thymidine phosphorylase" include wild-type forms of the TP gene or protein, as well as variants (e.g., splice variants, truncations, concatemers, and fusion constructs, among others) of wild-type TP proteins and nucleic acids encoding the same. Examples of such variants are proteins having at least 70% sequence identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.9% identity, or more) to any of the amino acid sequences of a wild-type TP protein (e.g., SEQ ID NO: 7), provided that the TP variant retains the function of a wild-type TP. Additionally, the terms "TP" and "thymidine phosphorylase" may refer to fusion proteins, or nucleic acids encoding the same, in which the TP is operably linked to another polypeptide, half-life-modifying agent, or therapeutic agent. The term "TP" may refer to the protein or the gene encoding this protein, depending upon the context, as will be appreciated by one of skill in the art.

```
Exemplary TP amino acid sequence (SEQ ID NO: 7):
MAALMTPGTGAPPAPGDFSGEGSQGLPDPSPEPKQLPELIRMKRDGGRLS

EADIRGFVAAVVNGSAQGAQIGAMLMAIRLRGMDLEETSVLTQALAQSGQ

QLEWPEAWRQQLVDKHSTGGVGDKVSLVLAPALAACGCKVPMISGRGLGH

TGGTLDKLESIPGFNVIQSPEQMQVLLDQAGCCIVGQSEQLVPADGILYA

ARDVTATVDSLPLITASILSKKLVEGLSALVVDVKFGGAAVFPNQEQARE

LAKTLVGVGASLGLRVAAALTAMDKPLGRCVGHALEVEEALLCMDGAGPP

DLRDLVTTLGGALLWLSGHAGTQAQGAARVAAALDDGSALGRFERMLAAQ

GVDPGLARALCSGSPAERRQLLPRAREQEELLAPADGTVELVRALPLALV

LHELGAGRSRAGEPLRLGVGAELLVDVGQRLRRGTPWLRVHRDGPALSGP

QSRALQEALVLSDRAPFAAPSPFAELVLPPQQ

Exemplary TP nucleic acid sequence (SEQ ID NO: 8):
CGACTGCCGAGCTCCGCCCTCCAGGCGGCCCCACCCGCCTGCCGTCCTGG

GGCGCCGCCGCCCCGCCGCCGGCAGTGGACCGCTGTGCGCGAACCCTGAA

CCCTACGGTCCCGACCCGCGGGCGAGGCCGGGTACCTGGGCTGGGATCCG

GAGCAAGCGGGCGAGGGCAGCGCCCTAAGCAGGCATCCCCGCAGGCCCGG

AGCGATGGCAGCCTTGATGACCCCGGGAACCGGGGCCCCACCCGCGCCTG

GTGACTTCTCCGGGGAAGGGAGCCAGGGACTTCCCGACCCTTCGCCAGAG

CCCAAGCAGCTCCCGGAGCTGATCCGCATGAAGCGAGACGGAGGCCGCCT

GAGCGAAGCGGACATCAGGGGCTTCGTGGCCGCTGTGGTGAATGGGAGCG

CGCAGGGCGCACAGATCGGGGCCATGCTGATGGCCATCCGACTTCGGGGC

ATGGATCTGGAGGAGACCTCGGTGCTGACCCAGGCCCTGGCTCAGTCGGG

ACAGCAGCTGGAGTGGCCAGAGGCCTGGCGCCAGCAGCTTGTGGACAAGC

ATTCCACAGGGGGTGTGGGTGACAAGGTCAGCCTGGTCCTCGCACCTGCC

CTGGCGGCATGTGGCTGCAAGGTGCCAATGATCAGCGGACGTGGTCTGGG

GCACACAGGAGGCACCTTGGATAAGCTGGAGTCTATTCCTGGATTCAATG

TCATCCAGAGCCCAGAGCAGATGCAAGTGCTGCTGGACCAGGCGGGCTGC

TGTATCGTGGGTCAGAGTGAGCAGCTGGTTCCTGCGGACGGAATCCTATA

TGCAGCCAGAGATGTGACAGCCACCGTGGACAGCCTGCCACTCATCACAG

CCTCCATTCTCAGTAAGAAACTCGTGGAGGGGCTGTCCGCTCTGGTGGTG

GACGTTAAGTTCGGAGGGGCCGCCGTCTTCCCCAACCAGGAGCAGGCCCG

GGAGCTGGCAAAGACGCTGGTTGGCGTGGGAGCCAGCCTAGGGCTTCGGG

TCGCGGCAGCGCTGACCGCCATGGACAAGCCCCTGGGTCGCTGCGTGGGC

CACGCCCTGGAGGTGGAGGAGGCGCTGCTCTGCATGGACGGCGCAGGCCC

GCCAGACTTAAGGGACCTGGTCACCACGCTCGGGGGCGCCCTGCTCTGGC

TCAGCGGACACGCGGGGACTCAGGCCCAGGGCGCTGCCCGGGTGGCCGCG

GCGCTGGACGACGGCTCGGCCCTTGGCCGCTTCGAGCGGATGCTGGCGGC

GCAGGGCGTGGATCCCGGTCTGGCCCGAGCCCTGTGCTCGGGAAGTCCCG

CAGAACGCCGGCAGCTGCTGCCTCGCGCCCGGGAGCAGGAGGAGCTGCTG

GCGCCCGCAGATGGCACCGTGGAGCTGGTCCGGGCGCTGCCGCTGGCGCT

GGTGCTGCACGAGCTCGGGGCCGGGCGCAGCCGCGCTGGGGAGCCGCTCC

GCCTGGGGGTGGGCGCAGAGCTGCTGGTCGACGTGGGTCAGAGGCTGCGC

CGTGGGACCCCCTGGCTCCGCGTGCACCGGGACGGCCCCGCGCTCAGCGG

CCCGCAGAGCCGCGCCCTGCAGGAGGCGCTCGTACTCTCCGACCGCGCGC

CATTCGCCGCCCCCTCGCCCTTCGCAGAGCTCGTTCTGCCGCCGCAGCAA

TAAAGCTCCTTTGCCGCGAAAAAAAAAAA
```

As used herein, the term "SUCLA2" refers to a gene encoding succinate-CoA ligase ADP-forming beta subunit, or the corresponding protein product. The terms "SUCLA2" and "succinate-CoA ligase ADP-forming beta subunit" include wild-type forms of the SUCLA2 gene or protein, as well as variants (e.g., splice variants, truncations, concatemers, and fusion constructs, among others) of wild-type SUCLA2 proteins and nucleic acids encoding the same. Examples of such variants are proteins having at least 70% sequence identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.9% identity, or more) to any of the amino acid sequences of a wild-type SUCLA2 protein (e.g., SEQ ID NO: 9), provided that the SUCLA2 variant retains the function of a wild-type SUCLA2. Additionally, the terms "SUCLA2" and "succinate-CoA ligase ADP-forming beta subunit" may refer to fusion proteins, or nucleic acids encoding the same, in which the SUCLA2 is operably linked to another polypeptide, half-life-modifying agent, or therapeutic agent. The term "SUCLA2" may refer to the protein or the gene encoding this protein, depending upon the context, as will be appreciated by one of skill in the art.

Exemplary SUCLA2 amino acid sequence (SEQ ID NO: 9):
MAASMFYGRLVAVATLRNHRPRTAQRAAAQVLGSSGLFNNHGLQVQQQQQ
RNLSLHEYMSMELLQEAGVSVPKGYVAKSPDEAYAIAKKLGSKDVVIKAQ
VLAGGRGKGTFESGLKGGVKIVFSPEEAKAVSSQMIGKKLFTKQTGEKGR
ICNQVLVCERKYPRREYYFAITMERSFQGPVLIGSSHGGVNIEDVAAESP
EAIIKEPIDIEEGIKKEQALQLAQKMGFPPNIVESAAENMVKLYSLFLKY
DATMIEINPMVEDSDGAVLCMDAKINFDSNSAYRQKKIFDLQDWTQEDER
DKDAAKANLNYIGLDGNIGCLVNGAGLAMATMDIIKLHGGTPANFLDVGG
GATVHQVTEAFKLITSDKKVLAILVNIFGGIMRCDVIAQGIVMAVKDLEI
KIPVVVRLQGTRVDDAKALIADSGLKILACDDLDEAARMVVKLSEIVTLA
KQAHVDVKFQLPI Exemplary SUCLA2 nucleic acid sequence (SEQ ID NO: 10):
CCGCCTGTCGCCTGTGCGCCTGCGCGCGGCGCCGAGGGGACGGGGTCCGA
CTCAGAAATGGCGGCCTCCATGTTCTACGGCAGGCTAGTGGCCGTGGCCA
CCCTTCGGAACCACCGGCCTCGGACGGCCCAGCGGGCTGCTGCTCAGGTT
CTGGGAAGTTCTGGATTGTTTAATAACCATGGACTCCAAGTACAGCAGCA
ACAGCAAAGGAATCTCTCACTACATGAATACATGAGTATGGAATTATTGC
AAGAAGCTGGTGTCTCCGTTCCCAAAGGATATGTGGCAAAGTCACCAGAT
GAAGCTTATGCAATTGCCAAAAAATTAGGTTCAAAAGATGTCGTGATAAA
GGCACAGGTTTTAGCTGGTGGTAGAGGAAAAGGAACATTTGAAAGTGGCC
TCAAAGGAGGAGTGAAGATAGTTTTCTCTCCAGAAGAAGCAAAAGCTGTT
TCTTCACAAATGATTGGGAAAAAATTGTTTACCAAGCAAACGGGAGAAAA
GGGCAGAATATGCAATCAAGTATTGGTCTGTGAGCGAAAATATCCCAGGA
GAGAATACTACTTTGCAATAACAATGGAAAGGTCATTTCAAGGTCCTGTA
TTAATAGGAAGTTCACATGGTGGTGTCAACATTGAAGATGTTGCTGCTGA
GTCTCCTGAAGCAATAATTAAAGAACCTATTGATATTGAAGAAGGCATCA
AAAAGGAACAAGCTCTCCAGCTTGCACAGAAGATGGGATTTCCACCTAAT
ATTGTGGAATCAGCAGCAGAAAACATGGTCAAGCTTTACAGCCTTTTTCT
GAAATACGATGCAACCATGATAGAAATAAATCCAATGGTGGAAGATTCAG
ATGGAGCTGTATTGTGTATGGATGCAAAGATCAATTTTGACTCTAATTCA
GCCTATCGCCAAAAGAAAATCTTTGATCTACAGGACTGGACCCAGGAAGA
TGAAAGGGACAAAGATGCTGCTAAGGCAAATCTCAACTACATTGGCCTCG
ATGGAAATATAGGCTGCCTAGTAAATGGTGCTGGTTTGGCTATGGCCACA
ATGGATATAATAAAACTTCATGGAGGGACTCCAGCCAACTTCCTTGATGT
TGGTGGTGGTGCTACAGTCCATCAAGTAACAGAAGCATTTAAGCTTATCA
CTTCAGATAAAAAGGTACTGGCTATTCTGGTCAACATTTTTGGAGGAATC
ATGCGCTGTGATGTTATTGCACAGGGTATAGTCATGGCAGTAAAAGACTT
GGAAATTAAAATACCTGTTGTGGTACGGTTACAAGGTACACGAGTCGATG ATGCTAAGGCACTGATAGCGGACAGTGGACTTAAAATACTTGCTTGTGAT
GACTTGGATGAAGCTGCTAGAATGGTTGTAAAGCTCTCTGAAATAGTGAC
CTTAGCGAAGCAAGCACATGTGGATGTGAAATTTCAGTTGCCAATATGAT
CTGAAAACCCAGTGGATGGCTGAAGGTGTTAAATGTGCTATAATCATTAA
GAATACTGTGTTCTGTGTTATTGTTCTTTTTCTTTTTAGTGTGTGGAGAT
TGTAATTGCCATCTAGGCACACAAACATTTAAAAGGATTTGGACTGCATT
TAATTGTACCATTCAGAATGGACTGTTTGTACGAAGCATGTATAATGCAG
TTATCTTCTTTCTTTTGTCGCAGCCAGTCTTTTTTGCTTCTCCTACAAAA
CGTAACTTGCAATTTGCCAGTTTATTATTGTTGGATACAAAGTTCTTCAT
TGATAAGAGTCCTATAAATAAGATAAATACGAAGATAAAGCTTTATTCTT
TAGTGTTAAAATACAGTATATCTAATAACTAGCCTCATTAGTAGAGCAGT
ATATTAAAACAATGTTTTATGTAAAAAGTGTTTATCTTCAGCACCAAATA
CATGATAAATGTATCAATCACTATTTATAAACAGAGCTTTCAAACACTCC
TCAGAATATTCTTCTAAGTATTTTGATGAAGTAACTTTGTAATTATTTGA
ACATTGTTTTAATCATTAGGAAACACTGATTAACTGCAAGTCTTCATGAT
TCTGTCATATTAAGAAACACCTGTAGGTTTGCTTCAAATAAAGGCATATA
TACCAAGGACTTACAGACAAAATTAAGAATGTCAATTTAAGTTAATAAAA
ATCTCCCAATATGAAAAAAAAAAAAAAAAAA As used herein, the term "SUCLG1" refers to a gene encoding succinate-CoA ligase ADP-forming alpha subunit, or the corresponding protein product. The terms "SUCLG1" and "succinate-CoA ligase ADP-forming alpha subunit" include wild-type forms of the SUCLG1 gene or protein, as well as variants (e.g., splice variants, truncations, concatemers, and fusion constructs, among others) of wild-type SUCLG1 proteins and nucleic acids encoding the same. Examples of such variants are proteins having at least 70% sequence identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.9% identity, or more) to any of the amino acid sequences of a wild-type SUCLG1 protein (e.g., SEQ ID NO: 11), provided that the SUCLG1 variant retains the function of a wild-type SUCLG1. Additionally, the terms "SUCLG1" and "succinate-CoA ligase ADP-forming alpha subunit" may refer to fusion proteins, or nucleic acids encoding the same, in which the SUCLG1 is operably linked to another polypeptide, half-life-modifying agent, or therapeutic agent. The term "SUCLG1" may refer to the protein or the gene encoding this protein, depending upon the context, as will be appreciated by one of skill in the art.

Exemplary SUCLG1 amino acid sequence (SEQ ID NO: 11):
MTATLAAAADIATMVSGSSGLAAARLLSRSFLLPQNGIRHCSYTASRQHL
YVDKNTKIICQGFTGKQGTFHSQQALEYGTKLVGGTTPGKGGQTHLGLPV
FNTVKEAKEQTGATASVIYVPPPFAAAAINEAIEAEIPLVVCITEGIPQQ
DMVRVKHKLLRQEKTRLIGPNCPGVINPGECKIGIMPGHIHKKGRIGIVS
RSGTLTYEAVHQTTQVGLGQSLCVGIGGDPFNGTDFIDCLEIFLNDSATE -continued

```
GIILIGEIGGNAEENAAEFLKQHNSGPNSKPVVSFIAGLTAPPGRRMGHA

GAIIAGGKGGAKEKISALQSAGVVVSMSPAQLGTTIYKEFEKRKML

Exemplary SUCLG1 nucleic acid sequence (SEQ ID NO:
12):
GTCATTGGCGTATGACCGCAACCCTTGCCGCTGCCGCTGACATCGCTACC

ATGGTCTCCGGCAGCAGCGGCCTCGCCGCCGCCCGTCTCCTGTCGCGCAG

CTTCCTCCTGCCGCAGAATGGAATTCGGCATTGTTCCTACACAGCTTCTC

GGCAACATCTCTATGTTGATAAAAATACAAAGATTATTTGCCAGGGTTTC

ACTGGCAAACAGGGCACCTTTCACAGCCAGCAGGCATTGGAATATGGCAC

CAAACTCGTTGGAGGAACCACTCCAGGGAAAGGAGGCCAGACACATCTGG

GCTTACCTGTCTTTAATACTGTGAAGGAGGCCAAAGAACAGACAGGAGCA

ACGGCTTCTGTCATTTATGTTCCTCCGCCTTTTGCTGCTGCTGCCATTAA

TGAAGCTATTGAGGCAGAAATTCCCTTGGTTGTGTGTATCACTGAAGGAA

TTCCCCAGCAGGACATGGTACGAGTCAAGCACAAACTGCTGCGCCAGGAA

AAGACAAGGCTAATTGGGCCCAACTGCCCTGGAGTCATCAATCCTGGAGA

ATGTAAAATTGGCATCATGCCTGGCCATATTCACAAAAAAGGAAGGATTG

GCATTGTGTCCAGATCTGGCACCCTGACTTATGAAGCAGTTCACCAAACA

ACGCAAGTTGGATTGGGGCAGTCTTTGTGCGTTGGCATTGGAGGTGATCC

TTTTAATGGAACAGATTTTATTGACTGCCTCGAAATCTTTTTGAACGATT

CTGCCACAGAAGGCATCATATTGATTGGTGAAATTGGTGGTAATGCAGAA

GAGAATGCTGCAGAATTTTTGAAGCAACATAATTCAGGTCCAAATTCCAA

GCCTGTAGTGTCCTTCATTGCTGGTTTAACTGCTCCTCCTGGGAGAAGAA

TGGGTCATGCCGGGGCAATTATTGCTGGAGGAAAAGGTGGAGCTAAAGAG

AAGATCTCTGCCCTTCAGAGTGCAGGAGTTGTGGTCAGTATGTCTCCTGC

ACAGCTGGGAACCACGATCTACAAGGAATTTGAAAAGAGGAAGATGCTAT

GAAAGAAAAAAAAATTCCTAAAACTGTGGAATGGATCACGTAGACATGT

AACCCAGCAGCAGTTTGCTTCTGTTGTCCACTGATTAATCAGCCTATGTG

CCTGACACTGGTCTTGCAGTACAACTGGAAGCCAAAACAAGGTGGAAGAT

GTCCTGAATTAAGATGTTTTCACCACATTGTATTACAGAGACAGCCAATA

AATCTACTATTTGATTTCAA
```

As used herein, the term "MPV17" refers to a gene encoding mitochondrial inner membrane protein MPV17, or the corresponding protein product. The terms "MPV17" and "mitochondrial inner membrane protein MPV17" include wild-type forms of the MPV17 gene or protein, as well as variants (e.g., splice variants, truncations, concatemers, and fusion constructs, among others) of wild-type MPV17 proteins and nucleic acids encoding the same. Examples of such variants are proteins having at least 70% sequence identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.9% identity, or more) to any of the amino acid sequences of a wild-type MPV17 protein (e.g., SEQ ID NO: 13), provided that the MPV17 variant retains the function of a wild-type MPV17. Additionally, the terms "MPV17" and "mitochondrial inner membrane protein MPV17" may refer to fusion proteins, or nucleic acids encoding the same, in which the MPV17 is operably linked to another polypeptide, half-life-modifying agent, or therapeutic agent. The term "MPV17" may refer to the protein or the gene encoding this protein, depending upon the context, as will be appreciated by one of skill in the art.

```
Exemplary MPV17 amino acid sequence (SEQ ID NO:
13):
MALWRAYQRALAAHPWKVQVLTAGSLMGLGDIISQQLVERRGLQEHQRGR

TLTMVSLGCGFVGPVVGGWYKVLDRFIPGTTKVDALKKMLLDQGGFAPCF

LGCFLPLVGALNGLSAQDNWAKLQRDYPDALITNYYLWPAVQLANFYLVP

LHYRLAVVQCVAVIWNSYLSWKAHRL

Exemplary MPV17 nucleic acid sequence (SEQ ID NO:
14):
AGTTCCTAGGCCAGCCTGTCACGTGGGAGGGAGGCTCGGCGCTCAGGAAG

CATGGCACTCTGGCGGGCATACCAGCGGGCCCTGGCCGCTCACCCGTGGA

AAGTACAGGTCCTGACAGCTGGGTCCCTGATGGGCCTGGGTGACATTATC

TCACAGCAGCTGGTGGAGAGGCGGGGTCTGCAGGAACACCAGAGAGGCCG

GACTCTGACCATGGTGTCCCTGGGCTGTGGCTTTGTGGGCCCTGTGGTAG

GAGGCTGGTACAAGGTTTTGGATCGGTTCATCCCTGGCACCACCAAAGTG

GATGCACTGAAGAAGATGTTGTTGGATCAGGGGGGCTTTGCCCCGTGTTT

TCTAGGCTGCTTTCTCCCACTGGTAGGGGCACTTAATGGACTGTCAGCCC

AGGACAACTGGGCCAAACTACAGCGGGATTATCCTGATGCCCTTATCACC

AACTACTATCTATGGCCTGCTGTGCAGTTAGCCAACTTCTACCTGGTCCC

CCTTCATTACAGGTTGGCCGTTGTCCAATGTGTTGCTGTTATCTGGAACT

CCTACCTGTCCTGGAAGGCACATCGGCTCTAAGCCTGCCTCACTCCATCG

TTTCCACCTTGCAGTGATGCAGCTTGACCCTGGAACGGTCAGACAACCTC

CTCAAAGTGGGCATACCAGTTTCCACGGGGTTGGGTTGCCGGTCAGAGCT

TAAGAGGACTAGCACCCTGCAATGCCCCTCTTCACTCTAAAATGTACACT

GACTGCTITAGAGCCCTTGATAATAGTCTTATTCCCACCACATACTAGGC

ACTCCATAAATATCTGTTGAACCTTCATGACCTTATCAACTTTACACCCA

TATCCCAGCAAATGCCACTCATCCCCACTCTTCATAGACACATTTGTTAC

TCTAACCCTGCCTAGGCTTCTTGTAGCTCCAGCTCTTTAGAGACTCCCGG

AACCCTTTATATGGTGCCTCAGTAAATATGTTATTAAATATGTAATCCGG

AA
```

As used herein, the term "POLG" refers to a gene encoding DNA polymerase gamma, catalytic subunit, or the corresponding protein product. The terms "POLG" and "DNA polymerase gamma, catalytic subunit" include wild-type forms of the POLG gene or protein, as well as variants (e.g., splice variants, truncations, concatemers, and fusion constructs, among others) of wild-type POLG proteins and nucleic acids encoding the same. Examples of such variants are proteins having at least 70% sequence identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.9% identity, or more) to any of the amino acid sequences of a wild-type POLG protein (e.g., SEQ ID NO: 15), provided that the POLG variant retains the function of a wild-type POLG. Additionally, the terms "POLG" and "DNA polymerase gamma, catalytic subunit" may refer to fusion proteins, or nucleic acids encoding the same, in which the POLG is operably linked to another polypeptide, half-life-modifying agent, or therapeutic agent. The term "POLL" may refer to the protein or the gene encoding this protein, depending upon the context, as will be appreciated by one of skill in the art.

```
Exemplary POLG amino acid sequence (SEQ ID NO: 15):
MSRLLWRKVAGATVGPGVPAPGRWVSSSVPASDPSDGQRRRQQQQQQQQQQQQQPQQPQVLSSEGGQLR
HNPLDIQMLSRGLHEQIFGQGGEMPGEAAVRRSVEHLQKHGLWGQPAVPLPDVELRLPPLYGDNLDQHFR
LLAQKQSLPYLEAANLLLQAQLPPKPPAWAWAEGWTRYGPEGEAVPVAIPEERALVFDVEVCLAEGTCPT
LAVAISPSAWYSWCSQRLVEERYSWTSQLSPADLIPLEVPTGASSPTQRDWQEQLVVGHNVSFDRAHIRE
QYLIQGSRMRFLDTMSMHMAISGLSSFQRSLWIAAKQGKHKVQPPTKQGQKSQRKARRGPAISSWDWLDI
SSVNSLAEVHRLYVGGPPLEKEPRELFVKGTMKDIRENFQDLMQYCAQDVWATHEVFQQQLPLFLERCPH
PVTLAGMLEMGVSYLPVNQNWERYLAEAQGTYEELQREMKKSLMDLANDACQLLSGERYKEDPWLWDLEW
DLQEFKQKKAKKVKKEPATASKLPIEGAGAPGDPMDQEDLGPCSEEEEFQQDVMARACLQKLKGTTELLP
KRPQHLPGHPGWYRKLCPRLDDPAWTPGPSLLSLQMRVTPKLMALTWDGFPLHYSERHGWGYLVPGRRDN
LAKLPTGTTLESAGVVCPYRAIESLYRKHCLEQGKQQLMPQEAGLAEEFLLTDNSAIWQTVEELDYLEVE
AEAKMENLRAAVPGQPLALTARGGPKDTQPSYHHGNGPYNDVDIPGCWFFKLPHKDGNSCNVGSPFAKDF
LPKMEDGTLQAGPGGASGPRALEINKMISFWRNAHKRISSQMVVWLPRSALPRAVIRHPDYDEEGLYGAI
LPQVVTAGTITRRAVEPTWLTASNARPDRVGSELKAMVQAPPGYTLVGADVDSQELWIAAVLGDAHFAGM
HGCTAFGWMTLQGRKSRGTDLHSKTATTVGISREHAKIFNYGRIYGAGQPFAERLLMQFNHRLTQQEAAE
KAQQMYAATKGLRWYRLSDEGEWLVRELNLPVDRTEGGWISLQDLRKVQRETARKSQWKKWEVVAERAWK
GGTESEMFNKLESIATSDIPRTPVLGCCISRALEPSAVQEEFMTSRVNWVVQSSAVDYLHLMLVAMKWLF
EEFAIDGRFCISIHDEVRYLVREEDRYRAALALQITNLLTRCMFAYKLGLNDLPQSVAFFSAVDIDRCLR
KEVTMDCKTPSNPTGMERRYGIPQGEALDIYQIIELTKGSLEKRSQPGP Exemplary POLG nucleic acid sequence (SEQ ID NO: 16):
GCGGACCGGCCGGGTGGAGGCCACACGCTACCCCGAGGCTGCGTAGGCCGCGCGAAGGGGACGCCGTGC
CGTGGGCCTGGGGTCGGGGGAGCAGCAGACCGGGAAGCACCGATTTGGGGTGGAAGGCAGGCATGGTCAA
ACCCATTTCACTGACAGGAGAGCAGAGACAGGACGTGTCTCTCTCCACGTCTTCCAGCCAGTAAAAGAAG
CCAAGCTGGAGCCCAAAGCCAGGTGTTCTGACTCCCAGCGTGGGGGTCCCTGCACCAACCATGAGCCGCC
TGCTCTGGAGGAAGGTGGCCGGCGCCACCGTCGGGCCAGGGCCGGTTCCAGCTCCGGGGCGCTGGGTCTC
CAGCTCCGTCCCCGCGTCCGACCCCAGCGACGGGCAGCGGCGGCGGCAGCAGCAGCAGCAGCAGCAGCAG
CAGCAGCAACAGCAGCCTCAGCAGCCGCAAGTGCTATCCTCGGAGGGCGGGCAGCTGCGGCACAACCCAT
TGGACATCCAGATGCTCTCGAGAGGGCTGCACGAGCAAATCTTCGGGCAAGGAGGGGAGATGCCTGGCGA
GGCCGCGGTGCGCCGCAGCGTCGAGCACCTGCAGAAGCACGGGCTCTGGGGGCAGCCAGCCGTGCCCTTG
CCCGACGTGGAGCTGCGCCTGCCGCCCCTCTACGGGGACAACCTGGACCAGCACTTCCGCCTCCTGGCCC
AGAAGCAGAGCCTGCCCTACCTGGAGGCGGCCAACTTGCTGTTGCAGGCCCAGCTGCCCCCGAAGCCCCC
GGCTTGGGCCTGGGCGGAGGGCTGGACCCGGTACGGCCCCGAGGGGAGGCCGTACCCGTGGCCATCCCC
GAGGAGCGGGCCCTGGTGTTCGACGTGGAGGTCTGCTTGGCAGAGGGAACTTGCCCCACATTGGCGGTGG
CCATATCCCCCTCGGCCTGGTATTCCTGGTGCAGCCAGCGGCTGGTGGAAGAGCGTTACTCTTGGACCAG
CCAGCTGTCGCCGGCTGACCTCATCCCCCTGGAGGTCCCTACTGGTGCCAGCAGCCCCACCCAGAGAGAC
TGGCAGGAGCAGTTAGTGGTGGGGCACAATGTTTCCTTTGACCGAGCTCATATCAGGGAGCAGTACCTGA
TCCAGGGTTCCCGCATGCGTTTCCTGGACACCATGAGCATGCACATGGCCATCTCAGGGCTAAGCAGCTT
CCAGCGCAGTCTGTGGATAGCAGCCAAGCAGGGCAAACACAAGGTCCAGCCCCCACAAAGCAAGGCCAG
AAGTCCCAGAGGAAAGCCAGAAGAGGCCCAGCGATCTCATCCTGGGACTGGCTGGACATCAGCAGTGTCA
```

-continued
ACAGTCTGGCAGAGGTGCACAGACTTTATGTAGGGGGCCTCCCTTAGAGAAGGAGCCTCGAGAACTGTT
TGTGAAGGGCACCATGAAGGACATTCGTGAGAACTTCCAGGACCTGATGCAGTACTGTGCCCAGGACGTG
TGGGCCACCCATGAGGTTTTCCAGCAGCAGCTACCGCTCTTCTTGGAGAGGTGTCCCCACCCAGTGACTC
TGGCCGGCATGCTGGAGATGGGTGTCTCCTACCTGCCTGTCAACCAGAACTGGGAGCGTTACCTGGCAGA
GGCACAGGGCACTTATGAGGAGCTCCAGCGGGAGATGAAGAAGTCGTTGATGGATCTGGCCAATGATGCC
TGCCAGCTGCTCTCAGGAGAGAGGTACAAAGAAGACCCCTGGCTCTGGGACCTGGAGTGGGACCTGCAAG
AATTTAAGCAGAAGAAAGCTAAGAAGGTGAAGAAGGAACCAGCCACAGCCAGCAAGTTGCCCATCGAGGG
GGCTGGGGCCCCTGGTGATCCCATGGATCAGGAAGACCTCGGCCCCTGCAGTGAGGAGGAGGAGTTTCAA
CAAGATGTCATGGCCCGCGCCTGCTTGCAGAAGCTGAAGGGGACCACAGAGCTCCTGCCCAAGCGGCCCC
AGCACCTTCCTGGACACCCTGGATGGTACCGGAAGCTCTGCCCCCGGCTAGACGACCCTGCATGGACCCC
GGGCCCCAGCCTCCTCAGCCTGCAGATGCGGGTCACACCTAAACTCATGGCACTTACCTGGGATGGCTTC
CCTCTGCACTACTCAGAGCGTCATGGCTGGGGCTACTTGGTGCCTGGGCGGCGGGACAACCTGGCCAAGC
TGCCGACAGGTACCACCCTGGAGTCAGCTGGGGTGGTCTGCCCCTACAGAGCCATCGAGTCCCTGTACAG
GAAGCACTGTCTCGAACAGGGGAAGCAGCAGCTGATGCCCCAGGAGGCCGGCCTGGCGGAGGAGTTCCTG
CTCACTGACAATAGTGCCATATGGCAAACGGTAGAAGAACTGGATTACTTAGAAGTGGAGGCTGAGGCCA
AGATGGAGAACTTGCGAGCTGCAGTGCCAGGTCAACCCCTAGCTCTGACTGCCCGTGGTGGCCCCAAGGA
CACCCAGCCCAGCTATCACCATGGCAATGGACCTTACAACGACGTGGACATCCCTGGCTGCTGGTTTTTC
AAGCTGCCTCACAAGGATGGTAATAGCTGTAATGTGGGAAGCCCCTTTGCCAAGGACTTCCTGCCCAAGA
TGGAGGATGGCACCCTGCAGGCTGGCCCAGGAGGTGCCAGTGGGCCCCGTGCTCTGGAAATCAACAAAAT
GATTTCTTTCTGGAGGAACGCCCATAAACGTATCAGCTCCCAGATGGTGGTGTGGCTGCCCAGGTCAGCT
CTGCCCCGTGCTGTGATCAGGCACCCCGACTATGATGAGGAAGGCCTCTATGGGGCCATCCTGCCCCAAG
TGGTGACTGCCGGCACCATCACTCGCCGGGCTGTGGAGCCCACATGGCTCACCGCCAGCAATGCCCGGCC
TGACCGAGTAGGCAGTGAGTTGAAAGCCATGGTGCAGGCCCCACCTGGCTACACCCTTGTGGGTGCTGAT
GTGGACTCCCAAGAGCTGTGGATTGCAGCTGTGCTTGGAGACGCCCACTTTGCCGGCATGCATGGCTGCA
CAGCCTTTGGGTGGATGACACTGCAGGGCAGGAAGAGCAGGGGCACTGATCTACACAGTAAGACAGCCAC
TACTGTGGGCATCAGCCGTGAGCATGCCAAAATCTTCAACTACGGCCGCATCTATGGTGCTGGGCAGCCC
TTTGCTGAGCGCTTACTAATGCAGTTTAACCACCGGCTCACACAGCAGGAGGCAGCTGAGAAGGCCCAGC
AGATGTACGCTGCCACCAAGGGCCTCCGCTGGTATCGGCTGTCGGATGAGGGCGAGTGGCTGGTGAGGGA
GTTGAACCTCCCAGTGGACAGGACTGAGGGTGGCTGGATTTCCCTGCAGGATCTGCGCAAGGTCCAGAGA
GAAACTGCAAGGAAGTCACAGTGGAAGAAGTGGGAGGTGGTTGCTGAACGGGCATGGAAGGGGGCACAG
AGTCAGAAATGTTCAATAAGCTTGAGAGCATTGCTACGTCTGACATACCACGTACCCCGGTGCTGGGCTG
CTGCATCAGCCGAGCCCTGGAGCCCTCGGCTGTCCAGGAAGAGTTTATGACCAGCCGTGTGAATTGGGTG
GTACAGAGCTCTGCTGTTGACTACTTACACCTCATGCTTGTGGCCATGAAGTGGCTGTTTGAAGAGTTTG
CCATAGATGGGCGCTTCTGCATCAGCATCCATGACGAGGTTCGCTACCTGGTGCGGGAGGAGGACCGCTA
CCGCGCTGCCCTGGCCTTGCAGATCACCAACCTCTTGACCAGGTGCATGTTTGCCTACAAGCTGGGTCTG
AATGACTTGCCCCAGTCAGTCGCCTTTTTCAGTGCAGTCGATATTGACCGGTGCCTCAGGAAGGAAGTGA
CCATGGATTGTAAAACCCCTTCCAACCCAACTGGGATGGAAAGGAGATACGGGATTCCCCAGGGTGAAGC
GCTGGATATTTACCAGATAATTGAACTCACCAAAGGCTCCTTGGAAAAACGAAGCCAGCCTGGACCATAG
CACTGCCTGGAGGCTCTGTATTTGCTCCCGTGGAGCTTCATCGGGGTGGTGCAGGCTCCCAAACTCAGGC
TTTCAGCTGTGCTTTTTGCAAAAGGGCTTGCCTAAGGCCAGCCATTTTTCAGTAGCAGGACCTGCCAAGA
AGATTCCTTCTAACTGAAGGTGCAGTTGAATTCAGTGGGTTCAGAACCAAGATGCCAACATCGGTGTGGA -continued

```
CTACAGGACAAGGGGCATTGTTGCTTGTTGGGTAAAAATGAAGCAGAAGCCCCAAAGTTCACATTAACTC

AGGCATTTCATTTATTTTTTCCTTTTCTTCTTGGCTGGTTCTTTGTTCTGTCCCCCATGCTCTGATGCAG

TGCCCTAGAAGGGGAAAGAATTAATGCTCTAACGTGATAAACCTGCTCCAAGGCAGTGGAAATAAAAGA

AGGAAAAAAAAGACTCTATCTTCTCAAAAAAAAAAAAAAAAA
```

Standard methods in molecular biology are described Sambrook, Fritsch and Maniatis Molecular Cloning, A Laboratory Manual, Cold Spring Harbor Laboratory Press, Cold Spring Harbor, NY (1982 & 1989 2nd Edition, 2001 3rd Edition); Sambrook and Russell Molecular Cloning, 3rd ed., Cold Spring Harbor Laboratory Press, Cold Spring Harbor, NY (2001); Wu *Recombinant DNA*, Vol. 217, Academic Press, San Diego, CA) (1993). Standard methods also appear in Ausbel, et al. *Current Protocols in Molecular Biology, Vols.* 1-4, John Wiley and Sons, Inc. New York, NY (2001).

Mitochondrial DNA Depletion Syndrome Treatment and Prevention

The compositions and methods of the present disclosure may be used to treat, prevent, and/or cure a variety of pathologies. For example, gene therapy methods described herein may involve administration of one or more compositions containing a nucleic acid encoding a functional protein so as to treat, prevent, and/or cure a disease associated with mitochondrial dysfunction. For the treatment of a mitochondrial DNA depletion syndrome, such as a deficiency of TK2, dGK, TP, p53R2, SUCLA2, SUCLG1, MPV17, and/or POLG, the gene therapy may involve administration of one or more compositions containing a gene encoding a functional form of the deficient protein. The treatment can also involve the administration of pharmacological therapy in conjunction with the gene therapy. Such a treatment protocol involving gene therapy alone or in combination with pharmacological therapy may be used to treat a variety of disorders characterized by unbalanced nucleoside pools, such as those found in mitochondrial DNA depletion syndrome.

Mitochondrial DNA (mtDNA) depletion syndrome (MDS) comprises several severe autosomal diseases characterized by a reduction in mtDNA copy number in affected tissues. Most of the MDS causative nuclear genes encode proteins that belong to the mtDNA replication machinery or are involved in deoxyribonucleoside triphosphate (dNTP) metabolism making all of these diseases candidates for gene therapy.

One form of MDS is thymidine kinase deficiency or TK2. TK2 encoded by the nuclear gene, TK2, is a mitochondrial matrix protein that phosphorylates thymidine and cytidine nucleosides to generate deoxythymidine monophosphate (TMP) and deoxycytidine monophosphate (dCMP), which in turn, are converted to deoxynucleotide triphosphates (dNTPs) required for mitochondrial DNA synthesis. Autosomal recessive TK2 mutations cause devastating neuromuscular weakness with severe depletion of mitochondrial DNA (mtDNA) in infants and children, as well as progressive external ophthalmoplegia with mtDNA multiple deletions in adults. Many patients cannot walk and require some type of mechanical ventilation and feeding tube. The central nervous system is variably involved in these disorders, with symptoms that include seizures, encephalopathy, cognitive impairment, and hearing loss. Less than 7% of patients live more than 42 years.

Based on clinical and molecular genetics findings of patients thus diagnosed, three disease presentations were identified: i) infantile-onset ($\leq 1$ year-old) myopathy with onset of weakness in the first year of life with severe mtDNA depletion and early mortality; ii) childhood-onset (>1-11 years-old) myopathy with severe mtDNA depletion; and iii) late-onset myopathy ($\geq 12$ years-old) with mild weakness at onset and slow progression to loss of ambulation, respiratory insufficiency, or both, often with chronic progressive external ophthalmoparesis in adolescence or adulthood in association with mtDNA multiple deletions, reduced mtDNA copy number, or both. See Garone, et al. 2018.

Attempts to study the pathogenesis and test therapies for TK2 deficiency using cultured fibroblasts from patients have been unsuccessful, because the replicating cells failed to manifest mtDNA depletion. In contrast, a homozygous Tk2 H126N knock-in mutant (Tk2$^{-/-}$) mouse model, manifests a phenotype that is strikingly similar to the human infantile encephalomyopathy caused by TK2 mutations, characterized by onset at age 10 days with decreased ambulation, unstable gait, coarse tremor, growth retardation, and depletion of mitochondrial DNA (mtDNA) progressing rapidly to early death at age 14 to 16 days, which is a time period analogous to the human infantile-onset disease (Akman, et al. 2008; Dorado, et al. 2011). This mouse model has been used to show the administration of oral dC/dT prolonged delayed the onset of clinical symptoms of TK2 deficiency and prolonged the lives of the mice by two- to three-fold ('092 application). It was also used to show the administration of oral dCMP/TMP delayed clinical symptoms and prolonged life ('207 application).

Exemplary Findings From AAV Vectors Encoding TK2 in Mouse Models of MDS

As shown herein using a mouse model of Tk2 deficiency, the disease can be cured by replacing the mutant gene with a normal gene that encodes a functional Tk2 protein. An exemplary gene therapy described herein involves the use of an AAV (e.g., an AAV2 or AAV9 virus) containing a transgene encoding TK2. It has been discovered that administration of an AAV9 virus expressing human TK2 (referred to as "AAV9-hTK2" in the Examples provided below) prolonged the lifespan of TK2 mutant mice up to a maximum lifespan of about 4 months and an average of about 3 months. This was more than double the lifespan of the oral dC/dT pharmacological-treated TK2 mutant mice, which was an average of 43 days, and five times longer than the untreated TK2 mutant mice which was 18 days (see, e.g., Example 2). Weight also increased from about 55% over mice with dC/dT treatment alone and about 80% over the weight of wild type mice (see, e.g., Example 3).

Muscle strength (normalized to weight) and motor function assessed by Rotarod test was performed at postnatal day 60 and showed no differences between the treated TK2 mutant mice and untreated wild-type mice (see, e.g., Examples 3 and 4). Wild-type mice showed no adverse side-effects related to the therapy and were overall healthy.

Activity and levels of OXPHOS enzyme complexes in brain of treated mutant mice were similar to that showed in untreated and treated wild-type mice (see, e.g., Examples 7 and 8).

Additionally, treated mutant mice never showed head tremor, characteristic of untreated and dC+dT treated Tk2$^{-/-}$ mice, confirming that rescue of mitochondrial function in central nervous system prevents pathology.

Mitochondrial DNA was also rescued by the AAV9 administration in most tissue of the mutant mice (see, e.g., Example 6).

Treatment with 4.2×10$^{11}$ vc of AAV9-hTK2 at P1 does not efficiently transduce kidney cells, as previously observed in other studies. Consequently, TK2 activity in treated mutant mice was very poor compared to wild-type mice and there were signs of mtDNA depletion as soon as post-natal day 29. Histology and biochemical analysis showed compromised kidney function, which may be the underlying condition leading to early death of Tk2$^{-/-}$ mice (see, e.g., Example 8).

However, when the TK2 mutant mice were administered with a combination of the AAV9-hTK2 and an AAV2 virus expressing human TK2 gene (AAV2-hTK2), they survived significantly longer despite having lower levels of total viral dose. The mutant mice treated with both constructs grew as much as the mice treated with only AAV9-hTK2 and had slightly higher levels of mtDNA than mice treated with only AAV9-hTK2. They had equal growth and strength and motor coordination as the mutant mice treated with AAV9-hTK2 only as well as a decrease of protein in their urine and lower levels of index BUN (see, e.g., Example 9).

Additionally, when the mutant mice were treated with both AAV9-hTK2 and AAV2-hTK2 were further administered oral dC+dT in water, they survived even longer and have increased growth and mtDNA levels in the liver and kidney and decreased protein in their urine (see, e.g., Example 10).

Additionally, the TK2 mutant mice are treated with the oral dC/dT as described in the '092 application or the oral dCMP/TMP as described in '207 application, starting at an early age, e.g., postnatal day 4, and subsequently administered the AAV9-hTK2 vector, alone or in combination with the AAV2-hTK2 vector, at a later age, ranging from one month to about two months, with about 21 days being ideal. The AAV2-hTK2 vector can be administered simultaneously with the AAV9-hTK2 vector or subsequently. These mutant mice survived longer than the mutant mice administered only the AAV9-hTK2 and have increased growth and strength, and mtDNA and RCEs are restored in all tissues including kidney (see, e.g., Examples 11 and 12).

Methods of Treating, Preventing, and/or Curing Mitochondrial Diseases in Patients Patients who would benefit from the administration of the described gene therapy include those diagnosed with a deficiency in one or more of TK2, dGK, TP, p53R2, SUCLA2, SUCLG1, MPV17, and/or POLG. In these patients, compositions containing a nucleic acid encoding one or more of the deficient proteins (e.g., viral vectors, such as AAV vectors, containing such nucleic acids) may be administered to the patient. These compositions may be administered alone or in combination with pharmacological agents, such as deoxynucleosides (e.g., dC and dT or mixtures thereof), or deoxyribonucleoside monophosphates (e.g., dCMP and TMP or mixtures thereof). For example, the subject may have a mitochondrial DNA depletion syndrome and the treatment comprises administering (i) a composition containing a viral vector (e.g. AAV, such as an AAV that targets at least muscle tissue, optionally at least muscle tissue and CNS, for example AAV9) containing a nucleic acid encoding one or more of the deficient proteins, and (ii) a composition comprising deoxynucleosides (e.g., dC and dT or mixtures thereof), or deoxyribonucleoside monophosphates (e.g., dCMP and TMP or mixtures thereof). In one embodiment, the mitochondrial DNA depletion syndrome is TK2 deficiency and the viral vector (e.g. AAV, such as an AAV that targets at least muscle tissue, optionally at least muscle tissue and CNS, for example AAV9) comprises a nucleic acid encoding TK2. In a particular embodiment, the mitochondrial DNA depletion syndrome is TK2 deficiency and the viral vector is AAV9 comprising a nucleic acid encoding TK2.

In some embodiments, the present disclosure provides methods of treating, preventing, curing, and/or reducing the severity or extent of TK2 deficiency by administering to a subject in need thereof a therapeutically effective amount of a composition, such as a viral vector (e.g., an AAV), comprising a nucleic acid encoding TK2. In some embodiments, the viral vector is an AAV, such as AAV9 or AAV2. In some embodiments, the composition (e.g., viral vector, such as an AAV) comprising a nucleic acid encoding TK2 is administered as soon as TK2 deficiency is diagnosed or suspected. In some embodiments, the amount of AAV comprising the transgene administered is about 4.2×10$^{11}$ or 4.2×10$^{10}$ genome or vector or vector copies.

The disclosure also provides methods of treating, preventing, curing, and/or reducing the severity or extent of TK2 deficiency by administering to a subject in need thereof a therapeutically effective amount of a first composition (e.g., viral vector, such as AAV) containing a nucleic acid encoding TK2 and further comprising administering to the subject a therapeutically effective amount of a second composition (e.g., viral vector, such as AAV) containing a nucleic acid encoding TK2. In some embodiments, the first and second AAV are each independently an AAV2 or AAV9 vector encoding TK2. In some embodiments, the first AAV vector is administered prior to the second AAV vector. In some embodiments, the first composition (e.g., AAV vector) is administered as soon as TK2 deficiency is diagnosed or suspected, and the second composition (e.g., AAV vector) is administered at a time point after the first composition. In some embodiments, the second composition (e.g., AAV vector) is administered within days of the first composition (e.g., AAV vector). In some embodiments, the second composition (e.g., AAV vector) is administered within weeks of the first composition (e.g., AAV vector). In some embodiments, the second composition (e.g., AAV vector) is administered months after the first composition (e.g., AAV vector). In some embodiments, the first composition (e.g., AAV vector) and the second composition (e.g., AAV vector) are administered simultaneously at any given time point. In some embodiments, the two compositions (e.g., AAV vectors) are present within the same larger composition, and in some embodiments, the two are separate compositions.

In some embodiments, the method further includes further administering a therapeutically effective amount of a pharmacological agent, such as dC and/or dT. The pharmacological agent may be administered at the same time that the first composition (e.g., viral vector, such as an AAV vector) is administered or at a time point after the first composition is administered. In some embodiments, the pharmacological agent, such as dC and/or dT, is administered within days of the first composition. In some embodiments, the pharmacological agent, such as dC and/or dT, is administered within weeks of the first composition, and in some embodiments, the pharmacological agent, such as dC and/or dT, is administered months after the first composition. In some embodiments, the first composition, second composition, and the pharmacological agent are administered simultaneously at any given time point.

In some embodiments, the first composition (e.g., viral vector, such as an AAV, encoding a transgene described herein, for example TK2) is administered as soon as TK2 deficiency is known or suspected. The pharmacological agent (e.g., dC and/or dT) may be administered starting from about 7 days to about 35 days after the administration of the first composition, starting from about 14 days to about 28 days after the administration of the first composition, starting from about 14 days to about 21 days after the administration of the first composition, or starting from about 21 days after the administration of the first composition. The second composition (e.g., viral vector, such as an AAV, encoding a transgene described herein, for example TK2) may be administered starting from about 14 days to about 45 days after the administration of the first composition, starting from about 21 days to about 35 days after the administration of the first composition, starting from about 21 days to about 30 days after the administration of the first composition, or starting from about 29 days after the administration of the first composition. In some embodiments, administration of the pharmacological agent (e.g., dC and/or dT) continues throughout the subject's lifetime.

In some embodiments, the disclosure provides methods of treating, preventing, curing, and/or reducing the severity or extent of TK2 deficiency by administering to a subject in need thereof a therapeutically effective amount of a pharmacological agent (e.g., dC and/or dT) and further includes administering to the subject a therapeutically effective amount of a composition containing a viral vector, such as an AAV vector (e.g. rAAV), containing a nucleic acid encoding TK2. For example, the composition may contain an AAV2 or AAV9 containing a nucleic acid encoding TK2. In certain embodiments, the AAV is AAV9. In some embodiments, the pharmacological agent is administered prior to the AAV vector. In some embodiments, the pharmacological agent is administered as soon as TK2 deficiency is diagnosed or suspected, and the AAV vector is administered at a time point after. In some embodiments, the AAV vector is administered within days of the pharmacological agent, and in some embodiments, the AAV vector is administered within weeks of the pharmacological agent. In some embodiments, the AAV vector is administered months after the pharmacological agent. In some embodiments, the pharmacological agent and the AAV vector are administered simultaneously at any given time point. In some embodiments, a second AAV vector (e.g., AAV2 or AAV9) encoding TK2 is also administered. The first and second AAV vector may be the same or different. For example, the first AAV vector may be an AAV2 vector (i.e., containing AAV2 ITRs and AAV2 capsid proteins) and the second AAV vector may be an AAV9 vector (e.g., containing AAV9 ITRs and AAV9 capsid proteins). In some embodiments, one or both of the first and second vectors is a pseudotyped AAV vector containing AAV2 ITRs and capsid proteins from a different AAV serotype (e.g., an AAV2/1, AAV2/8, or AAV2/9 vector). In some embodiments, the first AAV vector is administered simultaneously or later in time relative to administration of the second AAV vector. The first and second vectors may be administered in the same composition or in different compositions.

In some embodiments, the disclosure provides methods of treating, preventing and/or reducing the severity or extent of TK2 deficiency by administering to a subject in need thereof a therapeutically effective amount of a pharmacological agent containing dCMP and/or TMP and additionally administering to the subject a therapeutically effective amount of a composition containing an AAV vector (e.g., an AAV2 or AAV9) containing a nucleic acid encoding TK2. In some embodiments, the dCMP and/or TMP is administered prior to administration of the AAV vector. In some embodiments, the dCMP and/or TMP is administered as soon as TK2 deficiency is diagnosed or suspected, and the AAV vector is administered at a time point after. In some embodiments, the AAV vector is administered within days of dCMP and/or TMP administration, and in some embodiments, the AAV vector is administered within weeks of the dCMP and/or TMP. In some embodiments, the AAV vector is administered months after the dCMP and/or TMP. In some embodiments, the dCMP and/or TMP and the AAV vector are administered simultaneously at any time point. In some embodiments, an additional AAV vector (e.g., an AAV2 or AAV9 vector) containing a nucleic acid encoding TK2 is also administered to the subject. The second AAV vector can be administered simultaneously or later in time relative to administration of the first AAV vector. The first and second AAV vectors may be administered as part of the same composition or as different composition.

All of the aforementioned methods can be used to restore function of a dysfunctional TK2 protein in a subject with TK2 deficiency.

A parallel defect of dGK, due to autosomal recessive mutations in DGUOK with deficiencies in dGMP and dAMP, causes mtDNA depletion typically manifesting as early childhood-onset hepatocerebral disease (Mandel, et al. 2001). These patients would benefit from the administration of an AAV vector comprising the nucleic acid that encodes dGK and at least one deoxypurine, dG or dA, or mixtures thereof. Similarly, patients having deficiencies of TP, p53R2, SUCLA2, SUCLG1, MPV17, and/or POLG may be treated using the compositions and methods of the disclosure, for example, by providing such a patient with a therapeutically effective amount of a composition (e.g., a viral vector, such as an AAV vector) containing a transgene encoding the deficient protein. The composition may be provided to the patient alone or in combination with a pharmacological agent, such as a deoxynucleoside or deoxynucleoside monophosphate described herein.

For example, other forms of MDS, as well as other disorders related to unbalanced nucleotide pools, can be treated by administration of compositions (e.g., viral vectors, such as AAV vectors) containing nucleic acids encoding one or more of TK2, dGK, TP, p53R2, SUCLA2, SUCLG1, MPV17, and/or POLG. The composition may be administered alone or in combination with a pharmacological agent, such as a deoxynucleosides (e.g., dA, dG, dC, or dT, or mixture thereof) or deoxynucleoside monophosphate (e.g., dAMP, dGMP, dCMP, or TMP or mixture thereof). These disorders include, without limitation, deficiencies related to RRM2B (encoding p53R2, the p53 inducible small subunit of ribonucleotide reductase, RNR) and mutations in TYMP (encoding thymidine phosphorylase, TP) which cause mitochondrial neurogastrointestinal encephalomyopathy (MNGIE). Additional nuclear genes that disrupt mitochondrial dNTP pools include but are not limited to SUCLA2, SUCLG1 and MPV17.

Assessing the Condition of a Patient Having a Mitochondrial Disease

Patients that exhibit the phenotype discussed above for TK2 deficiency including the most typical presentation of progressive muscle disease characterized by generalized hypotonia, proximal muscle weakness, loss of previously acquired motor skills, poor feeding, and respiratory difficulties, can be tested to definitively diagnose the disease.

If the clinical presentation is highly suspicious for mtDNA depletion syndrome, molecular genetic testing using a panel of genes known to cause mtDNA depletion syndrome should be performed (Chanprasert, et al. 2012). The TK2 gene is the only gene in which mutations are known to cause TK2-related mitochondrial DNA depletion syndrome. This testing can include a sequence analysis of the entire coding and exon/intron junction regions of TK2 for sequence variants and deletion/duplication. If compound heterozygous or homozygous deleterious mutations are identified in the sequence analysis, the diagnosis of TK2 deficiency is confirmed, and thus, the subject would benefit from the therapy described herein. If sequence analysis does not identify two compound heterozygous or homozygous deleterious mutations, deletion/duplication analysis should be considered to determine and/or confirm a TK2 deficiency diagnosis.

Further tests to determine and/or confirm a TK2 deficiency diagnosis may include testing serum creatine kinase (CK) concentration, electromyography, histopathology on skeletal muscle, mitochondrial DNA (mtDNA) content (copy number), and electron transport chain (ETC) activity in skeletal muscle. If one or more of the following is found in these tests, the TK2 deficiency is determined and/or confirmed. Elevated CK concentration as compared to healthy controls can indicate TK2 deficiency. A skeletal muscle biopsy can be performed, and then a mtDNA content analysis in skeletal muscle performed. If the skeletal muscle biopsy shows prominent variance in fiber size, variable sarcoplasmic vacuoles, variable increased connective tissue, and ragged red fibers as well as increased succinate dehydrogenase (SDH) activity and low to absent cytochrome c oxidase (COX) activity, and mtDNA copy number is severely reduced (typically less than 20% of age- and tissue-matched healthy controls), a diagnosis of TK2 deficiency can be determined and/or confirmed (Chanprasert, et al. 2012).

Additionally, TK2 deficiency is inherited in an autosomal recessive manner Thus, a sibling of an affected patient can be tested as early as possible after birth to diagnose the disease.

In all of these examples, gene therapy alone or in combination with deoxynucleoside therapy or deoxyribonucleoside monophosphate therapy should be started as soon as possible after a diagnosis of TK2 deficiency.

Recombinant AAV Vectors

"Recombinant AAV (rAAV) vectors" described herein generally include a transgene (e.g., encoding TK2, dGK, TP, p53R2, SUCLA2, SUCLG1, MPV17, and/or POLG). The transgene is flanked by 5' and 3' ITRs, and may be operably linked to one or more regulatory elements in a manner that permits transgene transcription, translation, and/or expression in a cell of a target tissue. Such regulatory elements may include a promoter or enhancer, such as the chicken beta actin promoter or cytomegalovirus enhancer, among others described herein. The recombinant AAV genome is generally encapsidated by capsid proteins (e.g., from the same AAV serotype as that from which the ITRs are derived or from a different AAV serotype from that which the ITRs are derived). The AAV vector may then be delivered to a selected target cell. In some embodiments, the transgene is a nucleic acid sequence, heterologous to the vector sequences, which encodes a polypeptide, protein, functional RNA molecule (e.g., miRNA, miRNA inhibitor) or other gene product of interest (e.g., TK2). Components of exemplary AAV vectors that may be used in conjunction with the compositions and methods of the disclosure are described below.

Any AAV serotype or combination of AAV serotype can be used in the methods and compositions of the present invention. Because the methods and compositions of the present invention are for the treatment and cure of mitochondrial disorders, AAV serotypes that target at least muscle, or at least muscle and the central nervous system can be used in some embodiments and include but are not limited to AAV1, AAV2, AAV4, AAV5, AAV6, AAV7, AAV8, and AAV9.

In some embodiments, AAV9 serotype, which has a wide tropism, is used.

Components of AAV vectors

The AAV vectors described herein may contain cis-acting 5' and 3' ITRs (See, e.g., Carter, in "Handbook of Parvoviruses", ed., P. Tijsser, CRC Press, pp. 155 168 (1990)). The ITR sequences are typically about 145 bp in length. Preferably, substantially the entire sequences encoding the ITRs are used in the molecule, although some degree of minor modification of these sequences is permissible. (See, e.g., texts such as Sambrook et al, (1989) and Fisher et al., (1996)). An example of such a molecule is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types.

In addition to the elements identified above for recombinant AAV vectors, the vector may also include conventional control elements which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

As used herein, a nucleic acid sequence (e.g., coding sequence) and regulatory sequences are said to be operably linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., shRNA, miRNA).

For nucleic acids encoding proteins, a polyadenylation sequence generally is inserted following the transgene sequences and before the 3' AAV ITR sequence. An rAAV construct useful in the present invention may also contain an intron, desirably located between the promoter/enhancer sequence and the transgene. One possible intron sequence is derived from SV-40, and is referred to as the SV-40 T intron sequence.

Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional and many such sequences are available (see, e.g., Sambrook et al, and references cited). Such a motif may be useful, for example, for instances in which multiple genes or portions thereof are expressed from the same AAV vector.

The precise nature of the regulatory sequences needed for gene expression in host cells may vary between species, tissues or cell types, but shall in general include, as necessary, 5' non-transcribed and 5' non-translated sequences involved with the initiation of transcription and translation respectively, such as a TATA box, capping sequence, CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors may optionally include 5' leader or signal sequences.

Examples of constitutive promoters include, without limitation, a chicken beta actin promoter, a retroviral Rous sarcoma virus (RSV) LTR promoter (optionally with a RSV enhancer), a cytomegalovirus (CMV) promoter (optionally with a CMV enhancer), a SV40 promoter, a dihydrofolate reductase promoter, a 13-actin promoter, a phosphoglycerol kinase (PGK) promoter, and an EFla promoter (Invitrogen).

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Examples of inducible promoters regulated by exogenously supplied promoters include a zinc-inducible sheep metallothionine (MT) promoter, a dexamethasone (Dex)-inducible mouse mammary tumor virus (MMTV) promoter, a T7 polymerase promoter system (WO 98/10088); a ecdysone insect promoter (No et al., *Proc. Natl. Acad. Sci. USA* 93:3346-3351 (1996)), a tetracycline-repressible system (Gossen et al., *Proc. Natl. Acad. Sci. USA* 89:5547-5551 (1992)), a tetracycline-inducible system (Gossen et al., *Science* 268:1766-1769 (1995), a RU486-inducible system (Wang et al., *Nat. Biotech.* 15:239-243 (1997) and Wang et al., *Gene Ther.* 4:432-441 (1997)) and a rapamycin-inducible system (Magari et al., *J. Clin. Invest.* 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, a native promoter, or fragment thereof, for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner In some embodiments, one or more bindings sites for one or more of miRNAs are incorporated in a transgene of a rAAV vector, to inhibit the expression of the transgene in one or more tissues of a subject harboring the transgenes. The miRNA target sites in the mRNA may be in the 5' UTR, the 3' UTR or in the coding region. Typically, the target site is in the 3' UTR of the mRNA. Furthermore, the transgene may be designed such that multiple miRNAs regulate the mRNA by recognizing the same or multiple sites. The presence of multiple miRNA binding sites may result in the cooperative action of multiple RISCs and provide highly efficient inhibition of expression. The target site sequence may comprise a total of 5-100, 10-60, or more nucleotides. The target site sequence may comprise at least 5 nucleotides of the sequence of a target gene binding site.

For example, a 3'UTR site which would inhibit the expression of the transgene in the liver can be incorporated into a transgene. This would be beneficial for transgenes which encode therapeutic proteins which are toxic to the liver as most of the virus administered (approximately 60 to 90%) is eventually found in the liver. Thus suppressing the therapeutic gene expression in liver relieves the burden from liver cells.

In some embodiments, the AAV vector will be modified to be a self-complementing AAV. A self-complementing AAV carries complementary sequence of the transgene (i.e., a double copy of the transgene). Self complementation makes the gene more stable after it enters the cell.

Transgene Coding Sequences

Nucleic acid sequences of transgenes described herein may be designed based on the knowledge of the specific composition (e.g., viral vector) that will express the transgene. For example, one type of transgene sequence includes a reporter sequence, which upon expression produces a detectable signal. In another example, the transgene encodes a therapeutic protein or therapeutic functional RNA. In another example, the transgene encodes a protein or functional RNA that is intended to be used for research purposes, e.g., to create a somatic transgenic animal model harboring the transgene, e.g., to study the function of the transgene product. In another example, the transgene encodes a protein or functional RNA that is intended to be used to create an animal model of disease. Appropriate transgene coding sequences will be apparent to the skilled artisan.

In embodiments of the current invention the transgenes would encode a functional protein including but not limited to TK2, dGK, p53R2, TP, SUCLA2, SUCLG1, POLG1, and a mitochondrial membrane protein MPV17.

The human TK2 gene (Gene ID: 7084) can be used to obtain a transgene encoding a functional TK2 protein. The human DGUOK (Gene ID: 1716) can be used to obtain a transgene encoding a functional dGK protein. The human TYMP gene (Gene ID: 1890) can be used to obtain a transgene encoding a functional TP protein. The human RRM2B gene (Gene ID: 50584) can be used to obtain a transgene encoding a functional p53R2 protein. The human SUCLA2 gene (Gene ID: 8803) can be used to obtain a transgene encoding a functional SUCLA2 protein. The human SUCLG1 gene (Gene ID: 8802) can be used to obtain a transgene encoding a functional SUCLG1 protein. The human POLG gene (Gene ID: 5428) can be used to obtain a transgene encoding a functional POLG1 protein. The human MPV17 gene (Gene ID: 4538) can be used to obtain a transgene encoding a functional mitochondrial membrane protein MPV17.

Codon Optimization of Trans Gene Coding Sequences

Codon optimization of the transgene coding sequences can increase the efficiency of the gene therapy. Thus, in some embodiments, a nucleic acid that is at least 70% identical to the coding sequence of the transgene encoding the therapeutic protein (e.g., a nucleic acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence) is used.

Codon optimization tools are known in the art.

Exemplary codon optimized nucleic acids are as follows.

```
Exemplary codon optimized TK2 nucleic acid (SEQ ID NO: 17):
ATGGGAGCATTTTGCCAGCGACCTAGTTCCGATAAAGAACAGGAGAAAGAGAAGAAGAGCGTCATCTG

TGTGGAAGGTAACATCGCTAGTGGCAAAACGACCTGTTTGGAATTTTTCTCTAATGCCACCGATGTGG

AGGTGCTTACAGAGCCTGTTAGTAAATGGCGAAATGTTCGAGGACATAATCCGCTGGGACTGATGTAT

CACGATGCCTCCAGATGGGGACTGACCCTTCAGACTTATGTCCAACTTACAATGCTTGACAGGCACAC

TAGACCGCAGGTTAGCAGCGTGAGGCTGATGGAGCGCTCAATTCACTCTGCCAGGTATATATTCGTTG

AGAACCTCTACCGATCTGGTAAGATGCCTGAGGTAGATTACGTAGTGCTGAGTGAATGGTTTGACTGG

ATTCTTCGCAACATGGATGTATCAGTGGATCTCATTGTTTACCTTAGGACTAACCCGGAGACGTGTTA

TCAGCGCTTGAAAAAGCGCTGCCGGGAAGAGGAAAAAGTGATTCCTCTGGAATACTTGGAAGCTATTC

ATCACCTTCACGAAGAGTGGCTGATAAAAGGTTCCCTGTTTCCCATGGCGGCCCCCGTGCTTGTCATA

GAAGCGGATCACCACATGGAAAGGATGCTCGAACTTTTCGAGCAAAATCGAGACCGGATTCTCACGCC

GGAGAATCGAAAACATTGCCCATAG

Exemplary codon optimized dGK nucleic acid (SEQ ID NO: 18):
ATGGCTGCAGGGAGGCTTTTTTTGTCTAGATTGAGGGCACCTTTTAGCTCCATGGCGAAGTCTCCGCT

TGAGGGGGTGAGTAGCAGCCGGGGGCTCCATGCTGGCAGAGGGCCCCGGAGGCTGTCTATTGAGGGGA

ATATTGCAGTTGGTAAGAGCACGTTTGTTAAATTGCTCACGAAGACCTATCCAGAATGGCACGTTGCT

ACAGAACCAGTAGCTACATGGCAAAACATTCAAGCAGCAGGCACACAGAAGGCTTGCACTGCACAGTC

TCTCGGAAACCTGCTCGATATGATGTACAGAGAGCCCGCCCGGTGGTCATACACGTTTCAGACCTTCA

GCTTTCTTTCTCGGTTGAAGGTACAGTTGGAGCCCTTCCCAGAGAAGTTGCTTCAAGCACGGAAACCT

GTACAGATATTCGAACGATTGCATTTCGAGGCGCTGATGAACATACCTGTGCTTGTTCTGGATGTGAA

CGACGATTTTTCCGAGGAAGTTACTAAGCAAGAGGACCTCATGCGGGAGGTAAACACGTTCGTTAAGA

ACCTGTAA

Exemplary codon optimized TP nucleic acid (SEQ ID NO: 19):
ATGGCAGCATTGATGACACCAGGAACGGGGGCTCCGCCTGCGCCTGGCGATTTTTCAGGAGAGGGGAG

TCAAGGTCTGCCGGACCCTTCACCGGAACCCAAACAGCTTCCCGAGCTTATTAGAATGAAGCGAGATG

GGGGTCGCCTCTCTGAGGCTGACATACGCGCTTTGTTGCGGCGGTCGTCAACGGCTCAGCACAAGGT

GCGCAAATAGGAGCGATGCTGATGGCTATCAGGCTGAGGGGAATGGATTTGGAAGAGACCAGTGTGCT

GACTCAAGCGCTGGCACAGAGCGGCCAGCAGCTTGAATGGCCAGAAGCTTGGCGCCAACAATTGGTCG

ATAAACACTCAACCGGGGGCGTCGGGGACAAAGTCTCCCTTGTACTGGCACCTGCTCTGGCTGCGTGC

GGATGTAAGGTTCCTATGATTAGCGGGCGGGCTTGGGACATACGGGAGGAACGTTGGACAAACTCGA

ATCCATCCCTGGTTTCAACGTGATTCAGAGCCCTGAACAAATGCAAGTACTCCTGGATCAGGCAGGCT
```

```
GCTGTATTGTTGGCCAAAGCGAACAACTCGTGCCTGCGGATGGTATCCTCTATGCTGCCAGGGATGTG

ACCGCCACAGTTGACTCCCTCCCGCTGATAACAGCGTCAATTTTGAGTAAGAAGCTCGTCGAAGGGCT

CAGCGCTCTTGTGGTTGATGTAAAATTTGGGGGGGCCGCAGTATTCCCCAACCAGGAACAAGCACGGG

AACTGGCAAAAACCCTGGTTGGTGTGGGCGCTTCACTGGGCCTGAGAGTTGCCGCTGCCTTGACCGCC

ATGGATAAGCCGCTCGGTAGGTGCGTAGGTCATGCACTTGAAGTAGAAGAAGCCCTTTTGTGCATGGA

TGGGGCCGGTCCCCCTGACTTGCGGGATCTCGTAACCACGCTTGGCGGCGCGTTGCTTTGGCTTTCTG

GACACGCTGGTACCCAAGCGCAAGGGGCAGCAAGAGTCGCAGCAGCGCTTGATGACGGATCAGCTCTT

GGGCGATTTGAAAGAATGCTTGCAGCTCAGGGCGTAGATCCAGGGCTGGCGCGGGCCCTTTGCTCAGG

TTCTCCAGCAGAGCGCCGACAGCTCCTTCCCAGGGCGCGAGAGCAGGAAGAATTGCTGGCCCCGGCTG

ATGGTACCGTCGAACTCGTACGGGCTTTGCCGCTGGCTCTTGTTTTGCACGAACTGGGGGCTGGGCGG

AGTCGCGCCGGTGAACCTCTCAGACTCGGTGTGGGTGCGGAGCTCCTCGTTGACGTCGGGCAACGACT

TCGCAGGGGAACCCCTTGGCTTAGGGTACACAGGGACGGGCCAGCACTCAGCGGCCCTCAGTCCAGGG

CCCTTCAAGAAGCTCTCGTGCTGAGTGATCGAGCGCCTTTTGCCGCTCCCTCACCATTTGCTGAATTG

GTATTGCCACCCCAGCAGTAA

Exemplary codon optimized p53R2 nucleic acid (SEQ ID NO: 20):
ATGCTGCTTCTCAGACTGCCACCCCACCGCAGTCATGCTTCCCCACTTGACTGTAAACTTCA

AGATAGGTGCCGGAAGTGTTACTCACCCCGATCAGGACAAGCGTGCCCTCCTGCGTTGGCGG

CCGCCTGGCTTCGGCGGTGTGAACGCCGAGGAGGTCGGCCGAGGGGTGGGCGACGCAAGGAA

CTGACCCTTGGCCTGCGCCCTGCACGGTGTTCAGCTCCCGGTCCTGCCAAGGATGATGCATG

GAGACCTCAGGCAGGTCGCTCCTCCTCAGATACCAACGAGAGTGAAATTAAATCTAATGAAG

AACCCCTTCTTCGCAAGAGTAGTCGCAGGTTCGTGATATTCCCCATACAATATCCTGATATC

TGGAAAATGTACAAGCAAGCCCAAGCATCATTCTGGACCGCAGAAGAGGTTGATCTCAGTAA

GGACCTCCCACACTGGAACAAACTGAAAGCCGACGAAAAATATTTCATATCCCATATACTTG

CTTTCTTTGCAGCCTCAGATGGAATTGTGAATGAAAACTTGGTAGAGCGCTTCTCTCAAGAG

GTCCAAGTTCCTGAAGCACGATGCTTTTACGGATTTCAAATCCTGATAGAAAATGTACATTC

CGAAATGTATTCCTTGCTTATAGACACGTATATCAGAGATCCCAAAAAAGGGAGTTCTTGT

TCAATGCGATCGAGACCATGCCATATGTTAAGAAAAAAGCCGATTGGGCCCTGAGGTGGATA

GCTGATAGGAAGTCTACATTTGGGGAACGCGTTGTTGCCTTCGCCGCCGTCGAGGGAGTCTT

CTTCTCCGGATCCTTCGCTGCTATCTTTTGGCTGAAAAAACGCGGCTTGATGCCTGGTTTGA

CCTTTAGCAATGAGTTGATATCACGGGATGAAGGGCTGCATTGTGACTTTGCCTGCCTTATG

TTCCAGTACTTGGTGAACAAACCGTCTGAGGAACGGGTAAGGGAAATCATAGTGGATGCAGT

AAAAATAGAGCAGGAGTTCCTTACTGAAGCGCTCCCCGTAGGGCTCATTGGCATGAACTGCA

TTCTTATGAAGCAGTACATCGAGTTCGTGGCCGATAGACTTTTGGTGGAGCTCGGGTTCTCA

AAGGTTTTTCAGGCTGAAAATCCTTTTGATTTTATGGAGAACATATCTCTGGAGGGCAAGAC

TAACTTTTTTGAAAAAGAGTATCCGAGTATCAAAGGTTTGCCGTGATGGCAGAAACAACAG

ATAATGTCTTCACACTTGATGCGGATTTTTAA

Exemplary codon optimized SUCLA2 nucleic acid (SEQ ID NO: 21):
ATGGCGGCTTCTATGTTCTATGGACGCCTGGTCGCCGTTGCCACGTTGCGGAATCACAGGCCCCGAAC

TGCACAAAGGGCTGCCGCTCAGGTGCTTGAAGCAGCGGATTGTTCAACAATCACGGCCTCCAAGTTC

AGCAACAGCAGCAGAGAAACCTCTCTCTGCATGAGTATATGAGTATGGAACTGCTCCAGGAAGCAGGG

GTGTCTGTACCAAAGGGCTACGTAGCAAAAAGCCCCGACGAGGCGTACGCCATAGCTAAAAACTGGG

AAGTAAGGACGTAGTTATCAAAGCACAGGTTCTGGCCGGTGGCCGCGGTAAGGGAACCTTCGAGAGTG
```

GTTTGAAAGGCGGTGTCAAGATCGTATTTAGTCCCGAGGAGGCCAAGGCTGTAAGTTCCCAGATGATC

GGCAAAAAATTGTTCACAAAGCAAACCGGCGAAAAGGGTAGAATTTGCAACCAAGTACTTGTCTGCGA

AAGAAAGTATCCGAGAAGGGAGTATTATTTCGCTATAACCATGGAAAGATCATTCCAAGGTCCCGTGC

TCATCGGCAGTTCACACGGGGCGTTAATATAGAGGATGTCGCTGCAGAGTCTCCGGAGGCCATAATT

AAGGAGCCTATAGACATCGAGGAAGGCATTAAAAAAGAACAAGCCTTGCAACTGGCACAAAAAATGGG

TTTTCCTCCGAACATCGTCGAGAGTGCCGCAGAAAATATGGTGAAACTGTACAGCCTGTTTTTGAAGT

ACGATGCGACAATGATAGAAATTAATCCGATGGTCGAGGACTCAGATGGAGCCGTGCTTTGTATGGAC

GCCAAAATTAACTTCGATTCAAACAGCGCTTATCGACAGAAGAAAATTTTCGATTTGCAAGATTGGAC

CCAAGAGGATGAGCGAGACAAAGATGCCGCCAAAGCAAATCTCAATTATATAGGACTCGATGGTAATA

TTGGATGTTTGGTCAATGGTGCCGGTCTCGCGATGGCAACTATGGATATAATCAAGTTGCATGGTGGG

ACTCCCGCCAACTTTCTTGACGTCGGGGGAGGCGCCACCGTTCACCAAGTTACGGAGGCTTTCAAACT

CATAACCTCTGACAAGAAGGTGCTGGCGATTCTTGTAAATATCTTTGGTGGCATTATGCGGTGTGATG

TTATTGCCCAGGGAATAGTAATGGCTGTCAAAGATTTGGAGATTAAAATACCCGTCGTGGTGCGGCTC

CAAGGTACTCGAGTAGATGATGCTAAGGCTCTGATTGCCGACAGCGGGCTGAAGATTCTGGCATGTGA

TGATTTGGACGAGGCAGCGAGAATGGTCGTGAAGCTCTCAGAAATAGTAACTTTGGCGAAACAGGCTC

ATGTCGATGTAAAGTTCCAACTTCCTATATGA

Exemplary codon optimized SUCLG1 nucleic acid (SEQ ID NO: 22):
ATGACCGCTACGCTTGCGGCTGCAGCCGACATCGCGACAATGGTCTCTGGAAGTTCAGGCTTGGCCGC

GGCTCGGCTTCTGAGTAGAAGTTTCTTGTTGCCGCAAAACGGTATCAGGCACTGCTCCTACACCGCCA

GTAGACAACACCTTTATGTTGATAAGAACACGAAGATAATTTGCCAAGGATTCACCGGTAAACAGGGG

ACCTTCCATTCCCAGCAGGCACTGGAATATGGAACTAAATTGGTAGGCGGCACTACGCCTGGGAAGGG

TGGCCAAACACATCTTGGTCTTCCCGTTTTTAACACAGTGAAGGAGGCTAAAGAACAAACGGGGGCAA

CGGCTAGCGTTATCTATGTCCCACCCCCGTTTGCCGCTGCAGCCATAAATGAGGCGATTGAAGCCGAG

ATCCCGCTTGTAGTCTGCATAACGGAGGGAATTCCGCAACAAGACATGGTGCGAGTAAAGCACAAGCT

TCTTCGACAGGAAAAAACAAGACTGATAGGTCCGAATTGTCCTGGCGTAATTAACCCCGGTGAATGCA

AAATCGGAATTATGCCGGGACATATTCACAAAAAAGGCCGAATCGGGATAGTCAGCAGATCAGGCACC

TTGACATACGAAGCGGTTCACCAGACTACGCAAGTCGGTTTGGGACAAAGCCTTTGCGTCGGTATCGG

TGGCGACCCATTTAACGGGACGGATTTCATTGACTGTCTGGAGATCTTCCTCAACGATTCCGCGACAG

AAGGAATCATTTTGATAGGAGAAATAGGCGGGAACGCCGAAGAGAATGCAGCGGAATTCCTCAAACAA

CATAACTCTGGCCCTAATAGTAAGCCGGTGGTATCATTCATAGCCGGTCTTACAGCGCCGCCGGGTCG

CAGAATGGGCCACGCAGGTGCAATTATAGCGGGGGGCAAGGGAGGTGCCAAAGAAAAGATATCCGCTC

TTCAAAGCGCAGGTGTAGTAGTTAGTATGAGTCCAGCTCAACTGGGCACAACCATCTACAAAGAATTT

GAAAAGCGGAAAATGCTTTGA

Exemplary codon optimized MPV17 nucleic acid (SEQ ID NO: 23):
ATGGCCCTCTGGAGAGCTTACCAACGAGCCTTGGCCGCGCACCCTTGGAAGGTACAGGTCTTGACCGC

CGGATCTTTGATGGGTCTTGGAGATATTATTTCTCAACAGTTGGTTGAACGGCGAGGCCTCCAGGAAC

ACCAAAGGGGGAGAACCCTTACAATGGTAAGTCTGGGTTGCGGATTCGTCGGGCCTGTCGTGGGGGA

TGGTATAAGGTTCTGGATCGCTTTATACCGGGGACCACCAAGGTCGATGCCTTGAAGAAGATGTTGCT

GGATCAGGGAGGATTCGCTCCGTGTTTTTTGGGATGTTTTCTGCCACTTGTTGGGGCTCTGAACGGAC

TGTCCGCGCAGGATAACTGGGCGAAGTTGCAACGCGACTACCCAGAGCGCCCTGATAACAAATTACTAT

CTCTGGCCAGCAGTTCAGTTGGCCAATTTTTACCTGGTACCTCTCCACTATCGCCTTGCTGTAGTACA

-continued

GTGTGTCGCCGTCATCTGGAACTCATACCTTTCATGGAAGGCTCATAGATTGTAA

Exemplary codon optimized POLG nucleic acid (SEQ ID NO: 24):
ATGTCCAGGCTGCTCTGGCGGAAGGTCGCAGGCGCCACTGTCGGTCCAGGACCAGTTCCAGCTCCCGG

TCGCTGGGTGAGCAGCAGCGTGCCAGCTAGCGATCCGAGCGACGGTCAGCGGCGACGGCAACAACAGC

AGCAACAGCAACAACAGCAACAACAACAGCCCCAGCAGCCTCAGGTTCTCAGTTCCGAGGGTGGCCAA

CTCCGACACAACCCACTGGATATACAGATGCTCTCCCGCGGTCTCCACGAACAAATATTCGGACAAGG

GGGTGAGATGCCGGGAGAGGCTGCGGTCAGGCGCAGTGTAGAACATCTCCAGAAACACGGGTGTGGG

GCCAACCGGCCGTTCCTCTCCCCGATGTTGAACTGCGGCTTCCACCTCTCTACGGTGATAATCTGGAC

CAGCACTTTAGACTGCTCGCTCAAAAGCAGAGTCTCCCTTACCTGGAAGCCGCTAACCTCCTGCTCCA

AGCCCAATTGCCCCTAAACCGCCAGCCTGGGCTTGGGCGGAGGGATGGACGAGGTATGGACCCGAAG

GGGAGGCTGTGCCAGTTGCTATACCAGAGGAACGCGCTCTGGTTTTCGACGTAGAGGTTTGTCTCGCG

GAGGGAACTTGTCCTACACTGGCTGTAGCAATTTCCCCTTCAGCCTGGTACAGCTGGTGCTCTCAGAG

ATTGGTGGAAGAAAGGTATAGCTGGACTAGCCAGCTGAGTCCCGCGGACCTCATTCCACTTGAGGTAC

CCACCGGGGCGTCAAGCCCAACTCAGAGGGACTGGCAGGAACAATTGGTAGTTGGGCATAATGTGAGT

TTTGACAGGGCTCATATCCGCGAACAGTATCTTATCCAGGGCTCTAGAATGCGATTCCTTGACACGAT

GAGCATGCACATGGCAATCAGCGGACTTAGTTCCTTTCAGAGGTCATTGTGGATTGCAGCCAAGCAGG

GAAAGCATAAGGTCCAACCCCCGACAAAACAAGGTCAGAAATCCCAGAGAAAAGCCCGGCGAGGCCCC

GCCATCAGTTCCTGGGATTGGTTGGATATCAGTAGTGTGAATAGCCTTGCTGAGGTGCATCGCCTGTA

TGTGGGTGGACCCCCACTTGAGAAAGAGCCTAGGGAGCTCTTCGTCAAAGGCACCATGAAGGATATTA

GAGAGAATTTTCAAGATCTCATGCAATACTGCGCACAAGACGTATGGGCAACGCATGAGGTCTTTCAA

CAGCAACTCCCCCTCTTTTTGGAACGATGTCCACATCCCGTCACTCTTGCTGGGATGTTGGAAATGGG

TGTAAGTTATTTGCCAGTCAATCAAAATTGGGAGAGATACTTGGCTGAAGCGCAGGGTACATATGAGG

AACTTCAGCGAGAAATGAAAAAAAGTCTTATGGATTTGGCCAATGACGCCTGCCAGCTGCTTTCCGGT

GAGCGGTACAAAGAAGATCCATGGCTTTGGGATCTCGAATGGGATTTGCAGGAATTTAAACAGAAAAA

GGCCAAGAAGGTCAAGAAAGAGCCAGCTACAGCCTCAAAGCTCCCTATAGAGGGAGCGGGAGCACCGG

GTGATCCGATGGATCAAGAGGATTTGGGACCTTGCTCCGAAGAGGAGGAATTCCAACAAGATGTAATG

GCAAGGGCCTGCCTGCAAAAGCTCAAAGGGACAACAGAACTCTTGCCCAAGAGGCCTCAACATCTGCC

CGGCCATCCAGGTTGGTATCGCAAACTCTGTCCAAGGCTGGACGATCCCGCCTGGACCCCGGGGCCCT

CCCTTCTGAGTCTGCAGATGAGAGTGACACCTAAGCTGATGGCACTTACTTGGGATGGGTTCCCTCTT

CACTATTCAGAGAGACACGGGTGGGGATATCTTGTCCCAGGTCGAAGGGACAATCTGGCGAAGCTTCC

CACAGGAACTACCTTGGAGAGTGCGGGCGTAGTATGTCCTTATCGAGCCATAGAAAGTCTGTATAGAA

AGCATTGCCTTGAACAAGGCAAACAACAACTCATGCCTCAGGAAGCCGGCCTCGCTGAAGAATTTCTT

CTTACTGATAACTCTGCTATCTGGCAAACAGTGGAGGAACTGGATTACCTCGAAGTCGAGGCCGAAGC

GAAGATGGAAAATTTGCGGGCGGCGGTCCCAGGTCAGCCCCTTGCTTTGACAGCACGGGGGGCCCTA

AGGATACCCAGCCCAGCTATCATCACGGGAACGGTCCATATAATGATGTTGATATACCTGGTTGTTGG

TTTTTTAAACTTCCTCATAAAGATGGCAATTCATGTAACGTTGGATCCCCATTCGCAAAGGACTTCCT

CCCCAAAATGGAGGATGGGACGTTGCAAGCAGGTCCCGGTGGAGCTTCTGGGCCGCGAGCCCTGGAAA

TAAATAAGATGATTAGCTTCTGGAGGAATGCACACAAGCGCATTTCTTCACAGATGGTAGTGTGGCTG

CCTCGGAGTGCTTTGCCCAGGGCTGTGATCAGACACCCCGATTATGATGAAGAGGGACTGTACGGGGC

AATATTGCCCCAGGTGGTTACGGCTGGTACTATTACCCGCCGGGCAGTTGAGCCGACCTGGCTGACAG

CATCTAATGCCAGGCCTGATCGCGTGGGTTCTGAACTTAAAGCAATGGTCCAAGCTCCGCCTGGATAC

```
                                 -continued
ACGCTTGTCGGCGCGGACGTGGACTCCCAGGAACTTTGGATAGCGGCTGTCCTTGGCGATGCACATTT

TGCAGGGATGCACGGGTGCACGGCTTTTGGCTGGATGACACTTCAGGGGAGGAAATCAAGGGGGACCG

ACCTGCACTCCAAGACCGCGACAACGGTAGGAATCTCAAGGGAACACGCTAAAATTTTCAATTATGGG

AGAATATATGGTGCCGGTCAACCGTTCGCTGAGCGCCTTCTGATGCAGTTTAACCATAGGCTGACACA

GCAGGAGGCAGCGGAGAAGGCGCAGCAGATGTACGCCGCAACTAAGGGTCTCAGATGGTATCGCCTCT

CAGACGAGGGCGAGTGGCTTGTCCGGGAATTGAACCTCCCGGTCGATCGGACGGAAGGTGGTTGGATT

AGTCTTCAGGATCTCAGAAAGGTGCAGCGGGAAACAGCACGCAAGTCTCAGTGGAAGAAATGGGAGGT

GGTCGCCGAGCGGGCATGGAAGGGTGGAACAGAATCCGAGATGTTTAACAAGCTGGAGAGCATAGCAA

CTAGTGACATCCCTAGGACACCGGTCTTGGGATGTTGCATTAGCCGGGCACTCGAGCCATCTGCCGTA

CAGGAAGAATTCATGACGTCACGGGTCAACTGGGTTGTCCAGTCTTCAGCCGTCGATTATCTGCATTT

GATGCTGGTCGCGATGAAGTGGCTCTTCGAAGAGTTTGCTATAGATGGCCGATTTTGCATCTCTATTC

ACGATGAGGTGCGCTACCTGGTAAGGGAAGAAGACCGATACCGAGCCGCCCTCGCCCTTCAGATAACA

AATCTGCTTACCAGGTGTATGTTTGCATACAAGCTGGGGTTGAACGACCTTCCCCAGTCCGTCGCTTT

CTTTTCAGCTGTTGATATAGATCGCTGCCTGAGAAAAGAGGTTACGATGGACTGCAAAACGCCCTCAA

ACCCCACTGGTATGGAGCGCAGATATGGCATCCCCCAAGGAGAAGCCCTCGACATATACCAGATAATT

GAGCTCACGAAGGGCAGCCTGGAGAAGAGATCCCAACCTGGCCCATAG
```

Exemplary Recombinant AAV Compositions

The current disclosure provides for compositions containing a recombinant AAV containing a nucleic acid sequence that encodes a functional protein. Such proteins include, without limitation, TK2, dGK, p53R2, TP, SUCLA2, SUCLG1, POLG1, and a mitochondrial membrane protein MPV17. In some embodiments, the rAAV comprises a chicken beta-actin promoter. In some embodiments, the rAAV further comprises a CMV enhancer. In some embodiments, the rAAV further comprises ITRs. In some embodiments, the rAAV further comprises a 3'UTR. In some embodiments, the rAAV is AAV 2 or AAV9. In some embodiments, the transgene encodes a functional TK2 enzyme.

Figure 1:
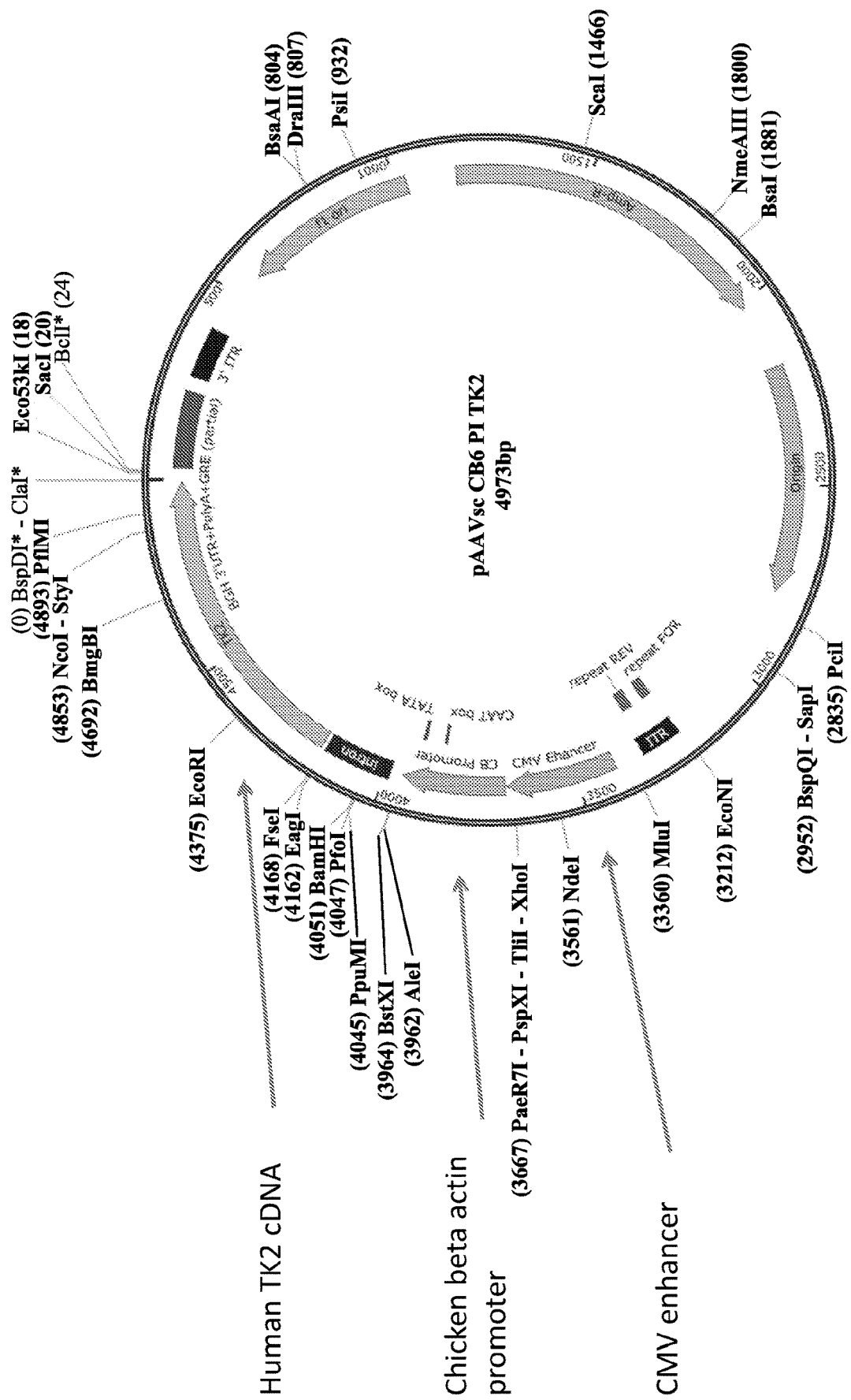
FIG. 1 is a schematic of a recombinant adeno-associated virus (AAV) vector comprising human TK2 cDNA.

An exemplary rAAV-hTK2 vector comprising the human TK2 transgene, a chicken beta-actin promoter, a CMV IE enhancer, a BGH 3'UTR, a poly A signal, and a 5' and 3'ITR is shown in FIG. 1.

Both an rAAV9-hTK2 and an rAAV2-hTK2 vector were used in the Examples. These constructs have the same ITR but different capsid protein sequences.

In some embodiments, the composition further comprises a pharmaceutical carrier.

In some embodiments, the composition comprises more than one rAAV comprising a transgene that encodes a functional protein including but not limited to TK2, dGK, p53R2, TP, SUCLA2, SUCLG1, POLG1, and a mitochondrial membrane protein MPV17.

Routes of Administration and Dosing

The current invention provides rAAV vectors for use in methods of treating, preventing, and/or curing a disease or disorder characterized by unbalanced nucleotide pools, and/or restoring function of a protein that is dysfunctional in a disease or disorder characterized by unbalanced nucleotide pools, and/or alleviating in a subject at least one of the symptoms associated with unbalanced nucleotide pools. In some embodiments, methods involve administration of a rAAV vector that encodes one or more therapeutic peptides, polypeptides, shRNAs, microRNAs, or antisense nucleotides, in a pharmaceutically-acceptable carrier to the subject in an amount and for a period of time sufficient to treat, prevent and/or cure the disease or disorder characterized by unbalanced nucleotide pools in the subject having or suspected of having such a disorder.

Diseases or disorders characterized by unbalanced nucleotide pools that can be treated, prevented and/or cured by the method of the current invention include, but are not limited to, those characterized by mutations in the following genes: TK2; DGUOK; TYMP; RRM2B; SUCLA2; SUCLG1; and MPV17. The proteins encoded by these genes can be restored by the method of the invention and include but are not limited to TK2, dGK, p53R2, TP, SUCLA2, SUCLG1, POLG1, and a mitochondrial membrane protein MPV17.

The rAAVs may be delivered to a subject in compositions according to any appropriate methods known in the art. The rAAV, preferably suspended in a physiologically compatible carrier (e.g., in a composition), may be administered to a subject. In certain embodiments, compositions may comprise a rAAV alone, or in combination with one or more other viruses (e.g., a second rAAV encoding having one or more different transgenes). In one embodiment, a composition can comprise an rAAV9 vector comprising a nucleic acid sequence comprising a transgene encoding a functional protein including but not limited to TK2, dGK, p53R2, TP, SUCLA2, SUCLG1, POLG1, and a mitochondrial membrane protein MPV17.

In a further embodiment, a composition can comprise an rAAV2 vector comprising a nucleic acid sequence comprising a transgene encoding a functional protein including but not limited to TK2, dGK, p53R2, TP, SUCLA2, SUCLG1, POLG1, and a mitochondrial membrane protein MPV17.

In yet a further embodiment, a composition can comprise an rAAV9 vector comprising a nucleic acid sequence comprising a transgene encoding a functional TK2. In a further embodiment, a composition can comprise an rAAV2 vector comprising a nucleic acid sequence comprising a transgene encoding a functional TK2. In a further embodiment, a composition can comprise an rAAV9 vector comprising a nucleic acid sequence comprising a transgene encoding TK2 and an rAAV2 vector comprising a nucleic acid sequence comprising a transgene encoding TK2.

Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present invention.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

In some embodiments, rAAV compositions are formulated to reduce aggregation of AAV particles in the composition, particularly where high rAAV concentrations are present (e.g., about $10^{13}$ GC/ml or more). Methods for reducing aggregation of rAAVs are well known in the art and, include, for example, addition of surfactants, pH adjustment, and salt concentration adjustment (see, e.g., Wright, et al., *Molecular Therapy* 12:171-178 (2005).

Formulation of pharmaceutically-acceptable excipients and carrier solutions is well-known to those of skill in the art, as is the development of suitable dosing and treatment regimens for using the particular compositions described herein in a variety of treatment regimens. Typically, these formulations may contain at least about 0.1% of the active ingredient or more, although the percentage of the active ingredient(s) may, of course, be varied and may conveniently be between about 1 or 2% and about 70% or 80% or more of the weight or volume of the total formulation. Naturally, the amount of active ingredient in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion. Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In addition to the methods of delivery described above, the following techniques are also contemplated as alternative methods of delivering the rAAV compositions to a host. Sonophoresis (i.e., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations, transdermal matrices (U.S. Pat. Nos. 5,770,219 and 5,783,208) and feedback-controlled delivery (U.S. Pat. No. 5,697,899).

rAAVS are administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected tissue (e.g., intracerebral administration, intrathecal administration), intravenous, oral, inhalation (including intranasal and intratracheal delivery), intraocular, intravenous, intramuscular, subcutaneous, intradermal, and other parental routes of administration. Routes of administration may be combined, if desired. The administration regimen depends on several factors, including the serum or tissue turnover rate of the therapeutic composition, the level of symptoms, and the accessibility of the target cells in the biological matrix. Preferably, the administration regimen delivers sufficient therapeutic composition to effect improvement in the target disease state, while simultaneously minimizing undesired side effects. Accordingly, the amount of biologic delivered depends in part on the particular therapeutic composition and the severity of the condition being treated.

The present invention provides stable pharmaceutical compositions comprising rAAV virions. The compositions remain stable and active even when subjected to freeze/thaw cycling and when stored in containers made of various materials, including glass.

Appropriate doses will depend on the subject being treated (e.g., human or nonhuman primate or other mammal), age and general condition of the subject to be treated, the severity of the condition being treated, the mode of administration of the rAAV virions, among other factors. An appropriate effective amount can be readily determined by one of skill in the art.

The dose of rAAV virions required to achieve a desired effect or "therapeutic effect," e.g., the units of dose in vector genomes/per kilogram of body weight (vg/kg), will vary based on several factors including, but not limited to: the route of rAAV administration; the level of gene or RNA expression required to achieve a therapeutic effect; the specific disease or disorder being treated; and the stability of the gene or RNA product. One of skill in the art can readily determine a rAAV virion dose range to treat a subject having a particular disease or disorder based on the aforementioned factors, as well as other factors that are well known in the art. An effective amount of the rAAV is generally in the range of from about 10 µl to about 100 ml of solution containing from about $10^9$ to $10^{16}$ genome copies per subject. Other volumes of solution may be used. The volume used will typically depend, among other things, on the size of the subject, the dose of the rAAV, and the route of administration. For example, for intrathecal or intracerebral administration a volume in range of 1 µl to 10 µl or 10 µl to 100 µl may be used. For intravenous administration a volume in range of 10 µl to 100 100 µl to 1 ml, 1 ml to 10 ml, or more may be used. In some cases, a dosage between about $10^{10}$ to $10^{12}$ rAAV genome copies per subject is appropriate. In certain embodiments, $10^{12}$ rAAV genome copies per subject is effective to target desired tissues. In some embodiments the rAAV is administered at a dose of $10^{10}$, $10^{11}$, $10^{12}$, $10^{13}$, $10^{14}$, or $10^{15}$ genome copies per subject. In some embodiments the rAAV is administered at a dose of $10^{10}$, $10^{11}$, $10^{12}$, $10^{13}$, or $10^{14}$ genome copies per kg.

Thus, a "therapeutically effective amount" will fall in a relatively broad range that can be determined through clinical trials. For example, for in vivo injection, i.e., injection directly to the subject, a therapeutically effective dose will be on the order of from about $10^5$ to $10^{16}$ of the rAAV virions, more preferably $10^8$ to $10^{14}$ rAAV virions. For in vitro transduction, an effective amount of rAAV virions to be delivered to cells will be on the order of $10^5$ to $10^{13}$, preferably $10^8$ to $10^{13}$ of the rAAV virions. If the composition comprises transduced cells to be delivered back to the subject, the amount of transduced cells in the pharmaceutical compositions will be from about $10^4$ to $10^{10}$ cells, more preferably $10^5$ to $10^8$ cells. The dose, of course, depends on the efficiency of transduction, promoter strength, the stability of the message and the protein encoded thereby, etc. Effective dosages can be readily established by one of ordinary skill in the art through routine trials establishing dose response curves.

Dosage treatment may be a single dose schedule or a multiple dose schedule to ultimately deliver the amount specified above. Moreover, the subject may be administered as many doses as appropriate. Thus, the subject may be given, e.g., $10^5$ to $10^{16}$ rAAV virions in a single dose, or two, four, five, six or more doses that collectively result in delivery of, e.g., $10^5$ to $10^{16}$ rAAV virions. One of skill in the art can readily determine an appropriate number of doses to administer.

Pharmaceutical compositions will thus comprise sufficient genetic material to produce a therapeutically effective amount of the protein of interest, i.e., an amount sufficient to reduce or ameliorate symptoms of the disease state in question or an amount sufficient to confer the desired benefit. Thus, rAAV virions will be present in the subject compositions in an amount sufficient to provide a therapeutic effect when given in one or more doses. The rAAV virions can be provided as lyophilized preparations and diluted in the virion-stabilizing compositions for immediate or future use. Alternatively, the rAAV virions may be provided immediately after production and stored for future use.

The pharmaceutical compositions will also contain a pharmaceutically acceptable excipient or carriers. Such excipients include any pharmaceutical agent that does not itself induce the production of antibodies harmful to the individual receiving the composition, and which may be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in *Remington's Pharmaceutical Sciences* and *U.S. Pharmacopeia: National Formulary*, Mack Publishing Company, Easton, PA (1984).

Formulations of therapeutic and diagnostic agents may be prepared by mixing with acceptable carriers, excipients, or stabilizers in the form of, e.g., lyophilized powders, slurries, aqueous solutions or suspensions.

Toxicity and therapeutic efficacy of the therapeutic compositions, administered alone or in combination with another agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). In particular aspects, therapeutic compositions exhibiting high therapeutic indices are desirable. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

Determination of the appropriate dose is made by the clinician, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that a biologic that will be used is derived from the same species as the animal targeted for treatment, thereby minimizing any immune response to the reagent.

A preferred route of administration of the AAVs is intravenously.

A preferred dose ranges from about $1\times10^{10}$ to about $8\times10^{11}$, from about $2\times10^{10}$ to about $6\times10^{11}$, from about $4\times10^{11}$ to about $4\times10^{11}$ genome or viral copy (vc) total administration. A preferred dose is about $4\times10^{11}$ genome or viral copy (vc) total administration of rAAV.

If more than one rAAV is used a preferred total dose of vector ranges from about $1\times10^{10}$ to about $6\times10^{11}$, from about $2\times10^{10}$ to about $5\times10^{11}$, from about $1\times10^{10}$ to about $4\times10^{11}$ genome or viral copy (vc) total administration. A preferred dose of total vector is about $3\times10^{11}$. The AAV can be administered in equal amounts, e.g., ratio of 50/50, or in or in ratios of about 5/95, 10/90, 15/85, 20/80, 25/75, 30/70, 35/65, 40/60, 45/55, 55/45, 60/40, 65/35, 70/30, 75/25, 80/20, 85/15, 90/10, and 95/5.

Doses can be adjusted to optimize the effects in the subject. Additionally, a subject can be monitored for improvement of their condition prior to increasing the dosage. A subject's response to the therapeutic administration of the rAAV can be monitored by observing a subject's muscle strength and control, and mobility as well as changes in height and weight. If one or more of these parameters increase after the administration, the treatment can be continued. If one or more of these parameters stays the same or decreases, the dosage can be increased.

Pharmacological Therapy—Methods of Administration and Dosing

The present invention encompasses the administration of deoxynucleosides, and/or deoxyribonucleoside monophosphates, in combination with the administration of a composition containing a transgene encoding a protein described herein.

Most preferred methods of administration are oral, intrathecal and parental including intravenous. The deoxynucleosides or deoxyribonucleoside monophosphates must be in the appropriate form for administration of choice.

Deoxynucleosides or deoxyribonucleoside monophosphates are easily dissolved in liquid are easily dissolved in liquid (such as water, formula or milk) whereas the free acid form does not readily dissolve in liquid.

Such pharmaceutical compositions comprising one of more deoxynucleosides or deoxyribonucleoside monophosphates for administration may comprise a therapeutically effective amount of the deoxynucleosides or deoxyribonucleoside monophosphates and a pharmaceutically acceptable carrier. Such pharmaceutical carriers can be sterile liquids, such as saline solutions in water and oils, including those of petroleum, animal, vegetable, or synthetic origin, such as peanut oil, soybean oil, mineral oil, sesame oil, and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents.

Oral administration is a preferred method of administration. The deoxynucleosides or deoxyribonucleoside monophosphates can be added to any form of liquid a patient would consume including but not limited to, milk, both cow's and human breast, infant formula, and water.

Additionally, pharmaceutical compositions adapted for oral administration may be capsules, tablets, powders, granules, solutions, syrups, suspensions (in non-aqueous or aqueous liquids), or emulsions. Tablets or hard gelatin capsules may comprise lactose, starch or derivatives thereof, magnesium stearate, sodium saccharine, cellulose, magnesium carbonate, stearic acid or salts thereof. Soft gelatin capsules may comprise vegetable oils, waxes, fats, semisolid, or liquid polyols. Solutions and syrups may comprise water, polyols, and sugars. An active agent intended for oral administration may be coated with or admixed with a material that delays disintegration and/or absorption of the active agent in the gastrointestinal tract. Thus, the sustained release may be achieved over many hours and if necessary, the active agent can be protected from degradation within the stomach. Pharmaceutical compositions for oral administration may be formulated to facilitate release of an active agent at a particular gastrointestinal location due to specific pH or enzymatic conditions.

In order to overcome any issue of the deoxynucleosides or deoxyribonucleoside monophosphates crossing the blood/brain barrier, intrathecal administration is an additional preferred form of administration (Galbiati, et al. 2006; Gotz, et al. 2008). Intrathecal administration involves injection of the drug into the spinal canal, more specifically the subarachnoid space such that it reaches the cerebrospinal fluid. This method is commonly used for spinal anesthesia, chemotherapy, and pain medication. Intrathecal administration can be performed by lumbar puncture (bolus injection) or by a port-catheter system (bolus or infusion). The catheter is most commonly inserted between the laminae of the lumbar vertebrae and the tip is threaded up the thecal space to the desired level (generally L3-L4). Intrathecal formulations most commonly use water, and saline as excipients but EDTA and lipids have been used as well.

A further preferred form of administration is parenteral including intravenous administration. Pharmaceutical compositions adapted for parenteral administration, including intravenous administration, include aqueous and non-aqueous sterile injectable solutions or suspensions, which may contain anti-oxidants, buffers, bacteriostats, and solutes that render the compositions substantially isotonic with the blood of the subject. Other components which may be present in such compositions include water, alcohols, polyols, glycerine, and vegetable oils. Compositions adapted for parental administration may be presented in unit-dose or multi-dose containers, such as sealed ampules and vials, and may be stored in a freeze-dried (lyophilized) condition requiring only the addition of a sterile carrier, immediately prior to use. Extemporaneous injection solutions and suspensions may be prepared from sterile powders, granules, and tablets. Suitable vehicles that can be used to provide parenteral dosage forms of the invention are well known to those skilled in the art. Examples include: Water for Injection USP; aqueous vehicles such as Sodium Chloride Injection, Ringer's Injection, Dextrose Injection, Dextrose and Sodium Chloride Injection, and Lactated Ringer's Injection; water-miscible vehicles such as ethyl alcohol, polyethylene glycol, and polypropylene glycol; and non-aqueous vehicles such as corn oil, cottonseed oil, peanut oil, sesame oil, ethyl oleate, isopropyl myristate, and benzyl benzoate.

Additionally, since some patients may be receiving enteral nutrition by the time the deoxynucleoside or deoxyribonucleoside monophosphates treatment begins, the dNs or dNMPs can be administered through a gastronomy feeding tube or other enteral nutrition means.

Further methods of administration include mucosal, such as nasal, sublingual, vaginal, buccal, or rectal; or transdermal administration to a subject.

Pharmaceutical compositions adapted for nasal and pulmonary administration may comprise solid carriers such as powders, which can be administered by rapid inhalation through the nose. Compositions for nasal administration may comprise liquid carriers, such as sprays or drops. Alternatively, inhalation directly through into the lungs may be accomplished by inhalation deeply or installation through a mouthpiece. These compositions may comprise aqueous or oil solutions of the active ingredient. Compositions for inhalation may be supplied in specially adapted devices including, but not limited to, pressurized aerosols, nebulizers or insufflators, which can be constructed so as to provide predetermined dosages of the active ingredient.

Pharmaceutical compositions adapted for rectal administration may be provided as suppositories or enemas. Pharmaceutical compositions adapted for vaginal administration may be provided as pessaries, tampons, creams, gels, pastes, foams or spray formulations.

Pharmaceutical compositions adapted for transdermal administration may be provided as discrete patches intended to remain in intimate contact with the epidermis of the recipient over a prolonged period of time.

The deoxynucleoside therapy comprises the administration of one or more deoxynucleosides chosen from the group consisting of deoxythymidine (dT), deoxycytidine (dC), deoxyadenosine (dA) and deoxyguanosine (dG).

A skilled practitioner can determine which deoxynucleosides are beneficial based upon the deficiency. It is also within the skill of the art for the practitioner to determine if mixtures of the deoxynucleosides should be administered and in what ratio. If two deoxynucleosides are to be administered, they can be in a ratio of 50/50 of each deoxynucleoside, e.g., dC and dT, or in ratios of about 5/95, 10/90, 15/85, 20/80, 25/75, 30/70, 35/65, 40/60, 45/55, 55/45, 60/40, 65/35, 70/30, 75/25, 80/20, 85/15, 90/10, and 95/5.

By way of example, dT and dC are administered in mixture of equal amounts for TK2 deficiency.

The deoxyribonucleoside monophosphates therapy comprises the administration of one or more deoxyribonucleoside monophosphates chosen from the group consisting of TMP, dCMP, dAMP, and dGMP. If two deoxyribonucleoside monophosphates, ratios can be determined.

By way of example, TMP and dCMP are administered in mixture of equal amounts for TK2 deficiency.

Selection of a therapeutically effective dose will be determined by the skilled artisan considering several factors, which will be known to one of ordinary skill in the art. Such factors include the particular form of the deoxynucleoside or deoxyribonucleoside monophosphate, and its pharmacokinetic parameters such as bioavailability, metabolism, and half-life, which will have been established during the usual development procedures typically employed in obtaining regulatory approval for a pharmaceutical compound. Further factors in considering the dose include the condition or disease to be treated or the benefit to be achieved in a normal individual, the body mass of the patient, the route of administration, whether the administration is acute or chronic, concomitant medications, and other factors well known to affect the efficacy of administered pharmaceutical agents. Thus, the precise dose should be decided according to the judgment of the person of skill in the art, and each patient's circumstances, and according to standard clinical techniques.

A preferred dose ranges from about 100 mg/kg/day to about 1,000 mg/kg/day. A further preferred dose ranges from about 200 mg/kg/day to about 800 mg/kg/day. A further preferred dose ranges from about 250 mg/kg/day to about 400 mg/kg/day. These dosage amounts are of individual deoxynucleosides or deoxyribonucleoside monophosphates or of a composition with a mixture of more than one deoxynucleosides, e.g., dT and dC or deoxyribonucleoside monophosphates. For example, a dose can comprise 400 mg/kg/day of dT alone. In a further example, a dose can comprise a mixture of 200 mg/kg/day of dT and 200 mg/kg/day of dC. In a further example, a dose can comprise 400 mg/kg/day of a mixture of dT and dC.

Administration of the deoxynucleosides or deoxyribonucleoside monophosphates can be once a day, twice a day, three times a day, four times a day, five times a day, up to six times a day, preferably at regular intervals. For example, when the deoxynucleosides are administered four times daily, doses would be at 8:00 AM, 12:00 PM, 4:00 PM, and 8:00 PM.

Doses can also be lowered if being administered intravenously or intrathecally. Preferred dose ranges for such administration are from about 50 mg/kg/day to about 500 mg/kg/day.

As shown in the '092 application, doses can be adjusted to optimize the effects in the subject. For example, the deoxynucleosides can be administered at 100 mg/kg/day to start, and then increased over time to 200 mg/kg/day, to 400 mg/kg/day, to 800 mg/kg/day, up to 1000 mg/kg/day, depending upon the subject's response and tolerability.

A subject can be monitored for improvement of their condition prior to increasing the dosage. A subject's response to the therapeutic administration of the deoxynucleosides or deoxyribonucleoside monophosphates can be monitored by observing a subject's muscle strength and control, and mobility as well as changes in height and weight. If one or more of these parameters increase after the administration, the treatment can be continued. If one or more of these parameters stays the same or decreases, the dosage of the deoxynucleosides can be increased.

As shown in the prior patent applications, the pharmacological therapy is well tolerated. Any observed adverse effects were minor and were mostly diarrhea, abdominal bloating and other gastrointestinal manifestations. A subject can also be monitored for any adverse effects, such as gastrointestinal intolerance, e.g., diarrhea. If one or more adverse effects are observed after administration, then the dosage can be decreased. If no such adverse effects are observed, then the dosage can be increased. Additionally, once a dosage is decreased due to the observation of an adverse effect, and the adverse effect is no longer observed, the dosage can be increased.

The deoxynucleosides or deoxyribonucleoside monophosphates can also be co-administered with other agents. Such agents would include therapeutic agents for treating the symptoms of the particular form of MDS. In particular, for TK2 deficiency, the dT and dC can be co-administered with an inhibitor of ubiquitous nucleoside catabolic enzymes, including but not limited to enzyme inhibitors such as tetrahydrouridine (inhibitor of cytidine deaminase) and immucillin H (inhibitor of purine nucleoside phosphorylase) and tipiracil (inhibitor of thymidine phosphorylase). Such inhibitors are known and used in the treatment of some cancers.

Kits

The present invention also provides kits comprising the components of the combinations of the invention in kit form. A kit of the present invention includes one or more components including, but not limited to, viral vectors (e.g., AAV vectors) and/or pharmacological agents (e.g., deoxynucleosides and/or nucleoside monophosphates) described herein. Kits may further include a pharmaceutically acceptable carrier, as discussed herein. The viral vector or pharmacological agent can be formulated as a pure composition or in combination with a pharmaceutically acceptable carrier, in a pharmaceutical composition.

In some embodiments, a kit includes an AAV vector containing a transgene described herein in one container (e.g., in a sterile glass or plastic vial).

In some embodiments, a kit includes an AAV vector containing a transgene described herein in one container (e.g., in a sterile glass or plastic vial) and a second AAV vector encoding a transgene described herein in another container (e.g., in a sterile glass or plastic vial).

In some embodiments, a kit includes an AAV vector containing a transgene described herein in one container (e.g., in a sterile glass or plastic vial) and a pharmacological agent in another container (e.g., in a sterile glass or plastic vial).

In some embodiments, a kit includes an AAV2 vector containing a transgene described herein in one container (e.g., in a sterile glass or plastic vial) and a pharmacological agent in another container (e.g., in a sterile glass or plastic vial).

In some embodiments, a kit includes an AAV9 vector containing a transgene described herein in one container (e.g., in a sterile glass or plastic vial) and a pharmacological agent in another container (e.g., in a sterile glass or plastic vial).

In some embodiments, a kit includes an AAV vector encoding TK2, dGK, p53R2, TP, SUCLA2, SUCLG1, POLG1, and/or a mitochondrial membrane protein MPV17, or a pharmaceutical composition thereof in one container (e.g., in a sterile glass or plastic vial).

If the kit includes one or more pharmaceutical compositions for parenteral administration to a subject, the kit can include a device for performing such administration. For example, the kit can include one or more hypodermic needles or other injection devices as discussed above.

The kit can include a package insert including information concerning the pharmaceutical compositions and dosage forms in the kit. Generally, such information aids patients and physicians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

Exemplary Embodiments of the Invention Include:

1. A method of preventing or treating thymidine kinase 2 (TK2) deficiency in a subject in need thereof comprising administering to the subject a therapeutically effective amount of a composition comprising a recombinant adeno-associated vector (rAAV) comprising a nucleic acid sequence comprising a transgene encoding a functional TK2 protein.
2. The method of embodiment 1, wherein the rAAV is chosen from the group consisting of AAV9 and AAV2.
3. The method of embodiment 1, wherein the subject is a mammal
4. The method of embodiment 1, wherein the subject is a human.
5. The method of embodiment 1, wherein the composition is a pharmaceutical composition.
6. The method of embodiment 1, wherein the composition is the first composition comprising a first rAAV, wherein the first rAAV is AAV9 and further comprising administering a therapeutically effective amount of a second composition comprising a second rAAV comprising a nucleic acid sequence comprising a transgene encoding a functional TK2 protein, wherein the second rAAV is AAV2 and is administered at a time point after the administration of the first rAAV.
7. The method of embodiment 6, wherein the second composition is a pharmaceutical composition.
8. The method of embodiment 6, wherein the first composition is administered as soon as the subject is diagnosed with TK2 deficiency or suspected of having TK2 deficiency, and is continued to be administered during the administration of the second composition.
9. The method of embodiment 6, wherein the second composition is administered within days of the first composition.
10. The method of embodiment 6, wherein the second composition is administered within weeks of the first composition.
11. The method of embodiment 6, wherein the second composition is administered at least a month after the first composition.
12. The method of embodiment 6, further comprising administering a therapeutically effective amount of a third composition comprising a pharmacological agent chosen from the group consisting of deoxycytidine (dC), deoxythymidine (dT), and mixtures thereof.
13. The method of embodiment 12, wherein the third composition is administered at the same time point as the second composition.
14. The method of embodiment 12, wherein the third composition is administered at a later time point as the second composition.
15. The method of embodiment 12, wherein the therapeutically effective amount of the third composition is between about 100 mg/kg/day and about 1000 mg/kg/day.
16. The method of embodiment 12, wherein the therapeutically effective amount of the third composition is between about 200 mg/kg/day and about 800 mg/kg/day.
17. The method of embodiment 12, wherein the therapeutically effective amount of the third composition is between about 250 mg/kg/day and about 400 mg/kg/day.
18. The method of embodiment 12, wherein the third composition is administered once daily, twice daily, three times daily, four times daily, five times daily or six times daily.
19. The method of embodiment 12, wherein the third composition is administered orally, intrathecally, enterally, or intravenously.
20. The method of embodiment 19, wherein the third composition is administered orally and comprises deoxynucleoside mixed with cow's milk, human breast milk, infant formula or water.
21. A method of preventing or treating thymidine kinase 2 (TK2) deficiency in a subject in need thereof comprising administering to the subject a therapeutically effective amount of a first composition comprising a pharmacological agent, and further administering a therapeutically effective amount of a second composition comprising a recombinant adeno-associated vector (rAAV) comprising a nucleic acid sequence comprising a transgene encoding a functional TK2 protein.

22. The method of embodiment 21, wherein the pharmacological agent is chosen from the group consisting of deoxycytidine (dC), deoxythymidine (dT), and mixtures thereof; and deoxycytidine monophosphate (dCMP), deoxythymidine monophosphate (dTMP), and mixtures thereof.

23. The method of embodiment 21, wherein the rAAV is AAV9.

24. The method of embodiment 21, wherein the second composition is a pharmaceutical composition.

25. The method of embodiment 21, wherein the first composition is administered as soon as the subject is diagnosed with TK2 deficiency or suspected of having TK2 deficiency, and is continued to be administered during the administration of the second composition.

26. The method of embodiment 21, wherein the second composition is administered within days of the first composition.

27. The method of embodiment 21, wherein the second composition is administered within weeks of the first composition.

28. The method of embodiment 21, wherein the second composition is administered at least a month after the first composition.

29. The method of embodiment 21, wherein the therapeutically effective amount of the first composition is between about 100 mg/kg/day and about 1000 mg/kg/day.

30. The method of embodiment 21, wherein the therapeutically effective amount of the first composition is between about 200 mg/kg/day and about 800 mg/kg/day.

31. The method of embodiment 21, wherein the therapeutically effective amount of the first composition is between about 250 mg/kg/day and about 400 mg/kg/day.

32. The method of embodiment 21, wherein the first composition is administered once daily, twice daily, three times daily, four times daily, five times daily or six times daily.

33. The method of embodiment 21, wherein the first composition is administered orally, intrathecally, enterally, or intravenously.

34. The method of embodiment 33, wherein the first composition is administered orally and comprises the pharmacological agent mixed with cow's milk, human breast milk, infant formula or water.

35. The method of embodiment 21, further comprising the administration of a third composition comprising a second rAAV comprising a recombinant adeno-associated vector (rAAV) comprising a nucleic acid sequence comprising a transgene encoding a functional TK2 protein wherein the second rAAV is AAV2.

36. A method of restoring thymidine kinase 2 enzyme activity in a subject in need thereof comprising administering to the subject a therapeutically effective amount of a composition comprising a recombinant adeno-associated vector (rAAV) comprising a nucleic acid sequence comprising a transgene encoding a functional TK2 protein.

37. The method of embodiment 36, wherein the rAAV is chosen from the group consisting of AAV9 and AAV2.

38. The method of embodiment 36, wherein the subject is a mammal.

39. The method of embodiment 36, wherein the subject is a human

40. The method of embodiment 36, wherein the composition is a pharmaceutical composition.

41. The method of embodiment 36, wherein the composition is the first composition comprising a first rAAV, wherein the first rAAV is AAV9 and further comprising administering a therapeutically effective amount of a second composition comprising a second rAAV comprising a nucleic acid sequence comprising a transgene encoding a functional TK2 protein, wherein the second rAAV is AAV2 and is administered at a time point after the administration of the first rAAV.

42. The method of embodiment 41, wherein the second composition is a pharmaceutical composition.

43. The method of embodiment 41, wherein the first composition is administered as soon as the subject is diagnosed with TK2 deficiency or suspected of having TK2 deficiency, and is continued to be administered during the administration of the second composition.

44. The method of embodiment 41, wherein the second composition is administered within days of the first composition.

45. The method of embodiment 41, wherein the second composition is administered within weeks of the first composition.

46. The method of embodiment 41, wherein the second composition is administered at least a month after the first composition.

47. The method of embodiment 41, further comprising administering a therapeutically effective amount of a third composition comprising a pharmacological agent chosen from the group consisting of deoxycytidine (dC), deoxythymidine (dT), and mixtures thereof.

48. The method of embodiment 47, wherein the third composition is administered at the same time point as the second composition.

49. The method of embodiment 47, wherein the third composition is administered at a later time point as the second composition.

50. The method of embodiment 47, wherein the therapeutically effective amount of the third composition is between about 100 mg/kg/day and about 1000 mg/kg/day.

51. The method of embodiment 47, wherein the therapeutically effective amount of the third composition is between about 200 mg/kg/day and about 800 mg/kg/day.

52. The method of embodiment 47, wherein the therapeutically effective amount of the third composition is between about 250 mg/kg/day and about 400 mg/kg/day.

53. The method of embodiment 47, wherein the third composition is administered once daily, twice daily, three times daily, four times daily, five times daily or six times daily.

54. The method of embodiment 47, wherein the third composition administered orally, intrathecally, enterally, or intravenously.

55. The method of embodiment 54, wherein the third composition is administered orally and comprises deoxynucleoside mixed with cow's milk, human breast milk, infant formula or water.

56. A method of restoring thymidine kinase 2 enzyme activity in a subject in need thereof comprising administering to the subject a therapeutically effective amount of a first composition comprising a pharmacological agent, and further administering a therapeutically effective amount of a second composition comprising a recombinant adeno-associated vector (rAAV) comprising a nucleic acid sequence comprising a transgene encoding a functional TK2 protein.

57. The method of embodiment 56, wherein the pharmacological agent is chosen from the group consisting of deoxycytidine (dC), deoxythymidine (dT), and mixtures thereof; and deoxycytidine monophosphate (dCMP), deoxythymidine monophosphate (dTMP), and mixtures thereof.

58. The method of embodiment 56, wherein the rAAV is AAV9.

59. The method of embodiment 56, wherein the second composition is a pharmaceutical composition.

60. The method of embodiment 56, wherein the first composition is administered as soon as the subject is diagnosed with TK2 deficiency or suspected of having TK2 deficiency, and is continued to be administered during the administration of the second composition.

61. The method of embodiment 56, wherein the second composition is administered within days of the first composition.

62. The method of embodiment 56, wherein the second composition is administered within weeks of the first composition.

63. The method of embodiment 56, wherein the second composition is administered at least a month after the first composition.

64. The method of embodiment 56, wherein the therapeutically effective amount of the first composition is between about 100 mg/kg/day and about 1000 mg/kg/day.

65. The method of embodiment 56, wherein the therapeutically effective amount of the first composition is between about 200 mg/kg/day and about 800 mg/kg/day.

66. The method of embodiment 56, wherein the therapeutically effective amount of the first composition is between about 250 mg/kg/day and about 400 mg/kg/day.

67. The method of embodiment 56, wherein the first composition is administered once daily, twice daily, three times daily, four times daily, five times daily or six times daily.

68. The method of embodiment 56, wherein the first composition administered orally, intrathecally, enterally, or intravenously.

69. The method of embodiment 56, wherein the first composition is administered orally and comprises the pharmacological agent mixed with cow's milk, human breast milk, infant formula or water.

70. The method of embodiment 56, further comprising the administration of a third composition comprising a second rAAV comprising a recombinant adeno-associated vector (rAAV) comprising a nucleic acid sequence comprising a transgene encoding a functional TK2 protein wherein the second rAAV is AAV2.

71. A method of preventing or treating a disease or disorder characterized by unbalanced nucleotide pools in a subject in need thereof comprising administering to the subject a therapeutically effective amount of a composition comprising a recombinant adeno-associated vector (rAAV) comprising a nucleic acid sequence comprising a transgene chosen from the group consisting of TK2; DGUOK; TYMP; RRM2B; SUCLA2; SUCLGJ; and MPV17.

72. A method of preventing or treating a disease or disorder characterized by unbalanced nucleotide pools in a subject in need thereof comprising administering to the subject a therapeutically effective amount of a first composition comprising a pharmacological agent, and further administering a therapeutically effective amount of a second composition comprising a recombinant adeno-associated vector (rAAV) comprising a nucleic acid sequence comprising a transgene chosen from the group consisting of TK2; DGUOK; TYMP; RRM2B; SUCLA2; SUCLGJ; and MPV17.

73. The method of embodiment 72, wherein the pharmacological agent is chosen from the group consisting of deoxycytidine (dC), deoxythymidine (dT), deoxyadenosine (dA), deoxyguanosine (dG), and mixtures thereof; and deoxycytidine monophosphate (dCMP), deoxythymidine monophosphate (dTMP), deoxyadenosine monophosphate (dAMP), deoxyguanosine monophosphate (dGMP) and mixtures thereof.

74. A method of restoring enzyme activity in a disease or disorder characterized by unbalanced nucleotide pools in a subject in need thereof comprising administering to the subject a therapeutically effective amount of a composition comprising a recombinant adeno-associated vector (rAAV) comprising a nucleic acid sequence comprising a transgene chosen from the group consisting of TK2; DGUOK; TYMP; RRM2B; SUCLA2; SUCLGJ; and MPV17.

75. A method of restoring enzyme activity in a disease or disorder characterized by unbalanced nucleotide pools in a subject in need thereof comprising administering to the subject a therapeutically effective amount of a first composition comprising a pharmacological agent, and further administering a therapeutically effective amount of a second composition comprising a recombinant adeno-associated vector (rAAV) comprising a nucleic acid sequence comprising a transgene chosen from the group consisting of TK2; DGUOK; TYMP; RRM2B; SUCLA2; SUCLGJ; and MPV17.

76. The method of embodiment 75, wherein the pharmacological agent is chosen from the group consisting of deoxycytidine (dC), deoxythymidine (dT), deoxyadenosine (dA), deoxyguanosine (dG), and mixtures thereof; and deoxycytidine monophosphate (dCMP), deoxythymidine monophosphate (dTMP), deoxyadenosine monophosphate (dAMP), deoxyguanosine monophosphate (dGMP) and mixtures thereof.

EXAMPLES

The present invention may be better understood by reference to the following non-limiting examples, which are presented in order to more fully illustrate the preferred embodiments of the invention. They should in no way be construed to limit the broad scope of the invention.

Example 1

Materials and Methods

Mouse Model of TK2 Deficiency

A homozygous Tk2 H126N knock-in mutant (Tk2$^{-/-}$) mouse that manifests a phenotype strikingly similar to the human infantile encephalomyopathy has been previously reported (Akman, et al. 2008). Between postnatal day 10 and 13, Tk2$^{-/-}$ mice rapidly develop fatal encephalomyopathy characterized by decreased ambulation, unstable gait, coarse tremor, growth retardation, and rapid progression to early death at age 14 to 16 days. Molecular and biochemical analyses of the mouse model demonstrated that the pathogenesis of the disease is due to loss of enzyme activity and ensuing dNTP pool imbalances with decreased dTTP levels in brain and both dTTP and dCTP levels in liver, which, in turn, produces mtDNA depletion and defects of respiratory chain enzymes containing mtDNA-encoded subunits, most prominently in the brain and spinal cord.

All experiments were performed according to a protocol approved by the Institutional Animal Care and Use Committee of the Columbia University Medical Center, and were consistent with the National Institutes of Health Guide for the Care and Use of Laboratory Animals Mice were housed and bred according to international standard conditions, with a 12-hour light, 12-hour dark cycle, and sacrificed at 4, 13, and 29 days of age.

Organs (brain, spinal cord, liver, heart, kidney, quadriceps muscle, lung, and gastrointestinal tract) were removed and either frozen in the liquid phase of isopentane, pre-cooled near its freezing point (−160° C.) with dry ice or fixed in 10% neutral buffered formalin and embedded in paraffin using standard procedures. Paraffin embedded tissue were then stained with hematoxylin and eosin (H&E) for morphological study or processed for immunostaining studies with GFAP, COX I, or complex I. Both heterozygous and homozygous wild type mice were considered as control group ($Tk2^+$) since no clinical and biochemical difference were previously described (Akman, et al. 2008; Dorado, et al. 2011).

hTK2 Construct

The vector comprising the human TK2 gene (pAAVsc CB6 PI TK2 is shown in FIG. 1). Key components of the construct include the human TK2 cDNA as well as 5'ITR, CMV IE enhancer, chicken beta actin promoter, BGH 3'UTR, Poly A signal, GRE, and 3' ITR.

This vector was encapsulated in both AAV9 and AAV2 capsids for the subsequent experiments.

Gene Therapy Administration

Based upon previous results using an AAV9-GFP vector in wild-type mice and analyzing the distribution of the vector showed that AAV9 virus does not target the brain when administered I.P. (Results not shown.) Based upon this work, the administration of the AAV9-hTK2 construct was done by intravenous (IV) injection.

The AAV9-hTK2 was administered via IV with a retro-orbital injection of a total volume of 35 µl of PBS 1× containing about $4.2 \times 10^{11}$ or $4.2 \times 10^{10}$ genome or vector copies at postnatal day 1.

Alternatively, AAV9-hTK2 was administered via IV with a retro-orbital injection of 35 µL of PBS 1× containing about $2.1 \times 10^{11}$ vector copies at postnatal day 1, followed by administration of 100 µL of AAV2-hTK2 via IV with a tail vein injection containing about $1.05 \times 10^{11}$ vector copies at day 29 and with and without supplementation with 520 mg/kg/day of oral dC+dT (in drinking water) from day 21 assuming a water consumption of 4 ml/day/mouse.

Pharmacological Treatment Administration and Experimental Plan

Deoxycytidine (dC) and deoxythymidine (dT) are administered in 50 µl of Esbilac milk formula for small pets (Pet-Ag) by daily oral gavage to $Tk2^{-/-}$ and aged matched control wild-type ($Tk2^+$) using a dose of 520 mg/kg/day, from postnatal day 4 to 29 days. At age postnatal 21 days, mice are separated from the mother and the treatment was continued by administration of dC and dT in drinking water assuming a water consumption of 4 ml/day/mouse. A negative control group of untreated Tk2 mutant and control wild-type mice are weighed and observed closely for comparison.

Deoxycytidine monophosphate (dCMP) and deoxythymidine monophosphate (TMP) (Hongene Biotech, Inc.) are administered in 50 µl of Esbilac milk formula for small pets (Pet-Ag) by daily oral gavage to Tk2 H126N knock-in mice ($Tk2^{-/-}$) and aged-matched control wild-type ($Tk2+$) using 2 doses, 200 mg/kg/day and 400 mg/kg/day, from postnatal day 4 to 29 days. At age 29 days, mice are separated from the mother and the treatment is continued by administration of dCMP and TMP in drinking water using a dose of 400 mg/kg/day.

Phenotype Assessment

Body weight was assessed daily, since it has been previously observed that incapacity of gaining weight is the first sign of disease (Akman, et al. 2008).

To define the degree of safety and efficacy of the gene therapy, survival time, age-at-onset of disease, type and severity of symptoms, occurrence of side effects, and proportion of treatment termination due to adverse events in treated and untreated Tk2 mice were compared. General behavior, survival time, and body weights of the mice were assessed daily beginning at postnatal day 4.

TK2 Enzyme Measurement

The activity of TK2 enzyme was measured as previously described in Franzolin, et al. 2006.

mtDNA Copy Number Measurement mtDNA copy number was measured as previously described in Spinazzola, et al. 2006

Mitochondrial Respiratory Chain Enzyme Activities

Mitochondrial RC enzymes analysis was performed in cerebrum tissue as previously described (DiMauro, et al. 1987; Birch-Machin, et al. 1994; Quinzii, et al. 2013).

Statistical Methods

Data are expressed as the mean±SD of at least 3 experiments per group. Gehan-Breslow-Wilcoxon test was used to compare the survival proportion of each group of mice. A p-value of <0.05 was considered to be statistically significant.

Example 2

Administration of AAV9-hTK2 Resulted in Prolonged Lifespan

The mutant mice described in Example 1 were administered via IV with a retro-orbital injection at postnatal day 1 with the AAV9-hTK2 construct (containing about $4.2 \times 10^{11}$ or $4.2 \times 10^{10}$ genome or vector copies) also described in Example 1.

Figure 2:
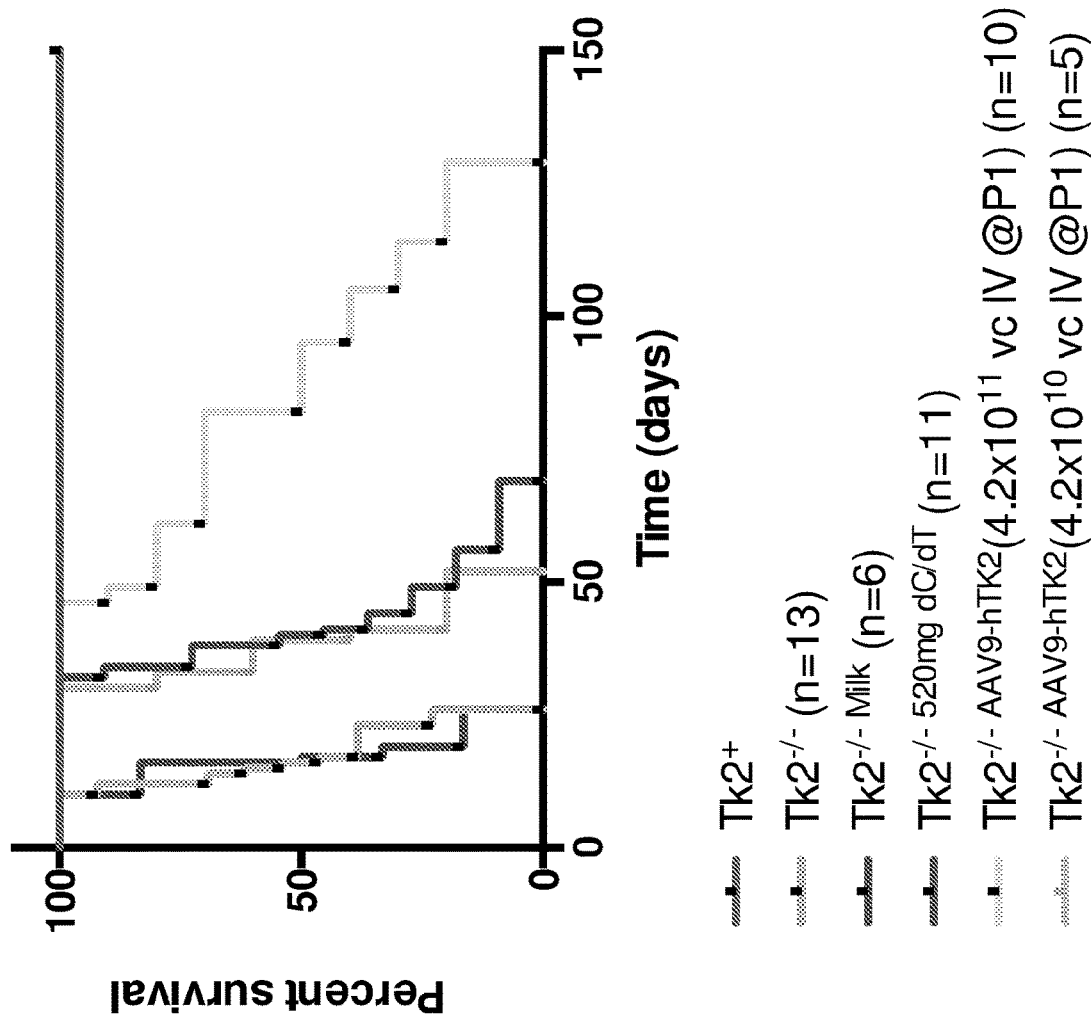
FIG. 2 shows the survival curves of the following mice (curves from left to right): $Tk2^{-/-}$ mice untreated (n=13); $Tk2^{-/-}$ mice administered milk only (n=6); $Tk2^{-/-}$ mice treated with AAV9-hTK2 at $4.2\times10^{10}$ vc by IV at postnatal day 1 (n=5); $Tk2^{-/-}$ mice treated with 520 mg of dC+dT (n=11); and $Tk2^{-/-}$ mice treated with AAV9-hTK2 at $4.2\times10^{11}$ vc by IV at postnatal day 1 (n=10). Survival of untreated Tk2+ (wild-type) is shown by the top horizontal line.

Treatment with AAV9-hTK2 resulted in a dose-dependent response with administration of $4.2 \times 10^{10}$ vc prolonging lifespan up to 3-fold (average of 39 days), similar to 520 mg/kg/day of dC+dT therapy. Administration of $4.2 \times 10^{11}$ vc prolonged lifespan up to 6-fold (average of 89 days) with a maximum of 129 days. See FIG. 2

Example 3

Administration of AAV9-hTK2 Resulted in Increased Growth, Strength and Motor Function in Mutant Mice The mice described in Example 1 were treated as described in Example 1 with the AAV9-hTK2 construct also described in Example 1.

The $Tk2^{-/-}$ mice treated with the lower dose of AAV9-hTK2 ($4.2 \times 10^{10}$ vc) grew at the same rate as those $Tk2^{-/-}$ mice treated with 520 mg/kg/day of dC+dT. They also grew at the same rate as $Tk2^+$ mice until postnatal day 20, when they reached a plateau.

The Tk2$^{-/-}$ mice treated with the higher dose of AAV9-hTK2 (4.2×10$^{11}$vc) grew at the same rate as Tk2$^+$ mice until P30.

Figure 3:
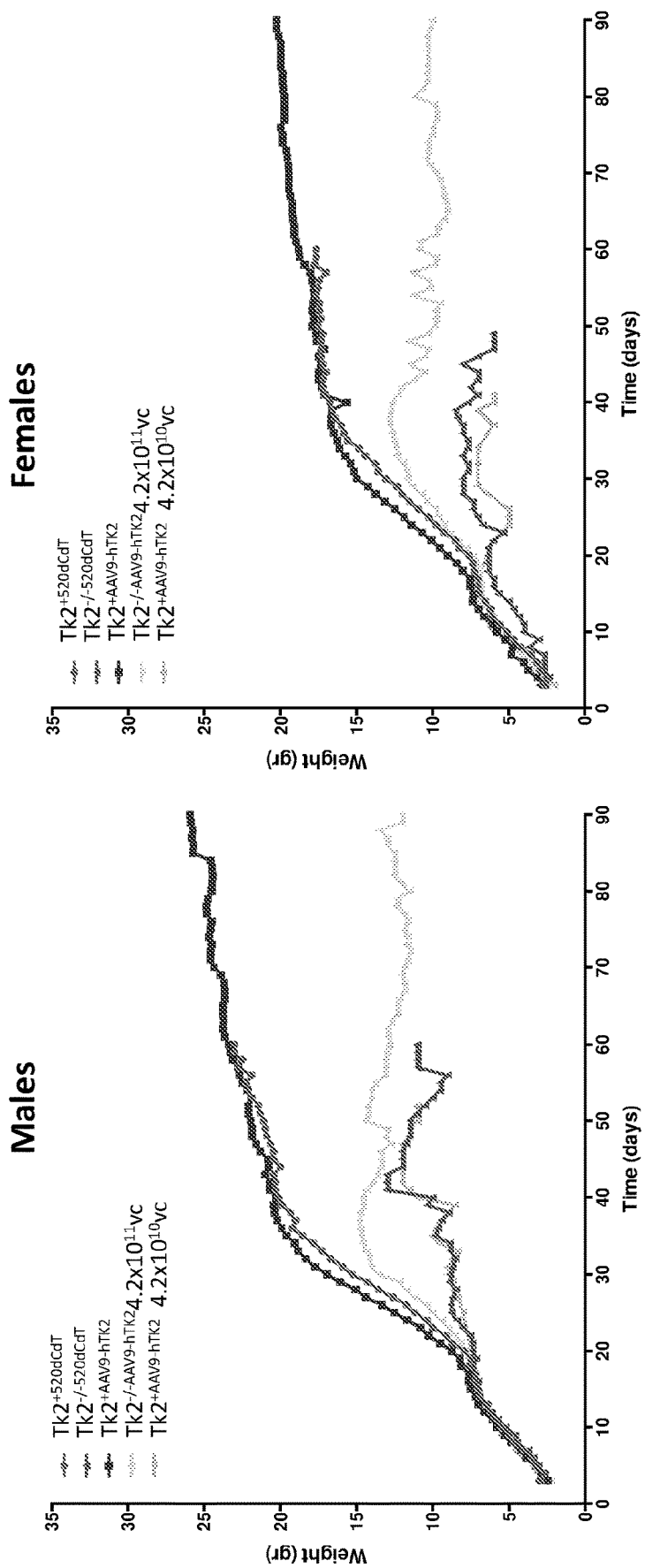
FIG. 3 shows graphs of weight versus time in the following male and female mice: Tk2+ treated with 520 mg of dC+dT; $Tk2^{-/-}$ mice treated with 520 mg of dC+dT; Tk2+ treated AAV9-hTK2; $Tk2^{-/-}$ mice treated with AAV9-hTK2 at $4.2\times10^{11}$ vc by IV at postnatal day 1; and $Tk2^{-/-}$ mice treated with AAV9-hTK2 at $4.2\times10^{10}$ vc by IV at postnatal day 1.

No differences were found between untreated Tk2$^+$, and Tk2$^+$ treated with the higher dose of AAV9-hTK2 (4.2×10$^{11}$vc). See FIG. 3.

Figure 4:
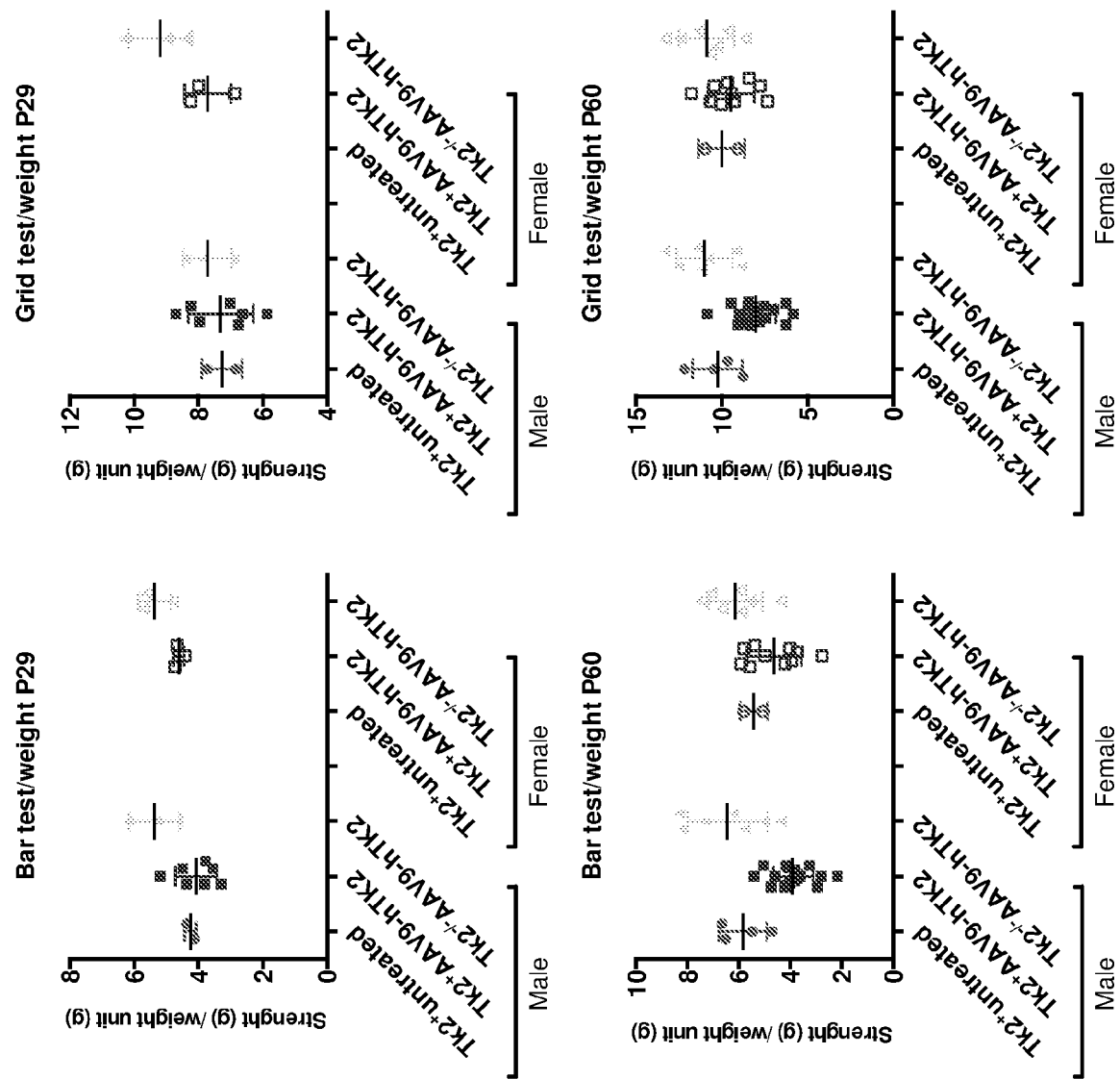
FIG. 4 shows graphs of the result of grip strength test of the fore limbs (bar test) and both fore and hind limbs (grid test) normalized by mouse weight at postnatal day 29 and postnatal day 60 of male and female mice including untreated Tk2+, Tk2+ treated with AAV9-hTK2 and $Tk2^{-/-}$ mice treated with AAV9-hTK2.

The Tk2$^{-/-}$ mice treated with 4.2×10$^{11}$ vc at P1 showed no differences in strength compared to untreated or AAV9-hTK2 treated wild-type mice. Strength was normalized by weight and measured at P29 and P60. See FIG. 4.

Figure 5:
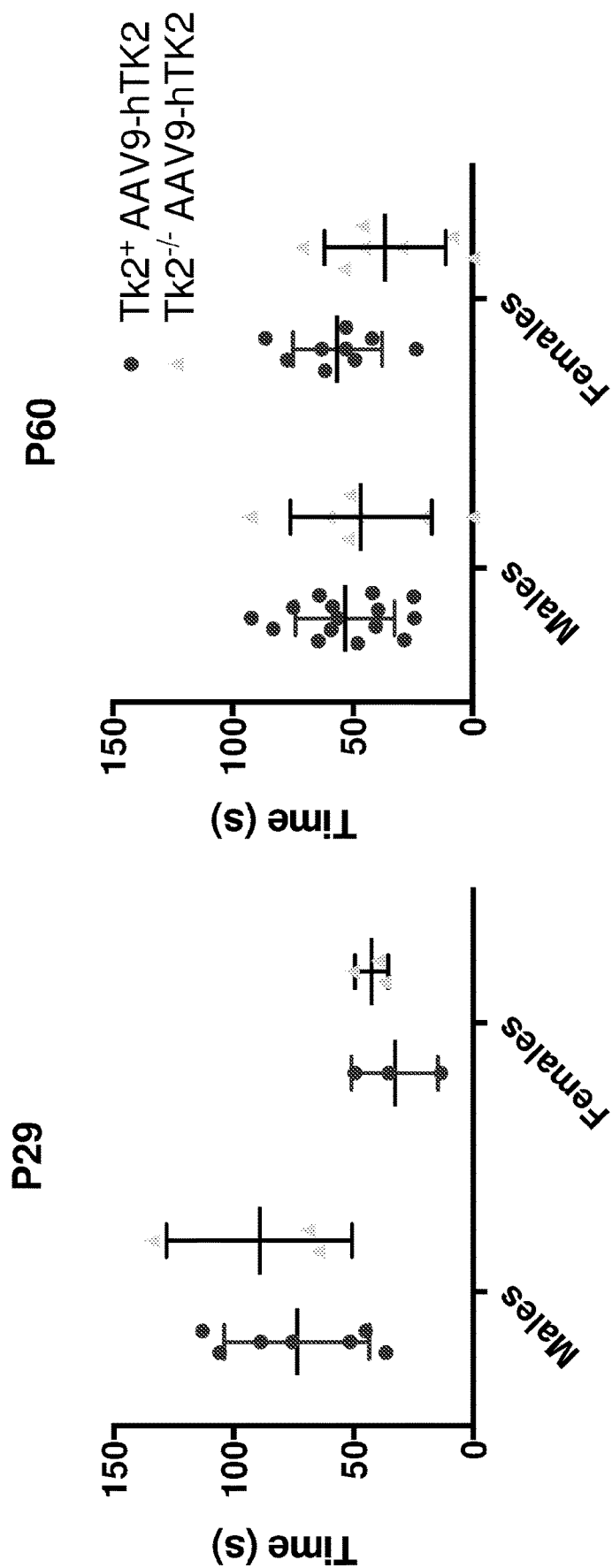
FIG. 5 shows graphs of the results of mice motor function as measured by accelerating rotarod performance test at postnatal day 29 and postnatal day 60 of male and female mice including Tk2+ treated with AAV9-hTK2 and $Tk2^{-/-}$ mice treated with AAV9-hTK2.

Rotarod testing, an outcome measure believed to model motor behavior defects, i.e. motor phenotypes, observed in human patients for assessing the motor function, was performed at postnatal day 29 and 60, and showed no differences between the treated mutant mice and treated wild-type mice, although two mutant, one male and one female, could not perform the test because of weakness and lack of balance. See FIG. 5.

Wild-type mice treated with the AAV9-hTK2 showed no adverse side-effects related to the therapy and were overall healthy.

The results regarding strength and motor function appear to rule out myopathy in the mutant mice and suggest that reduced weight showed in Tk2$^{-/-}$ may be caused by a non-muscle related health condition.

Example 4

Treatment with AAV9-Tk2 Restored TK2 Enzyme Activity in Most Tissues

Figure 6:
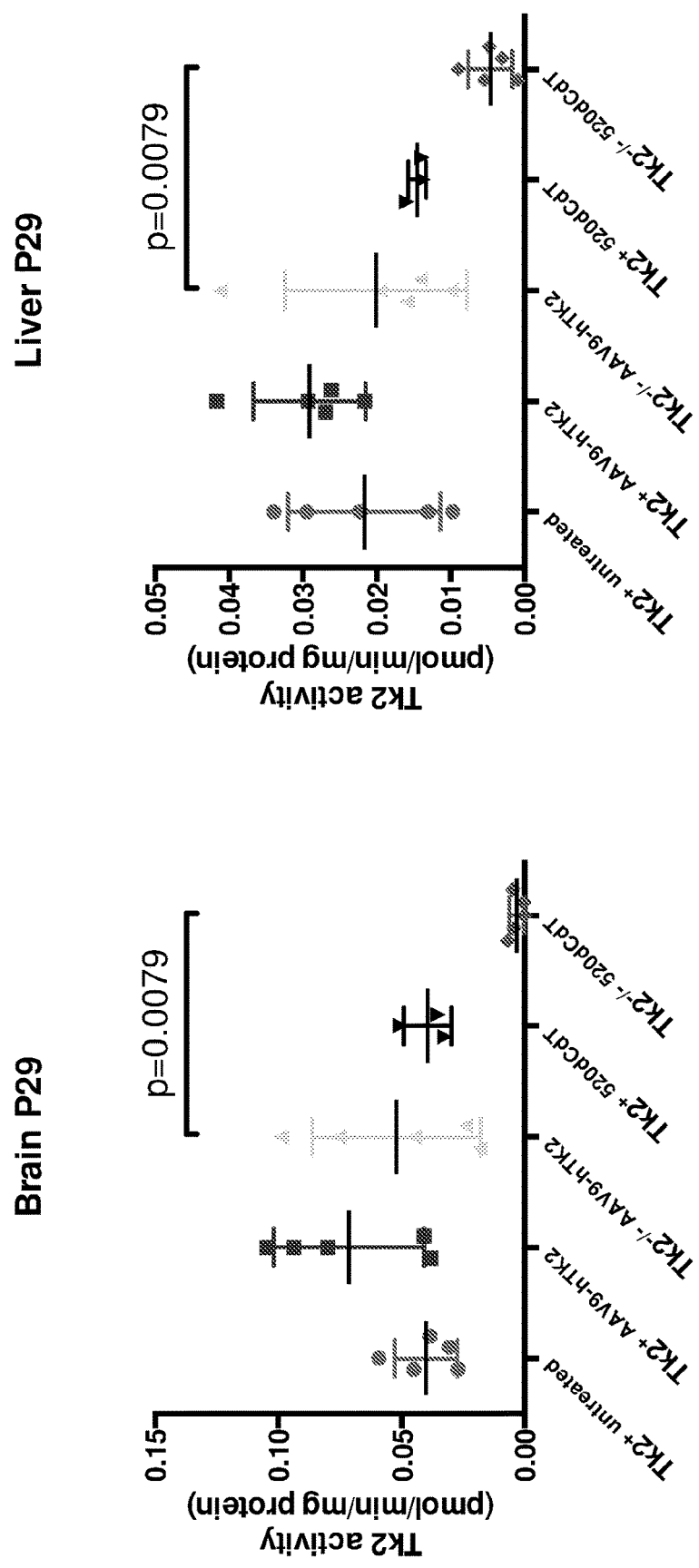
FIG. 6 shows graphs of the activity of TK2 enzyme measured as pmol/min/mg of protein at postnatal day 29 in brain, liver, muscle and kidney tissue of the following mice: untreated Tk2+; Tk2+ treated with AAV9-hTK2 at $4.2\times10^{11}$ vc; $Tk2^{-/-}$ mice treated with AAV9-hTK2 at $4.2\times10^{11}$ vc; Tk2+ treated with 520 mg of dC+dT; and $Tk2^{-/-}$ mice treated with 520 mg of dC+dT.
Figure 6:
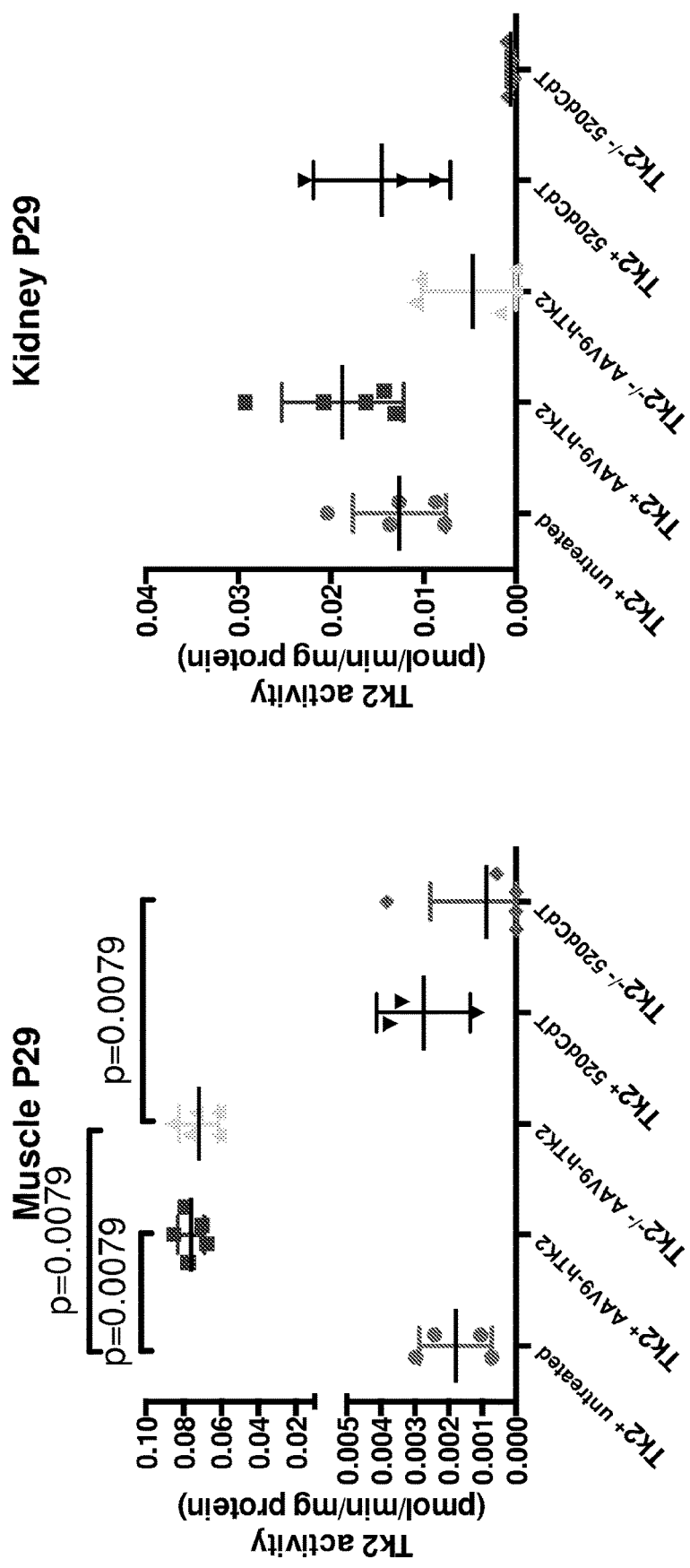

Using the methods described in Example 1, the activity of the TK2 enzyme was measured at P29 and shown to be restored in mutant mice treated with 4.2×10$^{11}$vc of AAV9-hTK2 at P1 in brain and liver to levels similar to those found in untreated wild-type mice. In muscle, AAV9-hTK2 increased 40-fold the TK2 activity as compared to untreated wild-type mice. However, the administration of the AAV9-hTK2 showed a poor efficiency restoring TK2 activity in kidney. See FIG. 6.

Example 5

Treatment with AAV9-hTk2 Increased the Expression of hTK2 in Most Tissues

Human TK2 was measured as a percentage with respect of mRNA expression of mouse TK2 as described in Example 1 in wild-type mice treated with AAV9-hTK2 (4×10$^{11}$ vc) at 1 month, 2 months, and 6 months in brain, liver, muscle, and kidney tissue.

Figure 7:
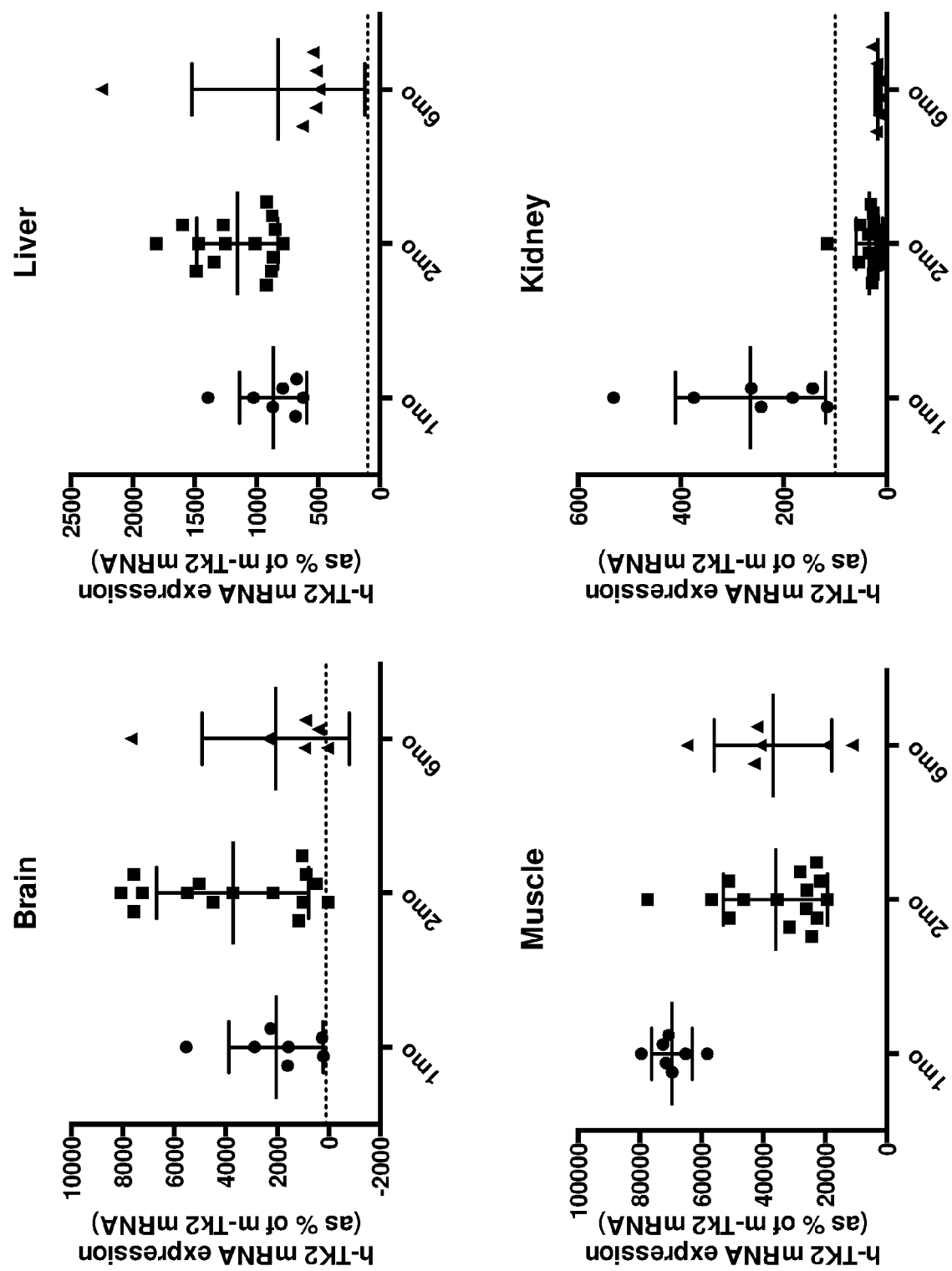
FIG. 7 shows graphs of mRNA expression of human TK2 measure as a percent of mouse TK2 mRNA in brain, liver, muscle and kidney tissue of Tk2+ treated with AAV9-hTK2 at one month, two months and six months.

Human TK2 was expressed in brain, liver and muscle above 100% of the expression of mouse TK2 on target tissue, even in wild-type mice after 6 months of treatment. In contrast, expression of human TK2 in kidney is very low 2 months after the treatment. See FIG. 7.

Example 6

Figure 8:
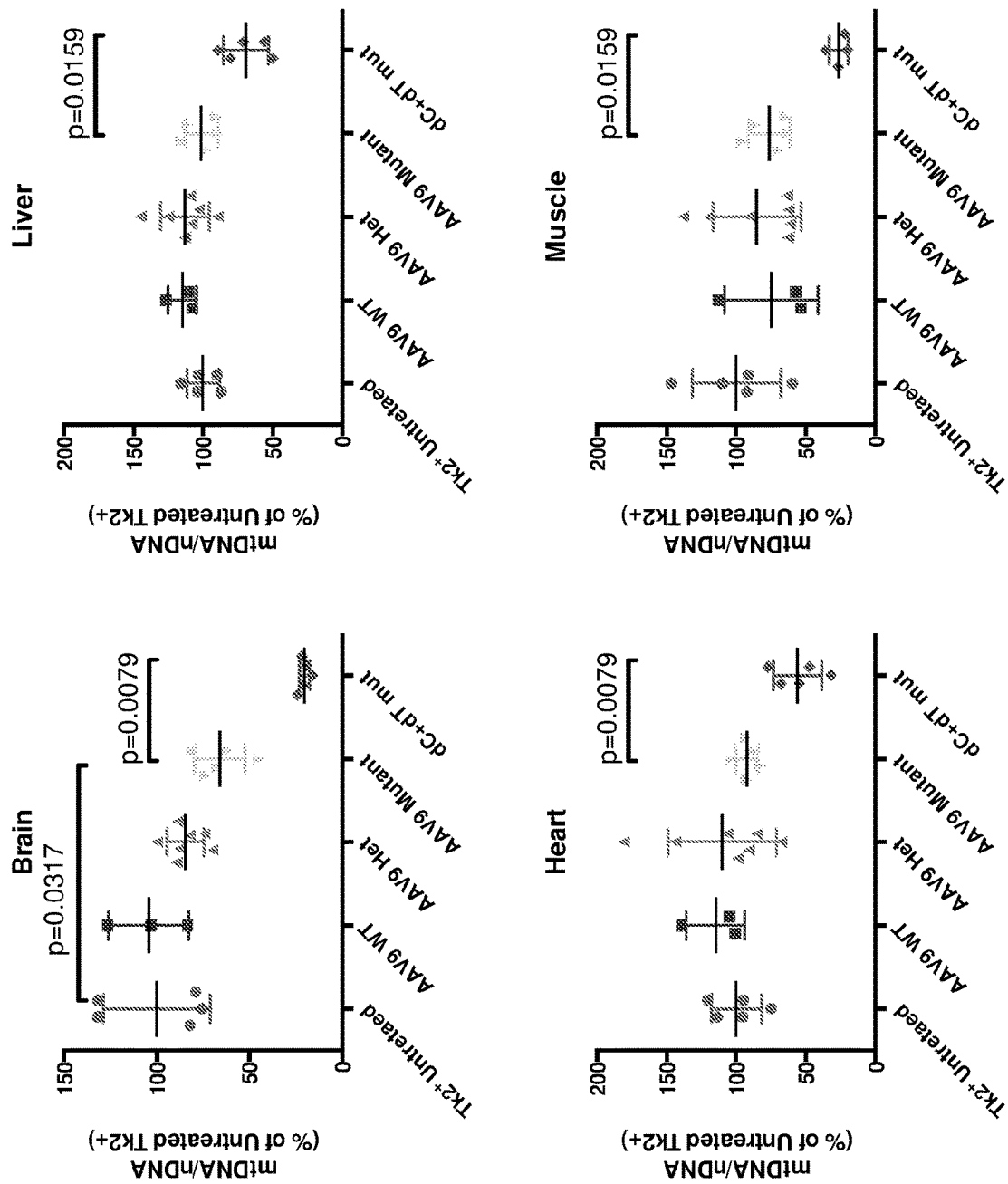
FIG. 8 shows graphs of showing mtDNA copy number (mtDNA/nDNA as a percent of untreated Tk2+) at postnatal day 29 in brain, liver, kidney, heart, muscle, and intestine tissue of the following mice: untreated Tk2+; Tk2+ treated with AAV9-hTK2; mice which are heterozygous for the Tk2 gene treated with AAV9-hTK2; $Tk2^{-/-}$ mice treated with AAV9-hTK2; and $Tk2^{-/-}$ mice treated with 520 mg of dC+dT.
Figure 8:
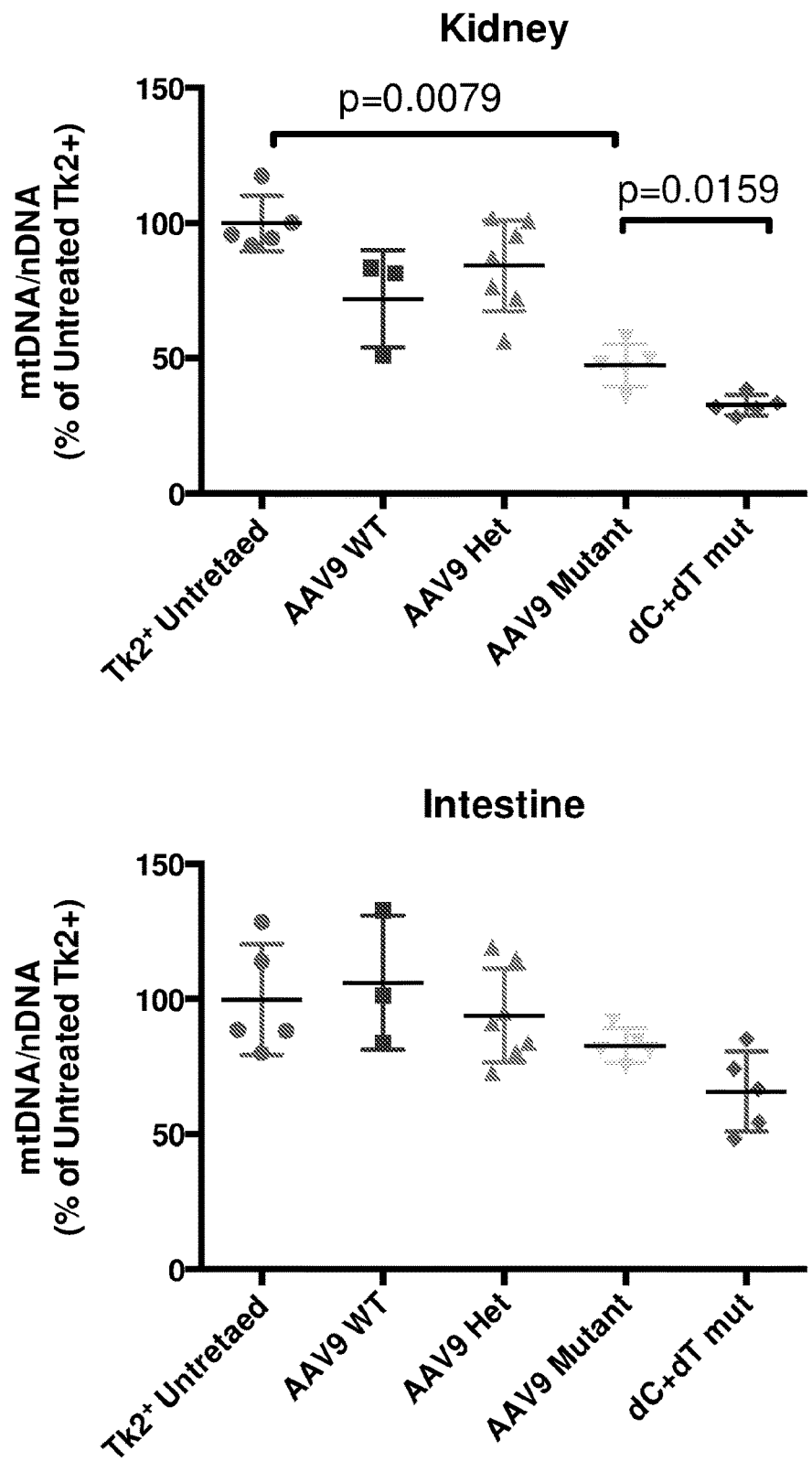

Treatment with AAV9-hTK2 Rescued mtDNA in Most Tissues mtDNA copy number was measured as described in Example 1. At postnatal day 29, Tk2$^{-/-}$ mice treated with AAV9-hTK2 (4×10$^{11}$ vc) at postnatal day 1 had signs of severe mtDNA depletion only in kidney tissue and mtDNA was partially rescued in brain, heart, liver, intestine and muscle (FIG. 8).

Figure 9:
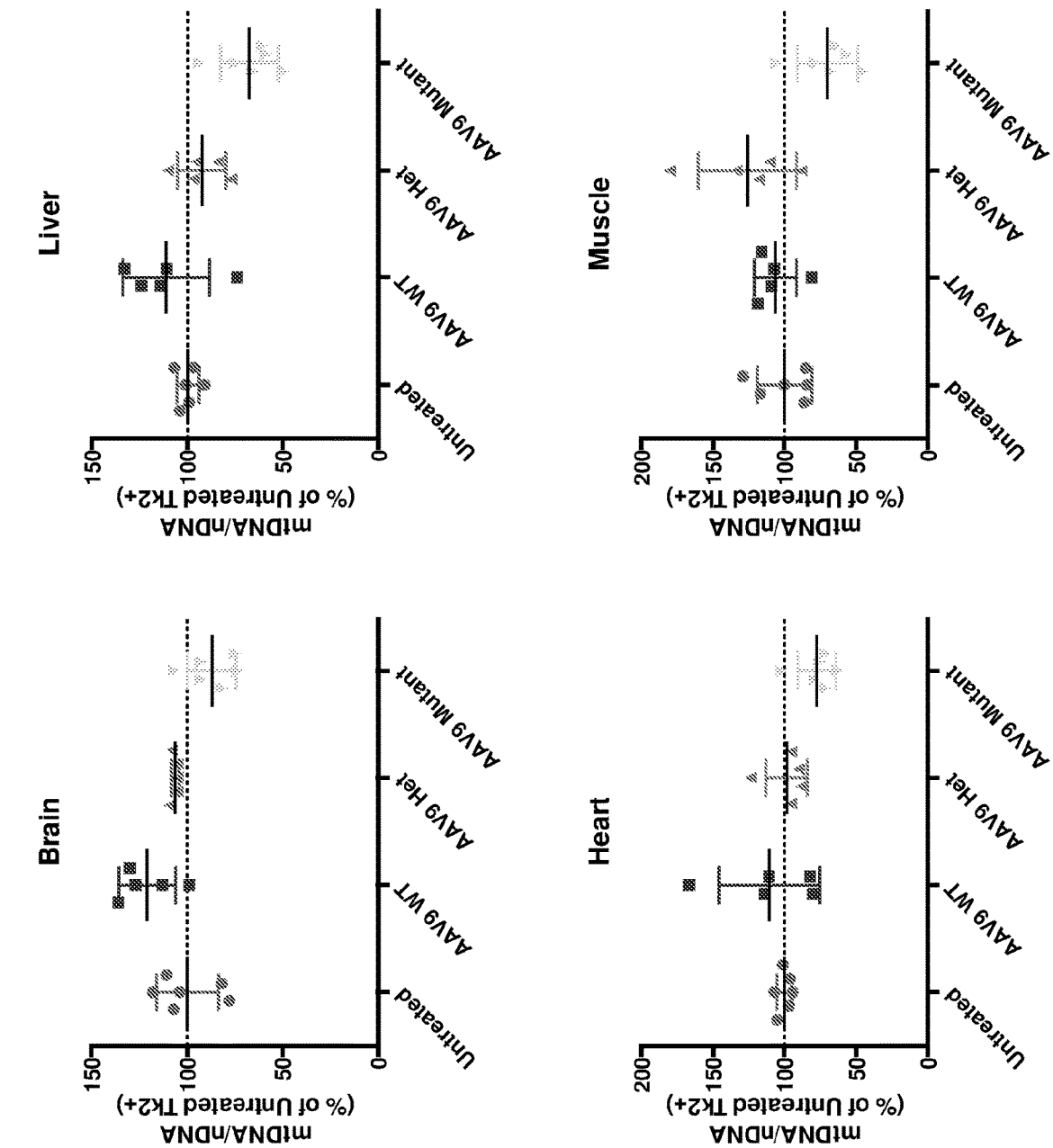
FIG. 9 shows graphs of showing mtDNA copy number (mtDNA/nDNA as a percent of untreated Tk2+) at postnatal day 60 in brain, liver, kidney, heart, muscle, and intestine tissue of the following mice: untreated Tk+; Tk2+ treated with AAV9-hTK2; mice which are heterozygous for the Tk2 gene treated with AAV9-hTK2; and $Tk2^{-/-}$ mice treated with AAV9-hTK2.
Figure 9:
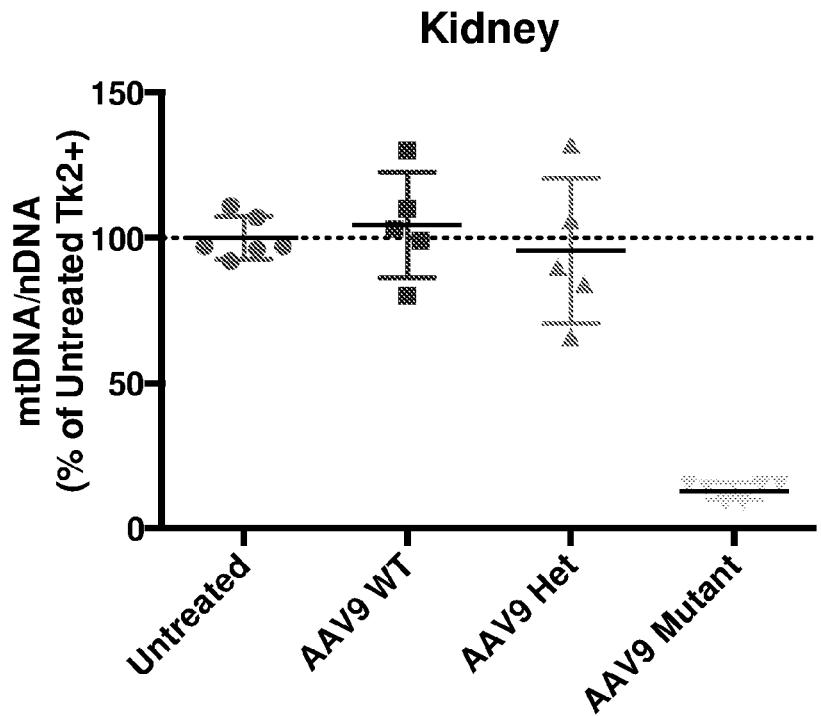
Figure 9:
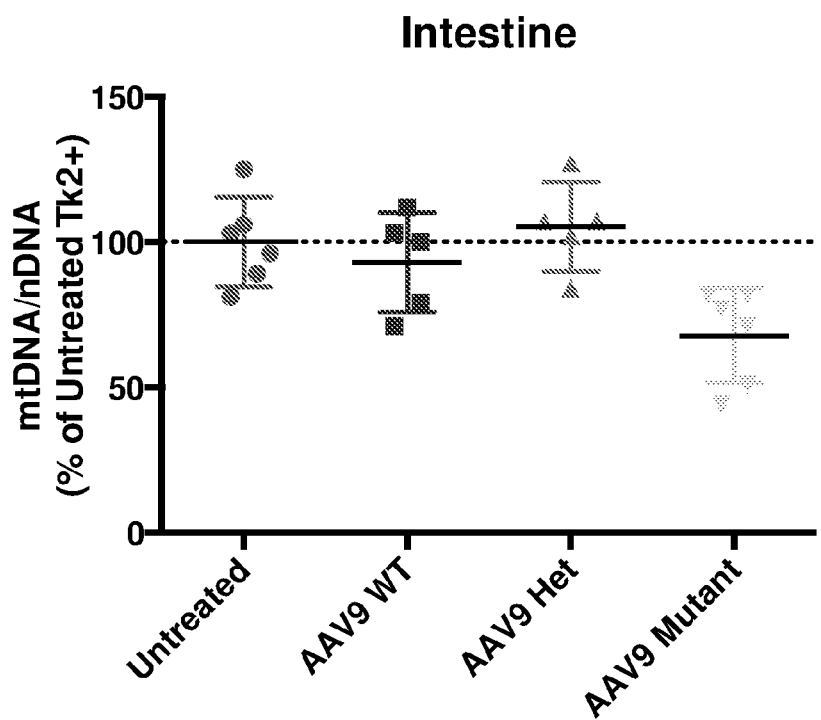

At postnatal day 60, there was very mild mtDNA depletion (65-80% of untreated wild-type mice) in liver, heart, muscle and intestine tissue of AAV9-hTK treated mutant mice. mtDNA in brain tissue of treated mutant mice was 87% that of untreated wild-type mice. This showed a rescue of mtDNA in most tissues of AAV9-hTK2 treated Tk2$^{-/-}$ mice. There was severe mtDNA depletion in kidney tissue of the same treated mutant mice. See FIG. 9.

Example 7

Treatment with AAV9-hTK2 Ameliorated Biochemical Abnormalities in Brain

Respiratory chain enzyme (RCE) activities and protein levels were measured as described in Example 1.

Figure 10:
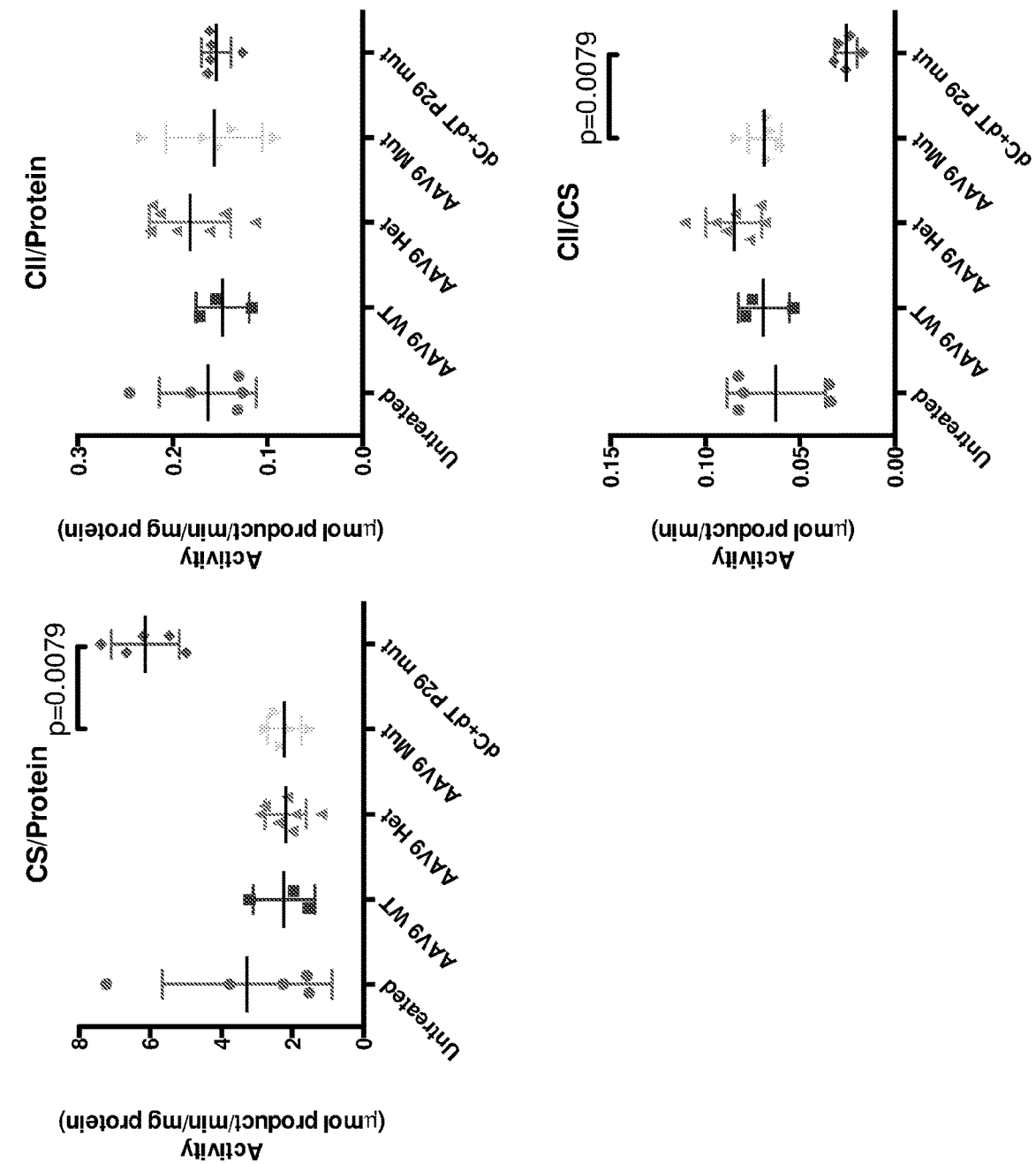
FIG. 10 shows graphs of respiratory chain enzyme activity at postnatal day 29 in brains of the following mice: untreated Tk+; Tk2+ treated with AAV9-hTK2; mice which are heterozygous for the Tk2 gene treated with AAV9-hTK2; $Tk2^{-/-}$ mice treated with AAV9-hTK2; and $Tk2^{-/-}$ mice treated with 520 mg of dC+dT.
Figure 10:
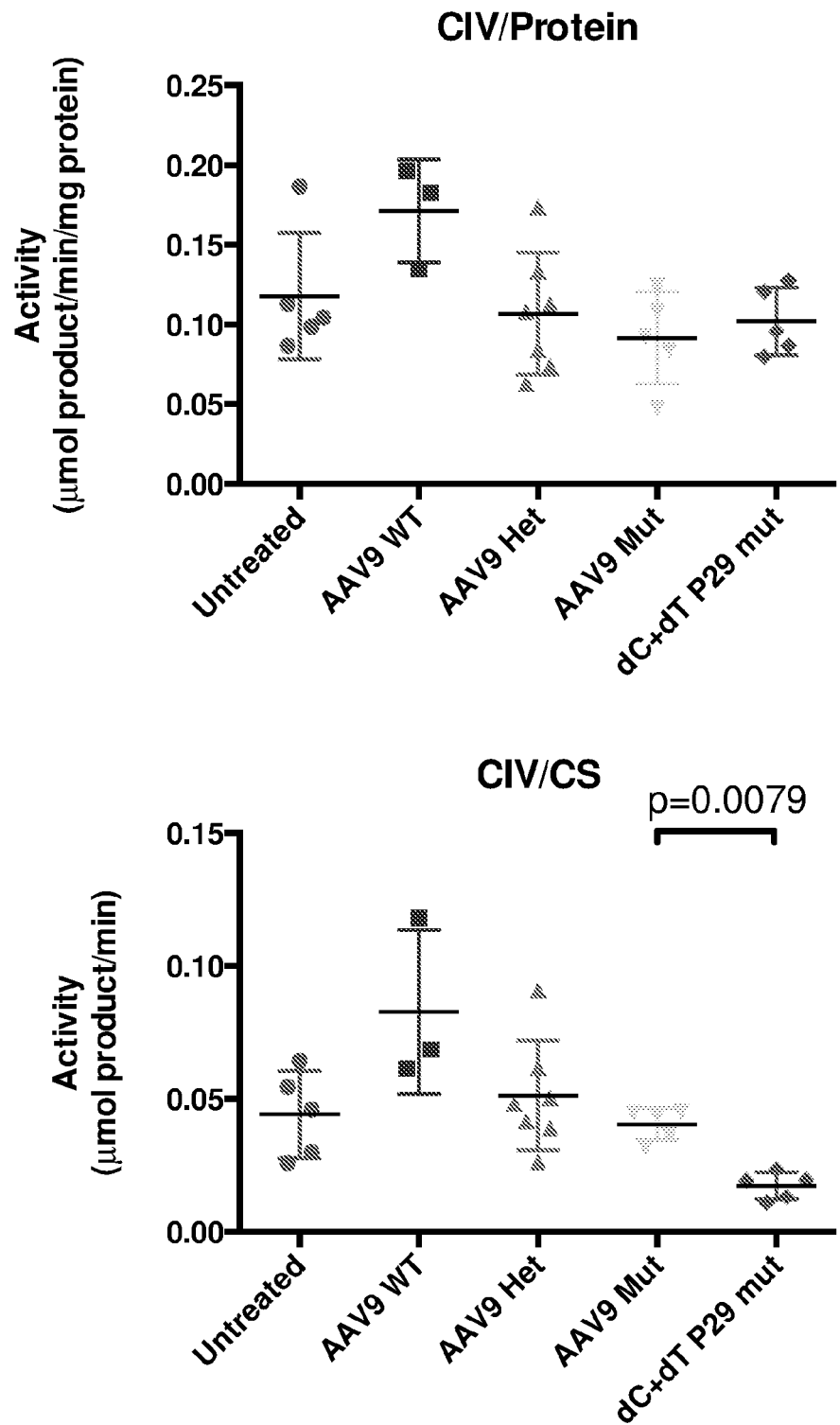
Figure 11:
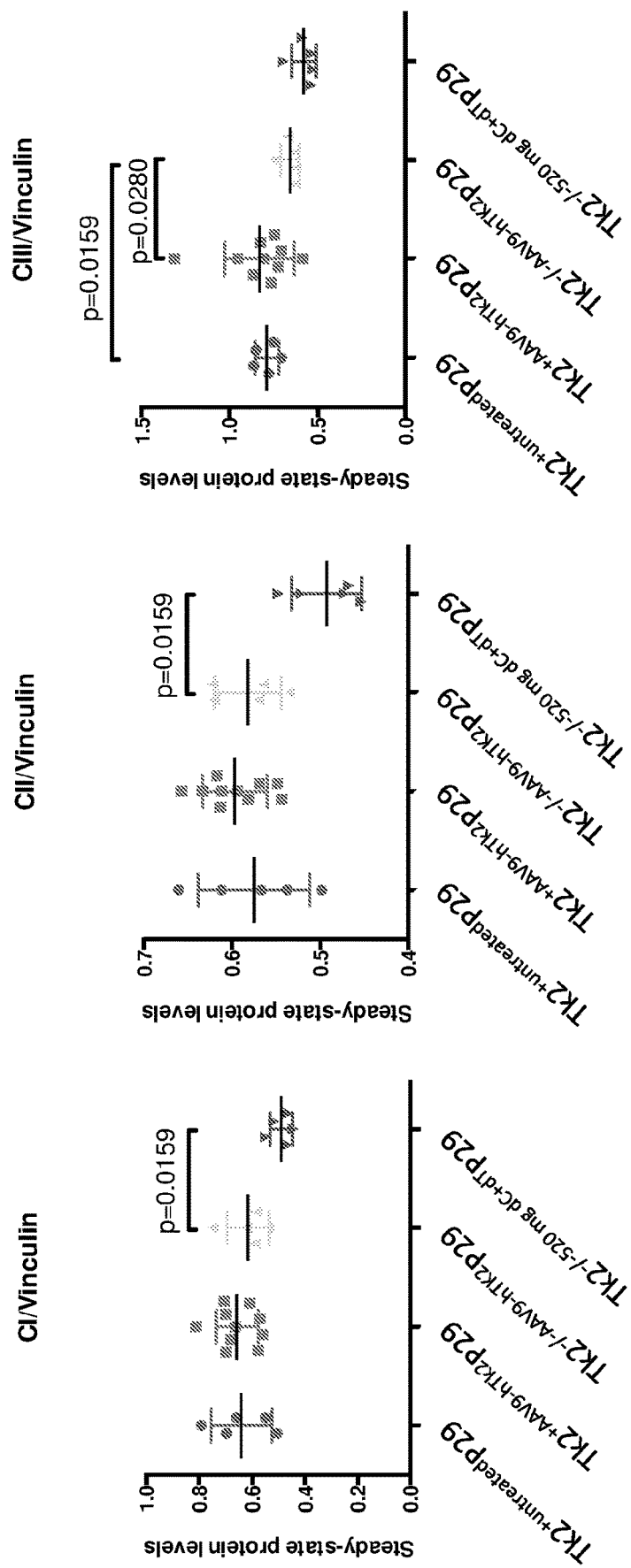
FIG. 11 shows graphs of respiratory chain enzyme levels (oxphos steady-state levels normalized to vinculin) at postnatal day 29 in brains of the following mice: untreated Tk+; Tk2+ treated with AAV9-hTK2; $Tk2^{-/-}$ mice treated with AAV9-hTK2; and $Tk2^{-/-}$ mice treated with 520 mg of dC+dT.
Figure 11:
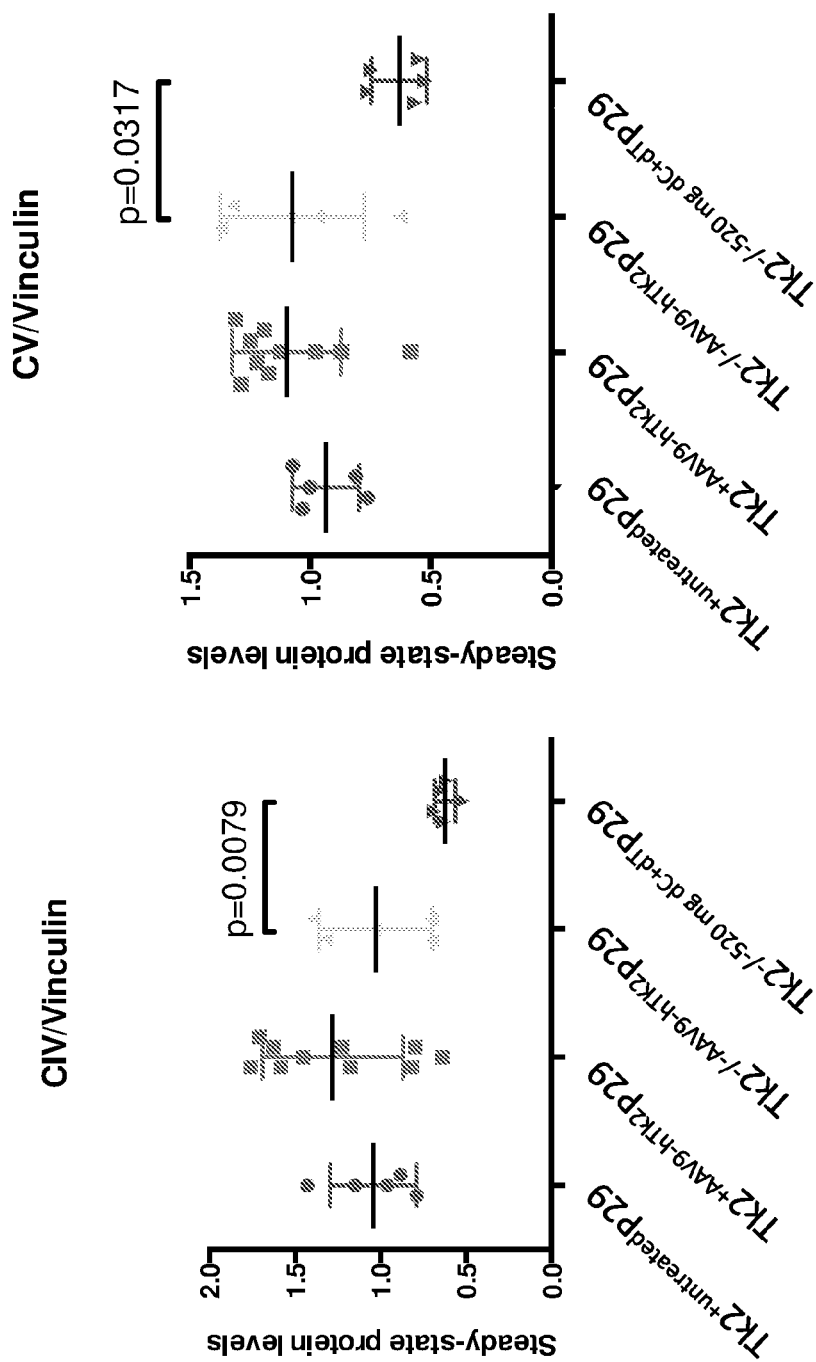

RCE activity in the brain at postnatal day 29 was completely restored in the brains of Tk2$^{-/-}$ mice treated with AAV9-hTK2 (4×10$^{11}$ vc) (FIG. 10). Only a slight reduction in complex III activity could be observed in AAV9-hTK2 treated Tk2$^{-/-}$ mice compared to untreated wild-type mice (FIG. 11).

Example 8

AAV9-hTK2 Does Not Rescue Kidney Function

Figure 12:
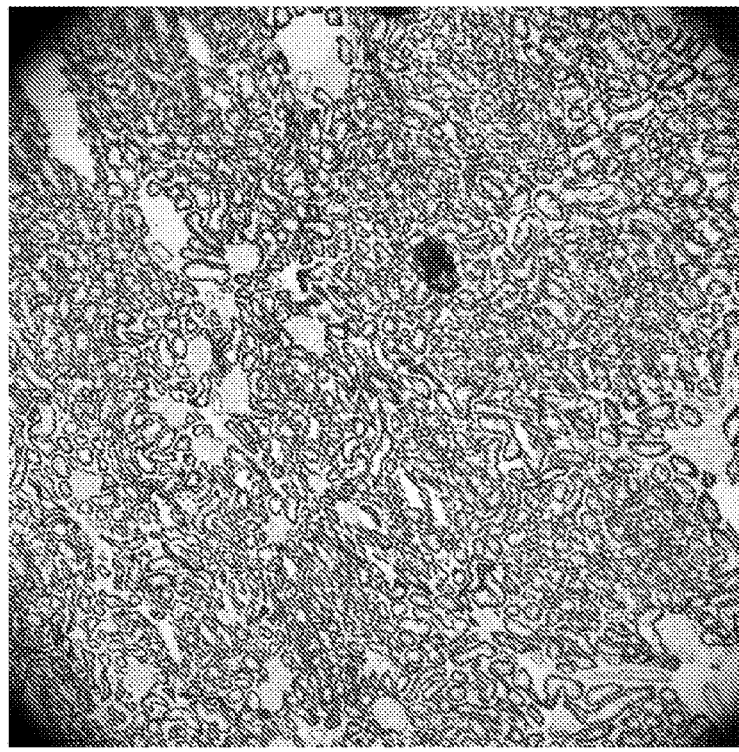
FIG. 12 shows images of stained (H & E) kidneys of AAV9-hTK2 treated mutant and wild-type mice at postnatal day 96.
Figure 12:
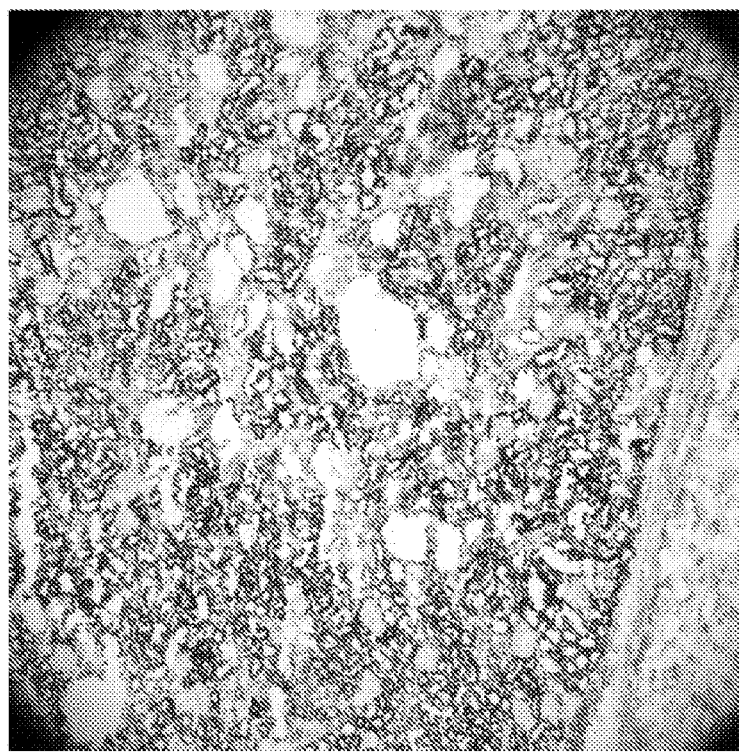

Using the methods in Example 1, kidney tissue of mutant mice treated with AAV9-hTK2 at 4.2×10$^{11}$ vc at their time of death at postnatal day 96 was stained with SDH and Cox. Kidney tissue of age matched wild-type mice treated with AAV9-hTK2 at 4.2×10$^{11}$ vc were stained as well. SDH (blue) staining showed no co-localization with Cox (brown) staining indicating Cox deficiency in the kidney tissue of the mutant mice and likely dysfunctional mitochondria (FIG. 12).

Figure 13:
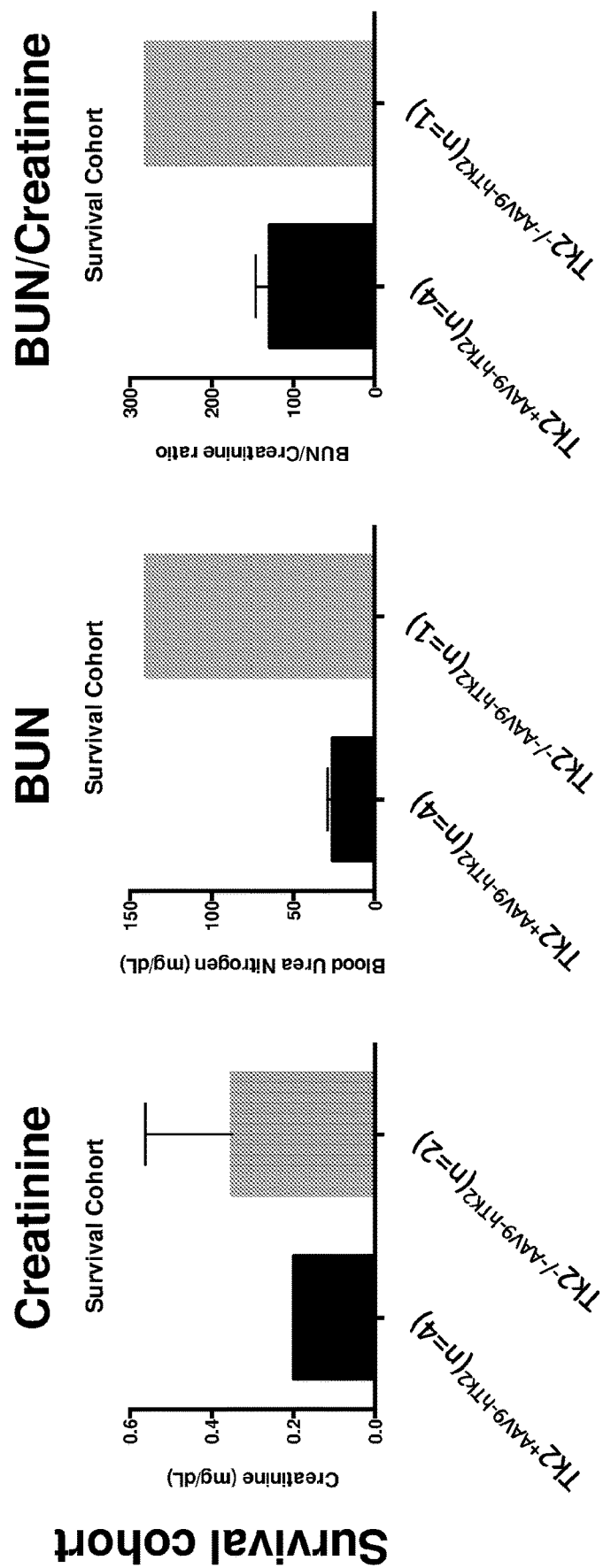
FIG. 13 shows graphs of creatinine and BUN index in AAV9-hTK2 treated mutant and wild-type mice in a survival cohort and a postnatal day 60 cohort.
Figure 13:
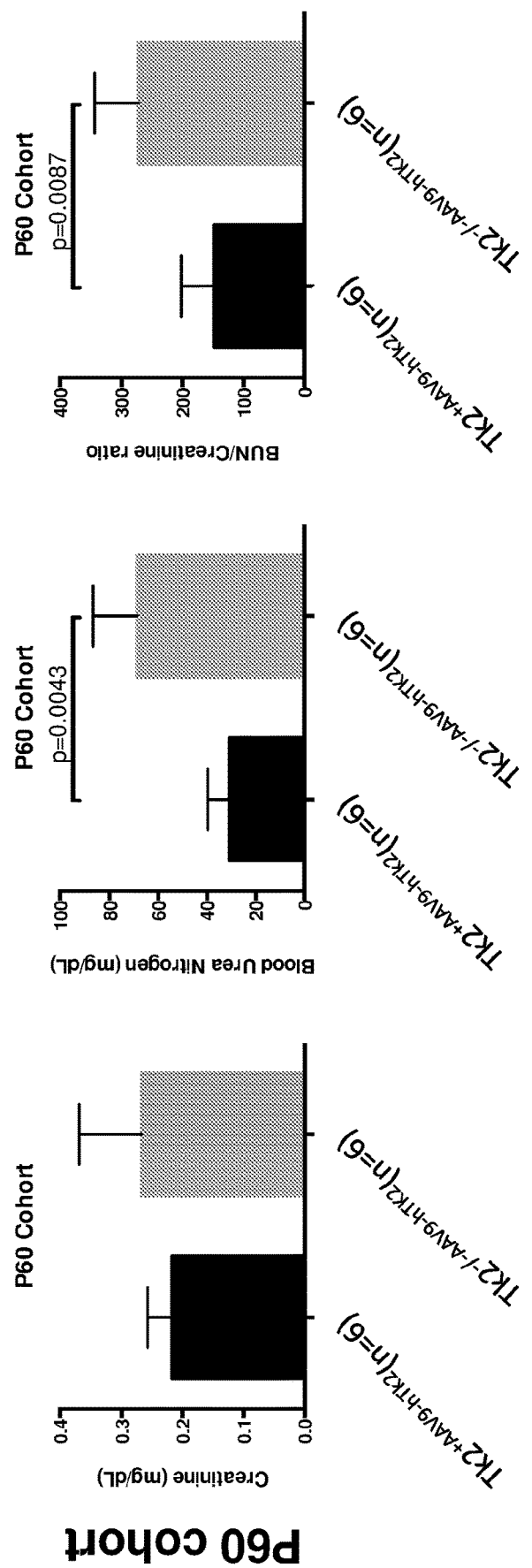

Creatinine and blood urea nitrogen (BUN) index were assessed in both mutant mice treated with AAV9-hTK2 at 4.2×10$^{11}$ vc and wild-type treated with AAV9-hTK2 at 4.2×10$^{11}$ vc both in the survival cohort and at postnatal day 60. Both creatinine and BUN were higher in the mutant mice in both cohorts suggesting kidney dysfunction (FIG. 13).

Example 9

Administration of AAV9-hTK2 in Combination with AAV2-hTK2 Increases Survival Over the Use of AAV9-hTK2 Alone Mutant mice as described in Example 1 were administered AAV9-hTK2 at 2.1×10$^{11}$ vc via retro-orbital injection of a total volume of 35 µl as also described in Example 1 at postnatal day 1. Wild-type mice are also treated at postnatal day 1.

At postnatal day 21, one third of these treated mutant and wild-type mice were supplemented with 520 mg/kg/day of oral dC+dT (in drinking water). At postnatal day 29 two thirds of the mice (all of those supplemented with dC+dT and half of the remaining mice) are administered with AAV2-hTK (Example 1) at 1.05×10$^{11}$ vc, via tail vein injection in a total volume of 100 ul.

Figure 14:
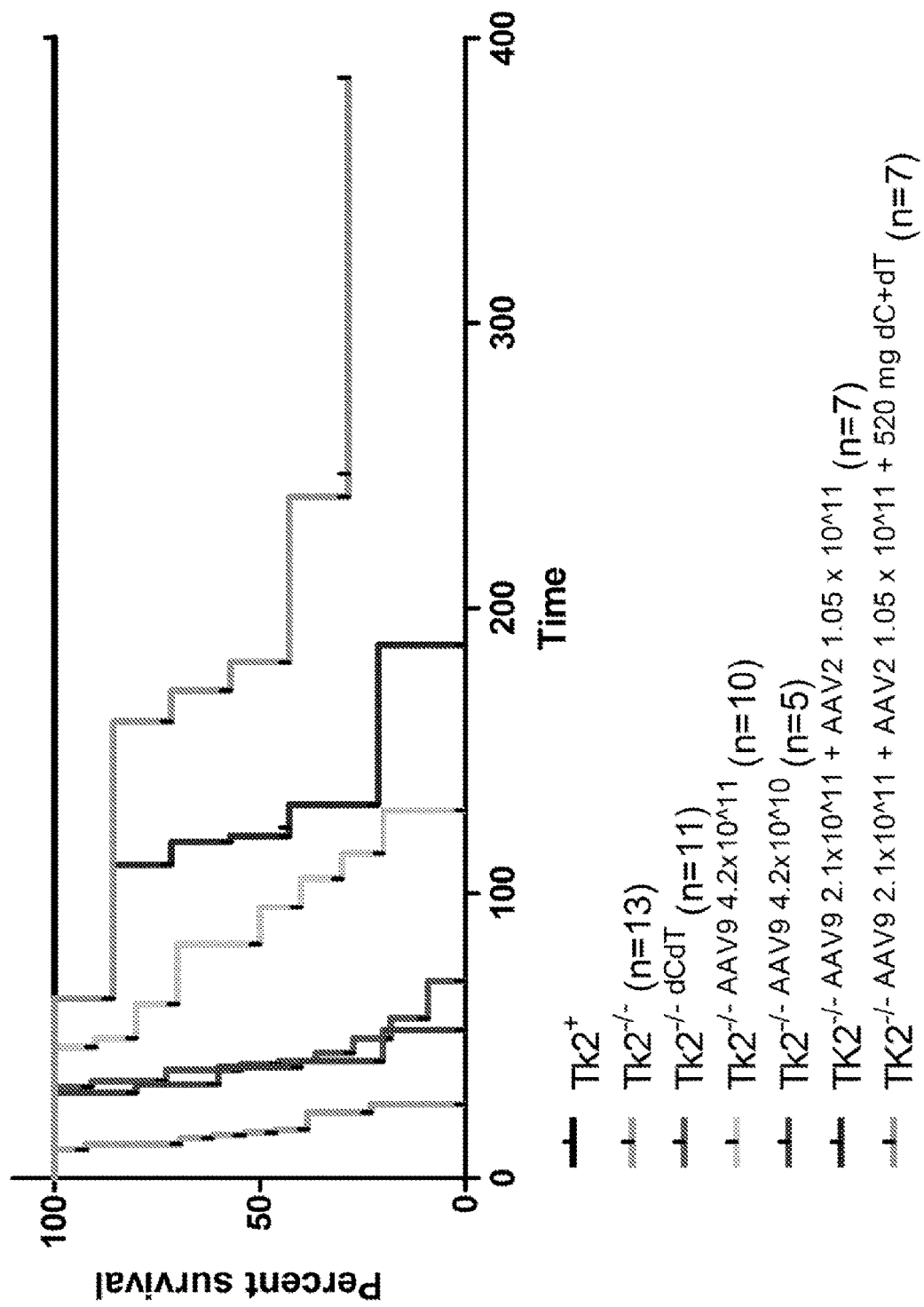
FIG. 14 shows the survival curve of the following mice (curves from left to right): $Tk2^{-/-}$ mice untreated (n=13); $Tk2^{-/-}$ mice treated with AAV9-hTK2 at $4.2\times10^{10}$ vc by IV at postnatal day 1 (n=5); $Tk2^{-/-}$ mice treated with 520 mg of dC+dT (n=11); $Tk2^{-/-}$ mice treated with AAV9-hTK2 at $4.2\times10^{11}$ vc by IV at postnatal day 1 (n=10); mice co-treated with AAV9-hTK2 at $2.1\times10^{11}$ at day 1 and AAV2-hTK2 at $1.05\times10^{11}$ at day 29 (n=7); and mice under co-treatment with AAV9-hTK2 at day 1, AAV2-hTK2 at day 29 and supplemented with 520 mg/kg/day of oral dC+dT from day 21 (n=7). Survival of untreated Tk2+ (wild-type) is shown by the top horizontal line.
Figure 15:
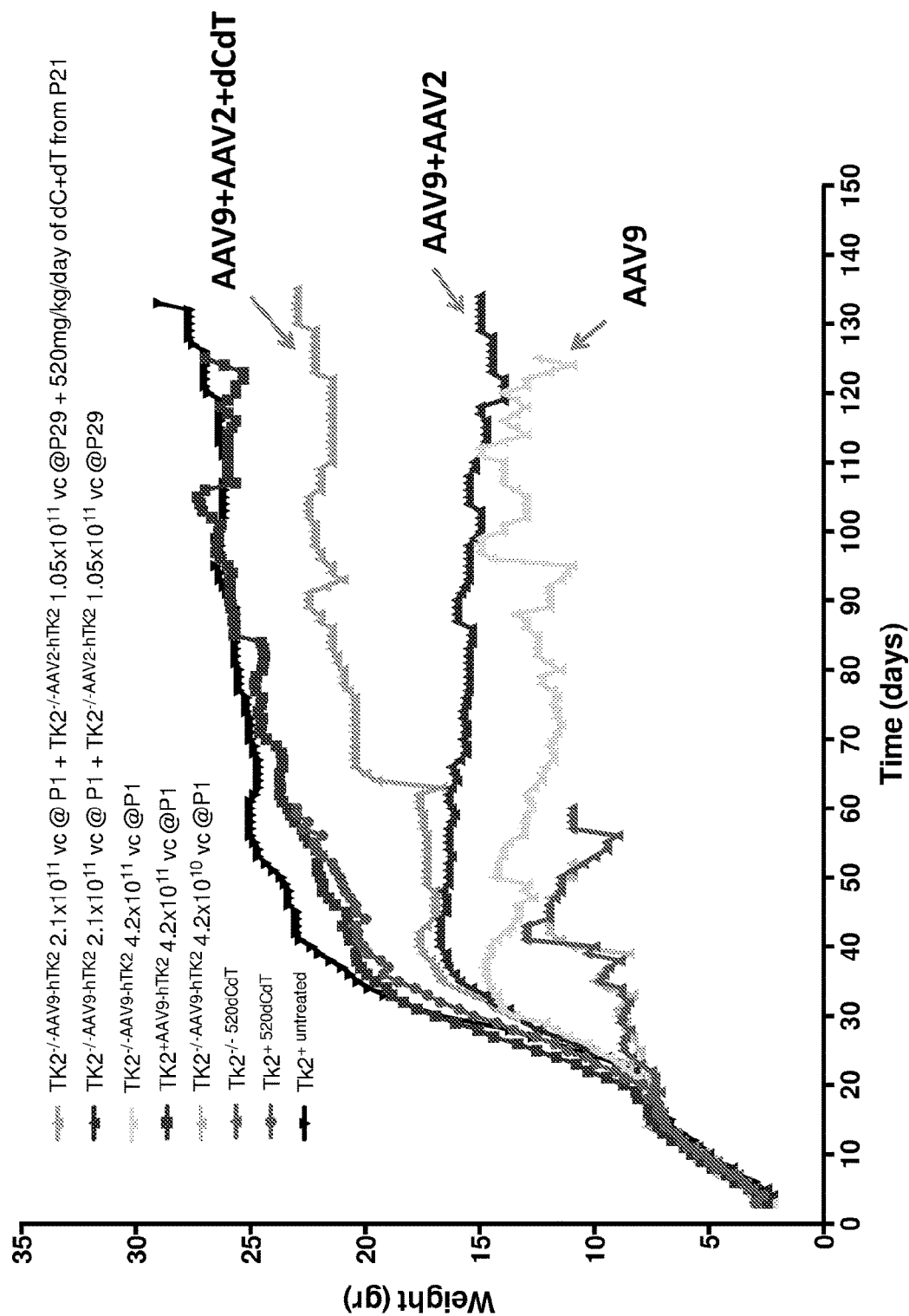
FIG. 15 shows weight versus time in the following male mice: Tk2+ untreated; Tk2+ treated with 520 mg of dC+dT; $Tk2^{-/-}$ mice treated with 520 mg of dC+dT; Tk2+ treated AAV9-hTK2 at $4.2\times10^{11}$ vc by IV at postnatal day 1; $Tk2^{-/-}$ mice treated with AAV9-hTK2 at $4.2\times10^{11}$ vc by IV at postnatal day 1 ("AAV9"); $Tk2^{-/-}$ mice treated with AAV9- hTK2 at 4.2×10¹⁰ vc by IV at postnatal day 1; Tk2⁻/⁻ mice treated with AAV9-hTK2 at 2.1×10¹¹ vc by IV at postnatal day 1 and AAV2-hTK2 at 1.05×10¹¹ vc by IV at postnatal day 29 ("AAV9+AAV2"); and Tk2⁻/⁻ mice treated with AAV9-hTK2 at 2.1×10¹¹ vc by IV at postnatal day 1, AAV2-hTK2 at 1.05×10¹¹ vc by IV at postnatal day 29 and 520 mg/kg/day of oral dC+dT from day 21 ("AAV9+AAV2+dCdT").

The mutant mice treated with only the AAV9-hTK2 survived an average of 89 days as consistent with the results in Example 2. The mutant mice who received both AAV9- hTK2 and AAV2-hTK2 lived significantly longer, about 120 days (FIG. 14). Despite having an overall lower dose of vector copies ($3.15 \times 10^{11}$ vc in total versus $4.2 \times 10^{11}$ vc), mutant mice treated with both constructs grew as much as mutant mice treated only with AAV9-hTK2 (FIGS. 15 and 16) and showed equal strength and motor coordination (FIGS. 17, 18 and 19). At day 60, mutant mice treated with both AAV9-hTK2 and AAV2-hTK2 showed slightly higher levels of mtDNA than those treated only with AAV9-hTK2 (FIG. 20). Mice treated with a combination of AAV9-hTK2 and AAV2-hTK2 also showed a decrease in the content of protein in the urine (FIG. 21) and slightly lower levels of the index BUN (FIG. 22) as compared to mice treated only with AAV9-hTK2, as well as higher Tk2 activity in liver (FIG. 23).

The combined data on mtDNA, protein in the urine and BUN showed that kidney dysfunction can be delayed in mice co-treated with AAV2 or AAV2+dN which also increases lifespan.

Example 10

Administration of Supplemental Nucleosides Enhances the Effects of the Gene Therapy Half of the mutant and wild-type mice treated with both the AAV9-hTK2 and the AAV2-hTK2 in Example 9 were further administered oral dC+dT at 520 mg/kg/day in drinking water as described in Example 1. It is assumed the mice ingest 4 ml a day per mouse.

The mutant mice who were given the supplemental nucleosides survive significantly longer, with a survival of more than 180 days (FIG. 14). They also had increased growth (FIGS. 15 and 16), and equal strength and motor coordination than mice treated with either AAV9-hTK2 or a combination of AAV9-hTK2 and AAV2-hTK2. Mice treated with the combination of AAV9-hTK2 and AAV2-hTK2 and further supplemented with dC+dT showed higher levels of mtDNA in liver.

Example 11

Administration of AAV9-hTK2 in Combination with dC+dT Increase Survival Over the Use of AAV9-hTK2 Alone Mutant mice as described in Example 1 are administered oral dC+dT (260 or 520 mg/kg/day each in milk) from postnatal day 4). At postnatal day 21, half the mice are administered with AAV9-hTK2 as described in Example 1.

The mutant mice given only the dC+dT treatment survived a mean of 31 and 40 days with the 260 and 520 mg/kg/day dose, respectively. The mutant mice who received the subsequent AAV9-hTK2 survive significantly longer.

Of the mice that received the AAV9-hTK2 half of these mice then are administered AAV2-hTK2 at postnatal day 30. These mice who received the dC+dT and the AAV9-hTK2 and the AAV2-hTK2 survive significantly longer than the mice receiving only the dC+dT and AAV9-hTK2.

Example 12

Administration of AAV9-hTK2 in Combination with dCMP+TMP Increase Survival Over the Use of AAV9-hTK2 Alone Mutant mice as described in Example 1 are administered dCMP+TMP (200 mg/kg/day or 400 mg/kg/day each in milk) from postnatal day 4. At postnatal day 21, half the mice are administered with AAV9-hTK2 as described in Example 1.

The mutant mice given only the dCMP+TMP treatment survive a mean of 35 and 44 days with the 200 and 400 mg/kg/day dose, respectively. The mutant mice who received the subsequent AAV9-hTK2 survive significantly longer.

Of the mice that received the AAV9-hTK2 half of these mice then are administered AAV2-hTK2 at postnatal day 30. These mice who received the dCMP+TMP and the AAV9-hTK2 and the AAV2-hTK2 survive significantly longer than the mice receiving only the dC+dT and AAV9-hTK2.

REFERENCES

Akman, et al. (2008) Thymidine kinase 2 (14126N) knock in mice show the essential role of balanced deoxynucleotide pools for mitochondrial DNA maintenance. *Hum. Mol. Genet.* 17:2433-2440

Béhin, et al. (2012) Adult cases of mitochondrial DNA depletion due to TK2 defect An expanding spectrum. *Neurology* 78:644-648

Birch-Machin, et al. (1994) An evaluation of the measurement of the activities of complexes I-IV in the respiratory chain of human skeletal muscle mitochondria. *Biochem Med Metab Biol* 51:35-42

Bourdon, et al. (2007) Mutation of RRM2B, encoding p53-controlled ribonucleotide reductase (p53R2), causes severe mitochondrial DNA depletion. *Nature Genetics* 39:776-780

Chanprasert, et al. (2012) TK2-Related Mitochondrial DNA Depletion Syndrome, Myopathic Form. *GeneReviews® Internet*, Dec. 6, 2012

Copeland (2008) Inherited mitochondrial diseases of DNA replication. *Ann. Rev. Med.* 59:131-146

DiMauro, et al. (1987) Cytochrome c oxidase deficiency in Leigh syndrome. *Ann. Neurol.* 22:498-506

DiMauro, Schon, (2003) Mitochondrial respiratory-chain diseases. *New England Journal of Medicine* 348:2656-2668

DiMauro, Hirano. (2005) Mitochondrial encephalomyopathics: an update. *Neuromuscul. Disord.* 15:276-286

Dorado, et al. (2011) Onset and organ specificity of Tk2 deficiency depends on Tk1 down-regulation and transcriptional compensation. *Hum. Mol. Genet.* 20:155-64

Elpeleg, et al. (2005) Deficiency of the ADP-forming succinyl-CoA synthase activity is associated with encephalomyopathy and mitochondrial DNA depletion. *Am. J. Hum. Genet.* 76:1081-1086

Franzolin, et al. (2006) Bromovinyl-deoxyuridine: a selective substrate for mitochondrial thymidine kinase in cell extracts. *Biochem. Biophy. Res. Commun.* 344(1):30-6

Galbiati, et al. (2006) New mutations in TK2 gene associated with mitochondrial DNA depletion. *Pediatr. Neurol.* 34:177-185

Garone, et al. (2012). MIN17 Mutations Causing Adult-Onset Multisystemic Disorder With Multiple Mitochondrial DNA Deletions. *Arch Neurol* 69:1648-1651

Garone, et al. (2018) Retrospective Natural History of Thymidine Kinase 2 Deficiency. *J. Med, Genetics* 55:515-21

Gotz, et al. (2008) Thymidine kinase 2 defects can cause multi-tissue mtDNA depletion syndrome. *Brain* 131:2841-2850

Hirano, et al. (2001) Defects of intergenomic communication: autosomal disorders that cause multiple deletions and depletion of mitochondrial DNA. *Semin. Cell. Develop. Biol.* 12:417-427

Longley, et al, (2006). Mutant POLG2 disrupts DNA polymerase gamma subunits and causes progressive external ophthalmoplegia. *Am J Hum Genet.* 78:1026-1034

Mandel, et al. (2001) The deoxyguanosine kinase gene is mutated in individuals with depleted hepatocerebral mitochondrial DNA. *Nature Genet.* 29:337-341

Naviaux, Nguyen. (2004) POLG mutations associated with Alpers' syndrome and mitochondrial DNA depletion. *Ann. Neurol.* 55:706-712

Nishino, et al. (1999). Thymidine phosphorylase gene mutations in MNGIE, a human mitochondrial disorder. *Science* 283:689-692.

Ostergaard, et al. (2007) Deficiency of the alpha subunit of succinate-coenzyme A ligase causes fatal infantile lactic acidosis with mitochondrial DNA depletion. *Am. J. Hum. Genet.* 81: 383-387

Paradas, et al. (2012) TK2 mutation presenting as indolent myopathy. *Neurology* 29:504-506

Quinzii, et al. (2013) Tissue-specific oxidative stress and loss of mitochondria in CoQ-deficient Pdss2 mutant mice. *FASEB J.* 27:612-621

Ronchi, et al. (2012). Next-generation sequencing reveals DGUOK mutations in adult patients with mitochondrial DNA multiple deletions. *Brain* 135:3404-3415.

Saada, et al. (2003) Mitochondrial deoxyribonucleoside triphosphate pools in thymidine kinase 2 deficiency. *Biochem. Biophys. Res, Commun.* 310:963-966

Sarzi, et al. (2007) Twinkle helicase (PEO1) gene mutation causes mitochondrial DNA depletion. *Ann. Neurol.* 62: 579-587

Spelbrink, et al. (2001). Human mitochondrial DNA deletions associated with mutations in the gene encoding Twinkle, a phage T7 gene 4-like protein localized in mitochondria. *Nature Genet.* 28:223-231

Spinazzola, et al. (2006) MPV17 encodes an inner mitochondrial membrane protein and is mutated in infantile hepatic mitochondrial DNA depletion. *Nature Genet.* 38:570-575

Tyynismaa, et al. (2012) Thymidine kinase 2 mutations in autosomal recessive progressive external ophthalmoplegia with multiple mitochondrial DNA deletions. *Hum. Mol. Genet.* 21:66-75

Tyynismaa, et al. (2009). A heterozygous truncating mutation in RRM2B causes autosomal-dominant progressive external ophthalmoplegia with multiple mtDNA deletions. *Am. J. Hum. Genet.* 85: 290-295

Van Goethem, et al. (2001) Mutation of POLO is associated with progressive external ophthalmoplegia characterized by mtDNA deletions. *Nature Genet.* 28:211-212.

---

The invention claimed is:

1. A method of increasing weight gain in a subject suffering from myopathic MDS characterized by one or more mutations in an endogenous gene encoding TK2, the method comprising administering to the subject a therapeutically effective amount of a composition comprising a vector of adeno-associated virus (AAV) and comprising a transgene encoding thymidine kinase 2 (TK2).

2. The method of claim 1 wherein the TK2 has the amino acid sequence of SEQ ID NO: 1.

3. The method of claim 1 wherein the composition comprises an AAV and is an AAV1, AAV2, AAV3, AAV4, AAV5, AAV6, AAV7, AAV8, AAV9, AAVrh74, AAVrh.8, or AAVrh.10.

4. The method of claim 1 wherein the AAV is AAV2/9 or AAV2/8.

5. The method of claim 1, further comprising administering one or more of dT, dC, TMP and dCMP to the subject.

6. The method of claim 3, wherein the AAV is AAV9.

* * * * *

SEQUENCE LISTING

```
<160> NUMBER OF SEQ ID NOS: 24

<210> SEQ ID NO 1
<211> LENGTH: 234
<212> TYPE: PRT
<213> ORGANISM: Homo sapiens

<400> SEQUENCE: 1

Met Gly Ala Phe Cys Gln Arg Pro Ser Ser Asp Lys Glu Gln Glu Lys
1               5                   10                  15

Glu Lys Lys Ser Val Ile Cys Val Glu Gly Asn Ile Ala Ser Gly Lys
            20                  25                  30

Thr Thr Cys Leu Glu Phe Phe Ser Asn Ala Thr Asp Val Glu Val Leu
        35                  40                  45

Thr Glu Pro Val Ser Lys Trp Arg Asn Val Arg Gly His Asn Pro Leu
    50                  55                  60

Gly Leu Met Tyr His Asp Ala Ser Arg Trp Gly Leu Thr Leu Gln Thr
65                  70                  75                  80

Tyr Val Gln Leu Thr Met Leu Asp Arg His Thr Arg Pro Gln Val Ser
                85                  90                  95

Ser Val Arg Leu Met Glu Arg Ser Ile His Ser Ala Arg Tyr Ile Phe
            100                 105                 110

Val Glu Asn Leu Tyr Arg Ser Gly Lys Met Pro Glu Val Asp Tyr Val
        115                 120                 125

Val Leu Ser Glu Trp Phe Asp Trp Ile Leu Arg Asn Met Asp Val Ser
    130                 135                 140

Val Asp Leu Ile Val Tyr Leu Arg Thr Asn Pro Glu Thr Cys Tyr Gln
145                 150                 155                 160

Arg Leu Lys Lys Arg Cys Arg Glu Glu Glu Lys Val Ile Pro Leu Glu
                165                 170                 175

Tyr Leu Glu Ala Ile His His Leu His Glu Glu Trp Leu Ile Lys Gly
            180                 185                 190
```

Ser Leu Phe Pro Met Ala Ala Pro Val Leu Val Ile Glu Ala Asp His
    195                 200                 205

His Met Glu Arg Met Leu Glu Leu Phe Glu Gln Asn Arg Asp Arg Ile
    210                 215                 220

Leu Thr Pro Glu Asn Arg Lys His Cys Pro
225                 230

<210> SEQ ID NO 2
<211> LENGTH: 4678
<212> TYPE: DNA
<213> ORGANISM: Homo sapiens

<400> SEQUENCE: 2

```
gccaagttat gggtgcgttc tgccagcgtc ctagcagtga taaagaacag gaaaaagaga      60
aaaaatcagt gatctgtgtc gagggcaata ttgcaagtgg gaagacgaca tgcctggaat     120
tcttctccaa cgcgacagac gtcgaggtgt taacggagcc tgtgtccaag tggagaaatg     180
tccgtggcca caatcctctg gcctgatgt accacgatgc ctctcgctgg ggtcttacgc      240
tacagactta tgtgcagctc accatgctgg acaggcatac tcgtcctcag gtgtcatctg     300
tacggttgat ggagaggtcg attcacagcg caagatacat ttttgtagaa aacctgtata     360
gaagtgggaa gatgccagaa gtggactatg tagttctgtc ggaatggttt gactggatct     420
tgaggaacat ggacgtgtct gttgatttga tagtttacct tcggaccaat cctgagactt     480
gttaccagag gttaaagaag agatgcaggg aagaggagaa ggtcattccg ctggaatacc     540
tggaagcaat tcaccatctc catgaggagt ggctcatcaa aggcagcctt tccccatgg      600 cagcccctgt tctggtgatt gaggctgacc accacatgga gaggatgtta aactctttg     660 aacaaaatcg ggatcgaata ttaactccag agaatcggaa gcattgccca taggaggcaa     720
aaggtctatg gctcatgtct gaaaaatgcc tgctgctgcc aagttagcta ttgggagcaa     780
tctggaaaaa cttgctccca ggagggcttt gtgtctggcc agcttgattt tcctaatggt     840
ctcatctcct ttgctagtgt ctttgtcatg cgtctctggc cctcgtgggt aaatgacaaa     900
cgggaccaat gggtttgcca agccctttgc tgttcgcagc ctcacattcc ccggtgcct      960 ctcccatggc tttgtgctgc tgagtcgctc tcatgaagcc cttagggaga gcacctgttg    1020
tgtgcctgac accacgctgg agctgtgtac caatcgtctc agccttcatt aggaggcga    1080 ggtaggagtc ttatatccca ggtgaggaat ttgaagctca gaaaggttga ggggctcccc    1140
agaggtcaca cagcctgtgt gcagtggagc tggcaccatt cagactttca gccgactcag    1200
caactttccc ttgccctggg ctgcctcctc ctgagagctg ttccccaccg ccctgcctct    1260
tccggttgga ggctctcatg tctctttggg gagagctggc agtgtgcgga gctgataaca    1320
ttttcccaat attgagcagt tcccaaggac agtcagcatt tctagacttc acaaaaatta    1380
tgctgcattt ggctggagcc cggtgttcag tggtttccct gcccgaggtc gctgcagccc    1440
catctaccac atcttcatgt ggacattgag attcacatgc tggctcctga agggtgctca    1500
gtctccttgg tgattaaggt cctgcttgaa ctgctgccaa ctccatgtca gggaagtcgc    1560
ttttggtgcc tggctggttt gcccagagcc aagctgggc aaggggcagc cagccctggc     1620
ttccaaggct cccgtactgt ctgtgtcctt gtataaggag cttttgctctt ggaattactg    1680 aaagtctgtg gcccaagaga gagacacaag tggccttaag tctttttgaa gtgttatttc    1740
atccagggaa atgcctcgag ccatagagcc tgaaatcatc tttgttggct cagaaaatac    1800
cttagcttca ctcagctgga ctgcattgaa ggcgaggctg ccccttggat caagcagaaa    1860
```

```
acaagagaaa gaaagaacgt tcccttggg gatagtctgg aaagttggga tttgcaaata    1920
aaggctctgg aagcattgct ggtcctgaag ctttggaggt gggcagagag agcttcaaga    1980
agactagatg caaaccctgg aaaggattaa ggctcaactc tggagaaaca ggccacagcc    2040
tctcagagca gctgttggct gtaaatagag gtagcaaggc cgctcccagg ccctgtgag     2100
tgtgggcacc tgtgcatgca atgctccgac tctgcagagg tgccaagtgc ccctgctggg    2160
ccagtcccag agagttagga agtcaaggcc tgcaactcct ggttcttcct gtttggacca    2220
gttcttgtgc cattggcagg atgagaggca gcagccaggc gggagctgtg tctagcagca    2280
cctgtagccc acgtgctgct aattagctgg aaaactggcg aaggcagaac ctttgctacc    2340
aggaatcttg acatgtgggg tctgtctttg agaatttgta aatgaacagt ccaatatttc    2400
ctctcggctc attttgcaca tccatttttg gggaaatgtg atttctctct cttttttttt    2460
ttttttttt gcctaaggca caatctcaag aggtcctgag accacgtacc catgattttt     2520
ttcttgctct gtgataccca ataactcctt cacctaagcc ctgttgttga ttttgaagtg    2580
cttcctaggc cagtgatttt agcttctgcc agctgctttt gccagtagat taacgtgttt    2640
ttattttca aactccgtgt ttcctaacgt ggagtgtatg ggtctaagag agcctgctgt     2700
cctccctgcc ttccaccttg gagaggaggc tggacgcatc agcagtggcc agggcaggtc    2760
gcaaaatctc ccagcctaga gaccacacct gaaacggctg aagccagctt gcacaagggc    2820
tgctgtccct ctgcggcagg cagagctggt gggggcaggg gtcacagagc agtcatagac    2880
accatggacc agggcaggag aagggcagat ggcacatggg cacaacaggg ccttgtcctt    2940
agagcactgg ggggtcatgg ctgggagggg catggcaggg gctggcatcc ctgtagagcc    3000
agaggggcca cccagggcag tgacattcca gatatgttgg gctcacctca tccttgctgt    3060
gagactggag ttccatgggg acatgaagtc agtacaccgc agagctgctc agctgctcta    3120
cctctcgctg actttttttgt tgcacatata cattttcttt caattagcat ttatttcagc    3180
ttttatttaa gcttttttgac agtacatgta aaatatatga ttataaccat ttaaaaatac    3240
cttatgtacc tggttttttt tggaaactag atagaaatat atttatcttt tacataaaag    3300
aagtgtgtag tggggtggtc cagggctttg tggtggctta gtggccatcg gggtcccagg    3360
ctcttcccac cttttctcttt tgggtccacc tcttggctcc tggcttcctt cctctggggc    3420
ctgactgtcc aggatggcag ctggagctcc tgctctgggc acggttggca tcagagccca    3480
ctgctcccca tccactcttt aatccagatg ctggtaatgt cccttccaa ggcataacta     3540
agataagctg gaaggttctt acgaggcttt gctagaggcc ctgggaggtg ggggaaagg     3600
caagagggca gtgcccaccc atagaccggg tcacatgacc tggcatcagc gccgtggggt    3660
cctttgggct tcacctccct ctcccctctg ccccacgtc atcccaccct catcctcacc      3720
ctcaccattc ccatcccgta ccgtaatgtc ccttgcaagg cctaactctg tgaggaatga    3780
aaccacctca tccttgttcc aataacatga gtgaccgaat ttacaaacga gtgaatgtgg    3840
acctctggaa acattaccca gcttgttttt acttttcact ttctctttct gccccttcca    3900
tttccgtagg agccctttac ctagatgaga agtgtccccc cgcctgggga atatatcagt    3960
cagaacaatc ttcctgcaga catgcaccat tagacccgag tgacggtggt gccatttaaa    4020
cctcagagca ggtaaaaggt ggtcctgaaa cctgtctacc cacagggtgc tatggaatct    4080
gaatcacttc ttttttccta gagccctggg gtggggagct ccctcaagtg ttcacatgtg    4140
tgtggaatga ggaacaccca tctccttggc cctctccacc ctgaagagtt agttattaaa    4200
```

-continued

```
ataattggca agctcttgca aatgtcagtc atccattgtt cagaatggaa tagcaataat    4260
acatccctgg ctgccctggg cttggccagg attactcact gaaggcctca gggttactgg    4320
cacacacttt cttttcctaa taatcccatc ccctcagctt tcctaaggct agagtgaatt    4380
tcgtgttcct ttagtttaca taagatggtg aacttggcaa aagctatcat taaacagaag    4440
ctaagagaaa gcctatgtcg tggaatccag aatgggtatt gccattcact gctgtccaca    4500
gaagctgtct tgaatttctt tctgtgtctt ttcttttttt ttctttaaga ctgttgttta    4560
ccagactggg ctctgtggaa cacaggtgtc ctgggagatg gttaatcatt acaaaatatt    4620
ggtaacaatc taaagatgca tacataagag agtggtcaaa taaaccattt tccattca     4678
```

<210> SEQ ID NO 3
<211> LENGTH: 183
<212> TYPE: PRT
<213> ORGANISM: Homo sapiens

<400> SEQUENCE: 3

```
Met Ala Gly Arg Leu Phe Leu Ser Arg Leu Arg Ala Pro Phe Ser
1               5                   10                  15

Ser Met Ala Lys Ser Pro Leu Glu Gly Val Ser Ser Arg Gly Leu
            20                  25                  30

His Ala Gly Arg Gly Pro Arg Arg Leu Ser Ile Glu Gly Asn Ile Ala
        35                  40                  45

Val Gly Lys Ser Thr Phe Val Lys Leu Leu Thr Lys Thr Tyr Pro Glu
    50                  55                  60

Trp His Val Ala Thr Glu Pro Val Ala Thr Trp Gln Asn Ile Gln Ala
65                  70                  75                  80

Ala Gly Thr Gln Lys Ala Cys Thr Ala Gln Ser Leu Gly Asn Leu Leu
                85                  90                  95

Asp Met Met Tyr Arg Glu Pro Ala Arg Trp Ser Tyr Thr Phe Gln Thr
            100                 105                 110

Phe Ser Phe Leu Ser Arg Leu Lys Val Gln Leu Glu Pro Phe Pro Glu
        115                 120                 125

Lys Leu Leu Gln Ala Arg Lys Pro Val Gln Ile Phe Glu Arg Leu His
    130                 135                 140

Phe Glu Ala Leu Met Asn Ile Pro Val Leu Val Leu Asp Val Asn Asp
145                 150                 155                 160

Asp Phe Ser Glu Glu Val Thr Lys Gln Glu Asp Leu Met Arg Glu Val
                165                 170                 175

Asn Thr Phe Val Lys Asn Leu
            180
```

<210> SEQ ID NO 4
<211> LENGTH: 879
<212> TYPE: DNA
<213> ORGANISM: Homo sapiens

<400> SEQUENCE: 4

```
aacggtgcgc tggagcgagt gagcagcgat acctagggcg gaagtgctct cggcggaagt     60
gatcgctgtg tgaatcgtgg gtgggatggc cgcgggccgc ctctttctaa gtcggcttcg    120
agcacccttc agttccatgg ccaagagccc actcgagggc gtttcctcct ccagaggcct    180
gcacgcgggg cgcgggcccc gaaggctctc catcgaaggc aacattgctg tgggaaagtc    240
cacgtttgtg aagttactca cgaaaactta cccagaatgg cacgtagcta cagaacctgt    300
agcaacatgg cagaatatcc aggctgctgg cacccaaaaa gcctgcactg cccaaagtct    360
```

-continued

```
tggaaacttg ctggatatga tgtaccggga gccagcacga tggtcctaca cattccagac    420 atttccttt tgagccgcc tgaaagtaca gctggagccc ttccctgaga aactcttaca      480
ggccaggaag ccagtacaga tctttgagag gctccacttt gaggctctga tgaacattcc    540
agtgctggtg ttggatgtca atgatgattt ttctgaggaa gtaaccaaac aagaagacct    600
catgagagag gtaaacacct tgtaaagaa tctgtaacca ataccatgaa gttcaggctg     660
tgatctgggc tccctgactt tctgaagcta gaaaaatgtt gtgtctccca accacctttc    720
catccccagc ccctctcatc cctggagcac tctgccgctc aagagctggt tgttaatta    780 ttgttagact ttgccattgt tttcttttgt acctgaagca ttttgaaaat aaagtttact    840
taagttatgc ttgttttct aaaaaaaaaa aaaaaaaa                              879
```

<210> SEQ ID NO 5
<211> LENGTH: 423
<212> TYPE: PRT
<213> ORGANISM: Homo sapiens

<400> SEQUENCE: 5

```
Met Leu Leu Leu Arg Leu Pro Pro His Arg Ser His Ala Ser Pro Leu
1               5                   10                  15

Asp Cys Lys Leu Gln Asp Arg Cys Arg Lys Cys Tyr Ser Pro Arg Ser
            20                  25                  30

Gly Gln Ala Cys Pro Pro Ala Leu Ala Ala Ala Trp Leu Arg Arg Cys
        35                  40                  45

Glu Arg Arg Gly Gly Arg Pro Arg Gly Gly Arg Lys Glu Leu Thr
    50                  55                  60

Leu Gly Leu Arg Pro Ala Arg Cys Ser Ala Pro Gly Pro Ala Lys Asp
65                  70                  75                  80

Asp Ala Trp Arg Pro Gln Ala Gly Arg Ser Ser Asp Thr Asn Glu
                85                  90                  95

Ser Glu Ile Lys Ser Asn Glu Glu Pro Leu Leu Arg Lys Ser Ser Arg
            100                 105                 110

Arg Phe Val Ile Phe Pro Ile Gln Tyr Pro Asp Ile Trp Lys Met Tyr
        115                 120                 125

Lys Gln Ala Gln Ala Ser Phe Trp Thr Ala Glu Glu Val Asp Leu Ser
    130                 135                 140

Lys Asp Leu Pro His Trp Asn Lys Leu Lys Ala Asp Glu Lys Tyr Phe
145                 150                 155                 160

Ile Ser His Ile Leu Ala Phe Phe Ala Ala Ser Asp Gly Ile Val Asn
                165                 170                 175

Glu Asn Leu Val Glu Arg Phe Ser Gln Glu Val Gln Val Pro Glu Ala
            180                 185                 190

Arg Cys Phe Tyr Gly Phe Gln Ile Leu Ile Glu Asn Val His Ser Glu
        195                 200                 205

Met Tyr Ser Leu Leu Ile Asp Thr Tyr Ile Arg Asp Pro Lys Lys Arg
    210                 215                 220

Glu Phe Leu Phe Asn Ala Ile Glu Thr Met Pro Tyr Val Lys Lys Lys
225                 230                 235                 240

Ala Asp Trp Ala Leu Arg Trp Ile Ala Asp Arg Lys Ser Thr Phe Gly
                245                 250                 255

Glu Arg Val Val Ala Phe Ala Val Glu Gly Val Phe Phe Ser Gly
            260                 265                 270

Ser Phe Ala Ala Ile Phe Trp Leu Lys Lys Arg Gly Leu Met Pro Gly
```

```
                      275                 280                 285
Leu Thr Phe Ser Asn Glu Leu Ile Ser Arg Asp Glu Gly Leu His Cys
    290                 295                 300

Asp Phe Ala Cys Leu Met Phe Gln Tyr Leu Val Asn Lys Pro Ser Glu
305                 310                 315                 320

Glu Arg Val Arg Glu Ile Ile Val Asp Ala Val Lys Ile Glu Gln Glu
                325                 330                 335

Phe Leu Thr Glu Ala Leu Pro Val Gly Leu Ile Gly Met Asn Cys Ile
                340                 345                 350

Leu Met Lys Gln Tyr Ile Glu Phe Val Ala Asp Arg Leu Leu Val Glu
                355                 360                 365

Leu Gly Phe Ser Lys Val Phe Gln Ala Glu Asn Pro Phe Asp Phe Met
    370                 375                 380

Glu Asn Ile Ser Leu Glu Gly Lys Thr Asn Phe Phe Glu Lys Arg Val
385                 390                 395                 400

Ser Glu Tyr Gln Arg Phe Ala Val Met Ala Glu Thr Thr Asp Asn Val
                405                 410                 415

Phe Thr Leu Asp Ala Asp Phe
                420

<210> SEQ ID NO 6
<211> LENGTH: 4913
<212> TYPE: DNA
<213> ORGANISM: Homo sapiens

<400> SEQUENCE: 6
atgaggtaaa tgttgctgtt gcgtcttccc cctcaccgca gtcacgccag cccgttagat    60
tgcaagttgc aggaccgctg taggaaatgt tattcgccgc ggtcaggaca ggcctgtccg   120
cccgccctcg ccgcagcctg gcttcgtcgt tgcgagcgcc ggggaggccg tccccgggga   180
gggcggagga aggagctgac tttgggtttg cgtcccgctc gctgctctgc ccgggggcca   240
gccaaggacg acgcttggag gcctcaggcc gggagatcat cttcagacac caacgaaagt   300
gaaataaagt caaatgaaga gccactccta agaaagagtt ctcgccggtt tgtcatcttt   360
ccaatccagt accctgatat tggaaaatg tataaacagg cacaggcttc cttctggaca   420
gcagaagagg tcgacttatc aaaggatctc cctcactgga caagcttaa agcagatgag   480 aagtacttca tctctcacat cttagccttt tttgcagcca gtgatggaat tgtaaatgaa   540
aatttggtgg agcgctttag tcaggaggtg caggttccag aggctcgctg tttctatggc   600
tttcaaattc tcatcgagaa tgttcactca gagatgtaca gttgctgat agacacttac   660 atcagagatc ccaagaaaag ggaatttta tttaatgcaa ttgaaaccat gccctatgtt   720
aagaaaaaag cagattgggc cttgcgatgg atagcagata gaaatctac tttggggaa   780 agagtggtgg cctttgctgc tgtagaagga gttttcttct caggatcttt tgctgctata   840
ttctggctaa agaagagagg tcttatgcca ggactcactt tttccaatga actcatcagc   900
agagatgaag gacttcactg tgactttgct tgcctgatgt tccaatactt agtaaataag   960
ccttcagaag aaagggtcag ggagatcatt gttgatgctg tcaaaattga gcaggagttt  1020
ttaacagaag cccttgccag tggcctcatt ggaatgaatt gcattttgat gaaacagtac  1080
attgagtttg tagctgacag attacttgtg gaacttggat tctcaaaggt ttttcaggca  1140
gaaaatcctt ttgatttat ggaaacatt tcttttagaag gaaaaacaaa tttctttgag  1200
aaacgagttt cagagtatca gcgttttgca gttatggcag aaaccacaga taacgtcttc  1260
```

```
accttggatg cagattttta aaaaacctct cgttttaaaa ctctataaac ttgtcattgg    1320
taaatagtag tctattttcc tctgcttaaa aaaaatttta agtatatcct ttaaaggact    1380
gggggtttgc tcaaaaggaa atccaaaacc tattctaaac aatttgcatt tatataattt    1440
tcctgtttaa caacaagagt gtgacctaaa tgcttttgtc ttgtcactga aataaaagat    1500
ggcattatgt ggttaagagc atggggcgag gggtcagaca tgagtctaag gttctgccct    1560
tactccagtg tgtgacccct tggcaagtcag ttaatcttgg taaacctcgg tgtacttatc    1620
tttaaaatgg gagtaatagt aggtcctaaa ttcatagagt ggatattagg attaggatgc    1680
aaaaataaat gcttaaccaa cactactact gttagcacca ctactaatta tcattcattg    1740
ataatattaa ttgcaatgat gttgtaataa aatactctca tttccttaaa ataattgtga    1800
ttctaggtcc taggatctag aattagatct ttgtatttt aatgcttagg ggaagaatat    1860
aagtatctcc ttaaaaagaa cataattctc attcacgcaa gaataagttc tttgaattcc    1920
ttagtatgta gtgaagaaaa tttagttgtt agttgctttg ggaagcctac ttatggagtg    1980
gaaaccagga ggttatcatg gtagttgacc ttataagaaa aatgattctt cttcagaaat    2040
taaaaacata actattgcca gatttagctc tggaatgttt agaatcaggc tagaatagca    2100
ttttccaaag aatattctaa gagctattag ctcctctaga tatttttttg ggggaaaaag    2160
gggattctgt ggtcagatga gtttgggaaa tgctgaacac ttcattcttc tttagcaagt    2220
acagtcagta catcaaagac tgagcagttc agtggtacat aaatttatct cgccctgcat    2280
attcccaaca tacttaacac agatgttttt tacctgttaa catctcaccc agctagtgtt    2340
cctcagaaca aagattggaa aaagctggcc gagaaccatt tatacataga ggaagggctt    2400
atggactgag aaagggagaa catggtaggg attattgaat catttcaaat ttataccagc    2460
ctgaatagtc taccagcaat tgacttaggc tgtgtttctt tatggttta aaactcttga    2520 gctgttataa gagatagttc ttttaatgtg actatgcaac atgatagcca atggtgaggg    2580
aaaaggaggt ttctctagaa gagtctgatg aaaggccggg aaccaaggtt tttgagaagt    2640 ctgccctat ttatttttag taagtatcaa gaggtagcct gagcctagtt agagttagac    2700 ctgtcttgg atgaagaagt cttaatactg aaatactgaa tttttaatac attattattt    2760
ggtattctgt atacccttc aagcagttgt ttcccattcc caacaaactg tactttatac    2820
aattctggat gctaaaactt agagattttc tctttgcata aattttggct ccattctttc    2880
cataacaatc taatcaaaac tgggagttct caagtgaatg caaaaggagc aggccataac    2940
tttatttgtt agatacactg tcagaaactt gagatctttt ggcctatgat aataccatta    3000
atttttgcat tgcttcagtt tgccaagtgt ttttacatca tctcatttga tctcaaaaca    3060
gcttgacaga gcaactgtta ttgaaatatt acagatggaa agaatgaggc tcagggaagt    3120
taaatgactt ggccaagatc tgctcatcgt cactgtctgt acagtatttt ttttttagagg    3180 ttgtaatgtc tcagatttag tcctttacca tctatgttga tttgcttttg tctatttcct    3240
cattaattga atatacttta aatatatata ttaaagtatc aaaatataga gagacatttg    3300
aactgtattc aggtaatatg tttaaagata tttatatatt gccatacaaa aacttaacat    3360
ttaaaactga taatatctgt aatgacatca gaatgaaaga aaaaaaattg tacagtgtat    3420
attcctttgt tttgaatcca aatctttttc ataggtaatg acagatgcct taatgtgaag    3480
cttatttata atagcaataa acctaactgg atttggatga agaagtctta atactgacat    3540
actggatttt taatgcactg gtttgttatt tggtattcta tctcttttc caggcctcca    3600 ggttgcacat ttattttatta tgttcaatac tttggttctt agttcttaaa gaatcaagaa    3660
```

```
gttgtgtaat cttttaaaaa tattatcttg cagataaaga aaaaaattaa gagtgtgttt    3720
acaactgttt tctctttttt acagtacatg tatttaaatc attgctataa taaagttaag    3780
ttcattagga atataaaaac ttgcagttct atgatagatt gcatttatta aaaatgtttc    3840
attgtatcac atagaaatat ggccaggaag gacttgagaa gacagtttga tccattgctt    3900
ttagacagga ctgggttttg ctgtccaatt atatacaata atagtttttc ttacaactaa    3960
gctggcccca gccttgtctt gatattaata catgaaattt ttataattgt ctcattgtct    4020
catttagaaa catccatatt tttctgcttt ttctattgcc attttttatt tgtgcatgaa    4080
ttgattattg agaaaatgta gcagtttgca tatttaaaaa ttaatcattt tgcattttac    4140
atttaaatat gctaacatca ctgtcataga attcccaaat ttcatttgta gatactgaac    4200
taagggctaa tgtcaggagc tgatttttaa tgataaagct gcagatgggc taaataaaag    4260
ccaaattaat cctacaatca ggtattatgt ttttaaacca agttgagtga attggtagtg    4320
gacttgggaa atcttcccca gcagaatctg gatgaatggc acagaattga aatctctttg    4380
tttcccacca tttcccttta agtgctctgc tcctttgtaa aaagttaaag atttgaaaga    4440
gaatctcata ttcccgaggc attaggaaga aaggatttaa tcccttcaat ttggggctta    4500
atcttgttta aaaaaatgta agtgaagatg gaaggctgga gagaatgatt gcttttttgta   4560 cagttaaata aggtcacaat attcttacat actttgtttt acaactgtgt ttcattttt     4620 tcaaatgtct ggccatttag caaagttatt tactatttac tgtgtacata gaaagcttta    4680
ttatgtgtgg tgtatctaaa ttttttttgc tgaaatacat tatggtcaat caagccaagc    4740
ctgcatgtac agaatttgtt ttttttttcaa ataaattagt tgttttctta ttttttttggc  4800 ttagtatgtt gaaataaact atggtatctt catcattttg tacatttcct ttttgaggaa    4860
ggtttcttta taagtgcaag ggctacccta ataaggaat gtatatactt act            4913

<210> SEQ ID NO 7
<211> LENGTH: 482
<212> TYPE: PRT
<213> ORGANISM: Homo sapiens

<400> SEQUENCE: 7

Met Ala Ala Leu Met Thr Pro Gly Thr Gly Ala Pro Pro Ala Pro Gly
1               5                   10                  15

Asp Phe Ser Gly Glu Gly Ser Gln Gly Leu Pro Asp Pro Ser Pro Glu
                20                  25                  30

Pro Lys Gln Leu Pro Glu Leu Ile Arg Met Lys Arg Asp Gly Gly Arg
            35                  40                  45

Leu Ser Glu Ala Asp Ile Arg Gly Phe Val Ala Val Val Asn Gly
        50                  55                  60

Ser Ala Gln Gly Ala Gln Ile Gly Ala Met Leu Met Ala Ile Arg Leu
65                  70                  75                  80

Arg Gly Met Asp Leu Glu Glu Thr Ser Val Leu Thr Gln Ala Leu Ala
                85                  90                  95

Gln Ser Gly Gln Gln Leu Glu Trp Pro Glu Ala Trp Arg Gln Gln Leu
            100                 105                 110

Val Asp Lys His Ser Thr Gly Gly Val Gly Asp Lys Val Ser Leu Val
        115                 120                 125

Leu Ala Pro Ala Leu Ala Ala Cys Gly Cys Lys Val Pro Met Ile Ser
    130                 135                 140

Gly Arg Gly Leu Gly His Thr Gly Gly Thr Leu Asp Lys Leu Glu Ser
```

```
                      145                 150                 155                 160
            Ile Pro Gly Phe Asn Val Ile Gln Ser Pro Glu Gln Met Gln Val Leu
                            165                 170                 175

Leu Asp Gln Ala Gly Cys Cys Ile Val Gly Gln Ser Glu Gln Leu Val
                            180                 185                 190

Pro Ala Asp Gly Ile Leu Tyr Ala Ala Arg Asp Val Thr Ala Thr Val
                            195                 200                 205

Asp Ser Leu Pro Leu Ile Thr Ala Ser Ile Leu Ser Lys Lys Leu Val
                210                 215                 220

Glu Gly Leu Ser Ala Leu Val Val Asp Val Lys Phe Gly Ala Ala
            225                 230                 235                 240

Val Phe Pro Asn Gln Glu Gln Ala Arg Glu Leu Ala Lys Thr Leu Val
                            245                 250                 255

Gly Val Gly Ala Ser Leu Gly Leu Arg Val Ala Ala Leu Thr Ala
                            260                 265                 270

Met Asp Lys Pro Leu Gly Arg Cys Val Gly His Ala Leu Glu Val Glu
                        275                 280                 285

Glu Ala Leu Leu Cys Met Asp Gly Ala Gly Pro Pro Asp Leu Arg Asp
                290                 295                 300

Leu Val Thr Thr Leu Gly Gly Ala Leu Leu Trp Leu Ser Gly His Ala
            305                 310                 315                 320

Gly Thr Gln Ala Gln Gly Ala Ala Arg Val Ala Ala Leu Asp Asp
                            325                 330                 335

Gly Ser Ala Leu Gly Arg Phe Glu Arg Met Leu Ala Ala Gln Gly Val
                        340                 345                 350

Asp Pro Gly Leu Ala Arg Ala Leu Cys Ser Gly Ser Pro Ala Glu Arg
                        355                 360                 365

Arg Gln Leu Leu Pro Arg Ala Arg Glu Gln Glu Leu Leu Ala Pro
                        370                 375                 380

Ala Asp Gly Thr Val Glu Leu Val Arg Ala Leu Pro Leu Ala Leu Val
            385                 390                 395                 400

Leu His Glu Leu Gly Ala Gly Arg Ser Arg Ala Gly Glu Pro Leu Arg
                            405                 410                 415

Leu Gly Val Gly Ala Glu Leu Leu Val Asp Val Gly Gln Arg Leu Arg
                            420                 425                 430

Arg Gly Thr Pro Trp Leu Arg Val His Arg Asp Gly Pro Ala Leu Ser
                        435                 440                 445

Gly Pro Gln Ser Arg Ala Leu Gln Glu Ala Leu Val Leu Ser Asp Arg
                450                 455                 460

Ala Pro Phe Ala Ala Pro Ser Pro Phe Ala Glu Leu Val Leu Pro Pro
            465                 470                 475                 480

Gln Gln

<210> SEQ ID NO 8
<211> LENGTH: 1679
<212> TYPE: DNA
<213> ORGANISM: Homo sapiens

<400> SEQUENCE: 8
cgactgccga gctccgccct ccaggcggcc ccacccgcct gccgtcctgg ggcgccgccg    60
ccccgccgcc ggcagtggac cgctgtgcgc gaaccctgaa ccctacggtc ccgaccccgcg   120 ggcgaggccg ggtacctggg ctgggatccg gagcaagcgg gcgagggcag cgccctaagc   180
aggcatcccc gcaggcccgg agcgatggca gccttgatga ccccgggaac cggggcccca   240
```

```
cccgcgcctg gtgacttctc cggggaaggg agccagggac ttcccgaccc ttcgccagag      300
cccaagcagc tcccggagct gatccgcatg aagcgagacg gaggccgcct gagcgaagcg      360
gacatcaggg gcttcgtggc cgctgtggtg aatgggagcg cgcagggcgc acagatcggg      420
gccatgctga tggccatccg acttcggggc atggatctgg aggagacctc ggtgctgacc      480
caggccctgg ctcagtcggg acagcagctg gagtggccag aggcctggcg ccagcagctt      540
gtggacaagc attccacagg gggtgtgggt gacaaggtca gcctggtcct cgcacctgcc      600
ctggcggcat gtggctgcaa ggtgccaatg atcagcggac gtggtctggg gcacacagga      660
ggcaccttgg ataagctgga gtctattcct ggattcaatg tcatccagag cccagagcag      720
atgcaagtgc tgctggacca ggcgggctgc tgtatcgtgg gtcagagtga gcagctggtt      780
cctgcggacg gaatcctata tgcagccaga gatgtgacag ccaccgtgga cagcctgcca      840
ctcatcacag cctccattct cagtaagaaa ctcgtggagg ggctgtccgc tctggtggtg      900
gacgttaagt tcggagggggc cgccgtcttc cccaaccagg agcaggcccg ggagctggca      960
aagacgctgg ttggcgtggg agccagccta gggcttcggg tcgcggcagc gctgaccgcc     1020
atggacaagc ccctgggtcg ctgcgtgggc acgccctgg aggtggagga ggcgctgctc     1080
tgcatggacg gcgcaggccc gccagactta agggacctgg tcaccacgct cgggggcgcc     1140
ctgctctggc tcagcggaca cgcgggggact caggcccagg gcgctgcccg ggtgccgcg     1200 gcgctggacg acggctcggc ccttggccgc ttcgagcgga tgctggcggc gcagggcgtg     1260
gatcccggtc tggcccgagc cctgtgctcg ggaagtcccg cagaacgccg gcagctgctg     1320
cctcgcgccc gggagcagga ggagctgctg gcgcccgcag atggcaccgt ggagctggtc     1380
cgggcgctgc cgctggcgct ggtgctgcac gagctcgggg ccgggcgcag ccgcgctggg     1440
gagccgctcc gcctgggggt gggcgcagag ctgctggtcg acgtgggtca gaggctgcgc     1500
cgtgggaccc cctggctccg cgtgcaccgg gacggccccg cgctcagcgg cccgcagagc     1560
cgcgccctgc aggaggcgct cgtactctcc gaccgcgcgc cattcgccgc ccctcgccc      1620 ttcgcagagc tcgttctgcc gccgcagcaa taaagctcct tgccgcgaa aaaaaaaa       1679
```

<210> SEQ ID NO 9
<211> LENGTH: 463
<212> TYPE: PRT
<213> ORGANISM: Homo sapiens

<400> SEQUENCE: 9

Met Ala Ala Ser Met Phe Tyr Gly Arg Leu Val Ala Val Ala Thr Leu
1               5                   10                  15

Arg Asn His Arg Pro Arg Thr Ala Gln Arg Ala Ala Gln Val Leu
            20                  25                  30

Gly Ser Ser Gly Leu Phe Asn Asn His Gly Leu Gln Val Gln Gln Gln
        35                  40                  45

Gln Gln Arg Asn Leu Ser Leu His Glu Tyr Met Ser Met Glu Leu Leu
    50                  55                  60

Gln Glu Ala Gly Val Ser Val Pro Lys Gly Tyr Val Ala Lys Ser Pro
65                  70                  75                  80

Asp Glu Ala Tyr Ala Ile Ala Lys Lys Leu Gly Ser Lys Asp Val Val
                85                  90                  95

Ile Lys Ala Gln Val Leu Ala Gly Gly Arg Gly Lys Gly Thr Phe Glu
            100                 105                 110

Ser Gly Leu Lys Gly Gly Val Lys Ile Val Phe Ser Pro Glu Glu Ala

```
            115                 120                 125
Lys Ala Val Ser Ser Gln Met Ile Gly Lys Lys Leu Phe Thr Lys Gln
    130                 135                 140

Thr Gly Glu Lys Gly Arg Ile Cys Asn Gln Val Leu Val Cys Glu Arg
145                 150                 155                 160

Lys Tyr Pro Arg Arg Glu Tyr Tyr Phe Ala Ile Thr Met Glu Arg Ser
                165                 170                 175

Phe Gln Gly Pro Val Leu Ile Gly Ser Ser His Gly Gly Val Asn Ile
            180                 185                 190

Glu Asp Val Ala Ala Glu Ser Pro Glu Ala Ile Ile Lys Glu Pro Ile
                195                 200                 205

Asp Ile Glu Glu Gly Ile Lys Lys Glu Gln Ala Leu Gln Leu Ala Gln
            210                 215                 220

Lys Met Gly Phe Pro Pro Asn Ile Val Glu Ser Ala Ala Glu Asn Met
225                 230                 235                 240

Val Lys Leu Tyr Ser Leu Phe Leu Lys Tyr Asp Ala Thr Met Ile Glu
                245                 250                 255

Ile Asn Pro Met Val Glu Asp Ser Asp Gly Ala Val Leu Cys Met Asp
            260                 265                 270

Ala Lys Ile Asn Phe Asp Ser Asn Ser Ala Tyr Arg Gln Lys Lys Ile
            275                 280                 285

Phe Asp Leu Gln Asp Trp Thr Gln Glu Asp Glu Arg Asp Lys Asp Ala
            290                 295                 300

Ala Lys Ala Asn Leu Asn Tyr Ile Gly Leu Asp Gly Asn Ile Gly Cys
305                 310                 315                 320

Leu Val Asn Gly Ala Gly Leu Ala Met Ala Thr Met Asp Ile Ile Lys
                325                 330                 335

Leu His Gly Gly Thr Pro Ala Asn Phe Leu Asp Val Gly Gly Gly Ala
            340                 345                 350

Thr Val His Gln Val Thr Glu Ala Phe Lys Leu Ile Thr Ser Asp Lys
            355                 360                 365

Lys Val Leu Ala Ile Leu Val Asn Ile Phe Gly Gly Ile Met Arg Cys
    370                 375                 380

Asp Val Ile Ala Gln Gly Ile Val Met Ala Val Lys Asp Leu Glu Ile
385                 390                 395                 400

Lys Ile Pro Val Val Val Arg Leu Gln Gly Thr Arg Val Asp Asp Ala
                405                 410                 415

Lys Ala Leu Ile Ala Asp Ser Gly Leu Lys Ile Leu Ala Cys Asp Asp
            420                 425                 430

Leu Asp Glu Ala Ala Arg Met Val Val Lys Leu Ser Glu Ile Val Thr
            435                 440                 445

Leu Ala Lys Gln Ala His Val Asp Val Lys Phe Gln Leu Pro Ile
    450                 455                 460
```

<210> SEQ ID NO 10
<211> LENGTH: 2182
<212> TYPE: DNA
<213> ORGANISM: Homo sapiens

<400> SEQUENCE: 10
ccgcctgtcg cctgtgcgcc tgcgcgcggc gccgagggga cggggtccga ctcagaaatg    60
gcggcctcca tgttctacgg caggctagtg gccgtggcca cccttcggaa ccaccggcct   120
cggacggccc agcgggctgc tgctcaggtt ctgggaagtt ctggattgtt taataaccat   180

```
ggactccaag tacagcagca acagcaaagg aatctctcac tacatgaata catgagtatg    240
gaattattgc aagaagctgg tgtctccgtt cccaaaggat atgtggcaaa gtcaccagat    300
gaagcttatg caattgccaa aaaattaggt tcaaagatg tcgtgataaa ggcacaggtt     360
ttagctggtg gtagaggaaa aggaacattt gaaagtggcc tcaaaggagg agtgaagata    420
gttttctctc cagaagaagc aaaagctgtt tcttcacaaa tgattgggaa aaaattgttt    480
accaagcaaa cggagaaaa gggcagaata tgcaatcaag tattggtctg tgagcgaaaa     540
tatcccagga gagaatacta ctttgcaata acaatggaaa ggtcatttca aggtcctgta    600
ttaataggaa gttcacatgg tggtgtcaac attgaagatg ttgctgctga gtctcctgaa    660
gcaataatta agaacctat tgatattgaa gaaggcatca aaaggaaca agctctccag      720 cttgcacaga agatgggatt tccacctaat attgtggaat cagcagcaga aaacatggtc    780
aagctttaca gccttttttct gaaatacgat gcaaccatga tagaaataaa tccaatggtg   840
gaagattcag atggagctgt attgtgtatg gatgcaaaga tcaattttga ctctaattca    900
gcctatcgcc aaaagaaaat cttttgatcta caggactgga cccaggaaga tgaaagggac   960
aaagatgctg ctaaggcaaa tctcaactac attggcctcg atggaaatat aggctgccta    1020
gtaaatggtg ctggtttggc tatggccaca atggatataa taaaacttca tggagggact   1080
ccagccaact tccttgatgt tggtggtggt gctacagtcc atcaagtaac agaagcattt    1140
aagcttatca cttcagataa aaaggtactg gctattctgg tcaacatttt tggaggaatc    1200
atgcgctgtg atgttattgc acagggtata gtcatggcag taaaagactt ggaaattaaa    1260
atacctgttg tggtacggtt acaaggtaca cgagtcgatg atgctaaggc actgatagcg    1320
gacagtggac ttaaaatact tgcttgtgat gacttggatg aagctgctag aatggttgta    1380
aagctctctg aaatagtgac cttagcgaag caagcacatg tggatgtgaa atttcagttg    1440
ccaatatgat ctgaaaaccc agtggatggc tgaaggtgtt aaatgtgcta taatcattaa    1500
gaatactgtg ttctgtgtta ttgttctttt tcttttttagt gtgtggagat tgtaattgcc   1560
atctaggcac acaaacattt aaaaggattt ggactgcatt taattgtacc attcagaatg    1620
gactgtttgt acgaagcatg tataatgcag ttatcttctt tcttttgtcg cagccagtct    1680
tttttgcttc tcctacaaaa cgtaacttgc aatttgccag tttattattg ttggatacaa    1740
agttcttcat tgataagagt cctataaata agataaatac gaagataaag ctttattctt    1800
tagtgttaaa atacagtata tctaataact agcctcatta gtagagcagt atattaaaac    1860
aatgttttat gtaaaaagtg tttatcttca gcaccaaata catgataaat gtatcaatca    1920
ctatttataa acagagcttt caaacactcc tcagaatatt cttctaagta ttttgatgaa    1980
gtaactttgt aattatttga acattgtttt aatcattagg aaacactgat taactgcaag    2040
tcttcatgat tctgtcatat taagaaacac ctgtaggttt gcttcaaata aaggcatata    2100
taccaaggac ttcagacaa aattaagaat gtcaatttaa gttaataaaa atctcccaat     2160
atgaaaaaaa aaaaaaaaaa aa                                             2182
```

<210> SEQ ID NO 11
<211> LENGTH: 346
<212> TYPE: PRT
<213> ORGANISM: Homo sapiens

<400> SEQUENCE: 11

Met Thr Ala Thr Leu Ala Ala Ala Ala Asp Ile Ala Thr Met Val Ser
1               5                   10                  15

Gly Ser Ser Gly Leu Ala Ala Ala Arg Leu Leu Ser Arg Ser Phe Leu
            20                  25                  30

Leu Pro Gln Asn Gly Ile Arg His Cys Ser Tyr Thr Ala Ser Arg Gln
            35                  40                  45

His Leu Tyr Val Asp Lys Asn Thr Lys Ile Ile Cys Gln Gly Phe Thr
 50                  55                  60

Gly Lys Gln Gly Thr Phe His Ser Gln Gln Ala Leu Glu Tyr Gly Thr
 65                  70                  75                  80

Lys Leu Val Gly Gly Thr Thr Pro Gly Lys Gly Gln Thr His Leu
                85                  90                  95

Gly Leu Pro Val Phe Asn Thr Val Lys Glu Ala Lys Glu Gln Thr Gly
            100                 105                 110

Ala Thr Ala Ser Val Ile Tyr Val Pro Pro Phe Ala Ala Ala
            115                 120                 125

Ile Asn Glu Ala Ile Glu Ala Glu Ile Pro Leu Val Val Cys Ile Thr
            130                 135                 140

Glu Gly Ile Pro Gln Gln Asp Met Val Arg Val Lys His Lys Leu Leu
145                 150                 155                 160

Arg Gln Glu Lys Thr Arg Leu Ile Gly Pro Asn Cys Pro Gly Val Ile
                165                 170                 175

Asn Pro Gly Glu Cys Lys Ile Gly Ile Met Pro Gly His Ile His Lys
            180                 185                 190

Lys Gly Arg Ile Gly Ile Val Ser Arg Ser Gly Thr Leu Thr Tyr Glu
            195                 200                 205

Ala Val His Gln Thr Thr Gln Val Gly Leu Gly Gln Ser Leu Cys Val
            210                 215                 220

Gly Ile Gly Gly Asp Pro Phe Asn Gly Thr Asp Phe Ile Asp Cys Leu
225                 230                 235                 240

Glu Ile Phe Leu Asn Asp Ser Ala Thr Glu Gly Ile Leu Ile Gly
                245                 250                 255

Glu Ile Gly Gly Asn Ala Glu Glu Asn Ala Ala Glu Phe Leu Lys Gln
            260                 265                 270

His Asn Ser Gly Pro Asn Ser Lys Pro Val Val Ser Phe Ile Ala Gly
            275                 280                 285

Leu Thr Ala Pro Pro Gly Arg Arg Met Gly His Ala Gly Ala Ile Ile
            290                 295                 300

Ala Gly Gly Lys Gly Gly Ala Lys Glu Lys Ile Ser Ala Leu Gln Ser
305                 310                 315                 320

Ala Gly Val Val Val Ser Met Ser Pro Ala Gln Leu Gly Thr Thr Ile
            325                 330                 335

Tyr Lys Glu Phe Glu Lys Arg Lys Met Leu
            340                 345

<210> SEQ ID NO 12
<211> LENGTH: 1270
<212> TYPE: DNA
<213> ORGANISM: Homo sapiens

<400> SEQUENCE: 12
gtcattggcg tatgaccgca acccttgccg ctgccgctga catcgctacc atggtctccg    60
gcagcagcgg cctcgccgcc gcccgtctcc tgtcgcgcag cttcctcctg ccgcagaatg   120
gaattcggca ttgttcctac acagcttctc ggcaacatct ctatgttgat aaaaatacaa   180
agattatttg ccagggtttc actggcaaac agggcacctt tcacagccag caggcattgg   240

```
aatatggcac caaactcgtt ggaggaacca ctccagggaa aggaggccag acacatctgg    300
gcttacctgt ctttaatact gtgaaggagg ccaaagaaca gacaggagca acggcttctg    360
tcatttatgt tcctccgcct tttgctgctg ctgccattaa tgaagctatt gaggcagaaa    420
ttcccttggt tgtgtgtatc actgaaggaa ttccccagca ggacatggta cgagtcaagc    480
acaaactgct gcgccaggaa aagacaaggc taattgggcc caactgccct ggagtcatca    540
atcctggaga atgtaaaatt ggcatcatgc ctggccatat tcacaaaaaa ggaaggattg    600
gcattgtgtc cagatctggc accctgactt atgaagcagt tcaccaaaca acgcaagttg    660
gattggggca gtctttgtgc gttggcattg gaggtgatcc ttttaatgga acagatttta    720
ttgactgcct cgaaatcttt ttgaacgatt ctgccacaga aggcatcata ttgattggtg    780
aaattggtgg taatgcagaa gagaatgctg cagaattttt gaagcaacat aattcaggtc    840
caaattccaa gcctgtagtg tccttcattg ctggtttaac tgctcctcct gggagaagaa    900
tgggtcatgc cggggcaatt attgctggag gaaaaggtgg agctaaagag aagatctctg    960
cccttcagag tgcaggagtt gtggtcagta tgtctcctgc acagctggga accacgatct   1020
acaaggaatt tgaaagagg aagatgctat gaaagaaaaa aaaaattcct aaaactgtgg   1080
aatggatcac gtagacatgt aacccagcag cagtttgctt ctgttgtcca ctgattaatc   1140
agcctatgtg cctgacactg gtcttgcagt acaactggaa gccaaaacaa ggtggaagat   1200
gtcctgaatt aagatgtttt caccacattg tattacagag acagccaata aatctactat   1260
ttgatttcaa                                                          1270

<210> SEQ ID NO 13
<211> LENGTH: 176
<212> TYPE: PRT
<213> ORGANISM: Homo sapiens

<400> SEQUENCE: 13

Met Ala Leu Trp Arg Ala Tyr Gln Arg Ala Leu Ala Ala His Pro Trp
1               5                   10                  15

Lys Val Gln Val Leu Thr Ala Gly Ser Leu Met Gly Leu Gly Asp Ile
            20                  25                  30

Ile Ser Gln Gln Leu Val Glu Arg Gly Leu Gln Glu His Gln Arg
        35                  40                  45

Gly Arg Thr Leu Thr Met Val Ser Leu Gly Cys Gly Phe Val Gly Pro
    50                  55                  60

Val Val Gly Gly Trp Tyr Lys Val Leu Asp Arg Phe Ile Pro Gly Thr
65                  70                  75                  80

Thr Lys Val Asp Ala Leu Lys Lys Met Leu Leu Asp Gln Gly Gly Phe
                85                  90                  95

Ala Pro Cys Phe Leu Gly Cys Phe Leu Pro Leu Val Gly Ala Leu Asn
            100                 105                 110

Gly Leu Ser Ala Gln Asp Asn Trp Ala Lys Leu Gln Arg Asp Tyr Pro
        115                 120                 125

Asp Ala Leu Ile Thr Asn Tyr Tyr Leu Trp Pro Ala Val Gln Leu Ala
    130                 135                 140

Asn Phe Tyr Leu Val Pro Leu His Tyr Arg Leu Ala Val Val Gln Cys
145                 150                 155                 160

Val Ala Val Ile Trp Asn Ser Tyr Leu Ser Trp Lys Ala His Arg Leu
                165                 170                 175

<210> SEQ ID NO 14
```

<211> LENGTH: 1002
<212> TYPE: DNA
<213> ORGANISM: Homo sapiens

<400> SEQUENCE: 14

```
agttcctagg ccagcctgtc acgtgggagg gaggctcggc gctcaggaag catggcactc      60
tggcgggcat accagcgggc cctggccgct cacccgtgga agtacaggt cctgacagct      120
gggtccctga tgggcctggg tgacattatc tcacagcagc tggtggagag gcggggtctg     180
caggaacacc agagaggccg gactctgacc atggtgtccc tgggctgtgg ctttgtgggc     240
cctgtggtag gaggctggta caaggttttg gatcggttca tccctggcac caccaaagtg     300
gatgcactga agaagatgtt gttggatcag gggggctttg ccccgtgttt tctaggctgc     360
tttctcccac tggtagggc acttaatgga ctgtcagccc aggacaactg gccaaacta      420
cagcgggatt atcctgatgc ccttatcacc aactactatc tatggcctgc tgtgcagtta    480
gccaacttct acctggtccc ccttcattac aggttggccg ttgtccaatg tgttgctgtt    540
atctggaact cctacctgtc ctggaaggca atcggctct aagcctgcct cactccatcg    600
tttccacctt gcagtgatgc agcttgaccc tggaacggtc agacaacctc ctcaaagtgg    660
gcataccagt ttcacgggg ttgggttgcc ggtcagagct aagaggact agcaccctgc      720
aatgccctc ttcactctaa aatgtacact gactgcttta gagcccttga taatagtctt     780
attcccacca catactaggc actccataaa tatctgttga accttcatga ccttatcaac    840
tttacacca tcccagca aatgccactc atccccactc ttcatagaca catttgttac      900
tctaaccctg cctaggcttc ttgtagctcc agctctttag agactcccgg aaccctttat    960
atggtgcctc agtaaatatg ttattaaata tgtaatccgg aa                       1002
```

<210> SEQ ID NO 15
<211> LENGTH: 1239
<212> TYPE: PRT
<213> ORGANISM: Homo sapiens

<400> SEQUENCE: 15

```
Met Ser Arg Leu Leu Trp Arg Lys Val Ala Gly Ala Thr Val Gly Pro
1               5                   10                  15

Gly Pro Val Pro Ala Pro Gly Arg Trp Val Ser Ser Val Pro Ala
            20                  25                  30

Ser Asp Pro Ser Asp Gly Gln Arg Arg Gln Gln Gln Gln Gln
        35                  40                  45

Gln Gln Gln Gln Gln Gln Gln Pro Gln Pro Gln Val Leu Ser Ser
    50                  55                  60

Glu Gly Gly Gln Leu Arg His Asn Pro Leu Asp Ile Gln Met Leu Ser
65                  70                  75                  80

Arg Gly Leu His Glu Gln Ile Phe Gly Gln Gly Glu Met Pro Gly
                85                  90                  95

Glu Ala Ala Val Arg Arg Ser Val Glu His Leu Gln Lys His Gly Leu
            100                 105                 110

Trp Gly Gln Pro Ala Val Pro Leu Pro Asp Val Glu Leu Arg Leu Pro
        115                 120                 125

Pro Leu Tyr Gly Asp Asn Leu Asp Gln His Phe Arg Leu Leu Ala Gln
    130                 135                 140

Lys Gln Ser Leu Pro Tyr Leu Glu Ala Ala Asn Leu Leu Leu Gln Ala
145                 150                 155                 160

Gln Leu Pro Pro Lys Pro Pro Ala Trp Ala Trp Ala Glu Gly Trp Thr
```

```
            165                 170                 175
Arg Tyr Gly Pro Glu Gly Glu Ala Val Pro Val Ala Ile Pro Glu Glu
            180                 185                 190

Arg Ala Leu Val Phe Asp Val Glu Val Cys Leu Ala Glu Gly Thr Cys
            195                 200                 205

Pro Thr Leu Ala Val Ala Ile Ser Pro Ser Ala Trp Tyr Ser Trp Cys
            210                 215                 220

Ser Gln Arg Leu Val Glu Glu Arg Tyr Ser Trp Thr Ser Gln Leu Ser
225                 230                 235                 240

Pro Ala Asp Leu Ile Pro Leu Glu Val Pro Thr Gly Ala Ser Ser Pro
                    245                 250                 255

Thr Gln Arg Asp Trp Gln Glu Gln Leu Val Val Gly His Asn Val Ser
                260                 265                 270

Phe Asp Arg Ala His Ile Arg Glu Gln Tyr Leu Ile Gln Gly Ser Arg
            275                 280                 285

Met Arg Phe Leu Asp Thr Met Ser Met His Met Ala Ile Ser Gly Leu
        290                 295                 300

Ser Ser Phe Gln Arg Ser Leu Trp Ile Ala Ala Lys Gln Gly Lys His
305                 310                 315                 320

Lys Val Gln Pro Pro Thr Lys Gln Gly Gln Lys Ser Gln Arg Lys Ala
                    325                 330                 335

Arg Arg Gly Pro Ala Ile Ser Ser Trp Asp Trp Leu Asp Ile Ser Ser
                340                 345                 350

Val Asn Ser Leu Ala Glu Val His Arg Leu Tyr Val Gly Gly Pro Pro
            355                 360                 365

Leu Glu Lys Glu Pro Arg Glu Leu Phe Val Lys Gly Thr Met Lys Asp
        370                 375                 380

Ile Arg Glu Asn Phe Gln Asp Leu Met Gln Tyr Cys Ala Gln Asp Val
385                 390                 395                 400

Trp Ala Thr His Glu Val Phe Gln Gln Gln Leu Pro Leu Phe Leu Glu
                    405                 410                 415

Arg Cys Pro His Pro Val Thr Leu Ala Gly Met Leu Glu Met Gly Val
                420                 425                 430

Ser Tyr Leu Pro Val Asn Gln Asn Trp Glu Arg Tyr Leu Ala Glu Ala
            435                 440                 445

Gln Gly Thr Tyr Glu Glu Leu Gln Arg Glu Met Lys Lys Ser Leu Met
        450                 455                 460

Asp Leu Ala Asn Asp Ala Cys Gln Leu Leu Ser Gly Glu Arg Tyr Lys
465                 470                 475                 480

Glu Asp Pro Trp Leu Trp Asp Leu Glu Trp Asp Leu Gln Glu Phe Lys
                    485                 490                 495

Gln Lys Lys Ala Lys Lys Val Lys Lys Glu Pro Ala Thr Ala Ser Lys
                500                 505                 510

Leu Pro Ile Glu Gly Ala Gly Ala Pro Gly Asp Pro Met Asp Gln Glu
            515                 520                 525

Asp Leu Gly Pro Cys Ser Glu Glu Glu Phe Gln Gln Asp Val Met
        530                 535                 540

Ala Arg Ala Cys Leu Gln Lys Leu Lys Gly Thr Thr Glu Leu Leu Pro
545                 550                 555                 560

Lys Arg Pro Gln His Leu Pro Gly His Pro Gly Trp Tyr Arg Lys Leu
                    565                 570                 575

Cys Pro Arg Leu Asp Asp Pro Ala Trp Thr Pro Gly Pro Ser Leu Leu
                580                 585                 590
```

Ser Leu Gln Met Arg Val Thr Pro Lys Leu Met Ala Leu Thr Trp Asp
            595                 600                 605

Gly Phe Pro Leu His Tyr Ser Glu Arg His Gly Trp Gly Tyr Leu Val
            610                 615                 620

Pro Gly Arg Arg Asp Asn Leu Ala Lys Leu Pro Thr Gly Thr Thr Leu
625                 630                 635                 640

Glu Ser Ala Gly Val Val Cys Pro Tyr Arg Ala Ile Glu Ser Leu Tyr
                645                 650                 655

Arg Lys His Cys Leu Glu Gln Gly Lys Gln Gln Leu Met Pro Gln Glu
            660                 665                 670

Ala Gly Leu Ala Glu Glu Phe Leu Leu Thr Asp Asn Ser Ala Ile Trp
            675                 680                 685

Gln Thr Val Glu Glu Leu Asp Tyr Leu Glu Val Glu Ala Glu Ala Lys
            690                 695                 700

Met Glu Asn Leu Arg Ala Ala Val Pro Gly Gln Pro Leu Ala Leu Thr
705                 710                 715                 720

Ala Arg Gly Gly Pro Lys Asp Thr Gln Pro Ser Tyr His His Gly Asn
                725                 730                 735

Gly Pro Tyr Asn Asp Val Asp Ile Pro Gly Cys Trp Phe Phe Lys Leu
            740                 745                 750

Pro His Lys Asp Gly Asn Ser Cys Asn Val Gly Ser Pro Phe Ala Lys
            755                 760                 765

Asp Phe Leu Pro Lys Met Glu Asp Gly Thr Leu Gln Ala Gly Pro Gly
            770                 775                 780

Gly Ala Ser Gly Pro Arg Ala Leu Glu Ile Asn Lys Met Ile Ser Phe
785                 790                 795                 800

Trp Arg Asn Ala His Lys Arg Ile Ser Ser Gln Met Val Val Trp Leu
                805                 810                 815

Pro Arg Ser Ala Leu Pro Arg Ala Val Ile Arg His Pro Asp Tyr Asp
            820                 825                 830

Glu Glu Gly Leu Tyr Gly Ala Ile Leu Pro Gln Val Val Thr Ala Gly
            835                 840                 845

Thr Ile Thr Arg Arg Ala Val Glu Pro Thr Trp Leu Thr Ala Ser Asn
            850                 855                 860

Ala Arg Pro Asp Arg Val Gly Ser Glu Leu Lys Ala Met Val Gln Ala
865                 870                 875                 880

Pro Pro Gly Tyr Thr Leu Val Gly Ala Asp Val Asp Ser Gln Glu Leu
                885                 890                 895

Trp Ile Ala Ala Val Leu Gly Asp Ala His Phe Ala Gly Met His Gly
            900                 905                 910

Cys Thr Ala Phe Gly Trp Met Thr Leu Gln Gly Arg Lys Ser Arg Gly
            915                 920                 925

Thr Asp Leu His Ser Lys Thr Ala Thr Thr Val Gly Ile Ser Arg Glu
            930                 935                 940

His Ala Lys Ile Phe Asn Tyr Gly Arg Ile Tyr Gly Ala Gly Gln Pro
945                 950                 955                 960

Phe Ala Glu Arg Leu Leu Met Gln Phe Asn His Arg Leu Thr Gln Gln
                965                 970                 975

Glu Ala Ala Glu Lys Ala Gln Gln Met Tyr Ala Ala Thr Lys Gly Leu
            980                 985                 990

Arg Trp Tyr Arg Leu Ser Asp Glu  Gly Glu Trp Leu Val  Arg Glu Leu
            995                  1000                 1005

```
Asn Leu Pro Val Asp Arg Thr Glu Gly Gly Trp Ile Ser Leu Gln
    1010                1015                1020

Asp Leu Arg Lys Val Gln Arg Glu Thr Ala Arg Lys Ser Gln Trp
    1025                1030                1035

Lys Lys Trp Glu Val Val Ala Glu Arg Ala Trp Lys Gly Gly Thr
    1040                1045                1050

Glu Ser Glu Met Phe Asn Lys Leu Glu Ser Ile Ala Thr Ser Asp
    1055                1060                1065

Ile Pro Arg Thr Pro Val Leu Gly Cys Cys Ile Ser Arg Ala Leu
    1070                1075                1080

Glu Pro Ser Ala Val Gln Glu Glu Phe Met Thr Ser Arg Val Asn
    1085                1090                1095

Trp Val Val Gln Ser Ser Ala Val Asp Tyr Leu His Leu Met Leu
    1100                1105                1110

Val Ala Met Lys Trp Leu Phe Glu Glu Phe Ala Ile Asp Gly Arg
    1115                1120                1125

Phe Cys Ile Ser Ile His Asp Glu Val Arg Tyr Leu Val Arg Glu
    1130                1135                1140

Glu Asp Arg Tyr Arg Ala Ala Leu Ala Leu Gln Ile Thr Asn Leu
    1145                1150                1155

Leu Thr Arg Cys Met Phe Ala Tyr Lys Leu Gly Leu Asn Asp Leu
    1160                1165                1170

Pro Gln Ser Val Ala Phe Phe Ser Ala Val Asp Ile Asp Arg Cys
    1175                1180                1185

Leu Arg Lys Glu Val Thr Met Asp Cys Lys Thr Pro Ser Asn Pro
    1190                1195                1200

Thr Gly Met Glu Arg Arg Tyr Gly Ile Pro Gln Gly Glu Ala Leu
    1205                1210                1215

Asp Ile Tyr Gln Ile Ile Glu Leu Thr Lys Gly Ser Leu Glu Lys
    1220                1225                1230

Arg Ser Gln Pro Gly Pro
    1235

<210> SEQ ID NO 16
<211> LENGTH: 4452
<212> TYPE: DNA
<213> ORGANISM: Homo sapiens

<400> SEQUENCE: 16
gcggaccggc cgggtggagg ccacacgcta ccccgaggct gcgtaggccg cgcgaagggg      60
gacgccgtgc cgtgggcctg ggtcggggg  agcagcagac cgggaagcac cgatttgggg     120
tggaaggcag gcatggtcaa acccatttca ctgacaggag agcagagaca ggacgtgtct    180
ctctccacgt cttccagcca gtaaaagaag ccaagctgga gcccaaagcc aggtgttctg    240
actcccagcg tggggtccc  tgcaccaacc atgagccgcc tgctctggag gaaggtggcc    300
ggcgccaccg tcgggccagg gccggttcca gctccggggc gctgggtctc cagctccgtc    360
cccgcgtccg accccagcga cgggcagcgg cggcggcagc agcagcagca gcagcagcag    420
cagcagcaac agcagcctca gcagccgcaa gtgctatcct cggagggcgg gcagctgcgg    480
cacaacccat tggacatcca gatgctctcg agagggctgc acgagcaaat cttcgggcaa    540
ggagggagag tgcctggcga ggccgcggtg cgccgcagcg tcgagcacct gcagaagcac    600
ggctctgggg gcagccagc  cgtgcccttg cccgacgtgg agctgcgcct gccgccctc    660 tacggggaca acctggacca gcacttccgc ctcctggccc agaagcagag cctgccctac    720
```

```
ctggaggcgg ccaacttgct gttgcaggcc cagctgcccc cgaagccccc ggcttgggcc      780
tgggcggagg gctggacccg gtacggcccc gaggggagg ccgtacccgt ggccatcccc       840
gaggagcggg ccctggtgtt cgacgtggag gtctgcttgg cagagggaac ttgccccaca      900
ttggcggtgg ccatatcccc ctcggcctgg tattcctggt gcagccagcg gctggtggaa      960
gagcgttact cttggaccag ccagctgtcg ccggctgacc tcatcccct ggaggtccct      1020 actggtgcca gcagccccac ccagagagac tggcaggagc agttagtggt ggggcacaat    1080
gtttcctttg accgagctca tatcagggag cagtacctga tccagggttc ccgcatgcgt    1140
ttcctggaca ccatgagcat gcacatggcc atctcagggc taagcagctt ccagcgcagt    1200
ctgtggatag cagccaagca gggcaaacac aaggtccagc cccccacaaa gcaaggccag    1260
aagtcccaga ggaaagccag aagaggccca gcgatctcat cctgggactg gctggacatc    1320
agcagtgtca acagtctggc agaggtgcac agactttatg tagggggggcc tcccttagag    1380 aaggagcctc gagaactgtt tgtgaagggc accatgaagg acattcgtga gaacttccag    1440
gacctgatgc agtactgtgc ccaggacgtg tgggccaccc atgaggtttt ccagcagcag    1500
ctaccgctct tcttggagag gtgtccccac ccagtgactc tggccggcat gctggagatg    1560
ggtgtctcct acctgcctgt caaccagaac tgggagcgtt acctggcaga ggcacagggc    1620
acttatgagg agctccagcg ggagatgaag aagtcgttga tggatctggc caatgatgcc    1680
tgccagctgc tctcaggaga gaggtacaaa gaagacccct ggctctggga cctggagtgg    1740
gacctgcaag aatttaagca gaagaaagct aagaaggtga agaaggaacc agccacagcc    1800
agcaagttgc ccatcgaggg ggctgggggcc cctggtgatc ccatggatca ggaagacctc    1860
ggcccctgca gtgaggagga ggagtttcaa caagatgtca tggcccgcgc ctgcttgcag    1920
aagctgaagg ggaccacaga gctcctgccc aagcggcccc agcaccttcc tggacaccct    1980
ggatggtacc ggaagctctg cccccggcta gacgaccctg catggacccc gggccccagc    2040
ctcctcagcc tgcagatgcg ggtcacacct aaactcatgg cacttacctg ggatggcttc    2100
cctctgcact actcagagcg tcatggctgg ggctacttgg tgcctgggcg gcgggacaac    2160
ctggccaagc tgccgacagg taccaccctg gagtcagctg gggtggtctg ccctacaga    2220 gccatcgagt ccctgtacag gaagcactgt ctcgaacagg ggaagcagca gctgatgccc    2280
caggaggccg gcctggcgga ggagttcctg ctcactgaca atagtgccat atggcaaacg    2340
gtagaagaac tggattactt agaagtggag gctgaggcca agatggagaa cttgcgagct    2400
gcagtgccag gtcaaccccct agctctgact gcccgtggtg gccccaagga cacccagccc    2460
agctatcacc atggcaatgg accttacaac gacgtggaca tccctggctg ctggtttttc    2520
aagctgcctc acaaggatgg taatagctgt aatgtgggaa gcccctttgc caaggacttc    2580
ctgcccaaga tggaggatgg caccctgcag gctggcccag gaggtgccag tgggccccgt    2640
gctctggaaa tcaacaaaat gatttctttc tggaggaacg cccataaacg tatcagctcc    2700
cagatggtgg tgtggctgcc caggtcagct ctgcccgtg ctgtgatcag gcaccccgac    2760
tatgatgagg aaggcctcta tggggccatc ctgccccaag tggtgactgc cggcaccatc    2820
actcgccggg ctgtggagcc cacatggctc accgccagca atgcccggcc tgaccgagta    2880
ggcagtgagt tgaaagccat ggtgcaggcc ccacctggct acacccttgt gggtgctgat    2940
gtggactccc aagagctgtg gattgcagct gtgcttggag acgccacctt tgccggcatg    3000
catggctgca cagcctttgg gtggatgaca ctgcagggca ggaagagcag gggcactgat    3060
```

```
ctacacagta agacagccac tactgtgggc atcagccgtg agcatgccaa aatcttcaac    3120
tacggccgca tctatggtgc tgggcagccc tttgctgagc gcttactaat gcagtttaac    3180
caccggctca cacagcagga ggcagctgag aaggcccagc agatgtacgc tgccaccaag    3240
ggcctccgct ggtatcggct gtcggatgag ggcgagtggc tggtgaggga gttgaacctc    3300
ccagtggaca ggactgaggg tggctggatt tccctgcagg atctgcgcaa ggtccagaga    3360
gaaactgcaa ggaagtcaca gtggaagaag tgggaggtgg ttgctgaacg ggcatggaag    3420
gggggcacag agtcagaaat gttcaataag cttgagagca ttgctacgtc tgacatacca    3480
cgtaccccgg tgctgggctg ctgcatcagc cgagccctgg agccctcggc tgtccaggaa    3540
gagtttatga ccagccgtgt gaattgggtg gtacagagct ctgctgttga ctacttacac    3600
ctcatgcttg tggccatgaa gtggctgttt gaagagtttg ccatagatgg gcgcttctgc    3660
atcagcatcc atgacgaggt tcgctacctg gtgcgggagg aggaccgcta ccgcgctgcc    3720
ctggccttgc agatcaccaa cctcttgacc aggtgcatgt ttgcctacaa gctgggtctg    3780
aatgacttgc cccagtcagt cgccttttc agtgcagtcg atattgaccg gtgcctcagg    3840
aaggaagtga ccatggattg taaaaccct tccaacccaa ctgggatgga aaggagatac    3900
gggattcccc agggtgaagc gctggatatt taccagataa ttgaactcac caaaggctcc    3960
ttggaaaaac gaagccagcc tggaccatag cactgcctgg aggctctgta tttgctcccg    4020
tggagcttca tcggggtggt gcaggctccc aaactcaggc tttcagctgt gcttttgca    4080 aaagggcttg cctaaggcca gccattttc agtagcagga cctgccaaga agattccttc    4140
taactgaagg tgcagttgaa ttcagtgggt tcagaaccaa gatgccaaca tcggtgtgga    4200
ctacaggaca aggggcattg ttgcttgttg ggtaaaaatg aagcagaagc cccaaagttc    4260
acattaactc aggcatttca tttattttt ccttttcttc ttggctggtt ctttgttctg    4320
tcccccatgc tctgatgcag tgccctagaa ggggaaagaa ttaatgctct aacgtgataa    4380
acctgctcca aggcagtgga aataaaaaga aggaaaaaaa agactctatc ttctcaaaaa    4440
aaaaaaaaaa aa                                                       4452
```

<210> SEQ ID NO 17
<211> LENGTH: 705
<212> TYPE: DNA
<213> ORGANISM: Homo sapiens

<400> SEQUENCE: 17

```
atgggagcat tttgccagcg acctagttcc gataaagaac aggagaaaga gaagaagagc     60
gtcatctgtg tggaaggtaa catcgctagt ggcaaaacga cctgtttgga atttttctct    120
aatgccaccg atgtggaggt gcttacagag cctgttagta aatggcgaaa tgttcgagga    180
cataatccgc tgggactgat gtatcacgat gcctccagat ggggactgac ccttcagact    240
tatgtccaac ttacaatgct tgacaggcac actagaccgc aggttagcag cgtgaggctg    300
atggagcgct caattcactc tgccaggtat atattcgttg agaacctcta ccgatctggt    360
aagatgcctg aggtagatta cgtagtgctg agtgaatggt ttgactggat tcttcgcaac    420
atggatgtat cagtggatct cattgtttac cttaggacta acccgagac gtgttatcag    480 cgcttgaaaa agcgctgccg ggaagaggaa aaagtgattc ctctggaata cttggaagct    540
attcatcacc ttcacgaaga gtggctgata aaaggttccc tgtttcccat ggcggccccc    600
gtgcttgtca tagaagcgga tcaccacatg gaaaggatgc tcgaactttt cgagcaaaat    660
cgagaccgga ttctcacgcc ggagaatcga aaacattgcc catag                     705
```

<210> SEQ ID NO 18
<211> LENGTH: 552
<212> TYPE: DNA
<213> ORGANISM: Homo sapiens

<400> SEQUENCE: 18

| | | | | | |
|---|---|---|---|---|---|
| atggctgcag | ggaggctttt | tttgtctaga | ttgagggcac | cttttagctc | catggcgaag | 60 |
| tctccgcttg | aggggtgag | tagcagccgg | gggctccatg | ctggcagagg | gccccggagg | 120 |
| ctgtctattg | agggaatat | tgcagttggt | aagagcacgt | tgttaaatt | gctcacgaag | 180 |
| acctatccag | aatggcacgt | tgctacagaa | ccagtagcta | catggcaaaa | cattcaagca | 240 |
| gcaggcacac | agaaggcttg | cactgcacag | tctctcggaa | acctgctcga | tatgatgtac | 300 |
| agagagcccg | cccggtggtc | atacacgttt | cagaccttca | gctttctttc | tcggttgaag | 360 |
| gtacagttgg | agcccttccc | agagaagttg | cttcaagcac | ggaaacctgt | acagatattc | 420 |
| gaacgattgc | atttcgaggc | gctgatgaac | atacctgtgc | ttgttctgga | tgtgaacgac | 480 |
| gatttttccg | aggaagttac | taagcaagag | gacctcatgc | gggaggtaaa | cacgttcgtt | 540 |
| aagaacctgt | aa | | | | | 552 |

<210> SEQ ID NO 19
<211> LENGTH: 1449
<212> TYPE: DNA
<213> ORGANISM: Homo sapiens

<400> SEQUENCE: 19

| | | | | | |
|---|---|---|---|---|---|
| atggcagcat | tgatgacacc | aggaacgggg | gctccgcctg | cgcctggcga | tttttcagga | 60 |
| gaggggagtc | aaggtctgcc | ggacccttca | ccggaaccca | aacagcttcc | cgagcttatt | 120 |
| agaatgaagc | gagatggggg | tcgcctctct | gaggctgaca | tacgcggctt | tgttgcggcg | 180 |
| gtcgtcaacg | gctcagcaca | aggtgcgcaa | ataggagcga | tgctgatggc | tatcaggctg | 240 |
| aggggaatgg | atttggaaga | gaccagtgtg | ctgactcaag | cgctggcaca | gagcggccag | 300 |
| cagcttgaat | ggccagaagc | ttggcgccaa | caattggtcg | ataaacactc | aaccgggggc | 360 |
| gtcggggaca | aagtctccct | tgtactggca | cctgctctgg | ctgcgtgcgg | atgtaaggtt | 420 |
| cctatgatta | gcgggcgggg | cttgggacat | acgggaggaa | cgttggacaa | actcgaatcc | 480 |
| atccctggtt | tcaacgtgat | tcagagccct | gaacaaatgc | aagtactcct | ggatcaggca | 540 |
| ggctgctgta | ttgttggcca | aagcgaacaa | ctcgtgcctg | cggatggtat | cctctatgct | 600 |
| gccagggatg | tgaccgccac | agttgactcc | ctcccgctga | taacagcgtc | aattttgagt | 660 |
| aagaagctcg | tcgaagggct | cagcgctctt | gtggttgatg | taaaatttgg | ggggccgca | 720 |
| gtattcccca | accaggaaca | agcacggaa | ctggcaaaaa | ccctggttgg | tgtgggcgct | 780 |
| tcactgggcc | tgagagttgc | cgctgccttg | accgccatgg | ataagccgct | cggtaggtgc | 840 |
| gtaggtcatg | cacttgaagt | agaagaagcc | cttttgtgca | tggatggggc | cggtcccct | 900 |
| gacttgcggg | atctcgtaac | cacgcttggc | ggcgcgttgc | tttggctttc | tggacacgct | 960 |
| ggtacccaag | cgcaagggc | agcaagagtc | gcagcagcgc | ttgatgacgg | atcagctctt | 1020 |
| gggcgatttg | aaagaatgct | tgcagctcag | gcgctagatc | cagggctggc | gcgggccctt | 1080 |
| tgctcaggtt | ctccagcaga | gcgccgacag | ctccttccca | gggcgcgaga | gcaggaagaa | 1140 |
| ttgctggccc | cggctgatgg | taccgtcgaa | ctcgtacggg | ctttgccgct | ggctcttgtt | 1200 |
| ttgcacgaac | tgggggctgg | gcggagtcgc | gccggtgaac | ctctcagact | cggtgtgggt | 1260 |

-continued

| | |
|---|---|
| gcggagctcc tcgttgacgt cgggcaacga cttcgcaggg gaaccccttg gcttagggta | 1320 |
| cacagggacg ggccagcact cagcggccct cagtccaggg cccttcaaga agctctcgtg | 1380 |
| ctgagtgatc gagcgccttt tgccgctccc tcaccatttg ctgaattggt attgccaccc | 1440 |
| cagcagtaa | 1449 |

<210> SEQ ID NO 20
<211> LENGTH: 1272
<212> TYPE: DNA
<213> ORGANISM: Homo sapiens

<400> SEQUENCE: 20

| | |
|---|---|
| atgctgcttc tcagactgcc accccaccgc agtcatgctt ccccacttga ctgtaaactt | 60 |
| caagataggt gccggaagtg ttactcaccc cgatcaggac aagcgtgccc tcctgcgttg | 120 |
| gcggccgcct ggcttcggcg gtgtgaacgc cgaggaggtc ggccgagggg tgggcgacgc | 180 |
| aaggaactga cccttggcct cgcgcctgca cggtgttcag ctcccggtcc tgccaaggat | 240 |
| gatgcatgga gacctcaggc aggtcgctcc tcctcagata ccaacgagag tgaaattaaa | 300 |
| tctaatgaag aaccccttct tcgcaagagt agtcgcaggt tcgtgatatt ccccatacaa | 360 |
| tatcctgata tctggaaaat gtacaagcaa gcccaagcat cattctggac cgcagaagag | 420 |
| gttgatctca gtaaggacct cccacactgg aacaaactga agccgacga aaaatatttc | 480 |
| atatcccata tacttgcttt cttttgcagcc tcagatggaa ttgtgaatga aacttggta | 540 |
| gagcgcttct ctcaagaggt ccaagttcct gaagcacgat gcttttacgg atttcaaatc | 600 |
| ctgatagaaa atgtacattc cgaaatgtat tccttgctta tagacacgta tatcagagat | 660 |
| cccaaaaaaa gggagttctt gttcaatgcg atcgagacca tgccatatgt taagaaaaaa | 720 |
| gccgattggg ccctgaggtg gatagctgat aggaagtcta catttgggga acgcgttgtt | 780 |
| gccttcgccg ccgtcgaggg agtcttcttc tccggatcct tcgctgctat ctttttggctg | 840 |
| aaaaaacgcg gcttgatgcc tggtttgacc tttagcaatg agttgatatc acggatgaa | 900 |
| gggctgcatt gtgactttgc ctgccttatg ttccagtact tggtgaacaa accgtctgag | 960 |
| gaacgggtaa gggaaatcat agtggatgca gtaaaaatag agcaggagtt ccttactgaa | 1020 |
| gcgctccccg tagggctcat tggcatgaac tgcattctta tgaagcagta catcgagttc | 1080 |
| gtggccgata gacttttggt ggagctcggg ttctcaaagg tttttcaggc tgaaaatcct | 1140 |
| tttgatttta tggagaacat atctctggag ggcaagacta acttttttga aaaaagagta | 1200 |
| tccgagtatc aaaggtttgc cgtgatggca gaaacaacag ataatgtctt cacacttgat | 1260 |
| gcggattttt aa | 1272 |

<210> SEQ ID NO 21
<211> LENGTH: 1392
<212> TYPE: DNA
<213> ORGANISM: Homo sapiens

<400> SEQUENCE: 21

| | |
|---|---|
| atggcggctt ctatgttcta tggacgcctg gtcgccgttg ccacgttgcg gaatcacagg | 60 |
| ccccgaactg cacaaagggc tgccgctcag gtgcttggaa gcagcggatt gttcaacaat | 120 |
| cacggcctcc aagttcagca acagcagcag agaaacctct ctctgcatga gtatatgagt | 180 |
| atggaactgc tccaggaagc aggggtgtct gtaccaaagg gctacgtagc aaaaagcccc | 240 |
| gacgaggcgt acgccatagc taaaaaactg ggaagtaagg acgtagttat caaagcacag | 300 |
| gttctggccg gtggccgcgg taagggaacc ttcgagagtg gtttgaaagg cggtgtcaag | 360 |

```
atcgtattta gtcccgagga ggccaaggct gtaagttccc agatgatcgg caaaaaattg    420
ttcacaaagc aaaccggcga aaagggtaga atttgcaacc aagtacttgt ctgcgaaaga    480
aagtatccga aagggagta ttatttcgct ataaccatgg aaagatcatt ccaaggtccc    540
gtgctcatcg gcagttcaca cggggggcgtt aatatagagg atgtcgctgc agagtctccg    600
gaggccataa ttaaggagcc tatagacatc gaggaaggca ttaaaaaaga caagccttg    660 caactggcac aaaaaatggg ttttcctccg aacatcgtcg agagtgccgc agaaaatatg    720
gtgaaactgt acagcctgtt tttgaagtac gatgcgacaa tgatagaaat taatccgatg    780
gtcgaggact cagatggagc cgtgctttgt atggacgcca aaattaactt cgattcaaac    840
agcgcttatc gacagaagaa aattttcgat ttgcaagatt ggacccaaga ggatgagcga    900
gacaaagatg ccgccaaagc aaatctcaat tatataggac tcgatggtaa tattggatgt    960
ttggtcaatg gtgccggtct cgcgatggca actatggata taatcaagtt gcatggtggg    1020
actcccgcca actttcttga cgtcggggga ggcgccaccg ttcaccaagt tacgaggct    1080 ttcaaactca taacctctga caagaaggtg ctggcgattc ttgtaaatat ctttggtggc    1140
attatgcggt gtgatgttat tgcccaggga atagtaatgg ctgtcaaaga tttggagatt    1200
aaaatacccg tcgtggtgcg gctccaaggt actcgagtag atgatgctaa ggctctgatt    1260
gccgacagcg ggctgaagat tctggcatgt gatgatttgg acgaggcagc gagaatggtc    1320
gtgaagctct cagaaatagt aactttggcg aaacaggctc atgtcgatgt aaagttccaa    1380
cttcctatat ga                                                        1392

<210> SEQ ID NO 22
<211> LENGTH: 1041
<212> TYPE: DNA
<213> ORGANISM: Homo sapiens

<400> SEQUENCE: 22
atgaccgcta cgcttgcggc tgcagccgac atcgcgacaa tggtctctgg aagttcaggc     60
ttggccgcgg ctcggcttct gagtagaagt ttcttgttgc cgcaaaacgg tatcaggcac    120
tgctcctaca ccgccagtag acaacacctt tatgttgata agaacacgaa gataatttgc    180
caaggattca ccgtaaaaca ggggacctcc cattcccagc aggcactgga atatggaact    240
aaattggtag cgcgcactac gcctgggaag ggtggccaaa cacatcttgg tcttcccgtt    300
tttaacacag tgaaggaggc taaagaacaa acgggggcaa cggctagcgt tatctatgtc    360 ccaccccgt tgccgctgc agccataaat gaggcgattg aagccgagat cccgcttgta    420
gtctgcataa cggagggaat tccgcaacaa gacatggtgc gagtaaagca caagcttctt    480
cgacaggaaa aaacaagact gataggtccg aattgtcctg cgtaattaa ccccggtgaa    540 tgcaaaatcg gaattatgcc gggacatatt cacaaaaaag gccgaatcgg atagtcagc    600 agatcaggca ccttgacata cgaagcggtt caccagacta cgcaagtcgg tttgggacaa    660
agcctttgcg tcggtatcgg tggcgaccca tttaacggga cggatttcat tgactgtctg    720
gagatcttcc tcaacgattc cgcgacagaa ggaatcattt tgataggaga aataggcggg    780
aacgccgaag agaatgcagc ggaattcctc aaacaacata actctggccc taatagtaag    840
ccggtggtat cattcatagc cggtcttaca gcgccgccgg tcgcagaat gggccacgca    900 ggtgcaatta tagcggggg caagggaggt gccaaagaaa agatatccgc tcttcaaagc    960
gcaggtgtag tagttagtat gagtccagct caactgggca caaccatcta caagaatttt    1020
```

```
gaaaagcgga aaatgctttg a                                             1041
```

<210> SEQ ID NO 23
<211> LENGTH: 531
<212> TYPE: DNA
<213> ORGANISM: Homo sapiens

<400> SEQUENCE: 23

```
atggccctct ggagagctta ccaacgagcc ttggccgcgc acccttggaa ggtacaggtc     60
ttgaccgccg gatctttgat gggtcttgga gatattattt ctcaacagtt ggttgaacgg    120
cgaggcctcc aggaacacca aggggagag accttacaa tggtaagtct gggttgcgga     180
ttcgtcgggc ctgtcgtggg gggatggtat aaggttctgg atcgctttat accggggacc    240
accaaggtcg atgccttgaa gagatgttg ctggatcagg gaggattcgc tccgtgtttt     300
ttgggatgtt ttctgccact tgttggggct ctgaacggac tgtccgcgca ggataactgg    360
gcgaagttgc aacgcgacta cccagacgcc ctgataacaa attactatct ctggccagca    420
gttcagttgg ccaatttta cctggtacct ctccactatc gccttgctgt agtacagtgt     480
gtcgccgtca tctggaactc ataccttca tggaaggctc atagattgta a              531
```

<210> SEQ ID NO 24
<211> LENGTH: 3720
<212> TYPE: DNA
<213> ORGANISM: Homo sapiens

<400> SEQUENCE: 24

```
atgtccaggc tgctctggcg gaaggtcgca ggcgccactg tcggtccagg accagttcca     60
gctcccggtc gctgggtgag cagcagcgtg ccagctagcg atccgagcga cggtcagcgg    120
cgacggcaac aacagcagca acagcaacaa cagcaacaac aacagcccca gcagcctcag    180
gttctcagtt ccgagggtgg ccaactccga cacaacccac tggatataca gatgctctcc    240
cgcggtctcc acgaacaaat attcggacaa ggggtgaga tgccgggaga ggctgcggtc      300
aggcgcagtg tagaacatct ccagaaacac gggttgtggg gccaaccggc cgttcctctc    360
cccgatgttg aactgcggct tccacctctc tacggtgata atctggacca gcactttaga    420
ctgctcgctc aaaagcagag tctcccttac ctggaagccg ctaacctcct gctccaagcc    480
caattgcccc ctaaaccgcc agcctgggct tgggcgagg gatggacgag gtatggaccc      540
gaaggggagg ctgtgccagt tgctatacca gaggaacgcg ctctggtttt cgacgtagag    600
gtttgtctcg cggagggaac ttgtcctaca ctggctgtag caatttcccc ttcagcctgg    660
tacagctggt gctctcagag attggtggaa gaaaggtata gctggactag ccagctgagt    720
cccgcggacc tcattccact tgaggtaccc accggggcgt caagcccaac tcagagggac    780
tggcaggaac aattggtagt tgggcataat gtgagttttg acagggctca tatccgcgaa    840
cagtatctta tccagggctc tagaatgcga ttccttgaca cgatgagcat gcacatggca    900
atcagcggac ttagttcctt tcagaggtca ttgtggattg cagccaagca gggaaagcat    960
aaggtccaac ccccgacaaa acaaggtcag aaatcccaga gaaaagcccg gcgaggcccc   1020
gccatcagtt cctgggattg gttggatatc agtagtgtga atagccttgc tgaggtgcat   1080
cgcctgtatg tgggtggacc cccacttgag aaagagccta gggagctctt cgtcaaaggc   1140
accatgaagg atattagaga gaattttcaa gatctcatgc aatactgcgc acaagacgta   1200
tgggcaacgc atgaggtctt tcaacagcaa ctccccctct ttttggaacg atgtccacat   1260
cccgtcactc ttgctgggat gttggaaatg ggtgtaagtt atttgccagt caatcaaaat   1320
```

```
tgggagagat acttggctga agcgcagggt acatatgagg aacttcagcg agaaatgaaa    1380
aaaagtctta tggatttggc caatgacgcc tgccagctgc tttccggtga gcggtacaaa    1440
gaagatccat ggctttggga tctcgaatgg gatttgcagg aatttaaaca gaaaaaggcc    1500
aagaaggtca agaaagagcc agctacagcc tcaaagctcc ctatagaggg agcgggagca    1560
ccgggtgatc cgatggatca agaggatttg ggaccttgct ccgaagagga ggaattccaa    1620
caagatgtaa tggcaagggc ctgcctgcaa aagctcaaag ggacaacaga actcttgccc    1680
aagaggcctc aacatctgcc cggccatcca ggttggtatc gcaaactctg tccaaggctg    1740
gacgatcccg cctggacccc ggggcccctcc cttctgagtc tgcagatgag agtgacacct    1800
aagctgatgg cacttacttg ggatgggttc cctcttcact attcagagag acacgggtgg    1860
ggatatcttg tcccaggtcg aagggacaat ctggcgaagc ttcccacagg aactaccttg    1920
gagagtgcgg gcgtagtatg tccttatcga gccatagaaa gtctgtatag aaagcattgc    1980
cttgaacaag gcaaacaaca actcatgcct caggaagccg gcctcgctga agaatttctt    2040
cttactgata actctgctat ctggcaaaca gtggaggaac tggattacct cgaagtcgag    2100
gccgaagcga agatggaaaa tttgcgggcg gcggtcccag gtcagcccct tgctttgaca    2160
gcacgggggg gccctaagga tacccagccc agctatcatc acgggaacgg tccatataat    2220
gatgttgata tacctggttg ttggtttttt aaacttcctc ataaagatgg caattcatgt    2280
aacgttggat ccccattcgc aaaggacttc ctccccaaaa tggaggatgg gacgttgcaa    2340
gcaggtcccg gtggagcttc tgggccgcga gccctggaaa taaataagat gattagcttc    2400
tggaggaatg cacacaagcg catttcttca cagatggtag tgtggctgcc tcggagtgct    2460
ttgcccaggg ctgtgatcag acaccccgat tatgatgaag agggactgta cggggcaata    2520
ttgccccagg tggttacggc tggtactatt acccgccggg cagttgagcc gacctggctg    2580
acagcatcta atgccaggcc tgatcgcgtg ggttctgaac ttaaagcaat ggtccaagct    2640
ccgcctggat acacgcttgt cggcgcggac gtggactccc aggaactttg gatagcggct    2700
gtccttggcg atgcacattt tgcagggatg cacggggtgca cggcttttgg ctggatgaca    2760
cttcagggga ggaaatcaag ggggaccgac ctgcactcca agaccgcgac aacggtagga    2820
atctcaaggg aacacgctaa aattttcaat tatgggagaa tatatggtgc cggtcaaccg    2880
ttcgctgagc gccttctgat gcagtttaac cataggctga cacagcagga ggcagcggag    2940
aaggcgcagc agatgtacgc cgcaactaag ggtctcagat ggtatcgcct ctcagacgag    3000
ggcgagtggc ttgtccggga attgaacctc ccggtcgatc ggacggaagg tggttggatt    3060
agtcttcagg atctcagaaa ggtgcagcgg gaaacagcac gcaagtctca gtggaagaaa    3120
tgggaggtgg tcgccgagcg ggcatggaag ggtggaacag aatccgagat gtttaacaag    3180
ctggagagca tagcaactag tgacatccct aggacaccgg tcttgggatg ttgcattagc    3240
cgggcactcg agccatctgc cgtacaggaa gaattcatga cgtcacgggt caactgggtt    3300
gtccagtctt cagccgtcga ttatctgcat ttgatgctgg tcgcgatgaa gtggctcttc    3360
gaagagtttg ctatagatgg ccgattttgc atctctattc acgatgaggt gcgctacctg    3420
```

-continued

```
gtaagggaag aagaccgata ccgagccgcc ctcgcccttc agataacaaa tctgcttacc    3480
aggtgtatgt ttgcatacaa gctggggttg aacgaccttc cccagtccgt cgctttcttt    3540
tcagctgttg atatagatcg ctgcctgaga aaagaggtta cgatggactg caaaacgccc    3600
tcaaacccca ctggtatgga gcgcagatat ggcatccccc aaggagaagc cctcgacata    3660
taccagataa ttgagctcac gaagggcagc ctggagaaga gatcccaacc tggcccatag    3720
```